US011633535B2

(12) United States Patent
Damiano et al.

(10) Patent No.: US 11,633,535 B2
(45) Date of Patent: Apr. 25, 2023

(54) AMBULATORY DEVICE AND COMPONENTS THEREOF

(71) Applicant: BETA BIONICS, Inc., Concord, MA (US)

(72) Inventors: Edward R. Damiano, Acton, MA (US); David Matthew Henderson, Mission Viejo, CA (US); Bryan Dale Knodel, Flagstaff, AZ (US); Michael J. Rosinko, Anaheim, CA (US)

(73) Assignee: BETA BIONICS, Inc., Concord, MA (US)

( * ) Notice: Subject to any disclaimer, the term of this patent is extended or adjusted under 35 U.S.C. 154(b) by 0 days.

(21) Appl. No.: 17/038,949

(22) Filed: Sep. 30, 2020

(65) Prior Publication Data

US 2021/0030949 A1    Feb. 4, 2021

Related U.S. Application Data

(63) Continuation of application No. PCT/US2020/042198, filed on Jul. 15, 2020.
(Continued)

(51) Int. Cl.
*A61M 5/14*          (2006.01)
*A61M 5/142*         (2006.01)
(Continued)

(52) U.S. Cl.
CPC .......... *A61M 5/1407* (2013.01); *A61M 5/142* (2013.01); *A61M 5/14244* (2013.01);
(Continued)

(58) Field of Classification Search
CPC ........ A61M 39/105; A61M 2039/1066; A61M 5/162; A61M 5/1407; A61M 2005/1587; A61M 5/14248
See application file for complete search history.

(56) References Cited

U.S. PATENT DOCUMENTS 1,930,929 A   10/1933  Eisenberg
3,807,467 A    4/1974  Tascher et al.
(Continued)

FOREIGN PATENT DOCUMENTS

EP    3 150 241    6/2018
EP    3 378 516    9/2018
(Continued)

OTHER PUBLICATIONS

Kolind et al., "Preservation-free drug for insulin pumps," Novo Nordisk Pharmaceutical company, Pump partner meeting ATTD 2020, WOP Technology Presentation, 26 pages.
(Continued)

*Primary Examiner* — Theodore J Stigell
(74) *Attorney, Agent, or Firm* — Patnstr®, APC

(57) ABSTRACT

Certain embodiments provide multi-medicament or single medicament infusion systems for preventing the cross-channeling or improper delivery of medicaments. The system may include one or more of an infusion pump, medicament cartridges, cartridge connectors, a multi-channel fluid conduit, and an infusion set. The medicament cartridges may be sized and shaped differently such that the medicament reservoirs can only be inserted into the pump under selected configurations.

29 Claims, 49 Drawing Sheets

Related U.S. Application Data

(60) Provisional application No. 63/037,472, filed on Jun. 10, 2020, provisional application No. 62/987,842, filed on Mar. 10, 2020, provisional application No. 62/874,977, filed on Jul. 16, 2019, provisional application No. 62/874,975, filed on Jul. 16, 2019, provisional application No. 62/874,972, filed on Jul. 16, 2019, provisional application No. 62/874,964, filed on Jul. 16, 2019, provisional application No. 62/874,959, filed on Jul. 16, 2019, provisional application No. 62/874,954, filed on Jul. 16, 2019, provisional application No. 62/874,928, filed on Jul. 16, 2019.

(51) Int. Cl.
*A61M 39/10* (2006.01)
*A61M 5/158* (2006.01)
*A61M 5/162* (2006.01)

(52) U.S. Cl.
CPC ............ *A61M 5/158* (2013.01); *A61M 5/162* (2013.01); *A61M 39/105* (2013.01); *A61M 5/14248* (2013.01); *A61M 2005/1587* (2013.01); *A61M 2205/13* (2013.01); *A61M 2205/3317* (2013.01); *A61M 2205/505* (2013.01); *A61M 2205/584* (2013.01); *A61M 2205/8206* (2013.01); *A61M 2205/8243* (2013.01)

(56) References Cited

U.S. PATENT DOCUMENTS

| | | |
|---|---|---|
| 4,150,673 A | 4/1979 | Watt |
| 4,253,501 A | 3/1981 | Ogle |
| 4,515,584 A | 5/1985 | Abe et al. |
| 4,585,439 A | 4/1986 | Michel |
| 4,608,042 A | 8/1986 | Vanderveen |
| 4,675,006 A | 6/1987 | Hrushesky |
| 4,955,861 A | 9/1990 | Enegren et al. |
| 5,085,643 A | 2/1992 | Larkin et al. |
| 5,147,323 A | 9/1992 | Haber |
| 5,243,982 A | 9/1993 | Mostl |
| 5,298,023 A | 3/1994 | Haber |
| 5,356,380 A | 10/1994 | Hoekwater et al. |
| 5,411,480 A | 5/1995 | Kriesel |
| 5,472,403 A | 12/1995 | Cornacchia |
| 5,505,704 A | 4/1996 | Pawelka et al. |
| 5,522,803 A | 6/1996 | Teissen-Simony |
| 5,529,463 A | 6/1996 | Layer |
| 5,545,152 A * | 8/1996 | Funderburk ........ A61M 39/14 604/535 |
| 5,616,124 A | 4/1997 | Hague et al. |
| 5,916,494 A | 6/1999 | Widman et al. |
| 5,954,697 A | 9/1999 | Srisathapat et al. |
| 5,961,494 A | 10/1999 | Hogan |
| 5,971,972 A | 10/1999 | Rosenbaum |
| 6,106,498 A | 8/2000 | Friedli et al. |
| 6,132,416 A | 10/2000 | Broselow |
| 6,248,067 B1 | 6/2001 | Causey, III et al. |
| 6,259,587 B1 | 7/2001 | Sheldon et al. |
| 6,360,784 B1 | 3/2002 | Philippens et al. |
| 6,362,591 B1 | 3/2002 | Moberg |
| 6,368,314 B1 | 4/2002 | Kipfer et al. |
| 6,390,130 B1 | 5/2002 | Guala |
| 6,485,465 B2 | 11/2002 | Moberg et al. |
| 6,551,276 B1 | 4/2003 | Mann et al. |
| 6,551,298 B1 | 4/2003 | Zhang et al. |
| 6,554,798 B1 | 4/2003 | Mann et al. |
| 6,555,986 B2 | 4/2003 | Moberg |
| 6,558,320 B1 | 5/2003 | Causey, III et al. |
| 6,572,545 B2 | 6/2003 | Knobbe et al. |
| 6,585,695 B1 | 7/2003 | Adair et al. |
| 6,620,138 B1 | 9/2003 | Marrgi et al. |
| 6,641,533 B2 | 11/2003 | Causey, III et al. |
| 6,652,483 B2 | 11/2003 | Slate |
| 6,656,148 B2 | 12/2003 | Das et al. |
| 6,659,980 B2 | 12/2003 | Moberg et al. |
| 6,719,728 B2 | 4/2004 | Mason et al. |
| 6,736,797 B1 | 5/2004 | Larsen et al. |
| 6,752,787 B1 | 6/2004 | Causey, III et al. |
| 6,801,420 B2 | 10/2004 | Talbot et al. |
| 6,809,653 B1 | 10/2004 | Mann et al. |
| 6,811,534 B2 | 11/2004 | Bowman et al. |
| 6,821,421 B2 | 11/2004 | Murakami |
| 6,854,620 B2 | 2/2005 | Ramey |
| 6,872,200 B2 | 3/2005 | Mann et al. |
| 6,878,132 B2 | 4/2005 | Kipfer |
| 6,936,029 B2 | 8/2005 | Mann et al. |
| 6,939,329 B1 | 9/2005 | Verkaart |
| 6,958,705 B2 | 10/2005 | Lebel et al. |
| 6,960,198 B2 | 11/2005 | Sarmiento |
| 6,979,326 B2 | 12/2005 | Mann et al. |
| 6,997,920 B2 | 2/2006 | Mann et al. |
| 7,025,226 B2 | 4/2006 | Ramey |
| 7,025,743 B2 | 4/2006 | Mann et al. |
| 7,098,803 B2 | 8/2006 | Mann et al. |
| 7,109,878 B2 | 9/2006 | Mann et al. |
| 7,187,528 B2 | 3/2007 | Talbot et al. |
| 7,193,521 B2 | 3/2007 | Moberg et al. |
| 7,281,314 B2 | 10/2007 | Hess et al. |
| 7,285,105 B2 | 10/2007 | Kim et al. |
| 7,291,133 B1 | 11/2007 | Kindler et al. |
| 7,324,012 B2 | 1/2008 | Mann et al. |
| 7,342,508 B2 | 3/2008 | Morgan et al. |
| 7,460,350 B2 | 12/2008 | Talbot et al. |
| 7,534,226 B2 | 5/2009 | Mernoe et al. |
| 7,602,310 B2 | 10/2009 | Mann et al. |
| 7,621,893 B2 | 11/2009 | Moberg et al. |
| 7,625,354 B2 | 12/2009 | Hochman |
| 7,628,772 B2 * | 12/2009 | McConnell ........ A61J 1/2096 604/181 |
| 7,628,782 B2 | 12/2009 | Adair et al. |
| 7,648,494 B2 | 1/2010 | Kornerup et al. |
| 7,654,127 B2 | 2/2010 | Krulevitch et al. |
| 7,655,618 B2 | 2/2010 | Green et al. |
| 7,658,734 B2 | 2/2010 | Adair et al. |
| 7,678,762 B2 | 3/2010 | Green et al. |
| 7,678,763 B2 | 3/2010 | Green et al. |
| 7,683,027 B2 | 3/2010 | Green et al. |
| 7,708,717 B2 | 5/2010 | Estes et al. |
| 7,749,185 B2 | 7/2010 | Wilson |
| 7,760,481 B2 | 7/2010 | Talbot et al. |
| 7,766,873 B2 | 8/2010 | Moberg et al. |
| 7,776,030 B2 | 8/2010 | Estes et al. |
| 7,789,859 B2 | 9/2010 | Estes et al. |
| 7,794,427 B2 | 9/2010 | Estes et al. |
| 7,794,428 B2 | 9/2010 | Estes et al. |
| 7,815,602 B2 | 10/2010 | Mann et al. |
| 7,819,843 B2 | 10/2010 | Mann et al. |
| 7,831,310 B2 | 11/2010 | Lebel et al. |
| 7,833,196 B2 | 11/2010 | Estes et al. |
| 7,879,010 B2 | 2/2011 | Hunn et al. |
| 7,879,026 B2 | 2/2011 | Estes et al. |
| 7,887,512 B2 | 2/2011 | Estes et al. |
| 7,892,206 B2 | 2/2011 | Moberg et al. |
| 7,914,449 B2 | 3/2011 | Kouchi et al. |
| 7,922,708 B2 | 4/2011 | Estes et al. |
| 7,951,112 B2 | 5/2011 | Patzer |
| 7,967,785 B2 | 6/2011 | Morgan et al. |
| 7,981,084 B2 | 7/2011 | Estes et al. |
| 7,981,105 B2 | 7/2011 | Adair et al. |
| 7,988,683 B2 | 8/2011 | Adair et al. |
| 7,998,111 B2 | 8/2011 | Moberg et al. |
| 7,998,131 B2 | 8/2011 | Adair et al. |
| 8,004,422 B2 | 8/2011 | Hess et al. |
| 7,938,803 B2 | 10/2011 | Mernoe et al. |
| 8,034,026 B2 | 10/2011 | Grant et al. |
| 8,057,436 B2 | 11/2011 | Causey et al. |
| 8,062,257 B2 | 11/2011 | Moberg et al. |
| 8,065,096 B2 | 11/2011 | Moberg et al. |
| 8,088,096 B2 | 1/2012 | Lauchard et al. |

(56) References Cited

U.S. PATENT DOCUMENTS

| | | |
|---|---|---|
| 8,105,279 B2 | 1/2012 | Mernoe et al. |
| 8,106,534 B2 | 1/2012 | Spurlin et al. |
| 8,142,397 B2 | 3/2012 | Patzer |
| 8,167,846 B2 | 5/2012 | Chong et al. |
| 8,177,767 B2 | 5/2012 | Kristensen et al. |
| 8,182,447 B2 | 5/2012 | Moberg et al. |
| 8,192,394 B2 | 6/2012 | Estes et al. |
| 8,197,444 B1 | 6/2012 | Bazargan et al. |
| 8,206,350 B2 | 6/2012 | Mann et al. |
| 8,206,353 B2 | 6/2012 | Chong et al. |
| 8,211,059 B2 | 7/2012 | Kriesel |
| 8,211,062 B2 | 7/2012 | Estes et al. |
| 8,251,959 B2 | 8/2012 | Johner et al. |
| 8,257,345 B2 | 9/2012 | Adair et al. |
| 8,267,893 B2 | 9/2012 | Moberg et al. |
| 8,273,061 B2 | 9/2012 | McConnell et al. |
| 8,282,601 B2 | 10/2012 | Mernoe et al. |
| 8,287,495 B2 | 10/2012 | Michaud et al. |
| 8,287,516 B2 | 10/2012 | Kornerup et al. |
| 8,298,184 B2 | 10/2012 | DiPerna et al. |
| 8,303,572 B2 | 11/2012 | Adair et al. |
| 8,372,039 B2 | 2/2013 | Mernoe et al. |
| 8,409,142 B2 | 4/2013 | Causey et al. |
| 8,430,847 B2 | 4/2013 | Mernoe et al. |
| 8,430,849 B2 | 4/2013 | Smith et al. |
| 8,454,575 B2 | 6/2013 | Estes et al. |
| 8,469,942 B2 | 6/2013 | Kow et al. |
| 8,475,408 B2 | 7/2013 | Mernoe et al. |
| 8,480,623 B2 | 7/2013 | Mernoe et al. |
| 8,483,980 B2 | 7/2013 | Moberg et al. |
| 8,500,716 B2 | 8/2013 | Adair et al. |
| 8,512,276 B2 | 8/2013 | Talbot et al. |
| 8,512,289 B2 | 8/2013 | Chong et al. |
| 8,523,803 B1 | 9/2013 | Favreau |
| 8,551,045 B2 | 10/2013 | Sie et al. |
| 8,551,046 B2 | 10/2013 | Causey et al. |
| 8,556,856 B2 | 10/2013 | Bazargan et al. |
| 8,556,866 B2 | 10/2013 | Krulevitch et al. |
| 8,562,565 B2 | 10/2013 | Fonacier et al. |
| 8,562,587 B2 | 10/2013 | Kovatchev et al. |
| 8,568,349 B2 | 10/2013 | Shergold |
| 8,573,027 B2 | 11/2013 | Rosinko et al. |
| 8,579,813 B2 | 11/2013 | Causey, III et al. |
| 8,597,269 B2 | 12/2013 | Chong et al. |
| 8,603,026 B2 | 12/2013 | Favreau |
| 8,603,027 B2 | 12/2013 | Favreau |
| 8,603,033 B2 | 12/2013 | Bazargan et al. |
| 8,613,726 B2 | 12/2013 | Causey, III et al. |
| 8,613,731 B2 | 12/2013 | Hansen et al. |
| 8,617,110 B2 | 12/2013 | Moberg et al. |
| 8,622,966 B2 | 1/2014 | Causey, III et al. |
| 8,628,510 B2 | 1/2014 | Bazargan et al. |
| 8,641,671 B2 | 2/2014 | Michaud et al. |
| 8,647,074 B2 | 2/2014 | Moberg et al. |
| 8,647,296 B2 | 2/2014 | Moberg et al. |
| 8,663,103 B2 | 3/2014 | Causey, III et al. |
| 8,674,288 B2 | 3/2014 | Hanson et al. |
| 8,679,060 B2 | 3/2014 | Mernoe et al. |
| 8,681,010 B2 | 3/2014 | Moberg et al. |
| 8,696,633 B2 | 4/2014 | Estes et al. |
| 8,747,368 B2 | 6/2014 | Mernoe et al. |
| 8,747,369 B2 | 6/2014 | Mernoe et al. |
| 8,758,323 B2 | 6/2014 | Michaud et al. |
| 8,771,229 B2 | 7/2014 | Amirouche et al. |
| 8,777,901 B2 | 7/2014 | Smith et al. |
| 8,790,307 B2 | 7/2014 | Amirouche et al. |
| 8,821,442 B2 | 9/2014 | Haaar |
| 8,823,528 B2 | 9/2014 | Blomquist |
| 8,834,420 B2 | 9/2014 | Estes et al. |
| 8,841,012 B2 | 9/2014 | Fonacier et al. |
| 8,864,726 B2 | 10/2014 | Halili et al. |
| 8,864,737 B2 | 10/2014 | Hasegawa et al. |
| 8,864,739 B2 | 10/2014 | Moberg et al. |
| 8,870,829 B2 | 10/2014 | Halili et al. |
| 8,876,770 B2 | 11/2014 | Kraft et al. |
| 8,900,206 B2 | 12/2014 | Halili et al. |
| 8,905,972 B2 | 12/2014 | Smith et al. |
| 8,915,879 B2 | 12/2014 | Smith et al. |
| 8,936,573 B2 | 1/2015 | Blomquist |
| 8,945,068 B2 | 2/2015 | Halili et al. |
| 8,974,435 B2 | 3/2015 | Friedli |
| 8,992,475 B2 | 3/2015 | Mann et al. |
| 8,992,507 B2 | 3/2015 | Aeschlimann et al. |
| 8,998,840 B2 | 4/2015 | Hanson et al. |
| 8,998,842 B2 | 4/2015 | Lauchard et al. |
| 8,998,856 B2 | 4/2015 | Eggert |
| 8,998,858 B2 | 4/2015 | Chong et al. |
| 9,011,371 B2 | 4/2015 | Moberg et al. |
| 9,033,925 B2 | 5/2015 | Moberg et al. |
| 9,033,951 B2 | 5/2015 | Kow et al. |
| 9,050,406 B2 | 6/2015 | Kow et al. |
| 9,101,710 B2 | 8/2015 | Yavorsky et al. |
| 9,101,715 B2 | 8/2015 | Causey, III et al. |
| 9,107,999 B2 | 8/2015 | Moberg et al. |
| 9,114,209 B2 | 8/2015 | Estes et al. |
| 9,114,213 B2 | 8/2015 | Murakami et al. |
| 9,119,917 B2 | 9/2015 | Blomquist |
| 9,132,228 B2 | 9/2015 | Yan |
| 9,173,998 B2 | 11/2015 | Rosinko et al. |
| 9,180,242 B2 | 11/2015 | Metzmaker et al. |
| 9,180,243 B2 | 11/2015 | Michaud |
| 9,180,254 B2 | 11/2015 | Avery et al. |
| 9,184,490 B2 | 11/2015 | Crouther et al. |
| 9,194,388 B2 | 11/2015 | Laermer |
| 9,205,192 B2 | 12/2015 | Estes et al. |
| 9,211,376 B2 | 12/2015 | Kouyoumjian et al. |
| 9,211,377 B2 | 12/2015 | DiPerna et al. |
| 9,216,249 B2 | 12/2015 | Smith et al. |
| 9,220,835 B2 | 12/2015 | Cane' |
| 9,250,106 B2 | 2/2016 | Rosinko et al. |
| 9,272,009 B2 | 3/2016 | Spencer |
| 9,283,318 B2 | 3/2016 | Yavorsky et al. |
| 9,295,826 B2 | 3/2016 | Bertrand et al. |
| 9,308,320 B2 | 4/2016 | Smith et al. |
| 9,308,321 B2 | 4/2016 | Alderete et al. |
| 9,314,569 B2 | 4/2016 | Causey et al. |
| 9,320,849 B2 | 4/2016 | Smith et al. |
| 9,327,073 B2 | 5/2016 | Moberg et al. |
| 9,335,910 B2 | 5/2016 | Farnan et al. |
| 9,339,639 B2 | 5/2016 | Halili et al. |
| 9,344,024 B2 | 5/2016 | Favreau |
| 9,345,643 B2 | 5/2016 | Okiyama |
| 9,364,608 B2 | 6/2016 | Moberg et al. |
| 9,379,652 B2 | 6/2016 | Favreau |
| 9,379,653 B2 | 6/2016 | Favreau |
| 9,381,297 B2 | 7/2016 | Brown et al. |
| 9,381,300 B2 | 7/2016 | Smith et al. |
| 9,393,399 B2 | 7/2016 | Yavorsky et al. |
| 9,415,157 B2 | 8/2016 | Mann et al. |
| 9,427,519 B2 | 8/2016 | Kraft et al. |
| 9,433,731 B2 | 9/2016 | Trock et al. |
| 9,433,732 B2 | 9/2016 | Moberg et al. |
| 9,433,733 B2 | 9/2016 | Moberg et al. |
| 9,452,255 B2 | 9/2016 | Tieck et al. |
| 9,452,256 B2 | 9/2016 | Tieck et al. |
| 9,463,309 B2 | 10/2016 | Yavorsky et al. |
| 9,494,147 B2 | 11/2016 | Chong et al. |
| 9,498,573 B2 | 11/2016 | Smith et al. |
| 9,514,518 B2 | 12/2016 | Gillespie et al. |
| 9,517,299 B2 | 12/2016 | Tieck et al. |
| 9,517,301 B2 | 12/2016 | Estes et al. |
| 9,533,132 B2 | 1/2017 | Halili et al. |
| 9,539,385 B2 | 1/2017 | Mathys |
| 9,539,388 B2 | 1/2017 | Causey et al. |
| 9,554,967 B2 | 1/2017 | Moia et al. |
| 9,579,452 B2 | 2/2017 | Adair et al. |
| 9,592,339 B2 | 3/2017 | Zhou |
| 9,597,462 B2 | 3/2017 | Moore |
| 9,610,431 B2 | 4/2017 | Halili et al. |
| 9,629,992 B2 | 4/2017 | Halili et al. |
| 9,636,453 B2 | 5/2017 | Monirabbasi et al. |
| 9,682,189 B2 | 6/2017 | Good et al. |
| 9,687,612 B2 | 6/2017 | Avery et al. |
| 9,707,339 B2 | 7/2017 | Chartrand |

(56) References Cited

U.S. PATENT DOCUMENTS

| | | | |
|---|---|---|---|
| 9,715,327 B2 | 7/2017 | Rosinko et al. |
| 9,717,845 B2 | 8/2017 | Istoc |
| 9,717,848 B2 | 8/2017 | Geismar et al. |
| 9,731,067 B2 | 8/2017 | Pananen |
| 9,744,290 B2 | 8/2017 | Tieck et al. |
| 9,744,291 B2 | 8/2017 | Tieck et al. |
| 9,744,301 B2 | 8/2017 | Mann et al. |
| 9,750,871 B2 | 9/2017 | Metzmaker et al. |
| 9,750,873 B2 | 9/2017 | Brown et al. |
| 9,750,875 B2 | 9/2017 | Smith et al. |
| 9,770,553 B2 | 9/2017 | Bazargan et al. |
| 9,782,536 B2 | 10/2017 | Skutnik et al. |
| 9,782,543 B2 | 10/2017 | Groeschke et al. |
| 9,789,245 B2 | 10/2017 | Tieck et al. |
| 9,795,732 B2 | 10/2017 | Track et al. |
| 9,801,787 B2 | 10/2017 | Py |
| 9,814,830 B2 | 11/2017 | Mernoe et al. |
| 9,814,872 B2 | 11/2017 | Eggert et al. |
| 9,839,741 B2 | 12/2017 | Yavorsky et al. |
| 9,841,014 B2 | 12/2017 | Yap et al. |
| 9,863,837 B2 | 1/2018 | Rule et al. |
| 9,872,957 B2 | 1/2018 | Causey et al. |
| 9,883,834 B2 | 2/2018 | Amirouche et al. |
| 9,889,256 B2 | 2/2018 | Cabiri et al. |
| 9,895,490 B2 | 2/2018 | Kow et al. |
| 9,925,330 B2 | 3/2018 | Tieck et al. |
| 9,931,459 B2 | 4/2018 | Tieck et al. |
| 9,931,460 B2 | 4/2018 | Tieck et al. |
| 9,943,645 B2 | 4/2018 | Monirabbasi et al. |
| 9,950,113 B2 | 4/2018 | Franke et al. |
| 9,987,420 B2 | 6/2018 | Pananen |
| 9,993,592 B2 | 6/2018 | Amirouche et al. |
| 9,993,594 B2 | 6/2018 | Bazargan et al. |
| 10,010,674 B2 | 7/2018 | Rosinko et al. |
| 10,010,678 B2 | 7/2018 | Schildt et al. |
| 10,016,564 B2 | 7/2018 | Piehl et al. |
| 10,029,045 B2 | 7/2018 | Smith et al. |
| 10,064,993 B2 | 9/2018 | Mernoe et al. |
| 10,071,200 B2 | 9/2018 | Alderete et al. |
| 10,080,839 B2 | 9/2018 | Cole et al. |
| 10,086,133 B2 | 10/2018 | Pananen et al. |
| 10,086,134 B2 | 10/2018 | Pananen et al. |
| 10,092,701 B2 | 10/2018 | Johansen et al. |
| 10,105,483 B2 | 10/2018 | Mernoe |
| 10,105,497 B2 | 10/2018 | Dreier et al. |
| 10,130,759 B2 | 11/2018 | Amirouche et al. |
| 10,130,763 B2 | 11/2018 | Lauchard et al. |
| 10,137,243 B2 | 11/2018 | Wang et al. |
| 10,141,882 B2 | 11/2018 | Favreau |
| 10,146,911 B2 | 12/2018 | Trock |
| 10,166,327 B2 | 1/2019 | Tieck et al. |
| 10,172,998 B2 | 1/2019 | Tieck et al. |
| 10,172,999 B2 | 1/2019 | Tieck et al. |
| 10,207,047 B2 | 2/2019 | Estes |
| 10,213,549 B2 | 2/2019 | Amirouche et al. |
| 10,220,143 B2 | 3/2019 | Moberg et al. |
| 10,228,663 B2 | 3/2019 | Favreau |
| 10,232,109 B2 | 3/2019 | Deak et al. |
| 10,238,030 B2 | 3/2019 | Urbani |
| 10,238,793 B2 | 3/2019 | Deak et al. |
| 10,252,001 B2 | 4/2019 | Geismar et al. |
| 10,258,736 B2 | 4/2019 | Metzmaker et al. |
| 10,272,196 B2 | 4/2019 | Smith et al. |
| 10,279,110 B2 | 5/2019 | Mann et al. |
| 10,300,264 B2 | 5/2019 | Halili et al. |
| 10,307,536 B2 | 6/2019 | Causey et al. |
| 10,322,227 B2 | 6/2019 | Piehl et al. |
| 10,363,365 B2 | 7/2019 | Bazargan |
| 10,376,631 B2 | 8/2019 | Tieck et al. |
| 10,376,632 B2 | 8/2019 | Tieck et al. |
| 10,384,013 B2 | 8/2019 | Krusell et al. |
| 10,391,257 B2 | 8/2019 | Piehl et al. |
| 10,478,554 B2 | 11/2019 | Bazargan et al. |
| 10,517,892 B2 | 12/2019 | Chattaraj et al. |
| 10,532,156 B2 | 1/2020 | Istoc |
| 10,552,580 B2 | 2/2020 | Bazargan |
| 10,603,431 B2 | 3/2020 | Mernoe et al. |
| 10,772,796 B2 | 9/2020 | Kavazov |
| 10,850,032 B2 | 12/2020 | Steck et al. |
| 10,857,287 B2 | 12/2020 | Damiano et al. |
| 10,861,591 B2 | 12/2020 | Grosman et al. |
| 10,881,789 B2 | 1/2021 | Damiano et al. |
| 10,960,136 B2 | 3/2021 | Palerm et al. |
| 2002/0038392 A1 | 3/2002 | De La Huerga |
| 2002/0055711 A1 | 5/2002 | Lavi et al. |
| 2002/0065484 A1 | 5/2002 | Douglas et al. |
| 2002/0161332 A1 | 10/2002 | Ramey |
| 2003/0009133 A1 | 1/2003 | Ramey |
| 2005/0015056 A1 | 1/2005 | Duchon et al. |
| 2005/0020980 A1 | 1/2005 | Inoue |
| 2005/0038387 A1 | 2/2005 | Kriesel |
| 2005/0051580 A1 | 3/2005 | Ramey |
| 2005/0154434 A1 | 7/2005 | Simon et al. |
| 2005/0256461 A1 | 11/2005 | DiFiore |
| 2006/0264908 A1 | 11/2006 | Ishii et al. |
| 2007/0088271 A1* | 4/2007 | Richards ............ A61M 5/14244 604/151 |
| 2007/0142786 A1 | 6/2007 | Lampropoulos |
| 2007/0161955 A1 | 7/2007 | Bynum et al. |
| 2007/0273671 A1 | 11/2007 | Zadesky et al. |
| 2007/0282294 A1 | 12/2007 | Sidler |
| 2008/0051719 A1 | 2/2008 | Moberg |
| 2008/0188813 A1 | 8/2008 | Miller et al. |
| 2008/0243085 A1 | 10/2008 | DeStefano |
| 2008/0262425 A1 | 10/2008 | Mogensen |
| 2008/0319383 A1 | 12/2008 | Byland |
| 2009/0062767 A1 | 3/2009 | Van Antwerp et al. |
| 2009/0326506 A1 | 12/2009 | Hasegawa et al. |
| 2010/0049144 A1 | 2/2010 | McConnell et al. |
| 2010/0145303 A1 | 6/2010 | Yodfat |
| 2010/0191165 A1 | 7/2010 | Appling |
| 2010/0217241 A1 | 8/2010 | Mann et al. |
| 2010/0241103 A1 | 9/2010 | Kraft et al. |
| 2011/0021905 A1 | 1/2011 | Patrick et al. |
| 2011/0118659 A1 | 5/2011 | Maaskamp |
| 2011/0160697 A1 | 6/2011 | Yodfat et al. |
| 2011/0230838 A1 | 9/2011 | Adams et al. |
| 2011/0288494 A1 | 11/2011 | Mendels |
| 2012/0078185 A1 | 3/2012 | Smith |
| 2012/0078197 A1 | 5/2012 | O'Connor et al. |
| 2012/0211946 A1 | 8/2012 | Halili et al. |
| 2012/0211947 A1 | 8/2012 | Halili et al. |
| 2012/0215177 A1 | 8/2012 | Halili et al. |
| 2012/0215178 A1 | 8/2012 | Halili et al. |
| 2012/0215179 A1 | 8/2012 | Halili et al. |
| 2012/0215180 A1 | 8/2012 | Halili et al. |
| 2012/0215183 A1* | 8/2012 | Halili .................. A61M 5/31 604/257 |
| 2012/0226234 A1 | 9/2012 | Bazargan et al. |
| 2013/0046253 A1 | 2/2013 | Yavorsky et al. |
| 2013/0085470 A1 | 4/2013 | O'Connor et al. |
| 2013/0245604 A1 | 9/2013 | Kouyoumjian et al. |
| 2013/0345641 A1 | 12/2013 | German |
| 2015/0057615 A1 | 2/2015 | Mernoe et al. |
| 2015/0073384 A1 | 3/2015 | Limaye |
| 2015/0105720 A1 | 4/2015 | Montalvo et al. |
| 2015/0202375 A1 | 7/2015 | Schabbach et al. |
| 2015/0265826 A1* | 9/2015 | Dudley ................ A61M 39/10 604/403 |
| 2015/0314063 A1 | 11/2015 | Nagar et al. |
| 2015/0357683 A1 | 12/2015 | Lohr |
| 2016/0015885 A1 | 1/2016 | Pananen et al. |
| 2016/0015886 A1 | 1/2016 | Pananen et al. |
| 2016/0015887 A1 | 1/2016 | Pananen et al. |
| 2016/0015911 A1 | 1/2016 | Bazargan et al. |
| 2016/0051760 A1 | 2/2016 | Krusell et al. |
| 2016/0058668 A1 | 3/2016 | Metzmaker et al. |
| 2016/0074587 A1 | 3/2016 | Searle et al. |
| 2016/0082182 A1 | 3/2016 | Gregory et al. |
| 2016/0089493 A1 | 3/2016 | Crouther et al. |
| 2016/0106919 A1 | 4/2016 | Hayter et al. |
| 2016/0184519 A1 | 6/2016 | Blundred et al. |
| 2016/0220754 A1 | 8/2016 | Shaanan et al. |
| 2016/0263324 A1 | 9/2016 | Shaanan et al. |

(56) References Cited

U.S. PATENT DOCUMENTS

| | | |
|---|---|---|
| 2016/0271322 A1 | 9/2016 | Ramey |
| 2016/0361494 A1 | 12/2016 | Jurg et al. |
| 2017/0056590 A1 | 3/2017 | DiPerna |
| 2017/0065768 A1 | 3/2017 | Moore |
| 2017/0182307 A1 | 6/2017 | Halili et al. |
| 2017/0189666 A1 | 7/2017 | Sealfon et al. |
| 2017/0192506 A1 | 7/2017 | Andersen et al. |
| 2017/0216523 A1 | 8/2017 | Neftel et al. |
| 2017/0235920 A1 | 8/2017 | Bauss et al. |
| 2017/0239422 A1 | 8/2017 | Kodgule et al. |
| 2017/0286638 A1 | 10/2017 | Searle et al. |
| 2017/0312454 A1 | 11/2017 | Chattaraj et al. |
| 2018/0036475 A1 | 2/2018 | Lin |
| 2018/0043104 A1 | 2/2018 | Mueller-Pathle |
| 2018/0043105 A1 | 2/2018 | Nazzaro et al. |
| 2018/0103897 A1 | 4/2018 | Amirouche |
| 2018/0104417 A1 | 4/2018 | Nessel et al. |
| 2018/0117248 A1 | 6/2018 | Cabiri et al. |
| 2018/0117296 A1 | 6/2018 | Damiano et al. |
| 2018/0207366 A1 | 7/2018 | Marcoz et al. |
| 2018/0228979 A1 | 8/2018 | Schildt et al. |
| 2018/0280624 A1 | 10/2018 | Bitton et al. |
| 2018/0311435 A1 | 11/2018 | Galasso |
| 2018/0318498 A1 | 11/2018 | Grant et al. |
| 2018/0318506 A1 | 11/2018 | Oakes et al. |
| 2018/0326164 A1 | 11/2018 | Bauss et al. |
| 2018/0353699 A1 | 12/2018 | Helmer et al. |
| 2019/0001060 A1 | 1/2019 | Gylleby et al. |
| 2019/0009032 A1 | 1/2019 | Hautaviita et al. |
| 2019/0015582 A1 | 1/2019 | Naftalovitz et al. |
| 2019/0030247 A1 | 1/2019 | Edwards et al. |
| 2019/0054251 A1 | 2/2019 | Pieronek et al. |
| 2019/0091460 A1 | 3/2019 | Yavorsky et al. |
| 2019/0134305 A1 | 5/2019 | Srinivasan et al. |
| 2019/0151559 A1 | 5/2019 | Byerly et al. |
| 2019/0167900 A1 | 6/2019 | Friedli et al. |
| 2019/0192762 A1 | 6/2019 | Metzmaker et al. |
| 2019/0209775 A1 | 7/2019 | Merchant |
| 2019/0217007 A1 | 7/2019 | Sasaki |
| 2019/0344009 A1* | 11/2019 | Damiano ............ A61M 5/1684 |
| 2020/0330719 A1 | 10/2020 | Segal |
| 2021/0030949 A1 | 2/2021 | Damiano et al. |
| 2021/0030957 A1 | 2/2021 | Damiano et al. |
| 2021/0093777 A1 | 4/2021 | Damiano et al. |
| 2021/0093849 A1 | 4/2021 | Stumpe et al. |
| 2021/0106750 A1 | 4/2021 | Damiano et al. |
| 2021/0283328 A1 | 9/2021 | Damiano et al. |
| 2022/0257853 A1 | 8/2022 | Henderson |

FOREIGN PATENT DOCUMENTS

| | | |
|---|---|---|
| JP | 57-124151 | 8/1982 |
| JP | 59-30241 | 2/1984 |
| JP | 2012-200381 | 10/2012 |
| JP | 3194787 | 12/2014 |
| RU | 2549310 | 4/2015 |
| WO | WO 99/64103 | 12/1999 |
| WO | WO 2002/094352 | 11/2002 |
| WO | WO 03/017915 | 3/2003 |
| WO | WO 04/045704 | 6/2004 |
| WO | WO 05/000378 | 1/2005 |
| WO | WO 05/004973 | 1/2005 |
| WO | WO 06/054367 | 5/2006 |
| WO | WO 2007/075677 | 7/2007 |
| WO | WO 09/069511 | 4/2009 |
| WO | WO 07/086186 | 5/2009 |
| WO | WO 09/060741 | 5/2009 |
| WO | WO 2011/079225 | 6/2011 |
| WO | WO 11/131778 | 10/2011 |
| WO | WO 2011/131775 | 10/2011 |
| WO | WO 12/008285 | 1/2012 |
| WO | WO 12/072555 | 6/2012 |
| WO | WO 12/110474 | 8/2012 |
| WO | WO 12/0115911 | 8/2012 |
| WO | WO 12/146670 | 11/2012 |
| WO | WO 12/160104 | 11/2012 |
| WO | WO 2013/093059 | 6/2013 |
| WO | WO 13/161979 | 10/2013 |
| WO | WO 14/104027 | 3/2014 |
| WO | WO 2014/159213 | 10/2014 |
| WO | WO 2015/027174 | 2/2015 |
| WO | WO 15/061690 | 4/2015 |
| WO | WO 15/061691 | 4/2015 |
| WO | WO 15/061693 | 4/2015 |
| WO | WO 15/155229 | 10/2015 |
| WO | WO 15/166993 | 11/2015 |
| WO | WO 17/007968 | 1/2017 |
| WO | WO 17/199012 | 11/2017 |
| WO | WO 17/217105 | 12/2017 |
| WO | WO 18/129354 | 7/2018 |
| WO | WO 19/021985 | 1/2019 |
| WO | WO 19/046593 | 3/2019 |

OTHER PUBLICATIONS

Ping One Touch Owner's Booklet, Dated Oct. 2014, (360 pages).
Renesas Synergy™ Platform, "Capacitive Touch Hardware Design and Layout Guidelines for Synergy, RX200, and RX100." R01AN3825EU0101 Rev.1.01, Jun. 14, 2017, pp. 1-18.
International Search Report and Written Opinion in PCT/U2020/042198 dated Nov. 24, 2020.
Boston University, Jan. 2014, Bionic Pancreas: Introducing the iLet 1294 1000, http://sites.bu.edu/bionicpacreas/introducing-the-ilet-1294-1000/, 3 pp.
Brown et al., Apr. 1, 2016, Introducing Beta Bionics: bringing the iLet bionic pancreas to market, https://diatribe.org/introducing-beta-bionics-bringing-ilet-bionic-pancreas-marekt, 3 pp.
Hoskins, Oct. 2, 2018, iLet "Bionic Pancreas" making progress with gen 4 device, Healthline, https//www.healthline.com/diabetesmine/beta-bionics-ilet-update#1, 15 pp.
Idlebrook, Jul. 30, 2019, Beta Bionics secures funding for pivotal iLet bionic pancreas trials, https://t1dexchange.org/welcome-glu-users/articles/beta-bionics-secures-funding-for-pivotal-ilet-bionic-pancreas-trials, 4 pp.
Krugman, Aug. 25, 2018, iLet Bionic Pancreas Interface, sarakrugman.com/ilet-interface, 3 pp.
Sifferlin, Apr. 1, 2016, The bionic pancreas is getting closer to reality, time.com, https://time.com/4278068/bionic-pancreas-company, 5 pp.

* cited by examiner

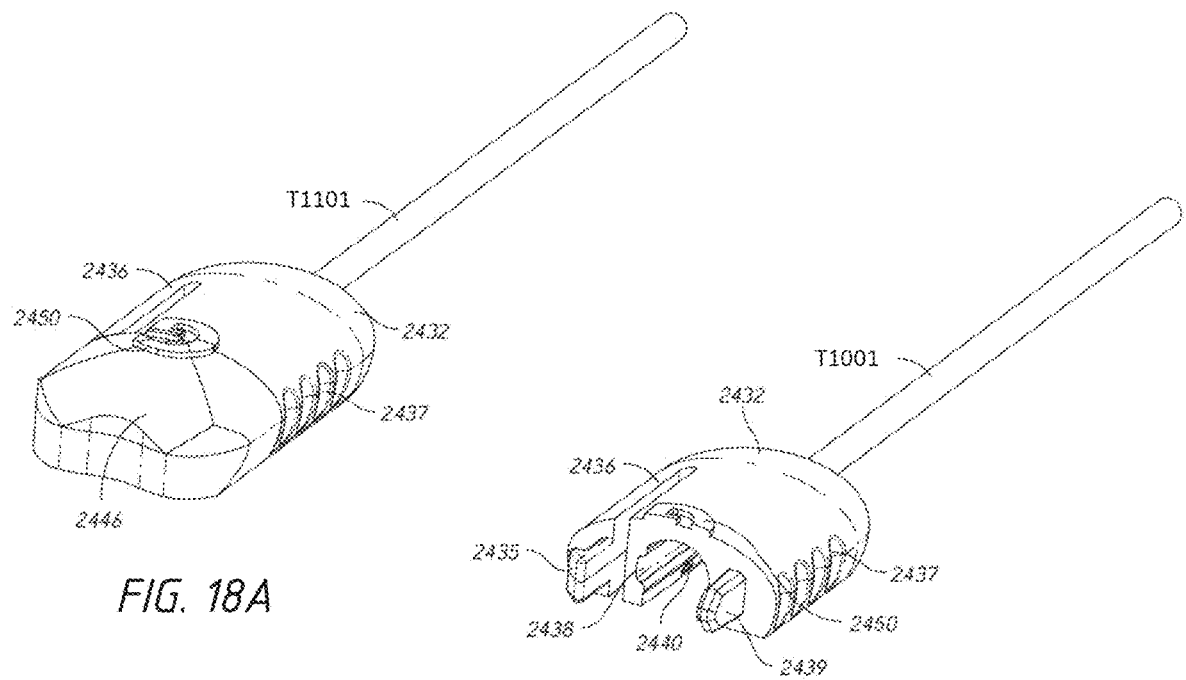
FIG. 18A
FIG. 18B
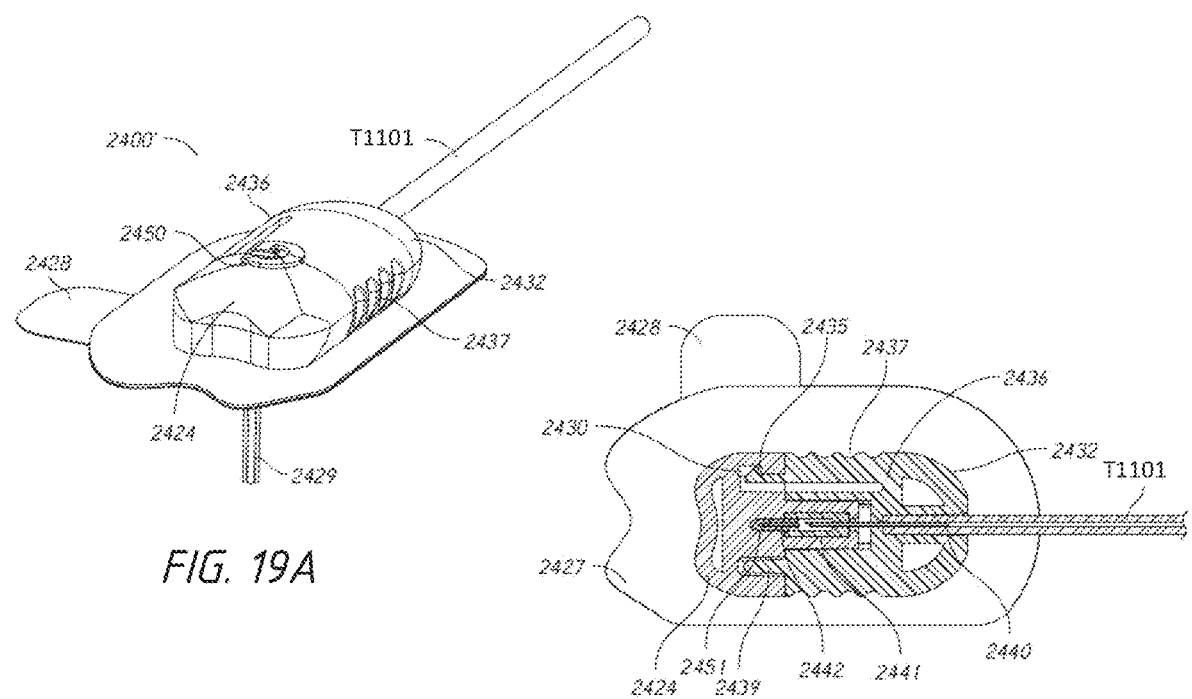
FIG. 19A
FIG. 19B

AMBULATORY DEVICE AND COMPONENTS THEREOF

CROSS REFERENCE TO RELATED APPLICATIONS

The present application is a continuation of International Patent Application No. PCT/US2020/042198, filed Jul. 15, 2020, which claims the benefit of priority to U.S. Provisional Patent Application No. 63/037,472, filed Jun. 10, 2020, U.S. Provisional Patent Application No. 62/987,842, filed Mar. 10, 2020, U.S. Provisional Patent Application No. 62/874,928, filed Jul. 16, 2019, U.S. Provisional Patent Application No. 62/874,954, filed Jul. 16, 2019, U.S. Provisional Patent Application No. 62/874,959, filed Jul. 16, 2019, U.S. Provisional Patent Application No. 62/874,964, filed Jul. 16, 2019, U.S. Provisional Patent Application No. 62/874,972, filed Jul. 16, 2019, U.S. Provisional Patent Application No. 62/874,975, filed Jul. 16, 2019, and U.S. Provisional Patent Application No. 62/874,977, filed Jul. 16, 2019, the entirety of each of which is hereby incorporated by reference herein. Any and all applications for which a foreign or domestic priority claim is identified in the Application Data Sheet as filed with the present application are hereby incorporated by reference under 37 CFR 1.57.

STATEMENT REGARDING FEDERALLY SPONSORED RESEARCH OR DEVELOPMENT

This invention was made with U.S. Government support under Contract No. DK120234, awarded by the National Institutes of Health. The Government has certain rights in the invention.

FIELD OF THE INVENTION

The disclosure relates generally to the field of medicament infusion systems (including systems configured to delivery multiple medicaments to a subject), components thereof (e.g., pump systems, cartridge connectors, cartridges, connector sets, multi-channel lumen assemblies, infusion sets, etc.), methods of making each of the foregoing, and methods of using each of the foregoing.

BACKGROUND

Sustained delivery, pump driven medicament injection devices generally include a delivery cannula mounted in a subcutaneous manner through the skin of the patient at an infusion site. The pump draws medicine from a reservoir and delivers it to the patient via the cannula. The injection device typically includes a channel that transmits a medicament from an inlet port to the delivery cannula which results in delivery to the subcutaneous tissue layer where the delivery cannula terminates. Some infusion devices are configured to deliver one medicament to a patient while others are configured to deliver multiple medicaments to patient.

SUMMARY

Some embodiments provide medicament infusion systems (including systems configured to delivery multiple medicaments to a subject), components thereof (e.g., pump systems, cartridge connectors, cartridges, connector sets, multi-channel lumen assemblies, infusion sets, etc.), methods of making each of the foregoing, and methods of using each of the foregoing.

Some embodiments pertain to an infusion pump for delivering medicaments to a patient. In some embodiments, the infusion pump comprises a pump housing. In some embodiments, the pump housing comprises a first receptacle port configured to engage a first cartridge connector. In some embodiments, the pump housing comprises a second receptacle port configured to engage a second cartridge connector. In some embodiments, the pump housing comprises a first medicament cartridge receptacle extending from the first receptacle port longitudinally along a first side of the infusion pump to a first cartridge receptacle aperture. In some embodiments, the pump housing comprises a second medicament cartridge receptacle extending from the second receptacle port longitudinally along a second side of the infusion pump to a second cartridge receptacle aperture. In some embodiments, the pump comprises an internal area. In some embodiments, the internal area comprises a power source located between the first medicament cartridge receptacle and the second medicament cartridge receptacle. In some embodiments, the internal area comprises a first motor in electronic communication with the power source. In some embodiments, the internal area comprises a second motor in electronic communication with the power source. In some embodiments, the internal area comprises a first stacked gear assembly. In some embodiments, the internal area comprises a second stacked gear assembly. In some embodiments, the internal area comprises a first lead screw. In some embodiments, the internal area comprises a second lead screw. In some embodiments, the first motor and second motor (where present) comprise a first pinion gear and a second pinion gear (where present), respectively, the first pinion gear being a member of the first stacked gear assembly and the second pinion gear being a member of the second stacked gear assembly (where present). In some embodiments, the first gear assembly extends laterally toward the first side of the infusion pump. In some embodiments, the second gear assembly extends laterally toward the second side of the infusion pump. In some embodiments, the first lead screw is in rotational communication with the first pinion gear through the first gear assembly. In some embodiments, the second lead screw is in rotational communication with the second pinion gear through the second gear assembly. In some embodiments, the pump comprises a first drive nut having a length extending longitudinally along the pump housing and being configured to travel into the first medicament cartridge receptacle via the first aperture, the first drive nut being in communication with the first lead screw and being configured to urge forward or backward in response to a first direction of rotation and a second direction of rotation, respectively, of the first lead screw. In some embodiments, the pump comprises a second drive nut having a length extending longitudinally along the pump housing and being configured to travel into the second medicament cartridge receptacle via the second aperture, the second drive nut being in communication with the second lead screw and being configured to urge forward or backward in response to a first direction of rotation and a second direction of rotation, respectively, of the second lead screw.

Any of the embodiments described above, or described elsewhere herein, can include one or more of the following features.

In some embodiments, the first receptacle port has one or more recognition features configured to engage with coinciding recognition features of the first cartridge connector. In some embodiments, the second receptacle port has one or more recognition features configured to engage with coinciding recognition features of the second cartridge connector. In some embodiments, the recognition features of the first receptacle port are different from the recognition features of the second receptacle port. In some embodiments, the first receptacle port is configured to not allow engagement of the second cartridge connector and the second receptacle port is configured to not allow engagement of the first cartridge connector.

In some embodiments, the pump comprises a first seal and/or a second seal. In some embodiments, the first seal provides a water resistant barrier between the internal area of the infusion pump and the first medicament cartridge receptacle. In some embodiments, the second seal provides a water resistant barrier between the internal area of the infusion pump and the second medicament cartridge receptacle. In some embodiments, the first seal is a first O-ring that circumferentially surrounds at least a portion of the first drive nut. In some embodiments, the second seal is a second O-ring that circumferentially surrounds at least a portion of the second drive nut. In some embodiments, the pump housing comprises a first saddle. In some embodiments, the pump housing comprises a second saddle. In some embodiments, the first saddle is configured to retain the first O-ring. In some embodiments, the second saddle is configured to retain the second O-ring. In some embodiments, the first saddle is positioned adjacent to the first cartridge receptacle aperture. In some embodiments, the second saddle is positioned adjacent to the second cartridge receptacle aperture.

In some embodiments, the first drive nut comprises a protrusion on a proximal portion of the first drive nut that remains within the internal area during extension of the drive nut into the first cartridge receptacle. In some embodiments, the pump housing comprises a groove configured to receive the protrusion of the first drive nut. In some embodiments, the protrusion of the first drive nut engages the groove thereby preventing rotation of the first drive nut. In some embodiments, the groove is provided as part or within the pump backing portion of the housing.

In some embodiments, the housing comprises a capacitive sensor configured to detect when a finger is touched to a surface. In some embodiments, the surface is a curved indentation on the housing and the capacitive sensor comprising an integrated circuit configured to measure a capacitance of a circuit. In some embodiments, a conductive foam fills a gap between the surface and the integrated circuit.

In some embodiments, the housing comprises a lower metal portion and a bezel that is attachable to the metal portion. In some embodiments, at least a portion of a sidewall of the ambulatory medical device is only covered by the bezel. In some embodiments, a circuit board positioned adjacent to an inner surface of the bezel. In some embodiments, a wireless antenna affixed to the circuit board such that the wireless antenna is positioned toward the portion of the sidewall of the ambulatory medical device that is only covered by the bezel.

In some embodiments, the bezel allows wireless signals to pass through and the metal portion does not interfere with a signal from the antenna. In some embodiments, the circuit board is configured to process wireless signals received by the antenna. In some embodiments, a first magnet is attached coaxially to a gear in the first gear assembly and a first rotary position sensor that measures an angular position of the first magnet.

In some embodiments, the first receptacle port comprises a snap arm recess extending longitudinally within the first medicament cartridge receptacle, the snap arm recess of the first medicament cartridge receptacle being configured to receive a snap arm of the first cartridge connector as the snap arm expands over a first medicament cartridge cap during engagement of a first medicament cartridge while the first medicament cartridge is housed in the first medicament cartridge receptacle. In some embodiments, the second receptacle port comprises a snap arm recess extending longitudinally within the second medicament cartridge receptacle, the snap arm recess of the second medicament cartridge receptacle being configured to receive a snap arm of the second cartridge connector as the snap arm expands over a second medicament cartridge cap during engagement of a second medicament cartridge while the second medicament cartridge is housed in the second medicament cartridge receptacle. In some embodiments, the snap arm recess of the first receptacle port is configured not to receive the snap arm of the second cartridge connector.

In some embodiments, the first receptacle port comprises lug opening and a radially extending lug track configured to receive a lug of the first cartridge connector as the first cartridge connector is inserted into the first receptacle port and turned into place. In some embodiments, the second receptacle port comprises lug opening and a radially extending lug track configured to receive a lug of the second cartridge connector as the second cartridge connector is inserted into the second receptacle port and turned into place.

In some embodiments, the first receptacle port comprises detent opening and a detent track, the detent track having a detent cam with a shallow first transition and a steep second transition, the detent opening and detent track being configured to receive a detent of the first cartridge connector as the first cartridge connector is inserted into the first receptacle port and turned into place, the shallow first transition being configured to allow the detent of the first cartridge connector to be turned into place within the infusion pump with less force than is required to remove the first cartridge connector from the first receptacle port along the direction of the steep second transition. In some embodiments, the second receptacle port comprises detent opening and a detent track, the detent track having a detent cam with a shallow first transition and a steep second transition, the detent opening and detent track being configured to receive a detent of the second cartridge connector as the second cartridge connector is inserted into the second receptacle port and turned into place, the shallow first transition being configured to allow the detent of the second cartridge connector to be turned into place within the infusion pump with less force than is required to remove the second cartridge connector from the second receptacle port along the direction of the steep second transition.

In some embodiments, the pump housing comprises a bezel and a display screen, the bezel being configured to engage a lower portion of the pump housing configured to hold the display screen.

Some embodiments provide an infusion pump comprising a housing having an interior space. In some embodiments, the pump housing comprises a bore through said housing, said bore having a first end and a second end, and the bore configured to receive a medicament cartridge. In some embodiments, the first end defines an opening into said housing and the second end is located in the interior space of the housing. In some embodiments, an elongate shaft disposed in the bore and configured to engage the medicament cartridge. In some embodiments, an O-ring circumferentially disposed on the elongate shaft adjacent to the second end of the bore.

Some embodiments provide an infusion pump for providing a therapy change. In some embodiments, the pump comprises a button that generates a wake signal after being pressed. In some embodiments, the pump comprises a touchscreen display that activates after receiving the wake signal. In some embodiments, the pump comprises a therapy change user interface that unlocks after receiving a first gesture on the touchscreen display. In some embodiments, the therapy change user interface is capable of receiving a therapy change selection from the touchscreen display. In some embodiments, a medicament infusion component delivers a medicament after receiving a second gesture on the touchscreen display.

Some embodiments provide an infusion pump a capacitive sensor that detects when a finger is touched to a surface. In some embodiments, the surface has a curved indentation. In some embodiments, the capacitive sensor comprises one or more of an integrated circuit that measures the capacitance of a circuit and/or a conductive foam that is between the surface and the integrated circuit.

Some embodiments provide an infusion pump comprising one or more of: a metal housing; a bezel that is attachable to the metal housing; at least a portion of a sidewall of the ambulatory medical device is only covered by the bezel; a circuit board positioned adjacent to the inner surface of the bezel; and/or a wireless antenna affixed to the circuit board such that the wireless antenna is positioned toward the portion of the sidewall of the ambulatory medical device that is only covered by the bezel.

Some embodiments provide an infusion pump comprising one or more of: an electric motor that rotates a shaft; a gear affixed to the end of the shaft that turns a gear assembly; a magnet attached coaxially to one of the gears in the gear assembly; and/or a rotary position sensor that measures an angular position of the magnet.

Some embodiments provide an infusion pump for delivering a medicament to a patient. In some embodiments, the infusion pump comprises a pump housing. In some embodiments, the infusion pump comprises a first receptacle port comprising a snap-arm extension recess configured to receive a first cartridge connector. In some embodiments, the infusion pump comprises a first medicament cartridge receptacle extending from the first receptacle port longitudinally along a first side of the infusion pump to a first cartridge receptacle aperture. In some embodiments, the infusion pump comprises an internal area. In some embodiments, the infusion pump comprises a power source. In some embodiments, the infusion pump comprises a first motor in electronic communication with the power source. In some embodiments, the infusion pump comprises a first gear assembly. In some embodiments, the infusion pump comprises a first lead screw. In some embodiments, the first motor comprises a first pinion gear, the first pinion gear being a member of the first gear assembly. In some embodiments, the first lead screw is in rotational communication with the first pinion gear through the first gear assembly. In some embodiments, the infusion pump comprises a first drive nut having a length extending longitudinally along the pump housing. In some embodiments, the first drive nut extends into the first medicament cartridge receptacle via the first aperture and is in communication with the first lead screw. In some embodiments, the first drive nut is configured to urge forward or backward in response to a first direction of rotation and a second direction of rotation, respectively, of the first lead screw.

Some embodiments provide an infusion pump for delivering a medicament to a patient. In some embodiments, the infusion pump comprises a pump housing. In some embodiments, the infusion pump comprises a first receptacle port configured to receive a first cartridge connector. In some embodiments, the infusion pump comprises a first medicament cartridge receptacle extending from the first receptacle port longitudinally along a first side of the infusion pump to a first cartridge receptacle aperture. In some embodiments, the infusion pump comprises an internal area. In some embodiments, the infusion pump comprises a power source. In some embodiments, the infusion pump comprises a first motor in electronic communication with the power source. In some embodiments, the infusion pump comprises a first stacked gear assembly. In some embodiments, the infusion pump comprises a first lead screw. In some embodiments, the first motor comprises a first pinion gear, the first pinion gear being a member of the first stacked gear assembly. In some embodiments, the first gear assembly extends laterally toward the first side of the infusion pump. In some embodiments, the first lead screw is in rotational communication with the first pinion gear through the first gear assembly. In some embodiments, the infusion pump comprises a first drive nut having a length extending longitudinally along the pump housing. In some embodiments, the first drive nut extends into the first medicament cartridge receptacle via the first aperture and in communication with the first lead screw. In some embodiments, the first drive nut is configured to urge forward or backward in response to a first direction of rotation and a second direction of rotation, respectively, of the first lead screw.

Any of the embodiments described above, or described elsewhere herein, can include one or more of the following features.

In some embodiments, the first receptacle port has one or more recognition features configured to engage with coinciding recognition features of the first cartridge connector.

In some embodiments, the infusion pump comprises a second receptacle port that has one or more features configured to engage with coinciding features of the second cartridge connector.

In some embodiments, the infusion pump comprises a first seal, the first seal providing a water resistant barrier between the internal area of the infusion pump and the first medicament cartridge receptacle. In some embodiments, the first seal is a first O-ring that surrounds at least a portion of the first drive nut. In some embodiments, the infusion pump comprises a first saddle, the first saddle being configured to retain the first O-ring. In some embodiments, the first drive nut comprises a protrusion and the pump housing comprises a groove configured to receive the protrusion, wherein the protrusion engages the groove and prevents rotation of the first drive nut.

In some embodiments, the infusion pump comprises a magnet attached coaxially to a gear of the first gear assembly and a rotary position sensor that measures an angular position of the magnet.

Some embodiments provide a cartridge connector. In some embodiments, the cartridge connector comprises a knob. In some embodiments, the knob is in the shape of a cam and having a flattened portion. In some embodiments, the cartridge connector comprises a body. In some embodiments, the body comprises a needle. In some embodiments, the body comprises a lower surface portion extending circumferentially from the needle. In some embodiments, the body comprises a shroud extending axially away from the lower surface portion. In some embodiments, the shroud is configured to receive and fit over a portion of a first medicament cartridge. In some embodiments, the first medicament cartridge is configured to hold a first medicament. In some embodiments, the lower surface portion is located within the shroud. In some embodiments, the lower surface portion is configured to contact a cap of the first medicament cartridge when the first medicament cartridge is inserted into the cartridge connector within the shroud. In some embodiments, the needle extends axially within the shroud away from the lower surface portion. In some embodiments, once inserted into the first pump receptacle, the first cartridge connector is configured to be positioned within the first pump receptacle using a quarter turn that aligns the flattened portion of the cam with a coinciding flat surface of the pump to indicate to a user that the first cartridge connector is correctly placed in the pump.

Some embodiments provide a cartridge connector. In some embodiments, the cartridge connector comprises a body. In some embodiments, the body comprises a needle. In some embodiments, the body comprises a lower surface portion extending circumferentially from the needle. In some embodiments, the body comprises a shroud extending axially away from the lower surface portion. In some embodiments, the shroud is configured to receive and fit over a portion of a first medicament cartridge that is configured to hold a first medicament. In some embodiments, the lower surface portion is located within the shroud. In some embodiments, the lower surface portion is configured to contact a cap of the first medicament cartridge when the first medicament cartridge is inserted into the cartridge connector within the shroud. In some embodiments, the needle extends axially within the shroud away from the lower surface portion. In some embodiments, the connector comprises a knob connected to the body. In some embodiments, the knob comprises a lower side extending circumferentially from the shroud of the body. In some embodiments, the knob comprises a fluid outlet configured to deliver the first medicament to a position outside the cartridge connector. In some embodiments, the lower side of the knob comprises one or more malleable nubs. In some embodiments, the malleable nubs are configured to contact an upper side surface of an infusion pump. In some embodiments, the malleable nubs are configured to deform (e.g., against the upper side surface of the infusion pump) when the cartridge connector is twisted into place within the infusion pump. In some embodiments, the one or more malleable nubs provides one or more contact points between the lower surface of the knob and the infusion pump.

Some embodiments provide a cartridge connector. In some embodiments, the cartridge connector comprises a body. In some embodiments, the body comprises a needle. In some embodiments, the body comprises a lower surface portion extending circumferentially from the needle. In some embodiments, the lower surface comprises a bowl-shaped concavity. In some embodiments, the lower surface comprises a surrounding lip. In some embodiments, the needle protrudes from and extends away from the bowl-shaped concavity. In some embodiments, the body comprises a shroud extending axially away from a circumference of the lower surface portion. In some embodiments, the shroud is configured to receive and fit over a portion of a first medicament cartridge that is configured to hold a first medicament. In some embodiments, the lower surface portion is located within the shroud and is configured to contact a cap of the first medicament cartridge when the first medicament cartridge is inserted into the cartridge connector within the shroud. In some embodiments, the needle extends axially from the lower surface portion and within the shroud. In some embodiments, the cartridge connector comprises a knob portion. In several embodiments, the cartridge connector comprises a fluid outlet configured to deliver the medicament to a position outside the cartridge connector. In some embodiments, the knob is fixed to or unitary with the body.

Some embodiments provide a cartridge connector. In some embodiments, the cartridge connector comprises a body. In some embodiments, the body comprises a needle. In some embodiments, the body comprises a lower surface portion extending circumferentially from the needle. In some embodiments, the body comprises a shroud extending axially away from the lower surface portion. In some embodiments, the shroud is configured to receive and fit over a portion of a first medicament cartridge that is configured to hold a first medicament. In some embodiments, the body comprises a projection extending axially upwardly from an upper surface of the body. In some embodiments, the projection comprises a fluid outlet. In some embodiments, the lower surface portion is located within the shroud. In some embodiments, the lower surface portion is configured to contact a cap of the first medicament cartridge when the first medicament cartridge is inserted into cartridge connector within the shroud. In some embodiments, the needle extends axially from the lower surface portion and within the shroud. In some embodiments, the body is configured to receive the medicament through the needle and to deliver the medicament out of the body from the fluid outlet of the body. In some embodiments, the needle and the fluid outlet of the body are in fluidic communication and provide a fluid path through the body. In some embodiments, the cartridge connector comprises a knob portion. In some embodiments, the knob portion is configured engage the body. In some embodiments, the knob portion comprises a receptacle section. In some embodiments, the receptacle section is configured to extend over and receive at least a portion of the projection of the body. In some embodiments, a fluid inlet is located within the receptacle section, the fluid inlet being configured to receive the medicament. In some embodiments, the knob comprises a fluid outlet configured to deliver the medicament to a position outside the cartridge connector. In some embodiments, the connector comprises an interstitial space (or area) located between the projection of the body and the receptacle section of the knob. In some embodiments, a flexible membrane is located within the interstitial space. In some embodiments, the flexible membrane extends over at least a portion of the projection of body. In some embodiments, the flexible membrane is configured to allow fluid to pass from the body outlet and into the knob inlet only after a threshold fluid pressure of the medicament is reached.

Any of the embodiments described above, or described elsewhere herein, can include one or more of the following features.

In some embodiments, the knob is in the shape of a cam having a flattened portion. In some embodiments, once inserted into the first pump receptacle, the first cartridge connector is configured to be positioned within the first pump receptacle using a quarter turn that aligns the flattened portion of the cam with a coinciding flat surface of the pump to indicate to a user that the first cartridge connector is correctly placed in the pump.

In some embodiments, the knob comprises a lower side extending circumferentially from the shroud of the body and wherein the lower side of the knob comprises one or more malleable nubs. In some embodiments, the malleable nubs are configured to contact an upper side surface of an infusion pump and to deform when the cartridge connector is twisted into place within the infusion pump. In some embodiments, the one or more malleable nubs provide one or more contact points between the lower surface of the knob and the infusion pump.

In some embodiments, the lower surface portion of the body comprises a bowl-shaped concavity and a surrounding lip. In some embodiments, the needle protrudes from and extends away from the bowl-shaped concavity.

In some embodiments, the body comprises a projection extending axially upwardly from an upper surface of the body. In some embodiments, the projection comprises a fluid outlet. In some embodiments, the body is configured to receive the medicament through the needle and to deliver the medicament out of the body from the fluid outlet of the body. In some embodiments, the needle and the fluid outlet of the body being in fluidic communication and providing a fluid path through the body. In some embodiments, the knob comprises a receptacle section. In some embodiments, the receptacle section is configured to extend over and receive at least a portion of the projection of the body. In some embodiments, a fluid inlet is located within the receptacle section, the fluid inlet being configured to receive the medicament. In some embodiments, a fluid outlet is configured to deliver the medicament to a position outside the cartridge connector. In some embodiments, the connector comprises an interstitial space located between the projection of the body and the receptacle section of the knob. In some embodiments, the connector comprises a flexible membrane located within the interstitial space and extending over at least a portion of the projection of the body. In some embodiments, the flexible membrane is configured to allow fluid to pass from the body outlet and into the knob inlet only after a threshold fluid pressure of the medicament is reached.

In some embodiments, the cartridge connector is also configured to engage a first port of an infusion pump.

In some embodiments, the needle of the cartridge connector is configured to pierce a septum of the cap of the first medicament cartridge.

In some embodiments, the knob is fixed to and/or unitary with the body.

In some embodiments, the shroud comprises one or more of a snap arm configured to engage the cap of the first medicament cartridge, a detent, and/or a lug.

Some embodiments pertain to a medicament connector set for delivering a single or multiple medicaments to a patient, the medicament connector set comprising a first cartridge connector as disclosed herein and a first fluid conduit configured to receive the first medicament from the first cartridge connector. In some embodiments, the connector set further comprising a first infusion connector in fluidic communication with the first fluid conduit (e.g., affixed and/or connected to the fluid conduit).

Some embodiments pertain to a medicament connector set for delivering a single or multiple medicaments to a patient comprising a cartridge connector as disclosed elsewhere herein as a first cartridge connector and a second cartridge connector configured to engage a second medicament cartridge. In some embodiments, the second medicament cartridge comprises a body. In some embodiments, the second medicament cartridge comprises a needle. In some embodiments, the second medicament cartridge comprises a lower surface portion extending circumferentially from the needle. In some embodiments, the second medicament cartridge comprises a shroud extending axially away from the lower surface portion and configured to receive and fit over a portion of a second medicament cartridge that is configured to hold a second medicament. In some embodiments, the lower surface portion is located within the shroud and is configured to contact a cap of the second medicament cartridge when the second medicament cartridge is inserted into the cartridge connector within the shroud. In some embodiments, the second medicament cartridge comprises a bowl-shaped concavity. In some embodiments, the needle extends axially within the shroud away from the lower surface portion. In some embodiments, the second medicament cartridge comprises a knob connected to the body. In some embodiments, the knob comprises a lower side extending circumferentially from the shroud of the body, the knob comprising a fluid outlet configured to deliver the first medicament to a position outside the cartridge connector. In some embodiments, the second medicament cartridge is configured to engage a second port of the infusion pump. In some embodiments, the shroud of the second cartridge connector comprises one or more of a snap arm configured to engage the cap of the second medicament cartridge, a detent, and/or a lug.

In some embodiments, one or more of the snap arm, the detent, and/or the lug of the first cartridge connector is different than the snap arm, the detent, and/or the lug of the second cartridge connector. In some embodiments, the first cartridge connector is configured to not engage the second medicament cartridge and/or the second cartridge connector is configured to not engage the first medicament cartridge. In some embodiments, the first cartridge connector is configured to not engage the second port of the infusion pump and/or wherein the second cartridge connector is configured to not engage the first port of the infusion pump.

Several embodiments pertain to an infusion system. In some embodiments, the system comprises a connector or connector set and an infusion pump as disclosed elsewhere herein.

Some embodiments disclosed herein pertain to an infusion pump for delivering multiple fluids to a patient. In some embodiments, the infusion pump comprises a pump housing. In some embodiments, the housing comprises a first receptacle port and a second receptacle port. In some embodiments, the infusion pump comprises a first medicament cartridge receptacle. In some embodiments, the receptacle extends from the first receptacle port longitudinally along a first side of the infusion pump to a first cartridge receptacle aperture. In some embodiments, the infusion pump comprises a second medicament cartridge receptacle extending from the second receptacle port longitudinally along a second side of the infusion pump to a second cartridge receptacle aperture. In some embodiments, the infusion pump comprises an internal area comprising one or more of a power source a first motor and a second motor. In some embodiments, the motor comprises a first pinion gear that is part of a first stacked gear assembly. In some embodiments, the pump comprises the first gear assembly, the first gear assembly extending laterally toward the first side of the infusion pump. In some embodiments, the pump comprises a first drive nut in rotational communication with the first pinion gear through the first gear assembly. In some embodiments, the pump comprises a first drive nut in communication with the first drive nut, the first piston residing within the internal area of the infusion pump when fully retracted and configured to extend outwardly from the internal area of the pump via first receptacle aperture when not fully retracted, the first drive nut configured to urge a plunger of a first medicament cartridge forward to distribute a first medicament from the first medicament cartridge. In some embodiments, the pump comprises a first O-ring surrounding at least a portion of the drive nut and providing a water resistant barrier to the internal area of the infusion pump.

In some embodiments, the housing comprises a capacitive sensor configured to detect when a finger is touched to a surface. In some embodiments, the surface is a curved indentation on the housing and the capacitive sensor comprises an integrated circuit configured to measure a capacitance of a circuit. In some embodiments, a conductive foam that fills a gap between the surface and the integrated circuit is provided. In some embodiments, the capacitive sensor generates a wake signal after being pressed. In some embodiments, a touchscreen display of the pump activates after receiving the wake signal. In some embodiments, a therapy change user interface unlocks after receiving a first gesture on the touchscreen display. In some embodiments, the therapy change user interface is capable of receiving a therapy change selection from the touchscreen display. In some embodiments, a medicament infusion component delivers a medicament after receiving a second gesture on the touchscreen display.

In some embodiments, the housing comprises a metal portion and a bezel that is attachable to the metal portion. In some embodiments, at least a portion of a sidewall of the ambulatory medical device is covered by the bezel and not the metal housing. In some embodiments, a circuit board is positioned adjacent to an inner surface of the bezel. In some embodiments, a wireless antenna is affixed to the circuit board such that the wireless antenna is positioned toward the portion of the sidewall of the ambulatory medical device that is only covered by the bezel.

In some embodiments, the first motor rotates a shaft. In some embodiments, the pump comprises a gear affixed to the end of the shaft that turns a gear assembly. In some embodiments, the pump comprises a magnet is attached coaxially to one of the gears in the gear assembly. In some embodiments, the pump comprises a rotary position sensor that measures an angular position of the magnet.

In some embodiments, the housing comprises an interior space. In some embodiments, the housing comprises a bore through said housing, said bore having a first end and a second end, and the bore configured to receive a medicament cartridge. In some embodiments, the first end defines an opening into said housing and the second end is located in the interior space of the housing. In some embodiments, the housing comprises an elongate shaft disposed in the bore and configured to engage the medicament cartridge. In some embodiments, the housing comprises an O-ring circumferentially disposed on the elongate shaft adjacent to the second end of the bore.

Some embodiments pertain to a medicament infusion system for delivering a single or multiple medicaments to a patient. In some embodiments, the medicament infusion system comprises a first cartridge connector configured to engage a first medicament cartridge and an infusion pump. In some embodiments, the first cartridge connector comprises a needle configured to allow access to a first medicament in the first medicament cartridge. In some embodiments, the first cartridge connector comprises a knob that is in the shape of a cam and having a flattened portion. In some embodiments, the knob comprises at least one detent. In some embodiments, the knob comprises a snap arm. In some embodiments, the knob comprises a skirt. In some embodiments, the knob comprises a grip rib. In some embodiments, the first cartridge connector is configured to engage a first pump receptacle of a pump. In some embodiments, the first pump receptacle has a receiving track coinciding to the position and shape of the at least one detent. In some embodiments, the once inserted into the first pump receptacle, the first cartridge connector is configured to be positioned within the first pump receptacle using a quarter turn that aligns the flattened portion of the cam with a coinciding flat surface of the pump (e.g., to indicate to a user that the first cartridge connector is correctly placed in the pump).

Some embodiments pertain to a cartridge connector. In some embodiments, the cartridge connector comprises body. In some embodiments, the body comprises a needle. In some embodiments, the body comprises a lower surface portion extending circumferentially from the needle. In some embodiments, the body comprises a shroud extending axially away from the lower surface portion and configured to receive and fit over a portion of a first medicament cartridge (e.g., that is configured to hold a first medicament) In some embodiments, the body comprises a projection extending axially upwardly from an upper surface of the body. In some embodiments, the projection comprises a fluid outlet. In some embodiments, the lower surface portion is located within the shroud and is configured to contact a cap of the medicament cartridge when the medicament cartridge is inserted into cartridge connector via the shroud. In some embodiments, the needle extends axially from the lower surface portion and within the shroud. In some embodiments, the body is configured to receive the medicament through the needle and to deliver the medicament out of the body from the fluid outlet of the body. In some embodiments, the needle and the fluid outlet of the body are in fluidic communication. In some embodiments, the needle and the fluid outlet of the body provide a fluid path through the body. In some embodiments, the connector comprises a knob portion configured engage the body. In some embodiments, the knob comprises a receptacle section. In some embodiments, the receptacle section is configured to extend over and receive at least a portion of the projection of the body. In some embodiments, a fluid inlet located is within the receptacle section, the fluid inlet being configured to receive the medicament. In some embodiments, a fluid outlet of the knob is configured to deliver the medicament to a position outside the cartridge connector. In some embodiments, the connector comprises an interstitial space located between the projection of the body and the receptacle section of the knob. In some embodiments, a flexible membrane is located within the interstitial space and extends over at least a portion of the projection of the body. In some embodiments, the flexible membrane is configured to allow fluid to pass from the body outlet and into the knob inlet only after a threshold fluid pressure of the medicament is reached.

Some embodiments provide an infusion system comprising a connector set and any pump disclosed above or elsewhere herein. Some embodiments provide an infusion system comprising any connector and any pump disclosed above or elsewhere herein. In some embodiments, the infusion system further comprises a infusion system.

Some embodiments provide an infusion pump. In some embodiments, the infusion pump comprises a housing comprising a capacitive sensor configured to detect when a finger is touched to a surface. In some embodiments, the surface is a curved indentation on the housing. In some embodiments, the capacitive sensor comprises an integrated circuit configured to measure a capacitance of a circuit. In some embodiments, the infusion pump comprises a conductive foam that fills a gap between the surface and the integrated circuit.

In some embodiments, the surface that has a curved indentation is integrated into a frame of the medical device.

In some embodiments, the curved indentation is formed to a dimension of the finger of a user. In some embodiments, the curved indentation has a haptic feedback. In some embodiments, the haptic feedback indicates when the capacitive sensor detects a finger that is touched to the surface. In some embodiments, the haptic feedback indicates when the capacitive sensor detects a finger continuously for about 0.5 seconds. In some embodiments, the infusion pump comprises a light under the curved indentation. In some embodiments, an output of the light is responsive based on input received from the capacitive sensor. In some embodiments, the infusion pump comprises pump chambers that deliver one or more hormones into a user. In some embodiments, the infusion pump comprises is activated when the capacitive sensor detects a finger continuously for more than about 0.5 seconds.

Some embodiments provide an infusion pump comprising a button that generates a wake signal after being pressed. In some embodiments, the infusion pump comprises a touchscreen display that activates after receiving the wake signal. In some embodiments, the infusion pump comprises a therapy change user interface that unlocks after receiving a first gesture on the touchscreen display (e.g., after it is unlocked). In some embodiments, the therapy change user interface is capable of receiving a therapy change selection from the touchscreen display. In some embodiments, a medicament infusion component delivers a medicament after receiving a second gesture on the touchscreen display.

In some embodiments, the therapy change selection comprises a reception of a selection between one or more hormones that regulate blood sugar level of a user. In some embodiments, the therapy change selection comprises an amount of the one or more hormones that regulate blood sugar level of the user. In some embodiments, the button does not generate a wake signal if it is pressed for less than about 0.5 seconds before being pressed. In some embodiments, the first gesture on the touchscreen display further comprises a predetermined sequence of inputs. In some embodiments, the button does not generate a wake signal after the button is pressed until the button is released. In some embodiments, the button does not generate a wake signal if it is released more than about 1.5 seconds after the button is pressed.

Some embodiments provide a method for preventing inadvertent therapy change on a medical device. In some embodiments, the method comprises generating a wake signal after a button is pressed. In some embodiments, the method comprises activating a touchscreen display after receiving the wake signal. In some embodiments, the method comprises unlocking a therapy change user interface after receiving a first gesture on the touchscreen display. In some embodiments, the method comprises receiving a therapy change selection on the touchscreen display. In some embodiments, the method comprises receiving a second gesture prior to delivering a medicament based on the therapy change selection.

In some embodiments, the method comprises receiving the therapy change selection further comprises receiving a selection between one or more hormones that regulate blood sugar level of a user. In some embodiments, the method comprises receiving the therapy change selection comprises receiving an amount of the one or more hormones that regulate blood sugar level of the user. In some embodiments, the therapy change selection further comprises the one or more hormones to include an option between insulin or glucagon. In some embodiments, receiving the second gesture is based on the therapy change selection. In some embodiments, the method comprises receiving a predetermined sequence of numerical inputs in order to deliver the therapy change selection. In some embodiments, the first gesture further comprises completing a predetermined sequence of inputs. In some embodiments, generating the wake signal further comprises that the button is pressed for at least about 0.5 seconds. In some embodiments, generating the wake signal further comprises releasing the button after the button is pressed. In some embodiments, the button is released less than about 1.5 seconds after the button is pressed.

Some embodiments provide a medical device for providing a therapy change. In some embodiments, the medical device comprises a button that generates a wake signal after being pressed. In some embodiments, the medical device comprises a touchscreen display that activates after receiving the wake signal. In some embodiments, the medical device comprises a therapy change user interface that unlocks after receiving a first gesture on the touchscreen display. In some embodiments, the therapy change user interface is capable of receiving a therapy change selection from the touchscreen display. In some embodiments, a medicament infusion component delivers a medicament after receiving a second gesture on the touchscreen display. In some embodiments, the therapy change selection comprises a reception of a selection between one or more hormones that regulate blood sugar level of a user. In some embodiments, the therapy change selection comprises an amount of the one or more hormones that regulate blood sugar level of the user. In some embodiments, the button does not generate a wake signal if it is pressed for less than about 0.5 seconds before being pressed. In some embodiments, the first gesture on the touchscreen display further comprises a predetermined sequence of inputs. In some embodiments, the button does not generate a wake signal after the button is pressed until the button is released. In some embodiments, the button does not generate a wake signal if it is released more than about 1.5 seconds after the button is pressed.

Some embodiments provide a method for preventing inadvertent therapy change on a medical device. In some embodiments, the method comprises activating a touchscreen display after receiving a signal from a wake button. In some embodiments, the method comprises unlocking a therapy change user interface after receiving a first gesture on the touchscreen display. In some embodiments, the method comprises receiving a therapy change selection on the touchscreen display. In some embodiments, the method comprises receiving a second gesture prior to delivering a therapy. In some embodiments, the method comprises receiving the therapy change selection further comprises receiving a selection between one or more hormones that regulate blood sugar level of a user. In some embodiments, receiving the therapy change selection comprises receiving an amount of the one or more hormones that regulate blood sugar level of the user. In some embodiments, the second gesture is in correspondence to the therapy change selection. In some embodiments, receiving the second gesture further comprises receiving a selection of an indicator box that correspond to either insulin or glucagon. In some embodiments, the method comprises receiving a predetermined sequence of numerical inputs in order to deliver the therapy change selection. In some embodiments, the method comprises receiving the second gesture further comprises confirming that the selection of the indicator box is in accordance with the therapy change selection. In some embodiments, receiving the first gesture further comprises completing a predetermined sequence of inputs to unlock the therapy change user interface. In some embodiments, delivering the therapy further comprises receiving, by a therapy delivering device, a wireless signal from the touchscreen display. In some embodiments, the touchscreen display comprises at least one of OLED, LCD, or E-ink display; and wherein the wake button comprises at least one of capacitive or mechanical form of single input button.

Some embodiments provide an infusion pump. In some embodiments, the infusion pump comprises a capacitive sensor that detects when a finger is touched to a surface. In some embodiments, the infusion pump comprises the surface has a curved indentation. In some embodiments, the capacitive sensor comprises an integrated circuit that measures the capacitance of a circuit. In some embodiments, the infusion pump comprises a conductive foam between the surface and the integrated circuit.

In some embodiments, the surface that has a curved indentation is integrated into a bezel of the medical device. In some embodiments, the size of curved indentation is modified to fit the shape of the finger of a user. In some embodiments, the curved indentation has a haptic feedback. In some embodiments, the haptic feedback indicates when the capacitive sensor detects a finger that is touched to the surface. In some embodiments, the haptic feedback indicates when the capacitive sensor detects a finger continuously for about 0.5 seconds.

In some embodiments, the infusion pump comprises a light under the curved indentation. In some embodiments, the output of the light is responsive based on the detection, by the capacitive sensor, of the finger.

In some embodiments, the infusion pump that delivers one or more hormones into a user. In some embodiments, the infusion pump is activated when the capacitive sensor detects a finger continuously for more than about 0.5 seconds.

Some embodiments provide a method for preventing inadvertent therapy change on a medical device. In some embodiments, the method comprises generating a wake signal after a capacitive sensor detects a touch of a user in a curved indentation of the medical device. In some embodiments, the method comprises activating a touchscreen display after receiving the wake signal. In some embodiments, the method comprises unlocking a therapy change user interface after receiving a first gesture on the touchscreen display. In some embodiments, the method comprises receiving a therapy change selection on the touchscreen display. In some embodiments, the method comprises receiving a second gesture prior to delivering a medicament based on the therapy change selection.

Some embodiments provide an infusion pump. In some embodiments, the infusion pump comprises a housing with a lower portion that is metal. In some embodiments, the infusion pump comprises a bezel that is attachable to the metal portion of the housing. In some embodiments, at least a portion of a sidewall of the ambulatory medical device is only covered by the bezel. In some embodiments, a circuit board is positioned adjacent to an inner surface of the bezel. In some embodiments, a wireless antenna is affixed to the circuit board such that the wireless antenna is positioned toward the portion of the sidewall of the ambulatory medical device that is only covered by the bezel.

Some embodiments comprise an ambulatory medical device. In some embodiments, the device comprises a metal housing. In some embodiments, the device comprises a bezel that is attachable to the metal housing. In some embodiments, at least a portion of a sidewall of the ambulatory medical device is only covered by the bezel. In some embodiments, the device comprises a circuit board positioned adjacent to an inner surface of the bezel. In some embodiments, the device comprises a wireless antenna affixed to the circuit board such that the wireless antenna is positioned toward the portion of the sidewall of the ambulatory medical device that is only covered by the bezel. In some embodiments, a conducting layer of the circuit board is removed from a portion of the circuit board that is affixed to the wireless antenna. In some embodiments, a portion of the circuit board is positioned inside the portion of the sidewall of the ambulatory medical device that is only covered by the bezel. In some embodiments, the wireless antenna extends toward the portion of the side of the ambulatory medical device that is only covered by the bezel. In some embodiments, the metal housing covers a length and a width of the ambulatory medical device on at least one side of the ambulatory medical device. In some embodiments, the metal housing covers a height of at least one side of the ambulatory medical device. In some embodiments, the metal housing is aluminum. In some embodiments, the bezel is plastic.

In some embodiments, the ambulatory device comprises a capacitive sensor affixed to the circuit board. In some embodiments, the ambulatory device comprises a curved indentation on the outside of the bezel that is on the opposite side of the capacitive sensor. In some embodiments, the ambulatory device comprises a display that is connected to a main circuit board. In some embodiments, the ambulatory device comprises the circuit board is positioned orthogonally to the main circuit board.

Some embodiments provide an infusion pump. In some embodiments, the infusion pump comprises an antenna affixed to a circuit board. In some embodiments, the infusion pump comprises a bezel surrounding the antenna. In some embodiments, a metal housing is attached to the bezel. In some embodiments, the antenna sends and receives wireless signals. In some embodiments, the bezel allows for wireless signals to pass through. In some embodiments, the bezel is made of plastic. In some embodiments, the metal housing is below the antenna. In some embodiments, the circuit board will process the wireless signals received by the antenna.

Some embodiments provide a method for detecting touch in an ambulatory medical device. In some embodiments, the method comprises receiving the touch of a finger to a bezel. In some embodiments, the method comprises measuring, by the capacitance touch pad that is positioned adjacent to the bezel, a change in capacitance. In some embodiments, the method comprises detecting the presence of the finger. In some embodiments, the bezel has a curved indentation. In some embodiments, the method comprises detecting a changing capacitance when the finger is removed from the bezel. In some embodiments, the method comprises generating an activation signal responsive to the detection of the finger.

Some embodiments provide a method for receiving an input in an ambulatory medical device. In some embodiments, the method comprises receiving the touch of a finger to a bezel. In some embodiments, the method comprises measuring, by a capacitance touch pad that is positioned adjacent to the bezel, a change in capacitance. In some embodiments, the method comprises detecting a presence of the finger. In some embodiments, the bezel has a curved indentation. In some embodiments, the method includes detecting a changing capacitance when the finger is removed from the bezel. In some embodiments, the method includes generating an activation signal responsive to the detection of the finger.

Some embodiments provide an ambulatory medical device (e.g., an infusion pump). In some embodiments, the infusion pump comprises an electric motor that rotates a shaft. In some embodiments, the infusion pump comprises a gear affixed to the end of the shaft that turns a gear assembly. In some embodiments, the infusion pump comprises a magnet attached coaxially to one of the gears in the gear assembly. In some embodiments, the infusion pump comprises a rotary position sensor that measures an angular position of the magnet.

In some embodiments, the pump comprises a circuit board that is positioned orthogonally to an angle of rotation of the gear to which the magnet is affixed. In some embodiments, the rotary position sensor is attached to the circuit board. In some embodiments, the pump comprises a sensor that measures the rotation of the shaft. In some embodiments, the pump comprises a computer that receives data from the sensor and the rotary position sensor. In some embodiments, the computer verifies that data from the sensor and data from the rotary position sensor are synchronized. In some embodiments, the pump comprises a first drive nut that is operated by turning the gear assembly. In some embodiments, the pump delivers a medicament to a user of the ambulatory medical device. In some embodiments, the computer generates an error signal if data from the sensor and data from the rotary position sensor are not synchronized. In some embodiments, the computer determines a volume of medicament delivered to the user based on data from the rotary position sensor.

In some embodiments, the pump comprises a second electric motor that operates a second drive nut. In some embodiments, the pump comprises a housing for a first medicament cartridge and a housing for a second medicament cartridge. In some embodiments, the first infusion drive nut delivers medicament from the first medicament cartridge. In some embodiments, the second drive nut delivers medicament from the second medicament cartridge. In some embodiments, the housing for the first medicament cartridge will not accept the second medicament cartridge. In some embodiments, the housing for the second medicament cartridge will not accept the first medicament cartridge. In some embodiments, the computer determines an amount of medicament to be delivered from the second infusion pump based on the verification that the data from the sensor and data from the rotary position sensor are synchronized.

Some embodiments provide a method of error detection in an ambulatory medical device. In some embodiments, the method comprises receiving, by one or more sensors, a rotational position of a motor. In some embodiments, the method comprises receiving, by a rotary position sensor, a rotary position of an output shaft. In some embodiments, the method comprises determining that the motor and output shaft are not rotating in sync. In some embodiments, the method comprises informing a user that the motor and output shaft are not rotating in sync.

Some embodiments provide a method of error detection in an ambulatory medical device. In some embodiments, the method comprises receiving, by one or more sensors, a rotational position of a first motor. In some embodiments, the method comprises receiving, by a rotary position sensor, the rotary position of an output shaft. In some embodiments, the method comprises determining that the first motor and output shaft are not rotating in sync. In some embodiments, the method comprises switching an operation of the ambulatory medical device to a second motor based on the determination that the first motor and output shaft are not rotating in a synchronously.

Some embodiments provide a method of error detection in an ambulatory medical device. In some embodiments, the method comprises providing an electric motor configured to rotate a shaft. In some embodiments, the method comprises providing a gear affixed to an end of the shaft that turns a gear assembly. In some embodiments, the method comprises providing a magnet attached coaxially to one of the gears in the gear assembly. In some embodiments, the method comprises measuring an angular position of the magnet using a rotary position sensor.

In some embodiments, the method comprises positioning a circuit board orthogonally to an angle of rotation of the gear to which the magnet is affixed. In some embodiments, the method comprises attaching the rotary position sensor to the circuit board. In some embodiments, the method comprises measuring the rotation of the shaft using a sensor. In some embodiments, the method comprises receiving, by a computer, data a computer from the sensor and the rotary position sensor. In some embodiments, the data is transmitted wirelessly. In some embodiments, the method comprises verifying, by the computer, that the data from the sensor and data from the rotary position sensor are synchronized. In some embodiments, the method comprises turning the gear assembly to operate a first drive nut. In some embodiments, the method comprises delivering a medicament, using activation of the first drive nut, to a user. In some embodiments, the method comprises generating an error signal, by the computer, in response to the data from the sensor and the data from the rotary position sensor are not in synchronized. In some embodiments, the computer determines a volume of medicament delivered to the user based on data from the rotary position sensor. In some embodiments, a second electric motor that operates a second drive nut is present. In some embodiments, a housing for a first medicament cartridge and a housing for a second medicament cartridge is provided. In some embodiments, the first drive nut causes medicament from the first medicament cartridge to be delivered. In some embodiments, the second drive nut causes medicament from the second medicament cartridge to be delivered. In some embodiments, the housing (e.g., cartridge chamber) for the first medicament cartridge will not accept the second medicament cartridge and/or the housing (e.g., cartridge chamber) for the second medicament cartridge will not accept the first medicament cartridge. In some embodiments, the computer determines an amount of medicament to be delivered from the second infusion medicament cartridge based on the verification that the data from the sensor and data from the rotary position sensor are in sync.

Some embodiments provide an infusion pump. In some embodiments, the infusion pump comprises a housing having an interior space. In some embodiments, the infusion pump comprises bore through said housing, said bore having a first end and a second end, and the bore configured to receive a medicament cartridge. In some embodiments, the first end defines an opening into said housing and the second end is located in the interior space of the housing. In some embodiments, an elongate shaft is disposed in the bore and configured to engage the medicament cartridge. In some embodiments, the infusion pump comprises an O-ring circumferentially disposed on the elongate shaft adjacent to the second end of the bore.

In some embodiments, the O-ring forms a barrier to water and debris from entering the interior space of the housing. In some embodiments, a position of the O-ring is configured to permit water or air movement around the medicament cartridge. In some embodiments, the O-ring is configured to permit pressure differential equalization between an infusion site and drug cartridge. In some embodiments, the O-ring exerts pressure on the elongated shaft when the O-ring is circumferentially disposed on the elongated shaft. In some embodiments, the O-ring comprises a lubricant to lubricate between the elongated shaft to reduce friction around between the O-ring and the elongated shaft. In some embodiments, the O-ring is configured to maintain a pressure differential between ambient pressure and the interior space of the housing. In some embodiments, the O-ring is configured to maintain a pressure differential between the interior space of the housing and an interior of the bore. In some embodiments, the bore is configured to be exposed to an ambient pressure and equalize the ambient pressure. In some embodiments, the bore is configured to be exposed to an ambient pressure and equalize to the ambient pressure around the medicament cartridge. In some embodiments, the O-ring is compression fit over on the elongate shaft is configured to create a barrier to water and air ingress into the interior space of the housing.

Some embodiments provide a method. In some embodiments, the method includes implementing a seal between an interface of a medicament cartridge receiving chamber and the medicament cartridge, the medicament cartridge receiving chamber being configured to mate with the medicament cartridge in an abutting relationship. In some embodiments, the method includes placing an O-ring adjacent to a first end of an elongate shaft, opposite to a second end of the elongate shaft, engaging a lead screw of the elongate shaft, connected to a lead screw nut. In some embodiments, the method includes driving a gear engaging the lead screw, so as to translate the lead screw nut longitudinally towards the first end of the elongate shaft during medicament delivery.

In some embodiments, the O-ring remains immobilized in a medicament cartridge receiving chamber and yet circumferentially disposed on the lead screw nut. In some embodiments, the O-ring exerts a pressure on the elongated shaft when the O-ring is circumferentially disposed on the elongated shaft. In some embodiments, a lubricant is used to lubricate the elongated shaft to reduce a friction between the O-ring and the elongated shaft. In some embodiments, the medicament cartridge is a glucagon cartridge. In some embodiments, the medicament cartridge is an insulin cartridge. In some embodiments, a drive train assembly and a spur gear act to mechanically actuate the elongate shaft. In some embodiments, the O-ring assists in maintaining a pressure differential between an ambient pressure and an interior of the medicament cartridge receiving chamber. In some embodiments, a position of the O-ring is configured to permit water or air movement around the medicament cartridge. In some embodiments, the O-ring comprises a polymeric material.

Some embodiments provide cartridge connector set. In some embodiments, cartridge connector set comprises a first cartridge connector configured to engage a first medicament cartridge and an infusion pump. In some embodiments, the first cartridge connector comprises a needle configured to allow access to a first medicament in the first medicament cartridge. In some embodiments, the first cartridge connector comprises a knob that is in the shape of a cam and having a flattened portion. In some embodiments, a body of the connector comprises the knob and one or more of a detent, a snap arm, a skirt, and/or a grip rib. In some embodiments, the first cartridge connector is configured to engage a first pump receptacle of a pump, the first pump receptacle having a receiving track coinciding to the position and shape of the at least one detent. In some embodiments, once inserted into the first pump receptacle, the first cartridge connector is configured to positioned within the first pump receptacle using a quarter turn that aligns the flattened portion of the cam with a coinciding flat surface of the pump to indicate to a user that the first cartridge connector is correctly placed in the pump.

Some embodiments provide an infusion pump. In some embodiments, the infusion pump comprises a housing having an interior space. In some embodiments, the infusion pump comprises a bore through said housing, said bore having a first end and a second end, and the bore configured to receive a medicament cartridge. In some embodiments, the first end defines an opening into said housing and the second end is located in the interior space of the housing. In some embodiments, an elongate shaft is disposed in the bore and configured to engage the medicament cartridge. In some embodiments, the infusion pump comprises an O-ring circumferentially disposed on the elongate shaft adjacent to the second end of the bore.

Some embodiments provide method for preventing damage to an infusion pump. In some embodiments, the method comprises implementing a seal between an interface of a medicament cartridge receiving chamber sand the medicament cartridge, the medicament cartridge receiving chamber being configured to mate with the medicament cartridge in an abutting relationship. In some embodiments, the method comprises placing an O-ring adjacent to a first end of an elongate shaft, opposite to a second end of the elongate shaft, engaging a lead screw of the elongate shaft, connected to a lead screw nut. In some embodiments, the method comprises driving a gear engaging the lead screw, so as to translate the lead screw nut longitudinally towards the first end of the elongate shaft during medicament delivery.

Some embodiments pertain to a cartridge connector. In some embodiments, the cartridge comprises a body. In some embodiments, the body comprises a needle. In some embodiments, the body comprises a lower surface portion extending circumferentially from the needle. In some embodiments, the body comprises a shroud extending axially away from the lower surface portion and configured to receive and fit over a portion of a first medicament cartridge that is configured to hold a first medicament. In some embodiments, the body comprises a projection extending axially upwardly from an upper surface of the body, the projection comprising a fluid outlet. In some embodiments, the lower surface portion is located within the shroud and is configured to contact a cap of the medicament cartridge when the medicament cartridge is inserted into cartridge connector within the shroud. In some embodiments, the needle extends axially from the lower surface portion and within the shroud. In some embodiments, the body is configured to receive the medicament through the needle and to deliver the medicament out of the body from the fluid outlet of the body, the needle and the fluid outlet of the body being in fluidic communication and providing a fluid path through the body. In some embodiments, the cartridge comprises a knob portion configured engage the body. In some embodiments, the knob comprises a receptacle section, the receptacle section configured to extend over and receive at least a portion of the projection of the body. In some embodiments, the knob comprises a fluid inlet located within the receptacle section, the fluid inlet being configured to receive the medicament. In some embodiments, the cartridge comprises a fluid outlet configured to deliver the medicament to a position outside the cartridge connector. In some embodiments, the cartridge comprises an interstitial space located between the projection of the body and the receptacle section of the knob. In some embodiments, the cartridge comprises a flexible membrane located within the interstitial space and extending over at least a portion of the projection of the body, the flexible membrane being configured to allow fluid to pass from the body outlet and into the knob inlet only after a threshold fluid pressure of the medicament is reached.

Some embodiments provide a medicament infusion system for delivering a single or multiple medicaments to a patient. In some embodiments, the infusion system comprises a first cartridge connector configured to engage a first medicament cartridge and an infusion pump. In some embodiments, the first cartridge connector comprises a needle configured to allow access to a first medicament in the first medicament cartridge. In some embodiments, the first cartridge connector comprises a knob that is in the shape of a cam and having a flattened portion. In some embodiments, the first cartridge connector comprises at least one detent. In some embodiments, the first cartridge connector comprises a snap arm. In some embodiments, the first cartridge connector comprises a skirt. In some embodiments, the skirt comprises one or more snap arms, detents, and/or lugs. In some embodiments, the knob comprises a grip rib. In some embodiments, the first cartridge connector is configured to engage a first pump receptacle of a pump, the first pump receptacle having a receiving track coinciding to the position and shape of the at least one detent. In some embodiments, the first cartridge connector, once inserted into the first pump receptacle, the first cartridge connector is configured to positioned within the first pump receptacle using a quarter turn that aligns the flattened portion of the cam with a coinciding flat surface of the pump to indicate to a user that the first cartridge connector is correctly placed in the pump.

In some embodiments, the connector set (or an infusion system as disclosed herein) comprises a second cartridge connector configured to engage a second medicament cartridge and the infusion pump. In some embodiments, the second cartridge connector comprises a needle configured to allow access to a second medicament in the second medicament cartridge. In some embodiments, the second cartridge connector comprises a knob that is in the shape of a cam and having a flattened portion. In some embodiments, the second cartridge connector comprises at least one detent. In some embodiments, the second cartridge connector comprises a snap arm. In some embodiments, the second cartridge connector comprises a skirt (e.g., a shroud). In some embodiments, the skirt comprises one or more snap arms, detents, and/or lugs. In some embodiments, the knob of the second cartridge connector comprises a grip rib.

In some embodiments, the second cartridge connector comprises is configured to engage a pump second receptacle of a pump. In some embodiments, the second pump receptacle having a receiving track coinciding to the position and shape of the at least one detent. In some embodiments, once inserted into the second pump receptacle, the second cartridge connector is configured to positioned within the second pump receptacle using a quarter turn that aligns the flattened portion of the cam with a second coinciding flat surface of the pump to indicate to a user that the second cartridge connector is correctly placed in the pump.

In some embodiments, an infusion system comprises the first connector and the second connector (e.g., a connector set) and further comprises the pump. In some embodiments, the connector set comprises the first and second connectors.

In some embodiments, the infusion system further comprises the first medicament cartridge and/or the second medicament cartridge.

In some embodiments, the skirt of the second cartridge connector is longer than the skirt of the first cartridge connector. In some embodiments, the skirt of the second cartridge connector is configured to block attachment of the second cartridge connector to the first medicament cartridge.

In some embodiments, a recognition feature of the second cartridge connector is configured to block attachment of the second cartridge connector within the first pump receptacle. In some embodiments, a recognition feature of the first cartridge connector is configured to block attachment of the first cartridge connector within the second pump receptacle.

In some embodiments, the first medicament is insulin and the second medicament is glucagon. In some embodiments, a rotational direction of the quarter turn that aligns the flattened portion of the cam of the first cartridge connector with the first coinciding flat surface of the pump is the opposite a rotational direction of the quarter turn that aligns the flattened portion of the cam of the second cartridge connector with the second coinciding flat surface of the pump. In some embodiments, the quarter turn that aligns the flattened portion of the cam of the first cartridge connector with the first coinciding flat surface of the pump is clockwise and the quarter turn that aligns the flattened portion of the cam of the second cartridge connector with the second coinciding flat surface of the pump is counter clockwise. In some embodiments, the first medicament and the second medicament are both insulin. In some embodiments, the first cartridge connector comprises a first check valve that allows fluid flow from the first reservoir after a first threshold pressure is reached.

In some embodiments, the pump of (e.g., of the infusion system) comprises a pump housing having a first inlet port configured to engage the first cartridge connector. In some embodiments, the pump comprises a power source located within the pump housing. In some embodiments, the pump comprises a first pump receptacle configured to receive the first medicament cartridge when inserted through the first inlet port. In some embodiments, the pump comprises a second inlet port configured to engage the second cartridge connector and the second pump receptacle configured to receive a second medicament cartridge when inserted through the second inlet port. In some embodiments, the first receptacle and the second receptacle are located within the pump housing and laterally spaced apart from each other. In some embodiments, the power source is located at a position within the pump housing and between the first receptacle and the second receptacle. In some embodiments, the first inlet port is configured to mate with the first cartridge connector and the second inlet port is configured to mate with the second cartridge connector. In some embodiments, the pump comprises a pumping mechanism configured to deliver the first medicament from the first medicament cartridge.

In some embodiments, the first receptacle comprises a first recognition feature that prevents proper docking of the second medicament cartridge in the first chamber. In some embodiments, the second receptacle comprises a second recognition feature that prevents proper docking of the first medicament cartridge in the second receptacle. In some embodiments, the power source is an inductively chargeable battery. In some embodiments, the infusion pump is water proof or water resistant.

Some embodiments provide an infusion pump comprising a housing having an interior space. In some embodiments, the infusion pump comprises a bore through said housing, said bore having a first end and a second end, and the bore configured to receive a medicament cartridge. In some embodiments, the first end defines an opening into said housing and the second end is located in the interior space of the housing. In some embodiments, the infusion pump comprises an elongate shaft disposed in the bore and configured to engage the medicament cartridge. In some embodiments, the infusion pump comprises an O-ring circumferentially disposed on the elongate shaft adjacent to the second end of the bore. In some embodiments, the O-ring forms a barrier to water and debris from entering the interior space of the housing. In some embodiments, a position of the O-ring is configured to permit water or air movement around the medicament cartridge. In some embodiments, the O-ring is configured to permit pressure differential equalization between an infusion site and drug cartridge. In some embodiments, the O-ring exerts pressure on the elongated shaft when the O-ring is circumferentially disposed on the elongated shaft; and further comprising a lubricant to lubricate between the elongated shaft to reduce friction around between the O-ring and the elongated shaft. In some embodiments, the O-ring is configured to maintain a pressure differential between ambient pressure and the interior space of the housing. In some embodiments, the O-ring is configured to maintain a pressure differential between the interior space of the housing and an interior of the bore. In some embodiments, the bore is configured to be exposed to an ambient pressure and equalize the ambient pressure. In some embodiments, the bore is configured to be exposed to an ambient pressure and equalize to the ambient pressure around the medicament cartridge. In some embodiments, the O-ring is compression fit over on the elongate shaft is configured to create a barrier to water and air ingress into the interior space of the housing.

Some embodiments provide a battery charging station comprising a docking area for inductive charging. In some embodiments, the docking area is configured to receive the an infusion pump as disclosed elsewhere herein.

Some embodiments provide a method comprising implementing a seal between an interface of a medicament cartridge receiving chamber sand the medicament cartridge. In some embodiments of the method, the medicament cartridge receiving chamber is configured to mate with the medicament cartridge in an abutting relationship. In some embodiments, the method comprises placing an O-ring adjacent to a first end of an elongate shaft, opposite to a second end of the elongate shaft, engaging a lead screw of the elongate shaft, connected to a lead screw nut. In some embodiments, the method comprises driving a gear engaging the lead screw, so as to translate the lead screw nut longitudinally towards the first end of the elongate shaft during medicament delivery. In some embodiments, the O-ring remains immobilized in a medicament cartridge receiving chamber and yet circumferentially disposed on the lead screw nut.

Some embodiments provide a cartridge connector. In some embodiments, the cartridge connector comprises a body. In some embodiments, the body comprises a needle. In some embodiments, the body comprises a lower surface portion extending circumferentially from the needle. In some embodiments, the body comprises a shroud extending axially away from the lower surface portion and configured to receive and fit over a portion of a first medicament cartridge that is configured to hold a first medicament. In some embodiments, the body comprises a projection extending axially upwardly from an upper surface of the body, the projection comprising a fluid outlet. In some embodiments, the lower surface portion is located within the shroud and is configured to contact a cap of the medicament cartridge when the medicament cartridge is inserted into cartridge connector within the shroud. In some embodiments, the needle extends axially from the lower surface portion and within the shroud. In some embodiments, the body is configured to receive the medicament through the needle and to deliver the medicament out of the body from the fluid outlet of the body, the needle and the fluid outlet of the body being in fluidic communication and providing a fluid path through the body. In some embodiments, the cartridge connector comprises a knob portion configured engage the body. In some embodiments, the knob comprises a receptacle section, the receptacle section configured to extend over and receive at least a portion of the projection of the body. In some embodiments, the knob comprises a fluid inlet located within the receptacle section, the fluid inlet being configured to receive the medicament. In some embodiments, the knob comprises a fluid outlet configured to deliver the medicament to a position outside the cartridge connector. In some embodiments, an interstitial space is located between the projection of the body and the receptacle section of the knob. In some embodiments, a flexible membrane is located within the interstitial space and extending over at least a portion of the projection of the body. In some embodiments, the flexible membrane being configured to allow fluid to pass from the body outlet and into the knob inlet only after a threshold fluid pressure of the medicament is reached.

In some embodiments, the knob is in the shape of a cam and has a flattened portion. In some embodiments, the knob comprises a grip rib configured to facilitate manipulation and/or twisting of the cartridge connector. In some embodiments, the grip rib is configured to fit between the index finger and thumb of a user. In some embodiments, the body comprises at least one detent. In some embodiments, the cartridge connector is configured to engage a first pump receptacle of a pump. In some embodiments, the first pump receptacle having a receiving track coinciding to the position and shape of the at least one detent. In some embodiments, the cartridge connector is configured lock within the first pump receptacle once inserted into the first pump receptacle through a quarter turn that aligns the flattened portion of the cam with a coinciding flat surface of the pump. In some embodiments, alignment of the flattened portion of the cam indicates to a user that the cartridge connector is correctly placed in the pump. In some embodiments, the cartridge connector comprises at least one snap arm configured to deform outwardly from the shroud as the cap of the first medicament cartridge is inserted into the shroud, the snap arm comprising a projection mate. In some embodiments, the snap arm is configured to snap back into place after the cap abuts the upper surface of the body of the cartridge connector, thereby engaging the cap via the projection mate. In some embodiments, the shroud abuts an upper surface of the cap of the medicament cartridge. In some embodiments, the body and the knob portion are unitary.

Some embodiments provide medicament infusion set comprising the cartridge connector or connectors disclosed above or elsewhere herein. In some embodiments, the infusion set further comprises a second cartridge connector configured to engage a second medicament cartridge and the infusion pump. In some embodiments, the second cartridge connector comprises a needle configured to allow access to a second medicament in the second medicament cartridge. In some embodiments, the second cartridge connector comprises a knob that is in the shape of a cam and having a flattened portion. In some embodiments, the second cartridge connector comprises at least one detent. In some embodiments, the second cartridge connector comprises a snap arm. In some embodiments, the second cartridge connector comprises a shroud. In some embodiments, the knob of the second cartridge connector comprises a grip rib. In some embodiments, the second cartridge connector is configured to engage a second receptacle of the pump, the second pump receptacle having a receiving track coinciding to the position and shape of the at least one detent of the second cartridge connector. In some embodiments, once inserted into the second pump receptacle, the second cartridge connector is configured to positioned within the second pump receptacle using a quarter turn that aligns the flattened portion of the cam with a second coinciding flat surface of the pump to indicate to a user that the second cartridge connector is correctly placed in the pump. In some embodiments, the shroud of the second cartridge connector is longer than the shroud of the first cartridge connector. In some embodiments, the shroud of the second cartridge connector is configured to block attachment of the second cartridge connector to the first medicament cartridge. In some embodiments, a recognition feature of the second cartridge connector is configured to block attachment of the second cartridge connector within the first pump receptacle. In some embodiments, the second cartridge connector comprises a recognition feature of the first cartridge connector is configured to block attachment of the first cartridge connector within the second pump receptacle.

In some embodiments, the first medicament is insulin and the second medicament is glucagon. In some embodiments, a rotational direction of the quarter turn that aligns the flattened portion of the cam of the first cartridge connector with the first coinciding flat surface of the pump is the opposite a rotational direction of the quarter turn that aligns the flattened portion of the cam of the second cartridge connector with the second coinciding flat surface of the pump. In some embodiments, the quarter turn that aligns the flattened portion of the cam of the first cartridge connector with the first coinciding flat surface of the pump is clockwise and the quarter turn that aligns the flattened portion of the cam of the second cartridge connector with the second coinciding flat surface of the pump is counter clockwise. In some embodiments, a rotational direction of the quarter turn that aligns the flattened portion of the cam of the first cartridge connector with the first coinciding flat surface of the pump is the same as a rotational direction of the quarter turn that aligns the flattened portion of the cam of the second cartridge connector with the second coinciding flat surface of the pump.

BRIEF DESCRIPTION OF THE DRAWINGS

Various embodiments are depicted in the accompanying drawings for illustrative purposes, and should in no way be interpreted as limiting the scope of the embodiments. Any features, structures, components, materials, and/or steps of any of the embodiments can be combined or replaced with any features, structures, components, materials, and/or steps of any other of the embodiments to form additional embodiments, which are part of this disclosure. The illustrated embodiments are intended to demonstrate, but not to limit, the present disclosure. The proportions and relative dimensions and sizes of each component as shown in these drawings forms part of the supporting disclosure of this specification, but should not be limiting on the scope of this specification, except to the extent that such proportions, dimensions, or sizes are included in any individual claims.

FIG. 2A shows a view of the embodiment of FIG. 1A with its display screen and pump face removed, revealing various internal components of the pump. FIG. 2B shows another view of the embodiment of FIG. 1A with its display screen and pump face removed, revealing various internal components of the pump. FIG. 2C shows a portion of the cartridge drive assembly of the pump of FIG. 1A.

As shown in FIG. 2H, the pump comprises a lead screw, a threaded insert, and a drive nut.

FIG. 9A shows a perspective view of the cartridge connectors (e.g., the connector set). FIG. 9B shows a bottom view of the cartridge connectors.

FIGS. 18A-B illustrate perspective views of a single medicament distribution connector where 18A also illustrates a cover for the distribution connector.

FIGS. 19A-B illustrate views of a single medicament infusion base set where 19B is a cross-sectional view from the top.

FIG. 20A shows an embodiment of with the right site base, connected to a right site base cover. FIG. 20B shows the second site base connected to a second site base cover. FIG. 20C shows the first site connector connected to a first site connector cover. FIG. 20D shows the second (left) site connector connected to a second (left) site connector cover. FIG. 20E shows the dual-medicament infusion site base connected to a dual-medicament site base cover.

DETAILED DESCRIPTION

Figure 1A:
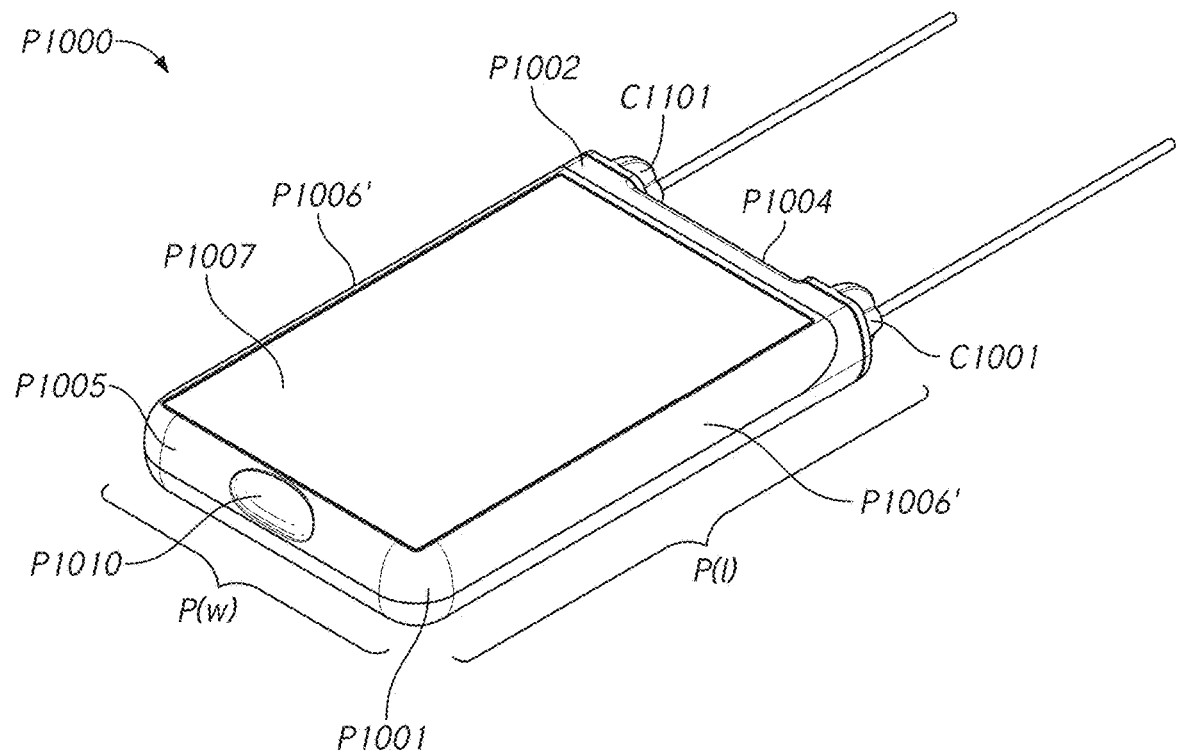
FIG. 1A illustrates perspective view of an embodiment of a pump system engaged to a cartridge connector set and fluid channels showing the lower surface of the pump.

Some embodiments described herein pertain to medicament infusion systems for one or more medicaments and the components of such systems (e.g., infusion pumps, medicament cartridges, cartridge connectors, lumen assemblies, infusion connectors, infusion sets, etc.). Some embodiments pertain to medicament re-filling systems. Some embodiments pertain to methods of manufacturing infusion systems and components thereof. Some embodiments pertain to methods for using any of the foregoing systems or components for infusing one or more medicaments to a patient. Several embodiments disclosed herein ensure proper channeling of medicaments to patients. While multiple recognition features can be used on the various components disclosed herein to reduce any opportunity for mischanneling, no single component or collection of components is essential or indispensable. For example, some embodiments may include each recognition feature and/or component disclosed herein, while others may not include or may lack one or more features or components disclosed herein while still achieving proper channeling. As an exemplary illustration, an infusion system may include an infusion pump, but not medicament cartridges. An infusion system may include medicament cartridges and cartridge connectors, but not a pump. An infusion system may include cartridge connectors and an infusion pump, but not medicament cartridges. An infusion system may include infusion connectors, a lumen assembly, cartridge connectors, an infusion pump, but not medicament cartridges or an infusion set. Any feature, structure, component, material, step, or method that is described and/or illustrated in any embodiment in this specification can be used with or instead of any feature, structure, component, material, step, or method that is described and/or illustrated in any other embodiment in this specification. Additionally, any feature, structure, component, material, step, or method that is described and/or illustrated in one embodiment may be absent from another embodiment.

INTRODUCTION

As disclosed elsewhere herein, sustained delivery, pump driven medicament injection devices generally include a delivery cannula mounted in a subcutaneous manner through the skin of the patient at an infusion site. A pump draws medicine from a reservoir and delivers it to the patient via the cannula. The injection device may include a channel that transmits a medicament, receiving it via an inlet port and providing a fluid path to the delivery cannula. The medicament may be transmitted to the patient via the cannula, which delivers the medicament to the subcutaneous tissue layer where the delivery cannula terminates. Infusion devices may be configured to deliver one medicament to a patient or multiple medicaments to a patient.

Though multi-medicament delivery systems exist, a drawback is that the patient or physician may accidentally load, and thus administer or cause to be administered, an incorrect medicament (e.g., pharmaceutical, hormone, etc.). For instance, in a multi-medicament infusion device, a user may load a medicament in an incorrect pump receptacle, which leads to the mistaken belief that he or she is administering one medicament when they are accidentally supplying a different one. The accidental administration of an incorrect medicament to the patient can have serious and potentially fatal consequences.

For example, standard-of-care insulin therapies for regulating blood glucose in diabetic patients may involve subcutaneous infusion of insulin via an insulin pump. If the amount of dosed insulin is excessive, it can lead to hypoglycemia or a situation of impending hypoglycemia. To combat and/or reverse such adverse situations, individuals typically consume additional carbohydrates (e.g. sweet juice or glucose tablets). Individuals can alternatively and/or additionally administer a so-called "rescue dose" of a counter-regulatory agent, such as glucagon. A counter-regulatory agent combats the effect of the excess regulatory agent dose (e.g., excess insulin) alleviating or substantially preventing adverse effects related to the excess dose. However, if a patient is given additional insulin instead of the intended rescue dose of glucagon, the results could be catastrophic, potentially leading to death. Similarly, during a diabetic episode, if a patient requires insulin but is given glucagon instead, that administration could exacerbate the episode and could lead to devastating effects and could be lethal.

The proper channeling in medicament dosing is, therefore, critical, especially where one medicament is used to achieve one effect while another is used to achieve a different and/or the opposite effect (e.g., as in the case of insulin and glucagon). In a multi-medicament automated system, if the medicaments are accidentally loaded in the incorrect cartridges or incorrect cartridge chambers of a pump, the automated system could deliver an ineffective (and/or potentially harmful) medicament to the patient. This phenomenon of incorrect medicament loading and/or administration in automated systems is called cross-channeling (or mischannelling). As illustrated above, cross-channeling is dangerous not only because the wrong medicament can lack the intended therapeutic effect, but also because the wrong medicament could have the opposite of an intended effect (or some other side effect that is unanticipated or undesired). Also as illustrated above, improper channeling not only fails to alleviate the patient's condition, but could make the patient's condition worse, or cause a new problem-state for the patient. Improper channeling (e.g., mischanneling) could cause a negative feedback loop, wherein the control system attempts to adjust the patient's disease state in one direction, but the delivery of the incorrect medicament exacerbates or causes no effect on the disease state. Sensing this, the control system can trigger further doses of the wrong medicament in an attempt to control the patient's condition, while actually causing the patient's condition to further deteriorate (or causing overdosing of the incorrect medicament).

Additionally, in certain circumstances or environments, commercial diabetic drug infusion systems may be inadequate to prevent improper dosing, even where the proper medicament is being administered. For example, runaway dosing can occur in some circumstances, or inadequate dosing in others.

While diabetic drugs (e.g., insulin and glucagon) are used as exemplary medicaments above and elsewhere herein, improper channeling (or dosing) can have deleterious effects in many multi-medicament regimens because a medicament is not administered to the patient at the necessary time (and/or at a necessary level), or an incorrect medicament is administered at a dangerous level. Mischanneling can be detrimental in other drug combinations that regulate pancreatic enzymes, other combinations of drugs meant to maintain the body's equilibrium in one direction or the other, or simply where a patient requires multiple drugs regardless of any relationship between the drugs or a common disease state (e.g., where one drug treats one disease state and another a completely unrelated disease state). Thus, the embodiments and considerations provided herein can be applied to any drug combination. Additionally, while cross-channeling can refer to systems with two medicaments, the term cross-channeling as used herein can also refer to systems where more than two medicaments are used and/or where a single medicament is used (for example, when a single medicament is improperly placed in a distribution system).

Some embodiments disclosed herein address one or more of problems associated with these problems (e.g., mischanneling, runaway or inadequate dosing, etc.) or others. Described herein are infusion systems for single or multiple medicaments and various connectors, tubes, cartridges, pumps, infusion sets, and/or systems comprising any one or more of the foregoing that ensure, help ensure, and/or substantially aid in providing proper channeling and/or dosing of each medicament to the patient. Certain embodiments of the infusion systems and components thereof described herein are configured to minimize, lessen, and/or otherwise help avoid the occurrence of cross-channeling and/or improper dosing of medicaments. In some embodiments, where medicaments are supplied by the infusion systems disclosed herein, components comprising recognition features as described herein are configured to impede, prevent, minimize the occurrence of, or otherwise inhibit any opportunity for a user to inadvertently place a medicament in the incorrect position and/or deliver an incorrect medicament (and/or an improper amount of a correct medicament).

Cross-channeling may be avoided by providing recognition features (e.g., unique differentiating recognition elements) that allow mating between only particularly shaped components within an infusion system. In some embodiments, the infusion system comprises an infusion pump with one, two, or more infusion chambers (or pump chambers) and one or more recognition features. In some embodiments, the system further comprises cartridges filled with different medicaments, and connectors and tubing having recognition features that connect to the cartridges to the infusion pump in such a way as to prevent mischanneling or cross-channeling of medicaments. In certain variants, each type of cartridge for each type of medicament has one or more unique differentiating features (either as an integral part of the cartridge or as a component attached or affixed to the cartridge). Recognition features can comprise, for example geometric or shape-based features, that allow for unique coupling between components of the system. A type of connector that has unique differentiating features can engage corresponding features in the pump housing and allow for insertion of a proper cartridge into the proper infusion chamber. A cartridge with unique features can interact with a pump infusion pump having corresponding features (e.g., a drive shaft or pump chamber with corresponding features). Improper dosing can be avoided with certain design features disclosed herein, including seals, valves, and other implements incorporated into the components disclosed herein.

The following disclosure provides additional details regarding configurations of systems and components for avoiding cross-channeling. While the following description provides context and examples, it should not be interpreted to limit the scope of the inventions covered by the claims that follow in this specification.

The Infusion System

Some embodiments disclosed herein pertain to infusion systems configured to delivery one or more medicaments without cross-channeling and/or configured to prevent improper dosing of a medicament. In certain variants, the system comprises one or more of the following: an infusion pump (configured to receive one or more medicament cartridges in one or more cartridge receptacles), one or more cartridge connectors (configured to engage one or more medicament cartridges, the infusion pump, and/or both simultaneously), one or more medicament cartridges, an infusion set (configured to deliver the medicament to the patient via a piercing element that may comprise a cannula or needle penetrating the skin of the patient), one or more infusion connectors configured to engage with the infusion set, and a fluid conduit in fluid communication with the one or more cartridge connectors and/or the one or more infusion connectors. In several embodiments, the infusion system (or components thereof) include one or more design features that make it compact. In some variants, the infusion system (or components thereof) are especially suitable to be ambulatory and/or wearable on a patient, allowing the patient freedom of movement (e.g., day-to-day activities, including but not limited to, work, engaging in exercise, swimming, air travel, etc.).

In some implementations, where the infusion system is configured to deliver multiple medicaments (instead of just one), the infusion system may be adapted to receive multiple medicaments from multiple medicament cartridges. As an illustration, in a two medicament infusion system, the system may comprise multiple different configurations of components, including or lacking one or more components selected from two medicament cartridges, an infusion pump configured to receive the two cartridges (e.g., in different cartridge receptacles), cartridge connectors configured to engage the medicament cartridges and/or the infusion pump (e.g., at or near the cartridge receptacles), an infusion set configured to deliver the medicaments to the patient (e.g., a piercing element for the first medicament and a piercing element for the second medicament), two infusion connectors configured to engage with the infusion set, and fluid conduits, each in fluid communication with one cartridge connector and one infusion connector (e.g., providing separate flow paths). of a A two medicament infusion system is shown in FIG. 1A, where the system comprises two different cartridge connectors with coinciding fluid conduits and a pump. Additionally, where the system is configured to delivery three or more medicaments, additional cartridges, cartridge receptacles, cartridge connectors, infusion connectors, and piercing elements may be provided as needed (though the system may also lack any one or more of these components). As disclosed elsewhere herein, while two or more medicaments may be delivered by the infusion system, several embodiments pertain to pumps that deliver a single medicament (e.g., having a pump with only one cartridge receptacle or multiple cartridge receptacles configured to receive a single type of medicament cartridge, for example, insulin).

In some embodiments, as disclosed elsewhere herein, the system and/or components thereof include unique mating features and design elements (recognition features). These recognition features may ensure that each portion of the system can only be connected within the system in a unique way or configuration (e.g., a proper way), thus preventing cross-channeling (e.g., mischanneling). In some embodiments, where different medicaments are delivered by a single system (or component thereof), the medicaments may be kept completely separate throughout their residency within the system (or components thereof) and may have different fluid paths to a patient. For example, cartridge connectors and fluid conduits may be used to provide separate fluid pathways that terminate at designated delivery members (e.g., needles, cannulas, etc.) within a base (e.g., the infusion set), thereby enabling independent delivery (e.g., subcutaneous or otherwise) of medicaments separately.

In certain embodiments, design features of the disclosed system (and/or components thereof) give rise to the following advantages or others: (1) allowing the user to easily connect and disconnect the components independently from any medicament sources as well as from the infusion ports or sites; (2) mitigating the possibility of mischanneling that occurs when a user accidentally connects the wrong components together; (3) mitigating possibility for improper dosing levels; (4) mitigating loss of and or contamination of medicaments; (5) allowing for a single or multistep insertion of the dual-cannula infusion site or port. In some embodiments, the system and components described herein can further comprise visual or brail call-outs in addition to or instead of various paired physical features disclosed herein. For instance, in some implementations, the components can comprise call-outs with wording indicating a proper medicament. In some variants, different colors (red, blue, yellow, green, orange, violet, etc.) or lengths (or other variables) to provide visual feedback regarding appropriate medicaments for appropriate components.

In some embodiments, as stated elsewhere herein, the infusion system can be used to provide separate fluid pathways for a variety of medicaments (e.g., drugs, hormones, proteins, pharmaceuticals, biologics, etc.) dissolved in a variety of liquid carriers (and/or liquid drugs). In certain embodiments, different liquid vehicles may be preferred based on the solubility, stability, or sensitivity of the medicament in a particular carrier. In some embodiments, aqueous solutions (buffers, etc.) are used as a delivery vehicle for the medicament. In certain variations, solvents such as DMSO are used to dissolve medicaments. In some embodiments, solvent/aqueous mixtures are used.

In some implementations, a dual medicament system configured to receive insulin and glucagon cartridges is provided. In another implementation, the system may comprise a pump with multiple cartridge receptacles (e.g., chambers) that are configured to receive medicament cartridges containing an identical medicament (and not a different medicament) and/or configured to interact with multiple identical cartridge connectors. For example, in some embodiments, the infusion pump may have two medicament receptacles that are identical and that include identical recognition features. These receptacles may both be configured to receive identical medicament cartridges and/or may be configured to engage cartridge connectors that are the same (e.g., two cartridges contain insulin and/or two cartridge connectors that are both configured to engage insulin cartridges). In such a configuration, the system and its components (e.g., the medicament cartridges, infusion pump, cartridge connectors, infusion set, infusion connectors, and a fluid conduit) are configured to receive two (or more) medicament cartridges comprising a particular medicament (e.g., insulin) and not a medicament cartridge comprising a different medicament (e.g., glucagon). By providing a system that accommodates two or more cartridges of the same medicament (and that prevents or inhibits the insertion or connection of cartridges having other medicaments), the system operates for a longer period of time without the need for refilling or adding additional cartridges. Moreover, an expended single cartridge (e.g., one that is empty or close to empty) can be changed on the fly by the user without disrupting and/or delaying the flow of medicine from a second cartridge that is providing the medicament to the patient. In some embodiments, the pump is configured to receive a single medicament cartridge and the system comprises single components to allow the delivery of the same (e.g., a single cartridge connector, a single channel lumen assembly (that may comprise the cartridge connector), a single infusion connector, a single infusion base, a single medicament cartridge, etc.).

The following sections provide additional information regarding individual components of the infusion systems disclosed herein. While these components may be described as being part of an infusion system, it is to be understood that, each of these components (e.g., the infusion pump, cartridge connectors, medicament cartridges, infusion set, infusion connectors, and fluid conduit) may be taken individually apart from the system. Likewise, where a component is described in isolation, it may be part of an infusion system, as disclosed herein. Any combination of recognition features within the infusion system can be mixed and matched to address the mischanneling problem just as any dosing safety features may be mixed and matched to address improper administration issues. In several implementations, not all the recognition features or safety features disclosed herein need to be used in a particular embodiment. For instance, as disclosed elsewhere herein, a cartridge connector may be uniquely shaped in a way to allows it to only engage with one medicament vial (and not others) and uniquely threaded so that it only engages a coinciding cartridge receptacle in a pump. In such an embodiment, such features may be sufficient to avoid mischanneling and other features need not be included. To illustrate, in such a configuration, the cartridge receptacle of the pump may lack a recognition feature configured prevent insertion of a cartridge and instead the connector is configured to engage a particular medicament cartridge and a particular cartridge port in the pump.

Pump System

As disclosed elsewhere herein, some embodiments, pertain to infusion pumps (e.g., pump systems). In some implementations, an infusion pump as disclosed herein is a part of and/or a component of an ambulatory infusion system.

Figure 1B:
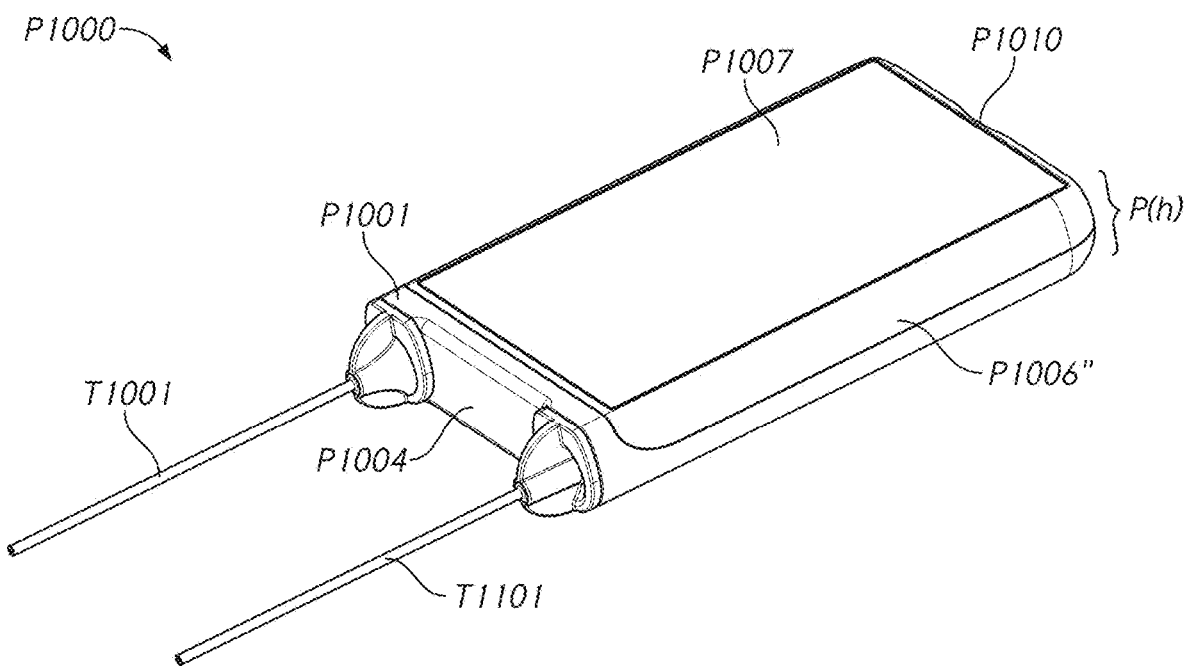
FIG. 1B is a second perspective view of the embodiment FIG. 1A, this time showing the upper surface of the pump.
Figure 1C:
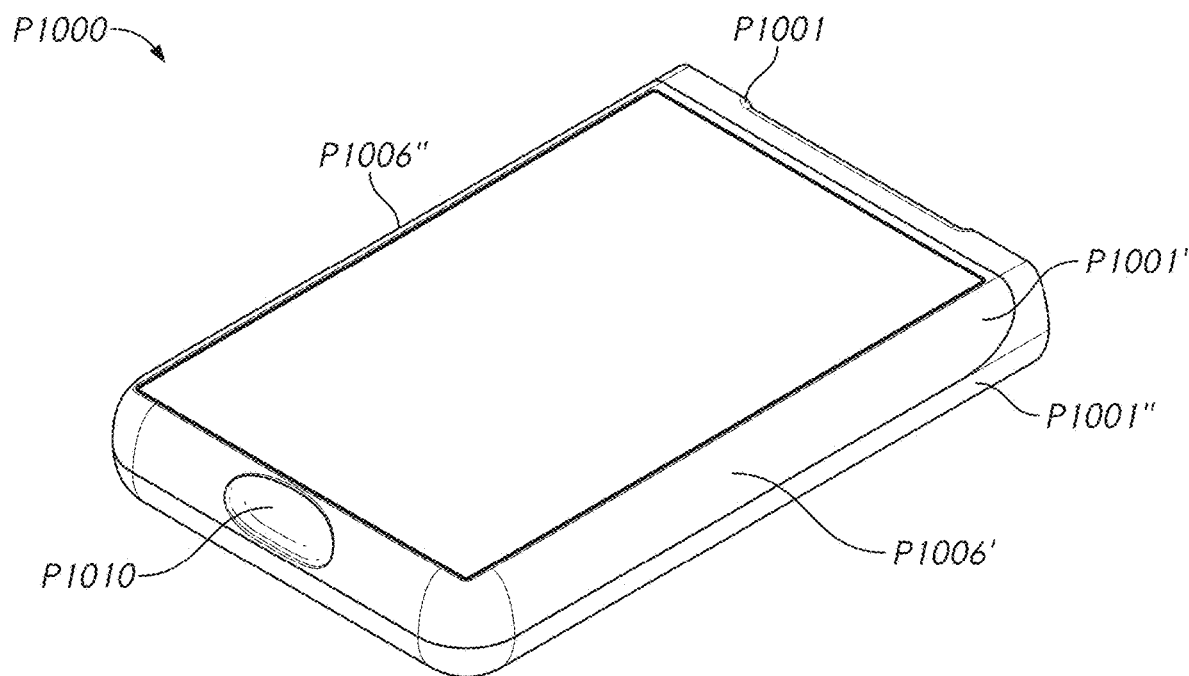
FIG. 1C is another perspective view of the embodiment FIG. 1A showing the upper surface of the pump device where the connector set has been removed.
Figure 1D:
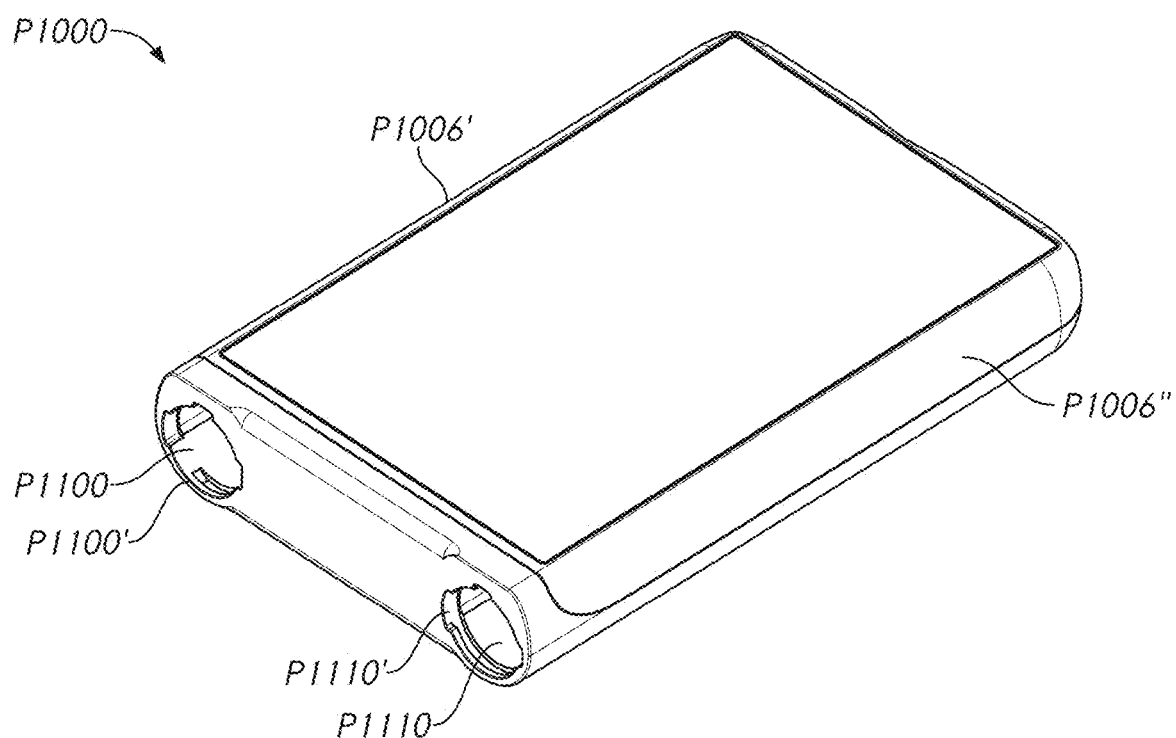
FIG. 1D is another perspective view of the embodiment FIG. 1A showing the upper surface of the pump.
Figure 1E:
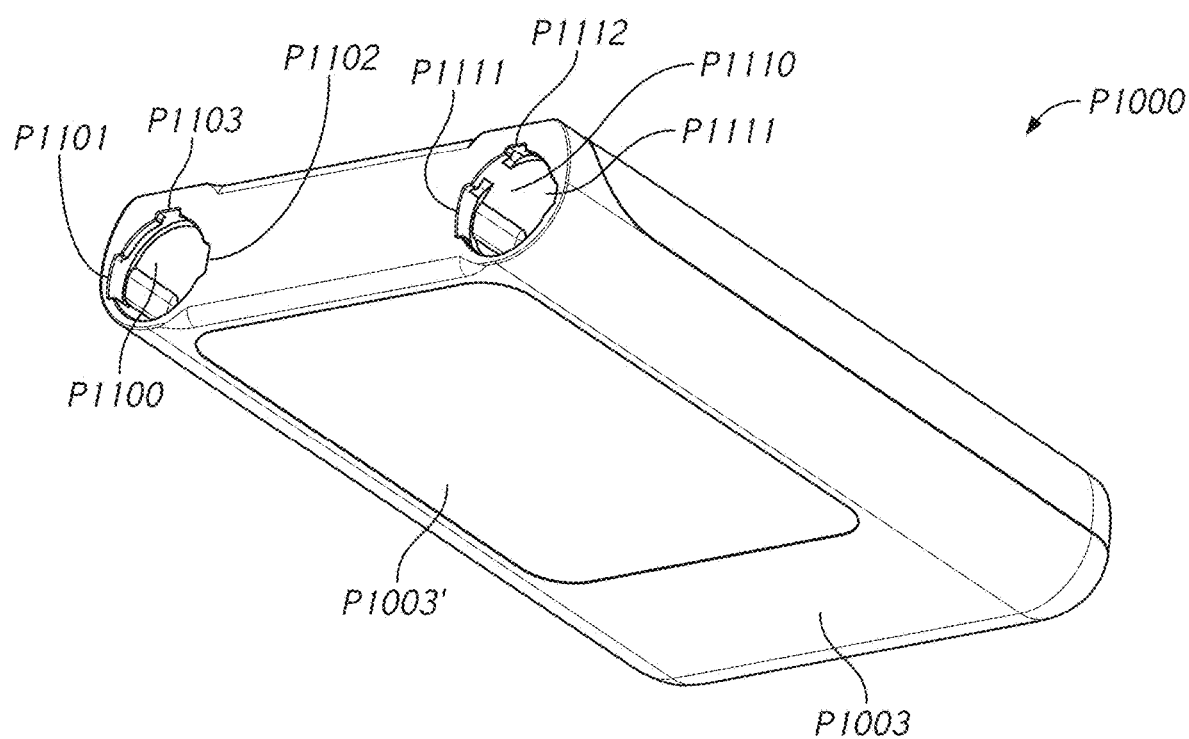
FIG. 1E is another perspective view of the embodiment FIG. 1A showing the lower surface of the pump.

In some embodiments, as shown in FIGS. 1A, 1B, and 1E, the pump may include a face P1002, a backing P1003, a bottom side P1005 (e.g., a lower side surface), a top side P1004 (e.g., an upper side surface), a first side surface P1006' (e.g., a right side surface), and a second side surface P1006" (a left side surface). As shown in FIGS. 1A and 1B, the pump face P1002 and pump backing P1003 may each extend (e.g., laterally as a plane) along the upper side surface P1004 and lower side surface P1005 of the pump P1000 providing a pump width P(w). The pump face P1002 and pump backing P1003 may each extend (e.g., longitudinally as a plane) between the lower side surface P1005 and upper side surface P1004 in a direction along the first side surface P1006' and second side surface P1006" of the pump P1000, providing a pump length P(l). As shown in FIG. 1A, the pump P1000 may also have a height P(h) extending between the pump face P1002 and the pump backing P1003 in a direction along the first side surface P1006' (and/or along the second side surface P1006"). In some embodiments, the face P1002, backing P1003, lower side surface P1005, upper side surface P1004, first side surface P1006', and second side surface P1006" of the pump provide an outer perimeter of the pump.

In several variants, the infusion pump P1000 includes a pump housing P1001 that encases and/or houses one or more internal components of the infusion pump. As shown in 1C (also visible in FIGS. 1A, 1B, and 1D-1F), in certain implementations, the pump housing P1001 can comprise a bezel P1001' and a lower portion P1001". In some embodiments, the lower portion P1001" provides a frame onto which the bezel fits and/or connects. As shown in FIG. 1C, a portion of the lower portion P1001" may extend to the pump face P1002. In some embodiments, the lower portion P1001" and/or the frame of the lower portion extends to the face of the pump to provides the upper side surface P1004 of the pump P1000. In some embodiments, the upper and lower portions of the housing may be sonically welded together, snap fit, glued or otherwise affixed to one another. In some embodiments, the connection between the bezel and the lower portion (in combination with one or more features) is waterproof and/or water resistant. In some embodiments, the pump is prevents water ingress at a depth 1 m for a period of equal to or at least about: 5 minutes, 10 minutes, 15 minutes, 30 minutes, or ranges spanning and/or including the aforementioned values. In some embodiments, the upper and lower portions of the housing may be different materials or the same. In certain implementations, for example, the lower portion is a metal and the upper portion is not. In some implementations, the upper portion is polymeric and/or plastic, and the lower portion is not. In some embodiments, both the lower portion and the upper portion are independently a polymeric material (e.g., a plastic) or a metal.

In several embodiments, a generally rectangular prism shaped configuration of the pump P1000 (as shown) has been found to advantageously accommodate internal pump components in a compact way (e.g., suitable for wearing). The compact nature of the rectangular prism configuration, along with one or more other design features disclosed, reduce bulk and increase the ease with which the disclosed infusion system can be worn and/or used. In several embodiments, the compact nature of the design increases user compliance and convenience. While a rectangular prism provides certain advantages with regard to the configuration of the internal components of the pump, in other embodiments, other shapes may be adopted (e.g., generally cube-shaped, oblong, cylindrical, oval cylindrical, etc.). In some embodiments, as disclosed elsewhere herein, the housing of the pump P1001 has rounded edges to improve shock absorption and/or resistance to cracking when impacted (e.g., by dropping, etc.).

In certain implementations, the ratio of the length of the pump P1000 to the width of the pump is equal to or at least about: 3:1, 5:2, 2:1, 5:3, 4:3, or ranges spanning and/or including the aforementioned ratios. For example, in some embodiments, the ratio of the length of the pump to the width of the pump can range from between 3:1 and 2:1, from 5:2 and 5:3, etc. In some configurations, the ratio of the width of the pump P1000 to the height of the pump P1000 is equal to or at least about: 7:1, 5:1, 4:1, 3:1, 5:2, or ranges spanning and/or including the aforementioned ratios. For example, in some embodiments, the ratio of the width of the pump to the height of the pump can range from between 7:1 and 4:1, etc.

In certain embodiments, as shown in FIG. 1A, the pump P1000 comprises a display region P1007. In some embodiments, as disclosed elsewhere herein, the display region P1007 is a display screen and/or a touch screen. In some variants, the display region P1007 may be configured to provide the user with data (e.g., alphanumeric, image-based, etc.) regarding medicament levels, drug dosing rates, information about blood sugar levels, and/or other diagnostic information. In certain configurations, as disclosed elsewhere herein, the display screen allows the user to adjust the distribution of medicaments or other pump and delivery settings (including one or more control features disclosed herein). In some embodiments, the bezel provides support for and/or engages the display screen, holding it in place.

In some embodiments, as shown in FIGS. 1A and 1B, the lower side surface P1005 of the pump P1000 may comprise a touch pad P1010. In some embodiments, the touch pad P1010 is a finger pad having a curved indentation configured to receive a finger of a user. In several variants, as disclosed elsewhere herein, a capacitive touch sensor may be located under the finger pad P1010 and/or is in electronic communication with the finger pad P1010. In other embodiments, additional capacitive touch sensors may be in communication with different surfaces of the pump (e.g., elsewhere on the pump face, pump backing, the upper side surface, the first side surface, or the second side surface).

In certain variants, additionally or alternatively, the display P1007 may be a capacitive touch sensor and/or a capacitive touch sensor may be located at or behind a portion of the pump face P1002 (e.g., making the display a touchscreen). In some embodiments, a capacitive touch sensor of the display P1007 may be activated by touching the display P1007 in designated locations and/or by touching the separate finger pad P1010 (and/or a different the surface) of the pump P1000. In some embodiments, the capacitive touch sensor of the display P1007 may be used to control and/or send signals to components within the pump P1000, for example, allowing a user to control one or more aspects of the drug delivered from the reservoirs located within the pump. For instance, in some embodiments, a user can swipe (or drag) a finger in one direction (i.e., left, right, down, up, or otherwise) over the capacitive touch sensor display P1007 to change delivery capabilities (e.g., rate, etc.).

Pump Cartridge Receptacles

FIGS. 1A and 1B show a multiple medicament pump P1000 engaged to two cartridge connectors C1001, C1101 (e.g., a first and a second cartridge connector). These cartridge connectors can be configured to attach to different medicament cartridges and to simultaneously engage the pump via cartridge receptacles (e.g., first and second cartridge receptacles). As show, a first and second fluid conduit T1001, T1101 are engaged to the first and second cartridge connectors C1001, C1101, respectively. Though not visible in FIGS. 1A and 1B, medicament cartridges may be housed in chambers that are engaged with the cartridge connectors C1001, C1101. Also visible in FIGS. 1A and 1B is tubing a first tube T4001 and a second tube T4002 that is configured to provide a fluid path to the infusion set and/or infusion connectors (not shown).

As shown in FIGS. 1C and 1D, the pump 1000 comprises cartridge receptacles P1100, P1110 (e.g., cartridge holders, cartridge chambers, and/or cartridge repositories). As shown, the cartridge receptacles include medicament receptacle inlet ports P1100', P1110". In FIGS. 1C-1F, the cartridge connectors C1001, C1002 shown in FIGS. 1A and 1B (and coinciding medicament cartridges M1001, M1101, visible in FIG. 2I) have been disengaged and removed from the pump P1000, making the cartridge receptacles P1100, P1110 and inlet ports P1100', P1110" visible. In some embodiments, these cartridge receptacles are configured to house (e.g., receive, secure in place, hold, etc.) the medicament cartridges M1001, M1101 (as shown in FIG. 2I).

As shown in FIGS. 1A, 1B, and 1D-1F, the pump P1000 may comprise a first medicament chamber P1100 that is different from a second medicament chamber P1110. In some variants, one or more design features (e.g., recognition features) of the inlet ports P1100', P1110' and/or other features within the cartridge receptacles P1100, P1110 prevent proper engagement of the cartridge connectors and/or prevent insertion of an improper cartridges into an incorrect chamber. For instance, as shown in FIGS. 1E-1J, these chambers P1100, P1110 or inlet ports P1100', P1110' may include one or more recognition features P1101, P1102, P1103, P1111, P1112, P1113 that prevent or inhibit coupling to improper components.

In some embodiments, the cartridge receptacles are configured to receive particular medicament vials and not others. For instance, a given receptacle can be configured to not receive an incorrect medicament cartridge (e.g., by virtue of the diameter, length, size, or shape of the medicament cartridge). In other embodiments, the cartridge receptacles may be configured to receive different types of cartridges indiscriminately. In such embodiments, even where a given cartridge receptacle can receive differently shaped medicament cartridges and/or cartridges for different medicaments (e.g., the first receptacle could receive either a glucagon cartridge or an insulin cartridge), mischanneling may still avoided by virtue of the cartridge connectors and the inlet ports P1100', P1110".

For instance, as disclosed elsewhere herein, a first cartridge connector C1001 may be configured to engage only a specific medicament cartridge M1001 (e.g., a first medicament cartridge) and a second cartridge connector C1101 may be configured to engage only a coinciding specific medicament cartridge M1101 (e.g., a second medicament cartridge). Though the pump receptacles P1100, P1110 themselves may not be configured to prevent the insertion of an incorrect medicament cartridge, the inlet ports P1100', P1110" may include unique mating features (e.g., recognition features) that allow them only to engage a specific medicament cartridge connector with coinciding mating features. To illustrate, the first receptacle may be configured to engage the first cartridge connector and not the second cartridge connector. The second receptacle may be configured to engage the second cartridge connector and not the first cartridge connector.

In other embodiments, a given receptacle can be configured to not receive an incorrect medicament cartridge (e.g., by virtue of the shape of the medicament cartridge) and to also not engage an incorrect cartridge connector.

In some embodiments, the pump is configured to receive a medicament cartridge that is already connected to a connector. To illustrate, a medicament cartridge may be connected to a cartridge connector, then the pump can receive the cartridge and connector simultaneously (only allowing engaging of an appropriate connector and/or cartridge). Alternatively, or additionally, in several embodiments, the pump may receive the medicament cartridge (e.g., loosely, without and/or free from the cartridge connector). Then, the pump may be configured to receive the cartridge connector into the cartridge receptacle over the cartridge, where the connector can be locked in position (e.g., twisted into place) within the pump. In such embodiments, the connector may be configured to simultaneously engage both the vial and the pump. Where the connector or medicament cartridge are improper for a given receptacle, certain recognition features can prevent engagement of the connector. For instance, where the cartridge and connector are not paired, the cartridge be of insufficient diameter to receive the cartridge, preventing the engagement of the cartridge connector to it and holding the cartridge connector in a position that is too far from the pump to engage the inlet port. Alternatively, the connector may receive the incorrect vial, but may travel too deep within the receptacle to engage the inlet recognition features of the pump.

As shown in FIG. 2I, the inlet port P1100' of the first medicament chamber P1100 may be configured to engage a first cartridge connector C1001 and/or receive a first cartridge M1001. In some embodiments, as shown, the inlet port P1110" of the second medicament chamber P1110 is configured to engage a second cartridge connector C1101 and/or receive a second cartridge M1101. In some embodiments, the inlet port P1100' of the first medicament chamber P1100 is configured not to engage a cartridge connector that engages the second inlet port P1110" (e.g., the second cartridge connector C1101). In some embodiments, additionally or alternatively, the inlet port P1110" of the second medicament chamber P1110 is configured not to engage a cartridge connector that engages the first inlet port P1100' (the first cartridge connector C1001). In the embodiment shown in FIG. 1D, the first receptacle P1100 is configured to house or receive a cartridge and cartridge connector for a regulatory agent (e.g., insulin) and the second medicament chamber P1110 is configured to house or receive a cartridge and cartridge connector for a counterregulatory agent (e.g., glucagon).

As shown in FIGS. 1D-1I, each of the pump chambers P1100, P1110 comprises one or more recognition features P1101, P1102, P1103, P1111, P1112, P1113 configured to prevent or inhibit mischannelling. As shown, the features may be protrusion-shaped openings (e.g., divots, apertures, pass-through spaces, detent slots, lug slots, radial lug or detent shaped notches, carve-outs, etc.) configured and/or shaped to receive corresponding protruding features (e.g., protrusions, tabs, lugs, detents) of a cartridge connector coinciding to the pump chamber. These mating features facilitate attachment of and/or to prevent connection of in appropriate components. While, in the depicted embodiment, radial divots (e.g., divots or notches shaped to receive coinciding protruding features) are distributed circumferentially about the inlet ports P1100', P1110", in other embodiments, protrusions (e.g., tabs, lugs, detents) and/or a mixture of protrusions and divots may be provided on or within the inlet ports to prevent or inhibit mischannelling (not shown). In such an embodiment, coinciding radial divots and/or protrusions may be provided on a corresponding cartridge connector.

Figure 9A:
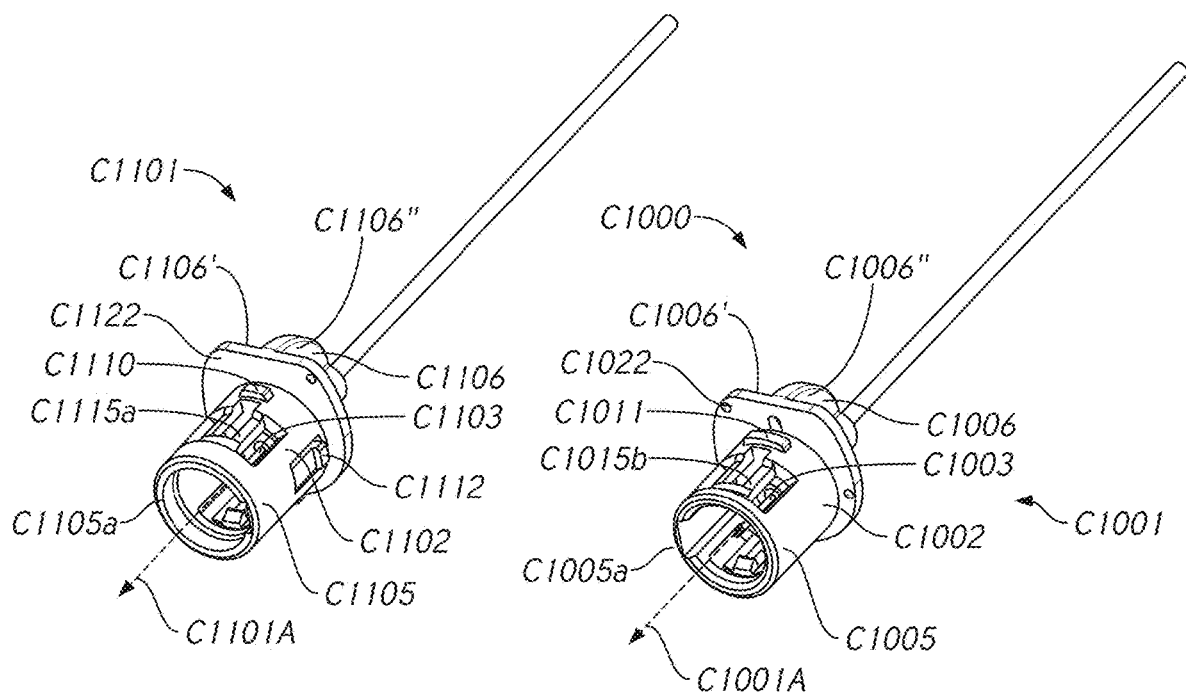
FIGS. 9A and 9B are views of a cartridge connector set comprising two cartridge connectors and coinciding fluid conduits (tubing).
Figure 9B:
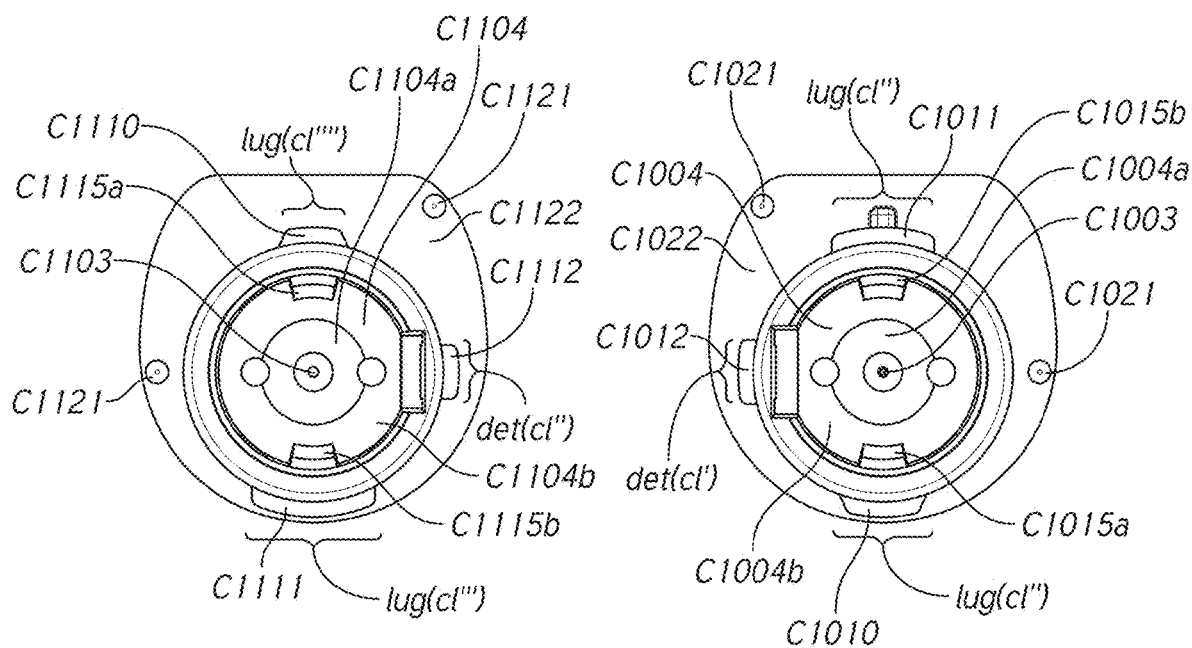

In some embodiments, as shown, the features of the pump receptacles P1100, P1110 may be located at a position proximal to the entrance of the receptacle (e.g., at the inlet ports P1100', P1110") to allow interaction with a corresponding cartridge connector. As shown in FIGS. 9A-9B, cartridge connectors C1001, C1101 corresponding to the pump receptacles P1100, P1110, respectively, comprise coinciding protrusions (e.g., tabs, lugs, detents). In some embodiments, these protrusions include lugs C1010, C1011, C1110, C1111 and/or detents C1012, C1112. In some embodiments, as described elsewhere herein, the protrusions (e.g., projections) are configured to mate with (e.g., slide into) coinciding openings configured to receive such projections. As illustrated in FIGS. 1D-1J and 9B, each cartridge chamber may have a plurality of recognition features configured to mate with corresponding recognition features of the cartridge connectors. In the illustrated embodiment of 1D-1J, each pump chamber P1100, P1110 comprises three radial carve-outs configured to engage coincidingly shaped lugs and detents of corresponding cartridge connectors C1001, C1101, respectively, shown in FIG. 9B. These recognition features may be configured to engage an appropriate connector, to prevent or inhibit engagement of an improper cartridge connector (e.g., that is not corresponding and that lacks one or more coinciding protrusions), or both.

While in the embodiment shown in FIGS. 1D-1J each inlet port 1100', 1110' has three radial divots as recognition features, in some embodiments, each pump chamber can independently have one, two, three, four five, or more recognition features (e.g., divots and/or protrusions) configured to receive coinciding recognitions features (e.g., protrusions and/or divots) from corresponding cartridge connectors. Additionally, as apparent here, while the cartridge receptacles have been described as comprising divots and the cartridge connectors as comprising protrusions, the opposite configuration is also possible (where divots are on the cartridge connectors and protrusions on the receptacles). Likewise, in some embodiments, types of recognition features could be mixed and matched on a particular receptacle or cartridge connector (so the receptacle comprises both protrusions and divots and the corresponding cartridge connector has coinciding divots and protrusions). In yet another variation, a cartridge receptacle can comprise only divots and a different cartridge receptacle in the same pump can comprise only protrusions. In such an embodiment, the corresponding cartridge connector set can comprise a connector with coinciding protrusions and a connector with coinciding divots, respectively. As exemplary embodiments, where a first cartridge connector comprises five protruding features (e.g., three lugs and two detents; not shown), a corresponding first receptacle (e.g., a first inlet port) would comprise five divots to receive those protrusions (e.g., three lug openings and two detent openings). A second cartridge connector could comprise four divots (e.g., two lug openings and two detent openings) configured to engage a corresponding second receptacle comprising four protrusions (e.g., two lugs and two detents) to be received within those divots.

Figure 1F:
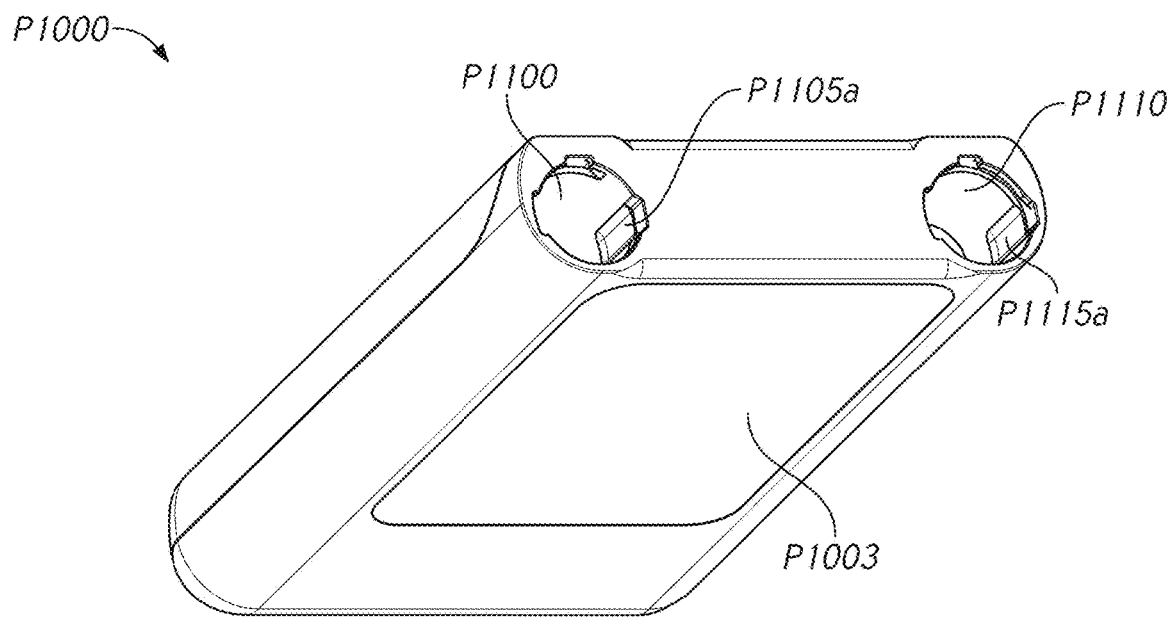
FIG. 1F is another perspective view of the embodiment FIG. 1A showing the lower surface of the pump and the cartridge receptacles.
Figure 1G:
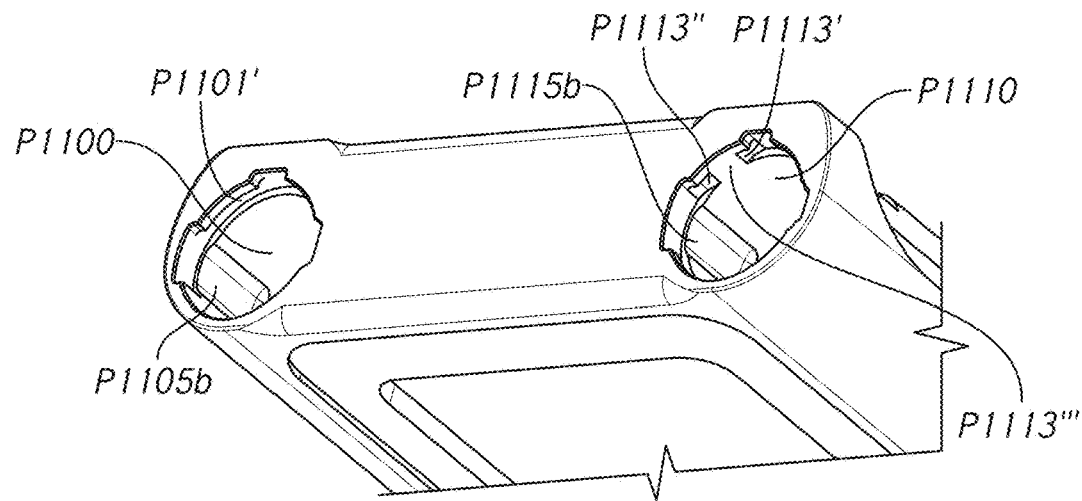
FIG. 1G is a view of the embodiment FIG. 1A showing the cartridge receptacles of the pump.
Figure 1H:
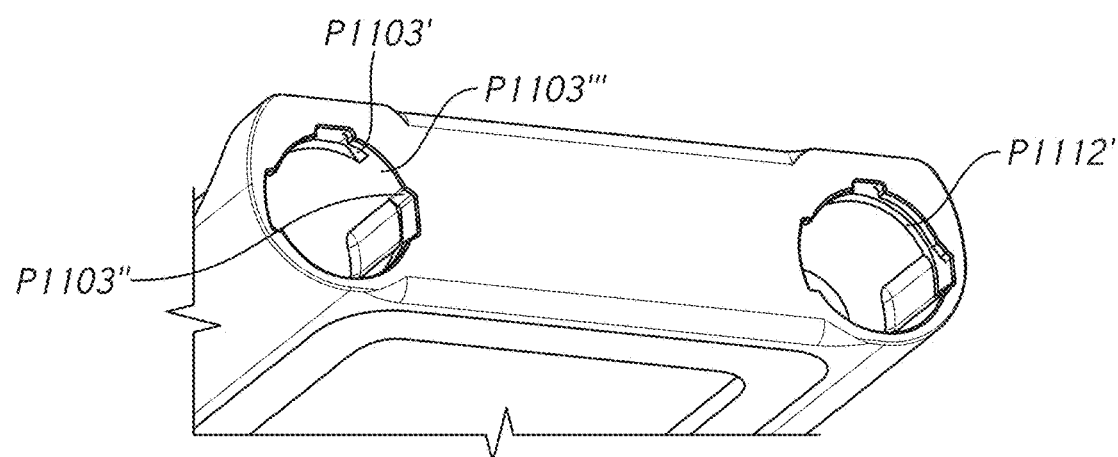
FIG. 1H is another view of the embodiment FIG. 1A showing the cartridge receptacles of the pump.
Figure 1I:
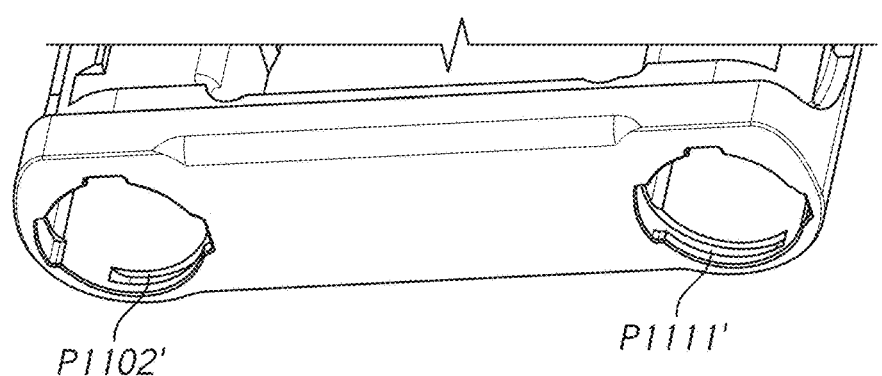
FIG. 1I is another view of the embodiment FIG. 1A showing the cartridge receptacles of the pump.
Figure 1J:
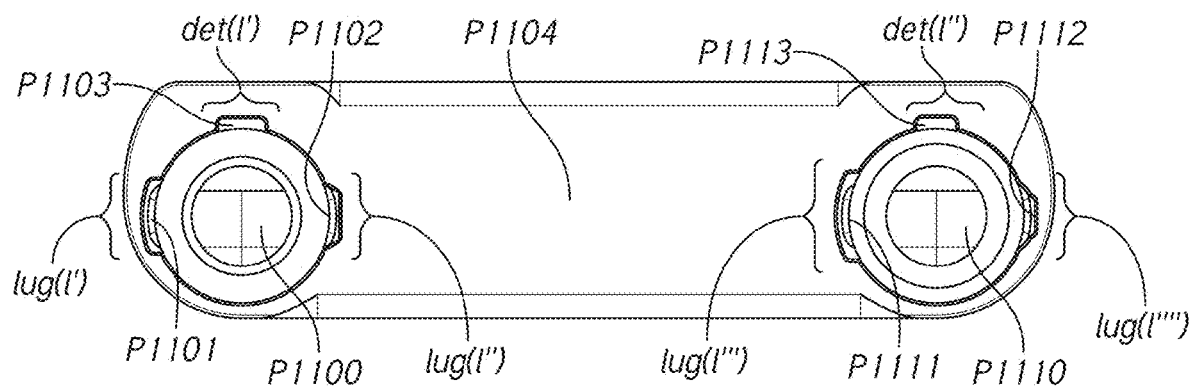
FIG. 1J is a view of the upper side surface of the embodiment FIG. 1A showing the cartridge receptacles of the pump

In some embodiments, as shown in FIGS. 1D-1J, the lug openings and detent openings may be various different sizes (e.g., circumferential lengths, radial heights, etc.). For example, as shown in FIG. 1J, a lug opening of one cartridge receptacle may be of one length lug(l'), a second may be of a second length lug(l"), these lengths may be different from each other and/or from the lug lengths of a second cartridge receptacle lug(l'''), lug(l''''). As shown, a detent opening of one cartridge receptacle may be of one length det(l') that is different from a detent opening length det(l") of the other cartridge receptacle. In some embodiments, these openings are configured to receive correspondingly sized lugs and detents (e.g., of coinciding lengths) located on corresponding cartridge connectors (as shown in, for example, FIG. 9B).

As shown in FIG. 1J, the detent and lug openings of two different medicament receptacles P1100, P1110 may have corresponding positions. For example, the detent openings P1103, P1113 for both inlets P1100', P1110" are located at 12 o'clock positions of the receptacles P1100, P1110, the first lug openings P1101, P1111 are at 9 o'clock, and the second lug openings P1102, P1112 are at 3 o'clock. In some variants, the lugs and detents are not in corresponding positions or only a portion of the lugs and detents are in corresponding positions. In some embodiments, even where lug openings and detent openings are in corresponding positions on separate inlets (or separate connectors), the attachment of an incorrect cartridge connector can be prevented and/or substantially hindered by providing different sizes of those equivalently positioned features. It has been found that that by providing a feature on a first receptacle (e.g., a lug opening, a detent opening, a lug, a detent, etc.) that is has a size difference of at least 15% (e.g., is 15% larger or smaller) than an equivalent feature on a second receptacle (e.g., a feature that is in the same relative position), mischanneling can be prevented and/or substantially inhibited. In certain implementations, the ratio of the length of a feature of one receptacle as compared to the length of an equivalent feature on a different receptacle is equal to or at least about: 3:1, 5:2, 2:1, 5:3, 4:3, 20:17, or ranges spanning and/or including the aforementioned ratios.

Figure 3A:
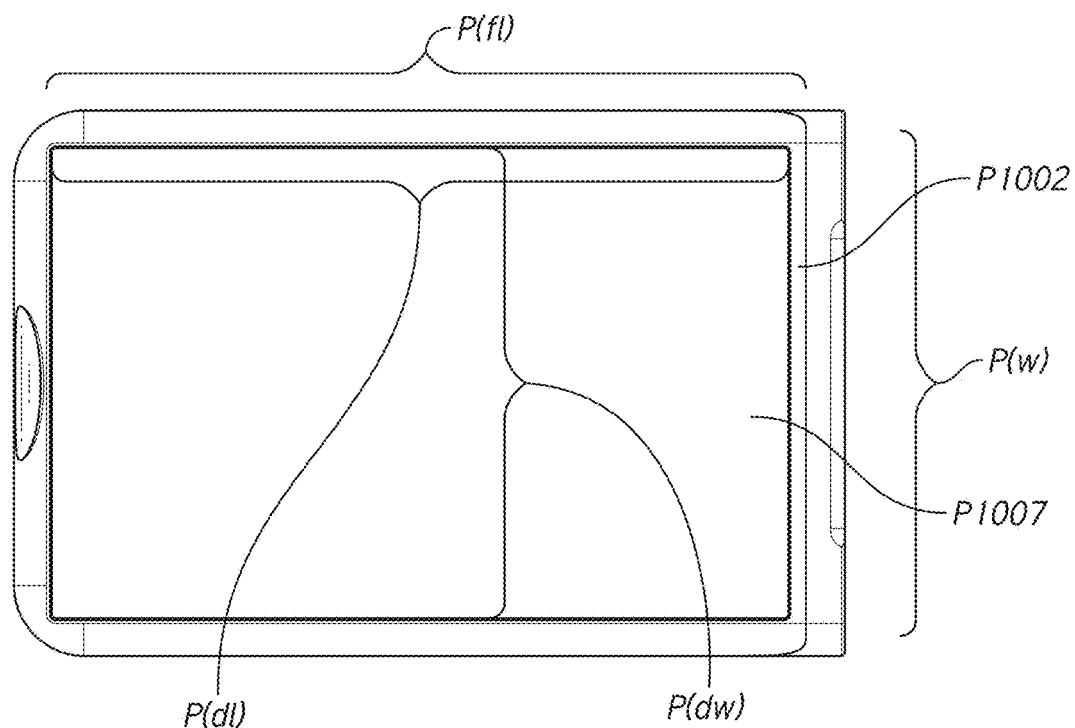
FIG. 3A shows a top view of the embodiment of FIG. 1A.
Figure 3B:
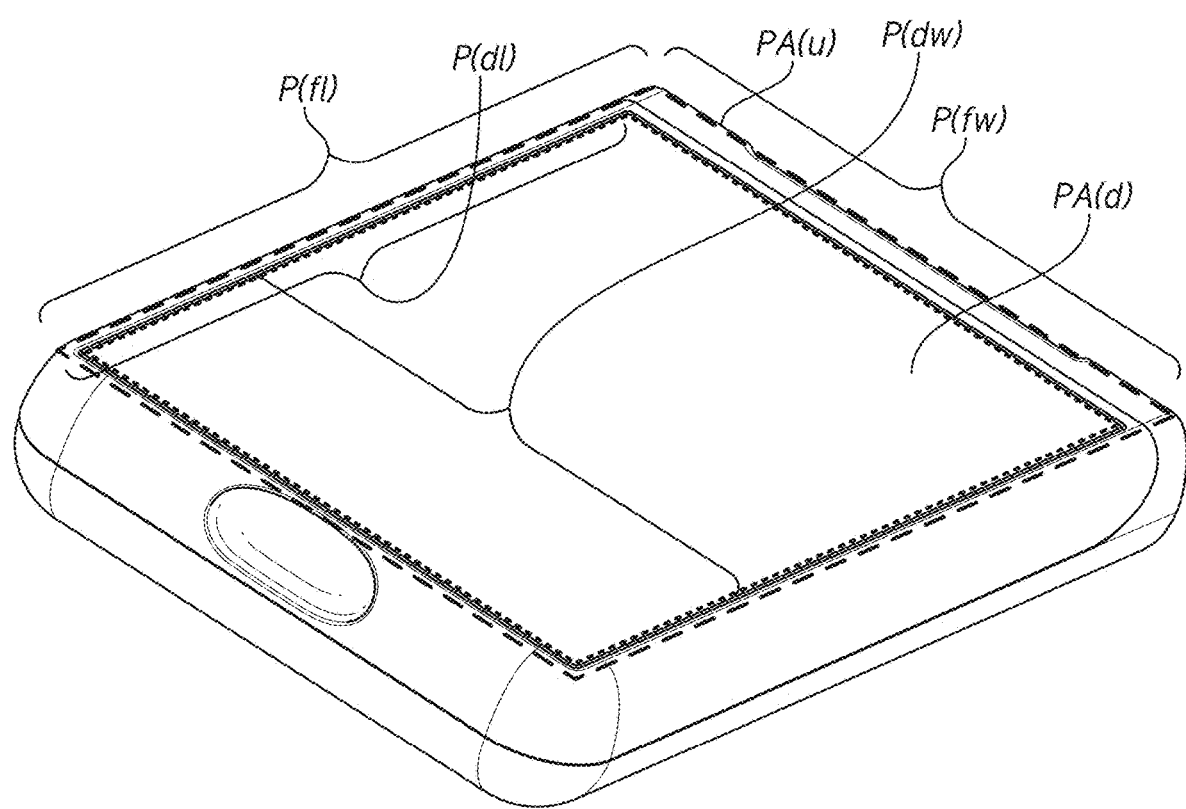
FIG. 3B shows a perspective view of the embodiment of FIG. 1A.
Figure 3C:
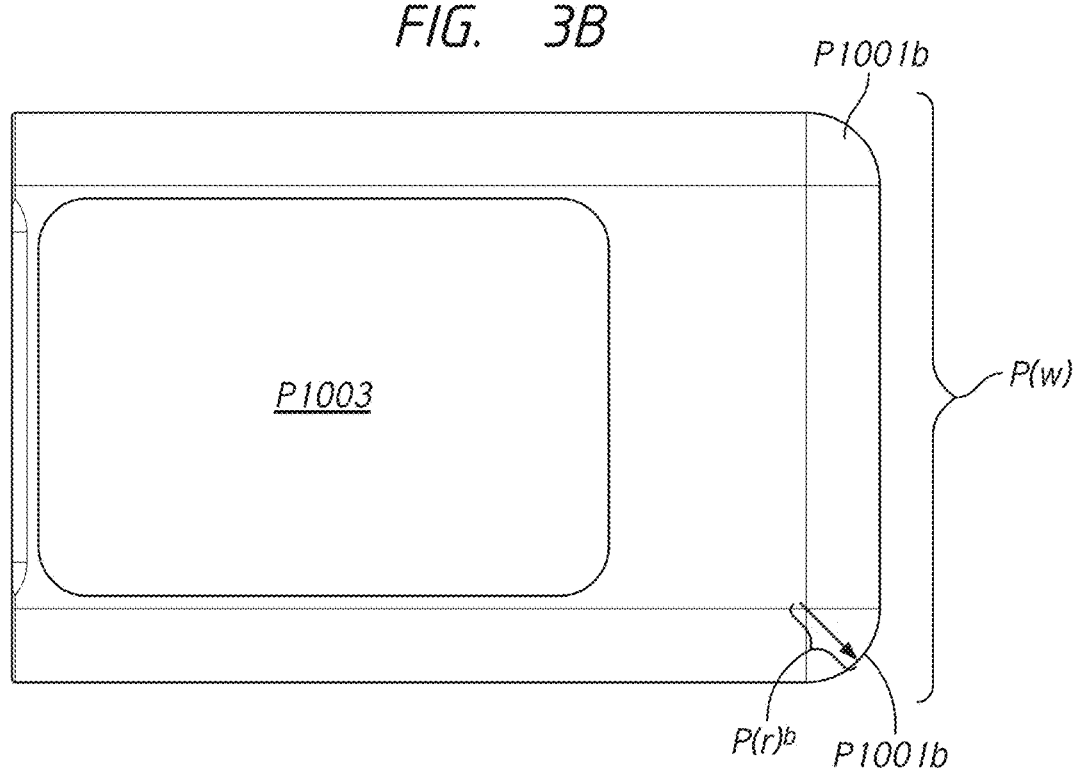
FIG. 3C shows a bottom view of the embodiment of FIG. 1A.
Figure 3D:
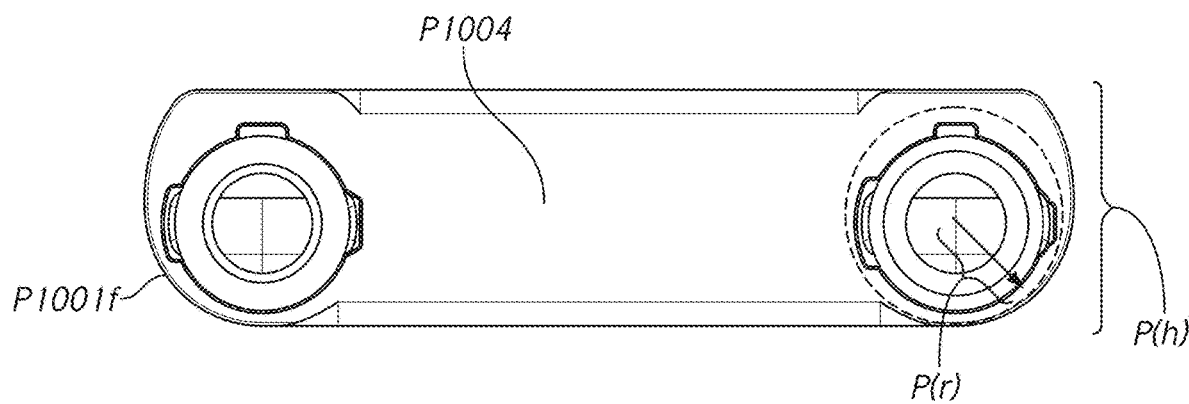
FIG. 3D shows a view of the upper side surface of the embodiment of FIG. 1A.

In certain embodiments, as shown in FIGS. 3D and 9B, one or more recognition features (e.g., lugs, detents, openings configured to receive lugs or detents, etc.) may be distributed around the periphery of the inlets P1100', P1110" or cartridge connectors C1001, C1101. For example, as shown in FIG. 1J, the mid-point of one recognition feature may be positioned at the 9 o'clock position and an adjacent recognition feature may have a midpoint at 12 o'clock, thereby being separated by 90°. In some embodiments, adjacent recognition features of the inlets P1100', P1110" or connectors C1001, C1101 may be separated by values independently selected from equal to or less than about: 180°, 160°, 140°, 120°, 100°, 90°, 80°, 70°, 60°, 50°, 40°, 30°, 20°, 10°, values between the aforementioned values or otherwise. As shown in FIGS. 1J and 9B, in some embodiments, non-adjacent recognition features of the inlets P1100', P1110" or connectors C1001, C1101 may be separated by values independently selected from equal to or less than about: 180°, 160°, 140°, 120°, 100°, 90°, 80°, 70°, 60°, 50°, 40°, 30°, 20°, 10°, values between the aforementioned values or otherwise.

It should be understood that, for any divot, any dimension of that divot, position of that divot, or relationship of that divot to another divot (e.g., a second divot) described herein also applies to protrusions or to relationships between protrusions. For brevity, such relationships have been shortened or omitted, as they will be readily appreciated in view of the disclosure. Likewise, as disclosed elsewhere herein, any recognition feature (e.g., notch, protrusion, etc.) described with respect to a cartridge receptacle applies to recognition features of cartridge connectors.

As shown in FIGS. 1D-1I, in some embodiments, divots (e.g., notches, protrusion shaped openings, etc.) may open to tracks P1101', P1103', P1111', P1113' (e.g., slots, paths, etc.). In some embodiments, these paths travel and/or are positioned circumferentially within the medicament receptacles P1100, P1110. In certain variants, once a cartridge connector is inserted into the pump chamber opening, the connector is rotated to lock the cartridge connector into the receptacle. For example, in the embodiment shown in FIGS. 1A-1J, the connectors may each be rotated a quarter turn to lock them each into place within the pump chambers. As shown, in some embodiments, a lug of the cartridge connector in initially inserted though the lug opening P1101 and then is rotated a quarter turn to a position it under the other detent opening P1102 of the pump chamber P1100. The lug travels along the lug path to its locked position. In other embodiments, a larger lug can be positioned under the opening for a smaller lug. In some embodiments, alignment of the lug under the smaller detent or smaller lug opening inhibits removal of the cartridge connector from the pump chamber once locked since the larger lug cannot pass through the smaller detent or lug opening. As noted above, where the receptacle inlet comprises protrusions (not shown), coinciding divots and tracks are located on a corresponding cartridge connector.

As would be appreciated from FIGS. 1E-1J, where different medicaments are used, the cartridge connectors may be configured to require a clockwise turn to lock one cartridge connector (and cartridge) in place in its corresponding receptacle and a counterclockwise turn to lock the other cartridge connector (and cartridge) in place in its corresponding receptacle. Thus, the direction of twisting is another optional indicator that allows a user to avoid mischanneling. In another embodiment, not shown, the cartridge connectors and cartridge receptacles may be configured to both allow clockwise turning to lock the cartridges in place. In another embodiment, not shown, the cartridge connectors and cartridge receptacles may be configured to both allow counterclockwise turning to lock the cartridges in place.

In some embodiments, as shown in FIGS. 1G and 1H, the cartridge receptacles P1100, P1110 may include a first "shallow" detent cam P1103', P1113' that comprises a smaller transition angle than a second "step" detent cam P1103", P1113" that comprises a larger transition angle. In some embodiments, as the cartridge connector (and corresponding detent lug) is inserted into the opening of the corresponding pump chamber, the cartridge connector is rotated in a first direction to lock the connector into the pump chamber. In some embodiments, while the connector is rotated within the receptacle, the detent may abut against and then travel over the first "shallow" detent cam until the detent reaches a transition P1103''', P1113'''. As rotation continues, the detent travels over the transition P1103''', P1113''' and passed the second steep detent cam P1103", P1113" reaching a detent clearance configured to receive the detent. At the same time, the lugs reach the end of their tracks, stopping or impeding further twisting of the cartridge connector. The detent clearance may be bordered on one side by the second "steep" detent cam P1103", P1113", which would require a greater rotating force in an opposite direction to permit the detent to overcome the second cam and to remove the detent from the clearance. In some embodiments, therefore, the combination of the different detent cams causes cartridge connector to require a greater amount of force to remove and/or unlock the cartridge connector from the pump chamber once it is locked into the pump than the initial amount of force that is required to lock the cartridge connector to the pump chamber. In certain implementations, the ratio of the angle of a steep cam as compared to angle of the shallow cam is equal to or at least about: 5:1, 3:1, 5:2, 2:1, 5:3, 4:3, or ranges spanning and/or including the aforementioned ratios. In other embodiments, the steep and shallow cam can be configured to lock lugs in position (instead of or in addition to the detents). As noted above, where the receptacle inlet comprises protrusions (not shown), coinciding cams and tracks are located on a corresponding cartridge connector.

In some embodiments, as shown in FIGS. 1F and 1G, the receptacles P1100, P1110 may comprise one or more snap-arm clearance recesses P1105a, P1105b, P1115a, P1115b (e.g., snap-arm extension recesses). In some embodiments, the snap-arm clearance recesses extend down (e.g., axially) a portion of one or more of the medicament receptacles. In some embodiments, these recesses are configured to allow and/or to provide space for the expansion of snap arms C1105a, C1105b, C1115a, C1115b (shown in FIG. 9D) on cartridge connectors C1001, C1101 to engage medicament cartridges that reside in the cartridge receptacles P1100, P1110. In other words, in some embodiments, as disclosed elsewhere herein, in order to secure a medicament cartridge in the pump, one or more cartridges are first placed in the pump via a pump receptacle P1100, P1110. In some embodiments, as disclosed elsewhere herein, the cartridge connectors can then be inserted into the receptacles. As an appropriate cartridge connector receives a corresponding cartridge via the cartridge connector shroud, the snap arms expand as the snap arm passes over the periphery of the medicament cartridge cap. The snap arm recess allows this expansion for an appropriately placed connector and/or cartridge. Once the cap is past the snap arm, the snap-arm snaps back into place where lip (e.g., tooth, edge, steps, or other cap locking mechanism) engages the medicament cartridge cap. Without the snap-arm clearance, the snap-arms are unable to expand over the cap of the cartridge, preventing and/or hindering the connection of an inappropriate medicament.

In certain variations, as noted elsewhere herein, the receptacles themselves may be different shapes or sizes such that they accept one type of medicament cartridge, but not another. For example, the chambers may have different diameters, shapes, or lengths such that one medicament may be received and or engaged, but not another. In some embodiments, for example, as shown in FIG. 2D, the chamber diameters may be different. As disclosed elsewhere herein, the glucagon chamber may have a lip that transitions it from one diameter to another smaller diameter traveling distally from the inlet. In such an embodiment, an insulin cartridge may not be insertable into glucagon chamber. In some embodiments, the glucagon cartridge (which is smaller diameter) can go into the insulin chamber. In some embodiments, however, a stop rib in the bottom of the chamber prevents full insertion of the glucagon cartridge. It will be appreciated that, likewise, the glucagon cartridge may be larger than the insulin chamber to achieve the opposite effect. In some embodiments, the glucagon cartridge includes an insertion stop rib. In some embodiments, the stop rib prevents the glucagon cartridge from seating low enough to allow the connection within the insulin chamber. In other embodiments, the cartridges are the same diameter and other aspects disclosed herein may be implemented to avoid mischanneling.

Pump Housing Configuration

In certain variants, as shown in FIGS. 2D-2I, the cartridge receptacles P1100, P1110 are laterally spaced apart within the housing P1001. As indicated elsewhere herein, in some embodiments, where the pump is configured to delivery different medicaments (as shown in FIGS. 1A-2I), each medicament cartridge receptacle (and/or an inlet thereof) can be different depending on the medicament it is configured to receive. Each different receptacle may be configured to receive only a specified medicament cartridge and/or cartridge connector and not another, incorrect medicament cartridge and/or cartridge connector. Alternatively, in a pump configured receive multiple medicament cartridges having the same medicament (not shown), that pump may have medicament receptacles that are identical or substantially identical (though located at different positions within the pump housing).

In some embodiments, as noted elsewhere herein, cross-channeling is avoided by providing design features and/or mating connectors or adapters on certain components of the infusion system. For instance, in some embodiments, the infusion system comprises an infusion pump with one, two, or more infusion chambers (or pump chambers). In some variants, the system further comprises cartridges filled with different medicaments, and cartridge connectors and tubing that connect to the cartridge to the infusion pump in such a way as to prevent mischanneling or cross-channeling of medicaments. In certain variants, for example, each type of cartridge for each type of medicament has one or more unique differentiating features (either as an integral part of the cartridge or as a component attached or affixed to the cartridge), for example geometric or shape-based features (e.g., protrusions, detents, tabs, apertures, feature receptacles, slots, etc.), that allow for unique coupling with a type of connector that itself has unique differentiating features (e.g., apertures, feature receptacles, slots, protrusions, detents, tabs, etc.) that engage corresponding features in the pump housing and allow for insertion of the proper cartridge into the proper pump chamber within the infusion pump. In certain embodiments, each type of cartridge for each type of medicament has one or more unique differentiating features (either as an integral part of the cartridge or as a component attached or affixed to the cartridge), for example geometric or shape-based features (e.g., protrusions, detents, tabs, apertures, feature receptacles, slots, etc.), that allow for unique coupling with a cartridge receptacle that has unique differentiating features (e.g., apertures, feature receptacles, slots, protrusions, detents, tabs, etc.)

As noted elsewhere herein, an improved infusion system comprising an infusion pump P1000 for multiple medicaments and multiple connectors ensures, helps to ensure, and/or substantially aids in providing proper channeling of each medicament to the patient. In other words, where multiple medicaments are supplied by the infusion systems, the features and/or components described herein are configured to prevent, minimize the occurrence of, or otherwise inhibit the opportunity for a user to inadvertently place a medicament in the incorrect cartridges or to place a cartridge in the incorrect pump chamber. In some embodiments, alternatively, where more than one cartridge is present, both cartridges may comprise a single medicament (e.g., insulin).

Figure 2A:
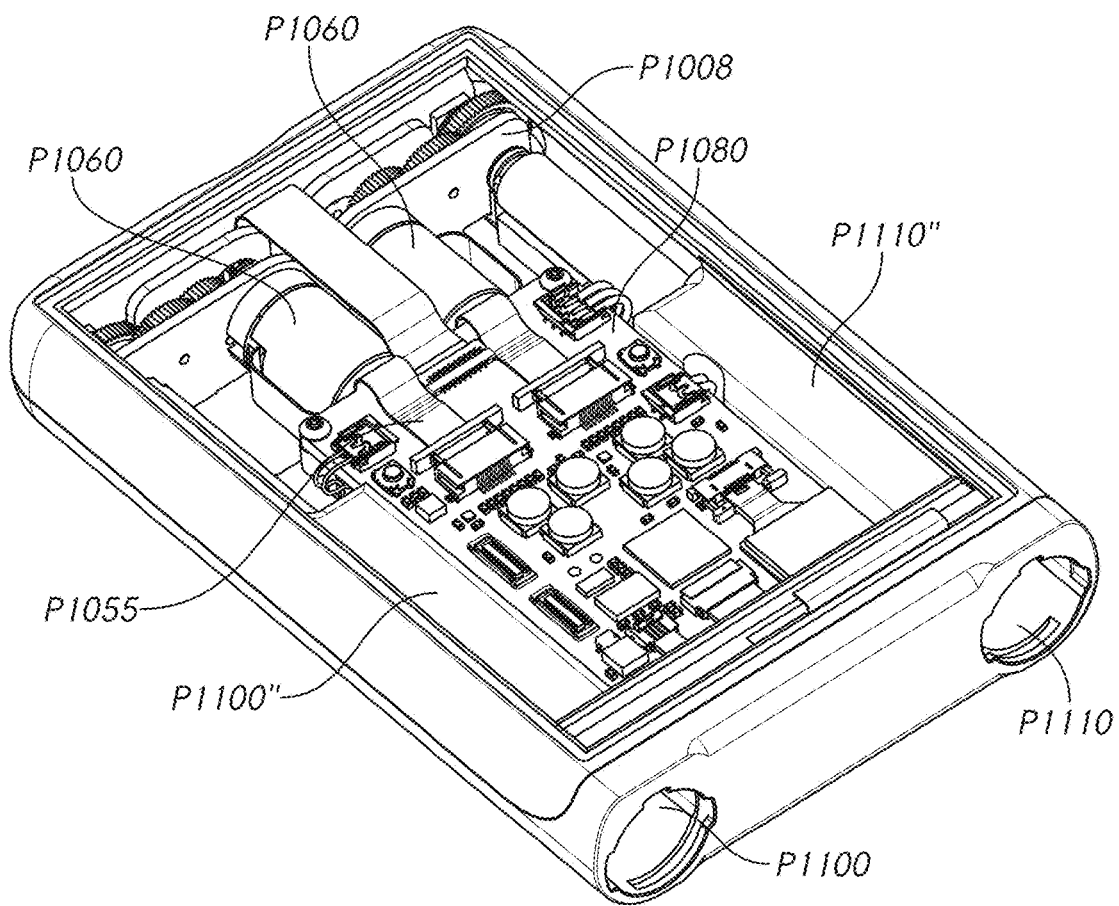
FIGS. 2A-2C show a views of the embodiment of FIG. 1A with its display screen and/or other portions of the pump face and housing removed, revealing various internal components of the pump.
Figure 2B:
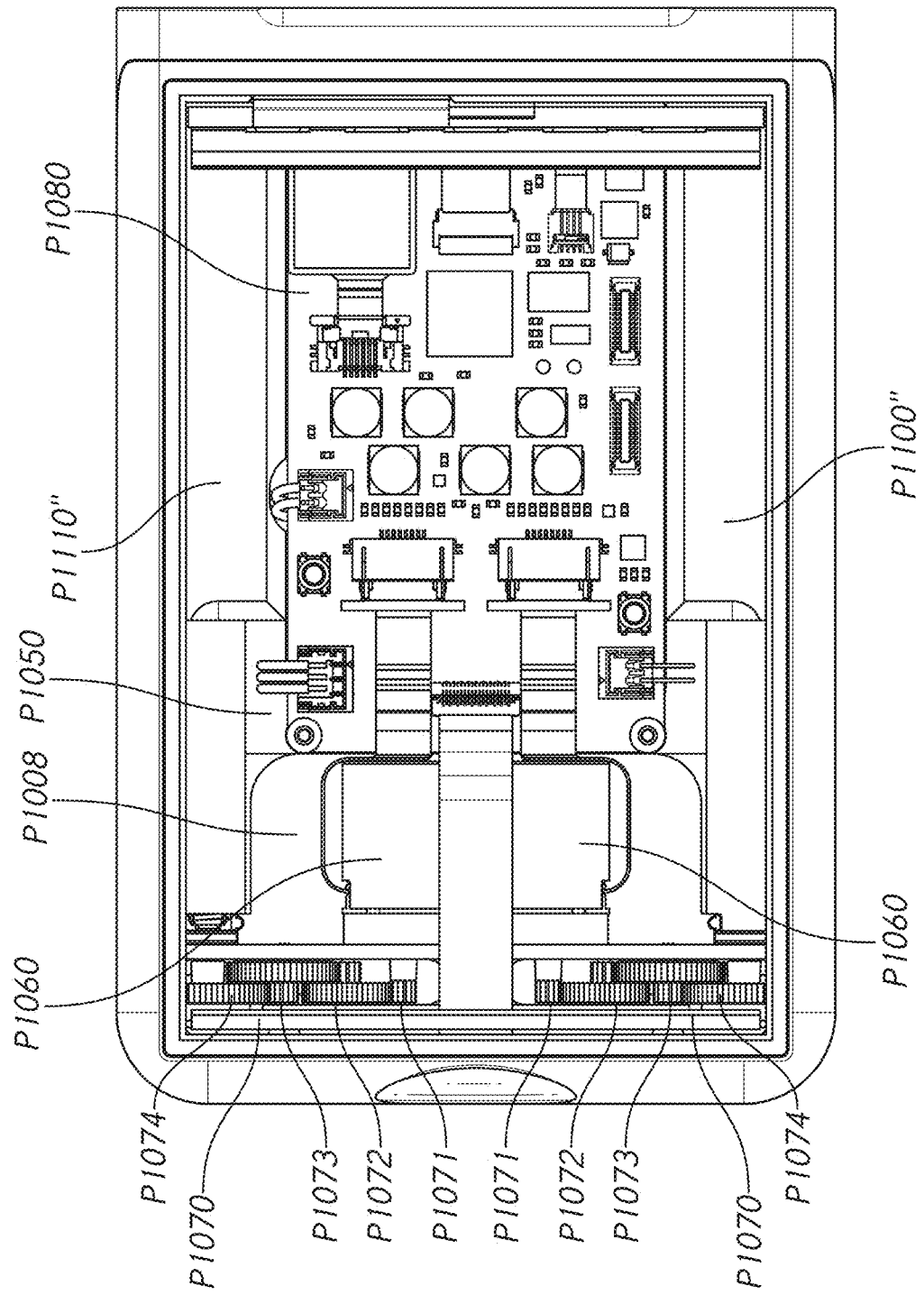
Figure 2C:
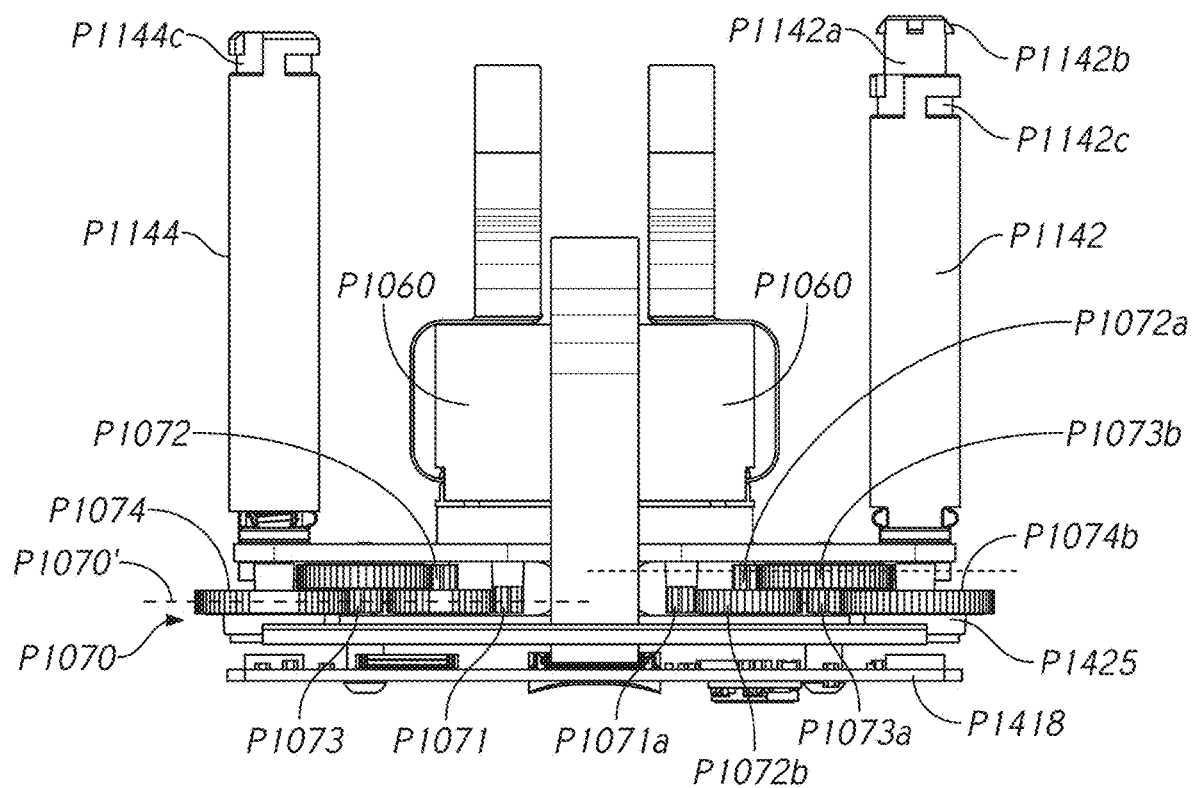
Figure 2D:
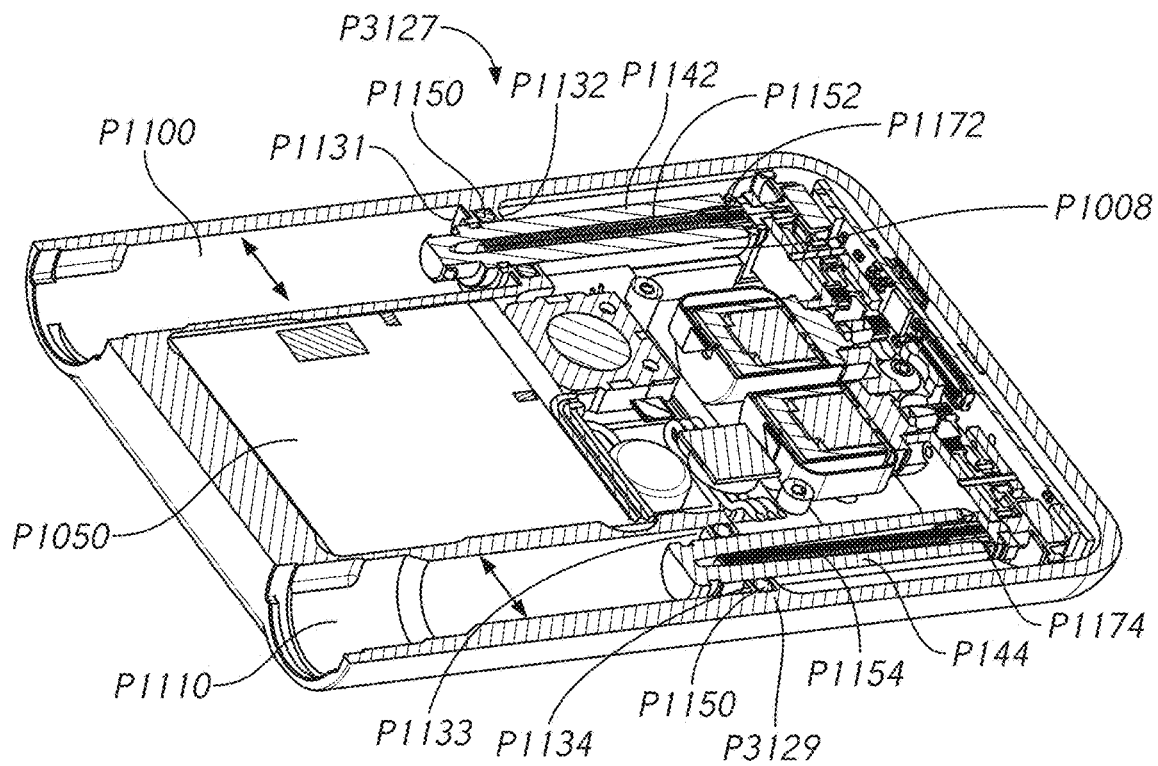
FIG. 2D shows a view of the embodiment of FIG. 1A bisected in a plane along the length and width of the pump.
Figure 2E:
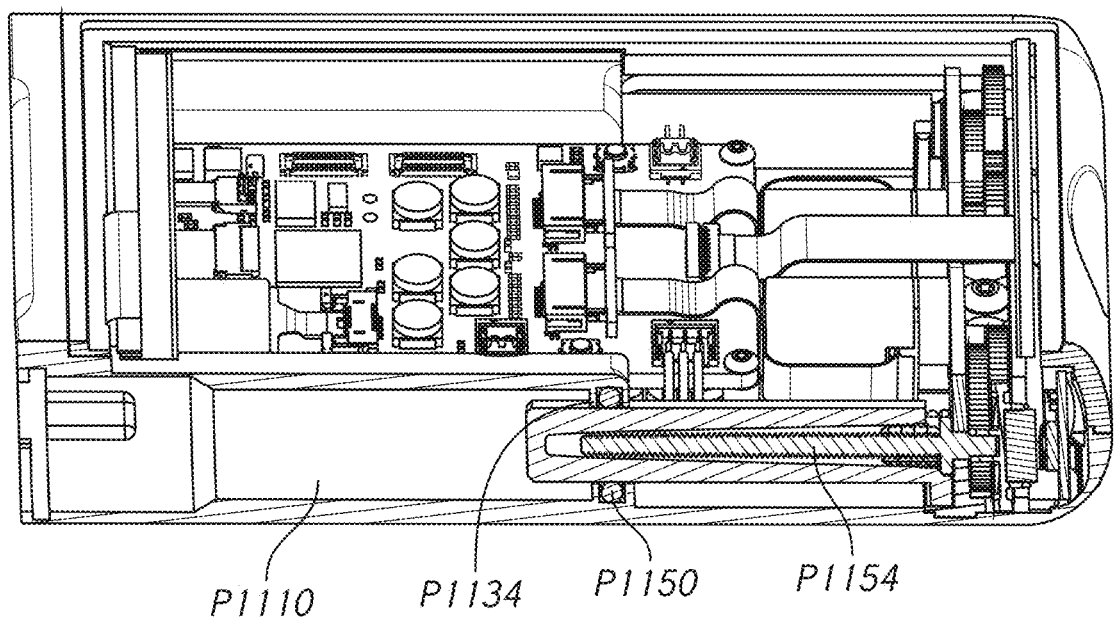
FIGS. 2E and 2F show cross-sectional views of the embodiment of FIG. 1A in planes along the length and height of the pump, cutting the first cartridge receptacle and the second cartridge receptacle, respectively.
Figure 2F:
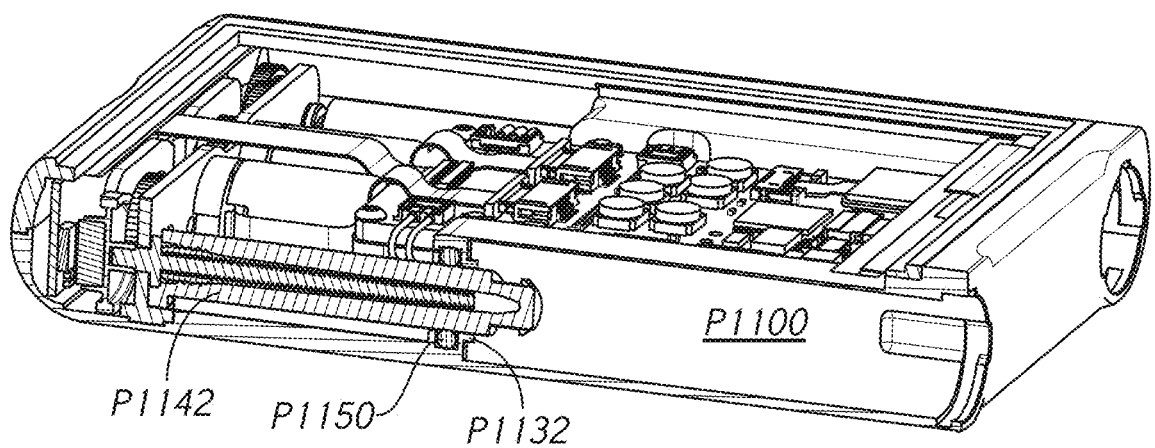
Figure 2G:
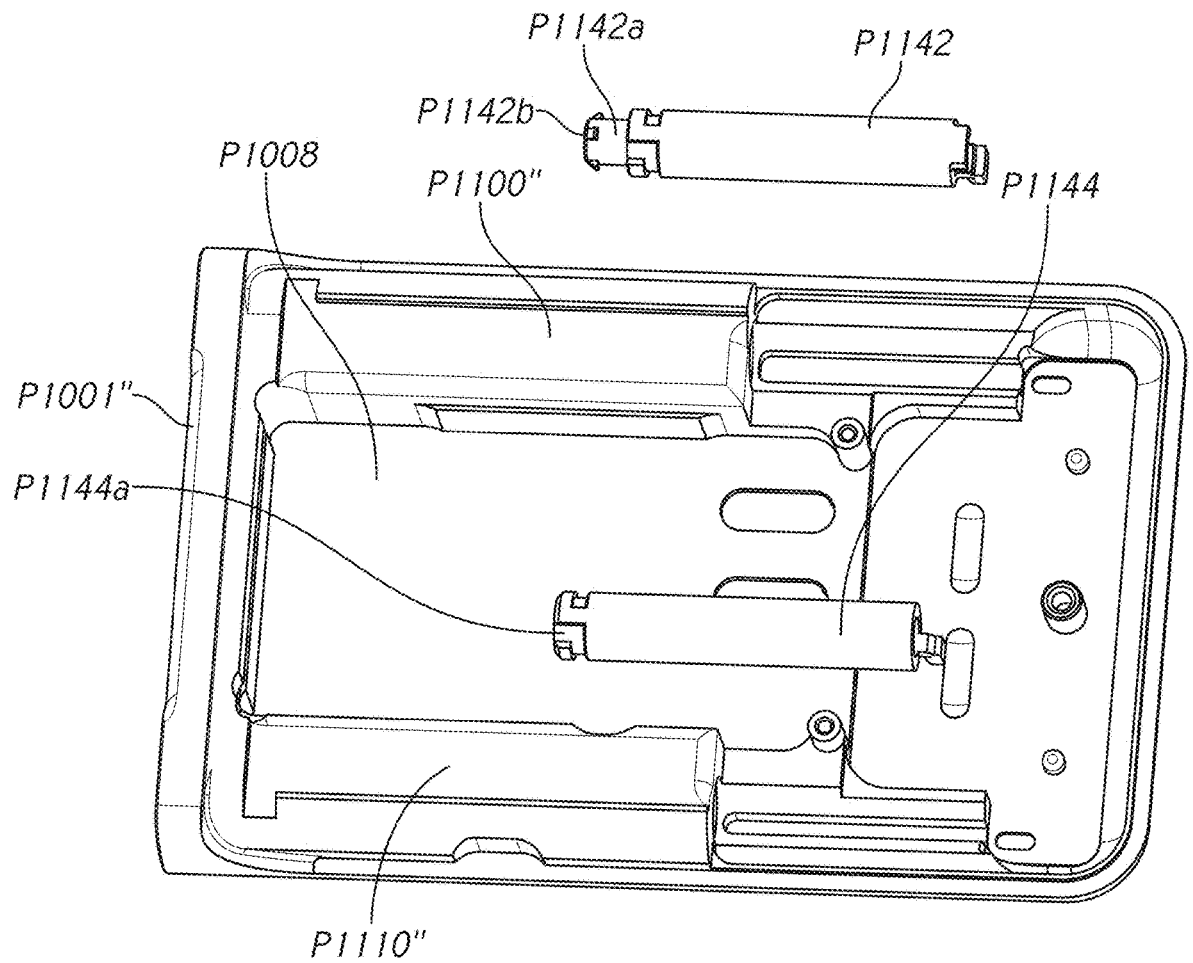
FIGS. 2G and 2H show partially exploded views of the embodiment of FIG. 1A with the display and bezel removed.
Figure 2H:
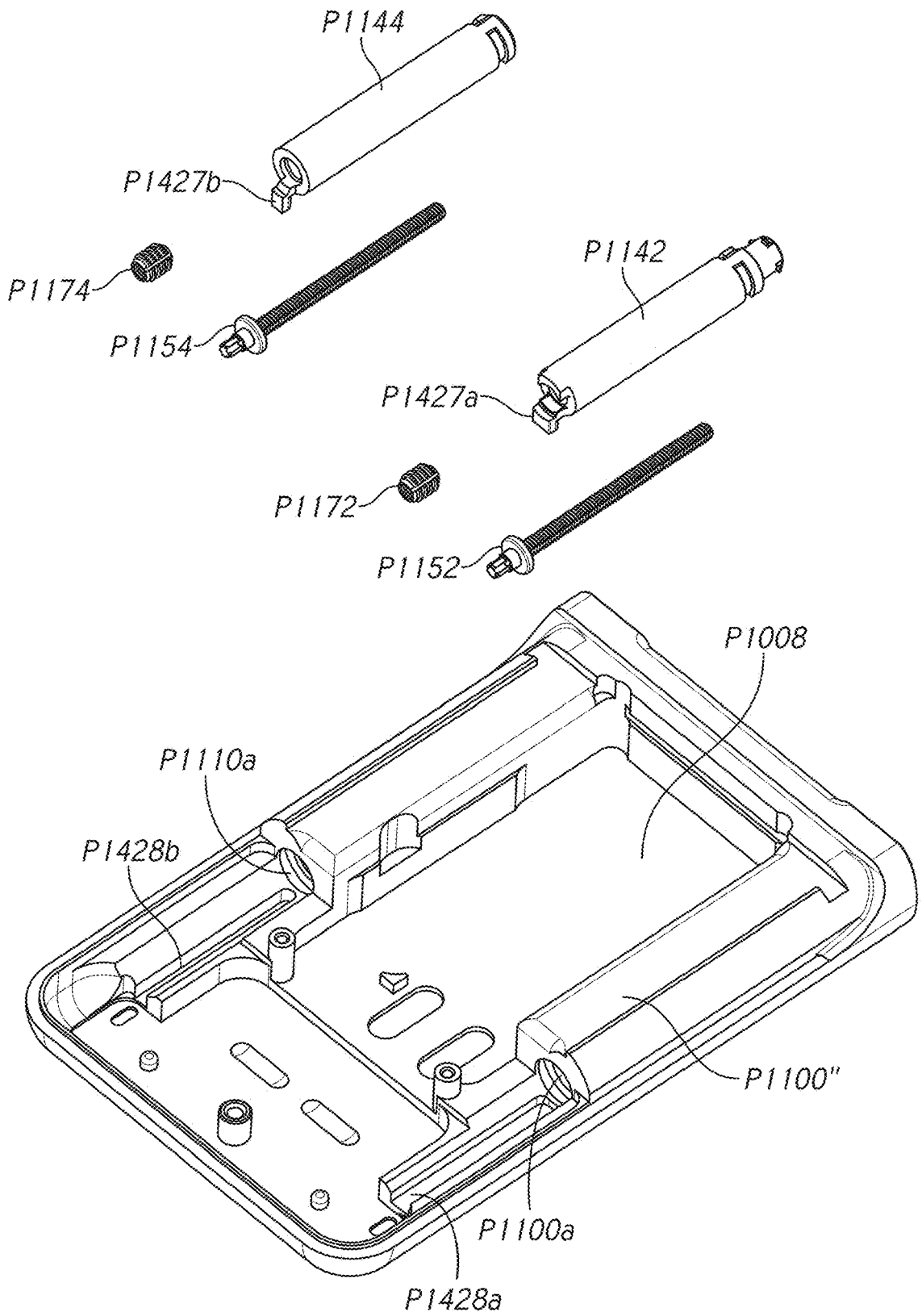
Figure 2I:
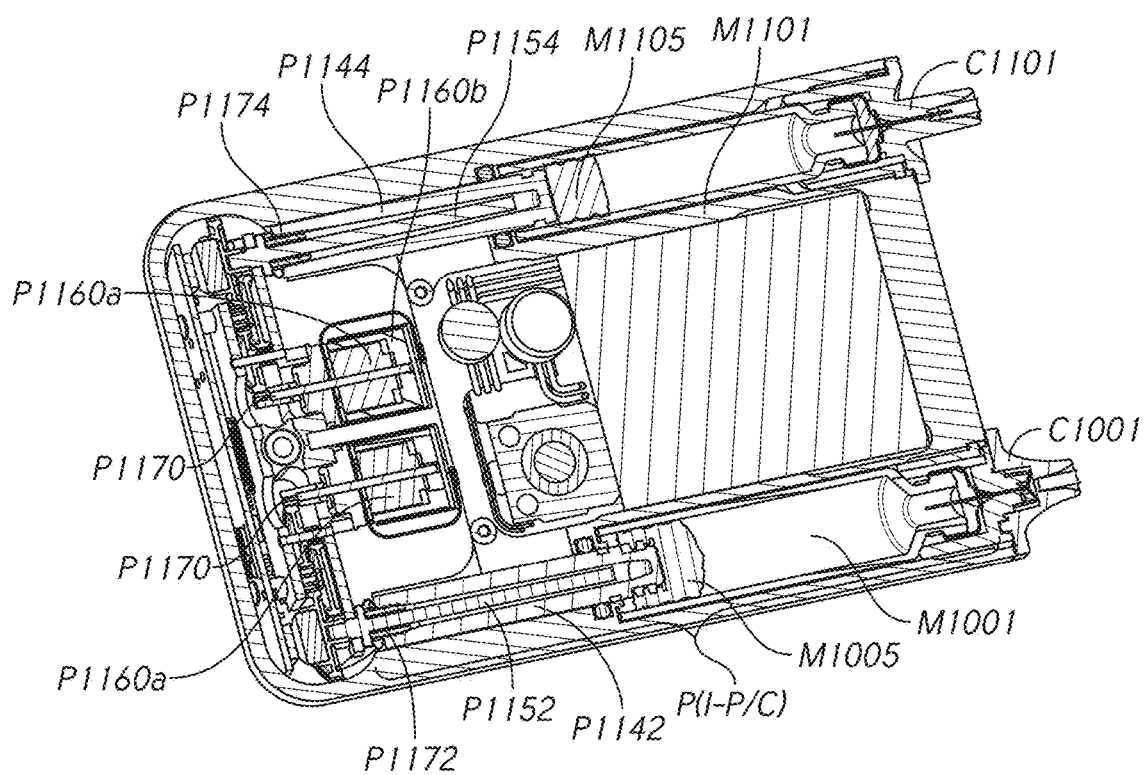
FIG. 2I shows a view of the embodiment of FIG. 1A bisected in a plane along the length and width of the pump. In this view, a medicament cartridge set and a cartridge connector set are present and/or engaged to the pump.

In some embodiments, as shown in FIGS. 2A-2I, a PCB P1080 (e.g., a primary PCB) may be located at a position within the pump housing P1001 and between the cartridge receptacles P1100, P1110. The pump P1001 has an internal area P1008 shown in FIG. 2A. As shown in FIG. 2A, the pump chambers are isolated from the internal area at least in part by chamber walls P1100", P1110". In some embodiments, a power source P1050 may be located at a position within the pump housing P1001 and between the cartridge receptacles P1100, P1110 (as shown in FIGS. 2B and 2D). In certain variants, the power source P1050 is an inductively chargeable battery, which may be located at a position below the PCB (as shown in FIGS. 2B and 2D). In some embodiments, the pump 1000 comprises an inductive charging pad P1003' (shown in FIG. 1E) configured to allow charging of the inductively chargeable battery P1050. In certain variants, as disclosed elsewhere herein, the infusion pump configuration is low profile to facilitate transport of the infusion pump in a pocket, on a belt, or under clothing. As shown in, for example, FIG. 2A, flex cables P1055 provide input to the motors P1060 of the infusion pump P1000. In some embodiments, the motors P1060 move a drive gear P1071 (e.g., a pinion gear) in a gear assembly comprising four gear components P1071, P1072, P1073, P1074 and facilitate movement of a lead screw P1152, P1154. The drive access of the motor and the lead screws are each configured to be parallel to each other and in the same axis as the reservoirs. In certain implementations, this configuration gives the infusion pump a compact design.

FIG. 2D provides a cross-sectional view of the pump cut through its height by a plane running along the length and width of the pump. In some embodiments, as shown in FIG. 2D, the first medicament receptacle P1100 may have a substantially equal internal diameter from the inlet port P1100' to the end of the bore. Also as shown in FIG. 2D, in some embodiments, the second medicament receptacle P1110 may have a lip or transition where the receptacle transitions from a first internal diameter to a second smaller internal diameter. In some embodiments, the second smaller internal diameter of the second receptacle P1110 is configured to receive the first medicament vial, but not the second. In some embodiments, the first medicament receptacle may be configured to receive either the first or the second medicament vial. In some embodiments, the smaller internal diameter is a diameter that is smaller than that of a medicament vial that is not configured to be distributed from the second medicament receptacle.

FIG. 2E shows a cross-sectional view with a cut through the second cartridge receptacle P1110 (where the bezel and display have been removed). FIG. 2F shows a cross-sectional view with a cut through the first cartridge receptacle P1100 (where the bezel and display have been removed). FIG. 2I provides another cross-sectional view of the pump cut through its height by a plane running along the length and width of the pump, this time with the cartridges M1001, M1101 and cartridge connectors C1001, C1101 engaged.

Figure 4A:
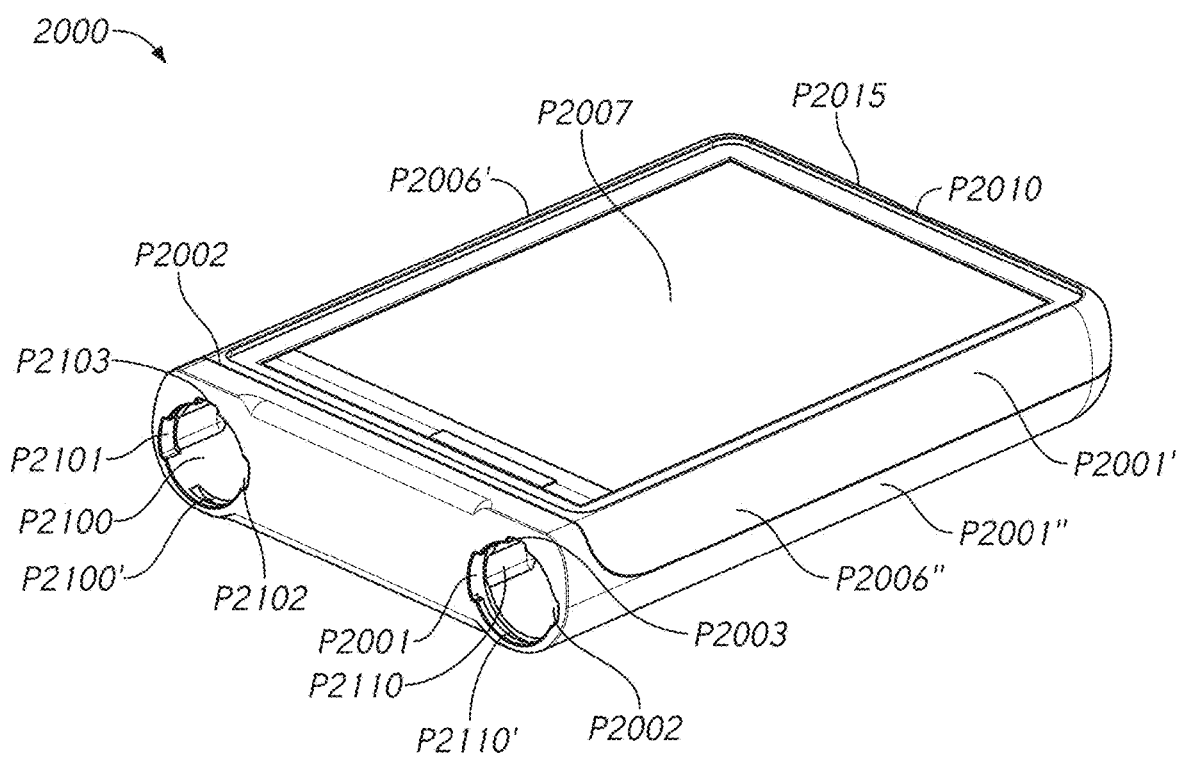
FIG. 4A illustrates a perspective view of another embodiment of a pump, showing the upper side surface of the pump.

FIG. 4A shows another embodiment of a pump P2000. Though for brevity not all of the features of the pump embodiment of FIG. 4A may be mentioned, pump 2000 may have each feature described with respect to the embodiment of FIG. 1A, except where such a feature is explicitly distinguished. Additionally, it should be recognized that, throughout this disclosure, similar and/or identical features for separate embodiments of a device or system component (e.g., pump, connectors, etc.), though not described for each different embodiment, are merely offset numerically by a factor of 1000 in the drawings (though they share hundreds, tens, and ones numerical values). For example, features of the receptacle inlet ports P2100', P2110' of the pump P2000 of FIG. 4A may be common to those of the receptacle inlet ports P1100', P1110' of the pump P1000 of FIG. 1A, though the features either of these inlet ports may not be detailed specifically where they are redundant of descriptions elsewhere in this disclosure. For the sake of convenience, certain features present or annotated with reference numerals in some figures and embodiments are not shown or annotated with reference numerals in other figures and embodiments. Unless the context clearly requires otherwise, these omissions should not be interpreted to mean that features omitted from the drawings of one figure could not be equally incorporated or implemented in the configurations of the disclosed methods, apparatus and systems related to or embodied in other figures. Conversely, unless the context clearly requires otherwise, it should not be assumed that the presence of certain features in some figures of the present disclosure means that the disclosed methods, apparatus and systems related to or embodied in such figures must necessarily include these features.

Figure 4B:
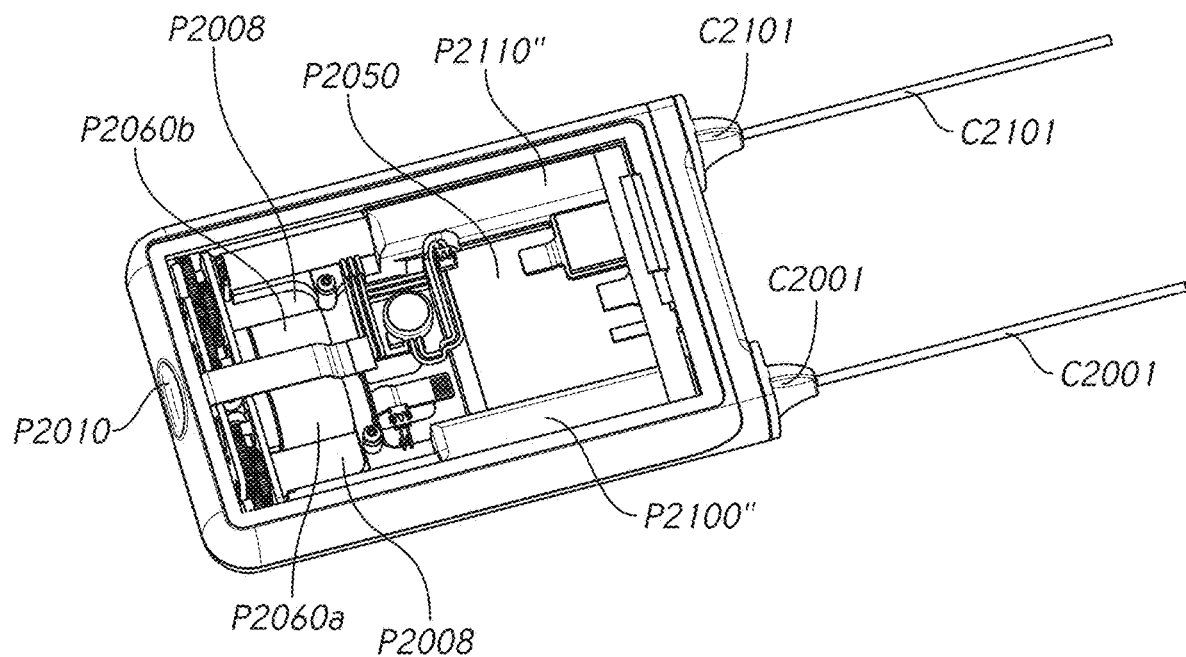
FIG. 4B illustrates a perspective view of the embodiment of 4A with the display removed.
Figure 4C:
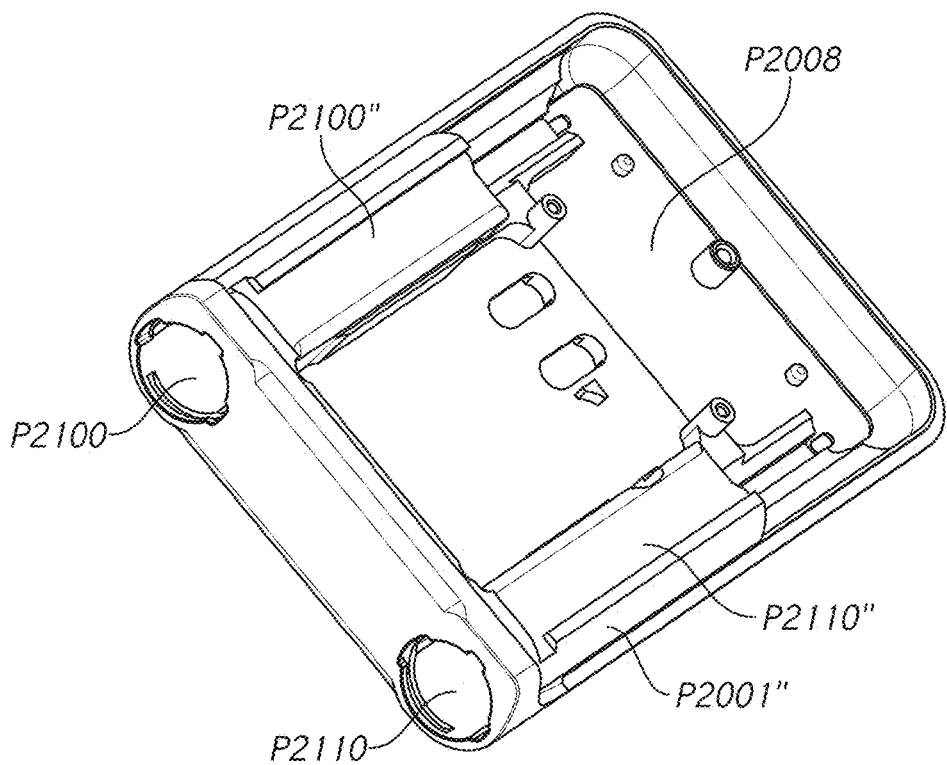
FIG. 4C illustrates a perspective view of the lower portion of the housing of the embodiment of 4A.
Figure 4D:
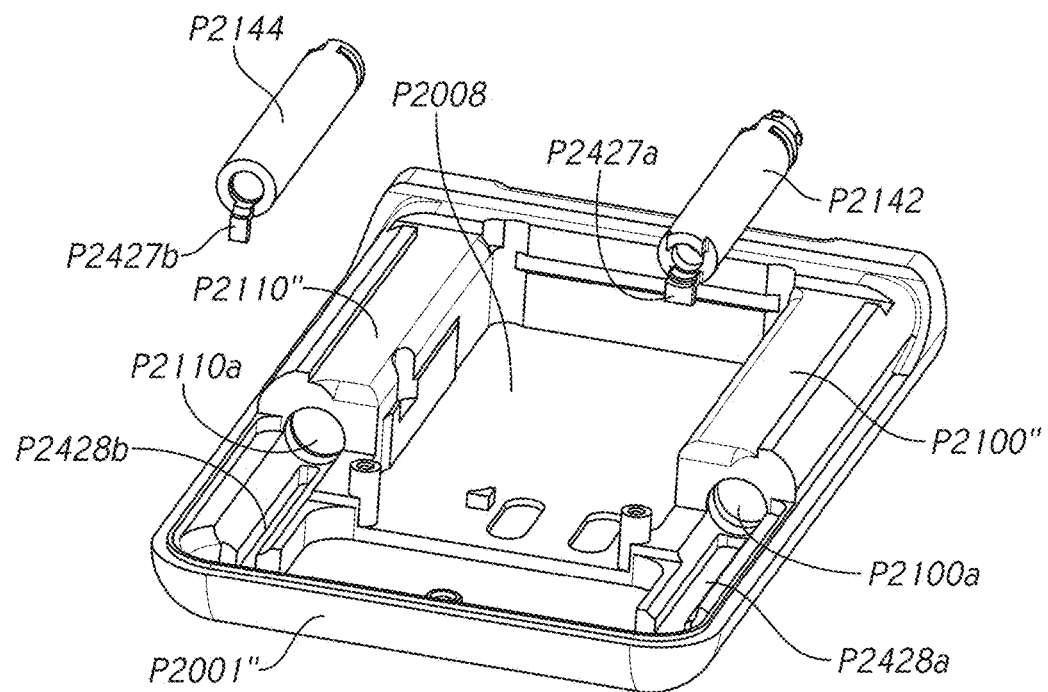
FIG. 4D illustrates a partially exploded perspective view of the lower portion of the housing and the drive nuts of the embodiment of 4A.
Figure 4E:
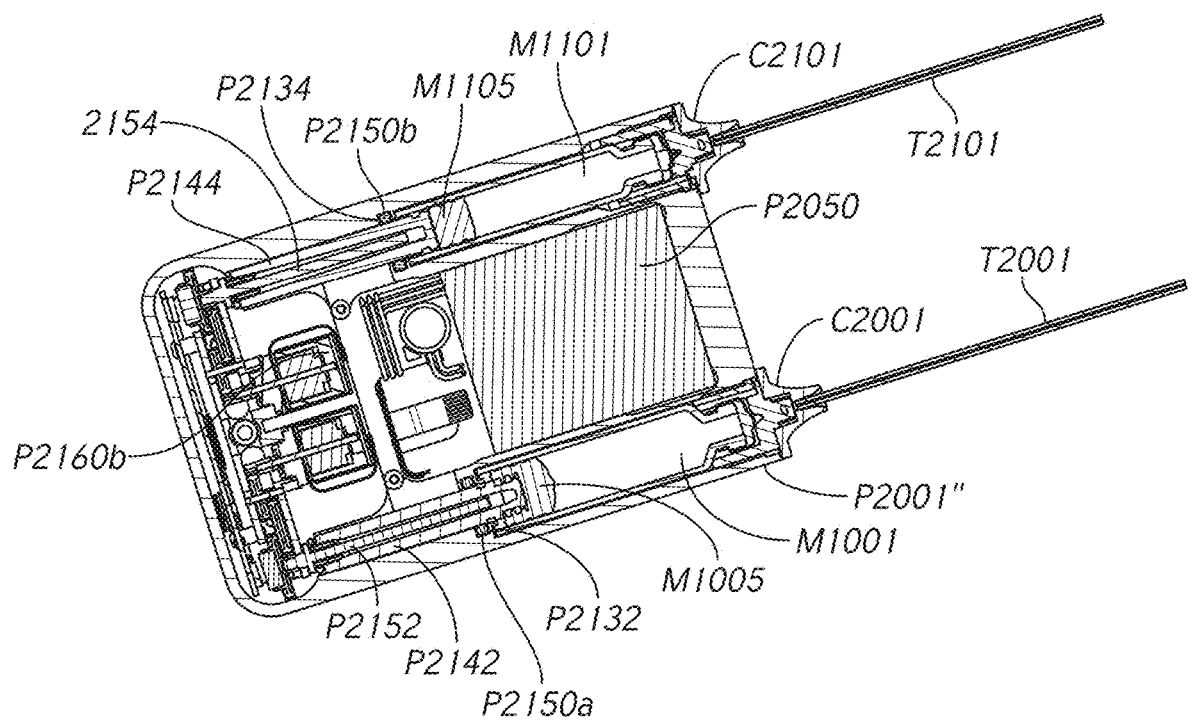
FIG. 4E shows a view of the embodiment of FIG. 4A bisected in a plane along the length and width of the pump. In this view, a medicament cartridge set and a cartridge connector set are present and/or engaged to the pump (along with coinciding fluid conduits).

FIG. 4B illustrates a perspective view of the embodiment of 4A with the display removed. FIG. 4C illustrates a perspective view of the lower portion of the housing of the embodiment of 4A. FIG. 4D illustrates a perspective view of the lower portion of the housing and drive nuts (e.g., piston shafts, etc.) of the embodiment of 4A. FIG. 4E shows the pump P2000 of FIG. 4A bisected through the height of the pump 2000. As shown, the pump 2000 is engaged to a connector set C2001, C2101 via the first and second cartridge receptacle inlets P2100', P2110', respectively. Also as shown, a first and second fluid conduit T2001, T2101 are engaged to the first and second cartridge connectors C2001, C2101, respectively.

As shown in FIGS. 2D-2I and 4E, in some embodiments, O-rings P1150a, P1150b, P2150a, P2150b are placed within saddles P1132, P1134, P2132, P2134. In several variants, as disclosed elsewhere herein, these O-rings provide a water resistant and/or waterproof barrier between the pump chambers P1100, P1110, P2100, P2110 and the internal area P1008, P2008 of the pump. In some embodiments, the saddles are molded within the lower portion of the pump housing P1001", P2001" and/or are unitary portions of the lower portion of the housing. In several embodiments, the saddles are located at the bottom of the pump chambers P1100, P1110, P2100, P2110 and/or make up a portion of the bottom of the pump chambers. In several embodiments, the saddles P1032, P1034, P2032, P2034 provide a circumferentially, inwardly extending bottom of the pump chambers P1100, P1110, P2100, P2110. In some embodiments, the saddles P1132, P1134, P2132, P2134 are configured to engage and/or hold the O-rings P1150a, P1150b, P2150a, P2150b in place. In some embodiments, the O-rings P1150a, P1150b, P2150a, P2150b are configured to seal against and/or engage two drive nuts P1142, P1144, P2142, P2144 (e.g., piston shafts). In some embodiments, a fully retracted drive nut P1142, P1144, P2142, P2144 along with the circumferentially inwardly extending saddles P1132, P1134, P2132, P2134 of the pump provide a distal end of the pump P1000, P2000 against which medicament cartridges abut when placed inside the pump P1000, P2000 (as shown in FIGS. 2I and 4E).

As evident in FIGS. 2A, 2B, 2D, 2G, 2H, and 4B-4E, though the display is removed, when fully assembled, the pump chambers P1100, P1110, P2100, P2110 are isolated and/or separated from the internal area P1008, P2008 of the pump P1000, P2000 by chamber walls P1100", P1110", P2100", P2110", the saddles P1132, P1134, P2132, P2134, the O-rings P1150a, P1150b, P2150a, P2150b, and the drive nuts P1142, P1144, P2142, P2144. In some embodiments, as evident from FIGS. 2D-2I and 4B-4E, the drive nuts P1142, P1144, P2142, P2144, enter the pump receptacles P1100, P1110, P2100, P2110 via receptacle apertures P1100a, P1110a, P2100a, P2110a. In some embodiments, as disclosed elsewhere herein, the O-rings engage the drive nuts P1142, P1144, P2142, P2144 to prevent ingress of dirt, grime, water, and/or air into the pump internal area P1008, P2008 from the medicament cartridge receptacles P1100, P1110, P2100, P2110. In some embodiments, as disclosed elsewhere herein, the seal between the O-rings 1150a, P1150b, P2150a, P2150b and the drive nuts P1142, P1144, P2142, P2144 are airtight and/or watertight. In some embodiments, the seal between the O-rings 1150a, P1150b, P2150a, P2150b and the drive nuts P1142, P1144, P2142, P2144 seal the internal area of the pump from the pump chambers in an airtight and/or watertight manner.

In some embodiments, as shown in FIGS. 2D-2I and 4A-4E, the drive nuts P1142, P1144, P2142, P2144 engage with and/or interact with longitudinally extending and/or internally embedded lead screws P1152, P1154, P2152, P2154. In some embodiments, the lead screws P1152, P1153 threadedly engaged with threaded inserts P1172, P1174, P2172, P2174 as shown in FIG. 2D. In some embodiments, as discussed elsewhere herein, the drive nut and the threaded insert are fixed together (e.g., the threaded insert is sonically welded, glued, or otherwise fixed within the drive nut). In some embodiments, as shown in FIG. 2I and FIG. 4B, the motors P1160a, P1160b, P2160a, P2160b drive the gears of the gear assembly P1070, P2070 engaging the lead screws P1152, P1154, P2152, P2154 which translates rotational motion to the threaded inserts P1172, P1174, P2172, P2174. In several embodiments, the threaded inserts advance along the lead screws, urging the drive nuts P1142, P1144, P2142, P2144 forward or backward longitudinally (e.g., along the length of the pump). In some embodiments, as the drive nuts P1142, P1144, P2142, P2144 are urged forward or backward, the rotational motion of the lead screws P1152, P1154, P2152, P2154 does not rotate the drive nut. In some embodiments, the lack of rotation of the first and second drive nuts P1142, P1144, P2142, P2144 lowers rotational friction between the drive nuts and the first and second O-rings P1150a, P1150b, P2150a, P2150b, respectively, and/or the medicament cartridge plungers M1005, M1105, respectively.

As shown in FIGS. 2G, 2H, 4C, 4D and as disclosed elsewhere herein, in some embodiments the O-rings 1150a, P1150b, P2150a, P2150b are housed within the medicament chambers via the chamber walls P1100", P1110", P2100", P2110". In some embodiments, the threaded insert P1172, P1174, P2172, P2174 is fixed within the drive nut P1142, P1144, P2142, P2144 and, as the lead screw P1152, P1154, P2152, P2154 rotates, the threaded insert creeps longitudinally along lead screw causing the drive nut to extend within the medicament chamber P1100, P1110, P2100, P2110 longitudinally towards the first end of the bore. In some embodiments, as the drive nut is urged forward or backward, the rotational motion of the lead screw against the threaded insert is not translated to the drive nut. For instance, as shown in FIGS. 2H and 4D, in several embodiments, the first and second drive nuts P1142, P1144, P2142, P2144 have first and second tongues P1427a, P1427b, P2427a, P2427b (e.g., protrusions, tab, etc.), respectively, that are seated within and/or that are configured to engage with first and second grooves P3128a, 3128b, P2428a, P2428b (e.g., tracks, protrusion receptacle, etc.) that prevent rotation of the drive nuts P1142, P1144, P2142, P2144. In some embodiments, one tongue may be larger and the other smaller (or differently shaped) to fit into correspondingly shaped troughs of the pump housing. In some embodiments, the O-ring, which is immobilized in and/or at the aperture of the cartridge chambers, remains in place and circumferentially disposed on the drive nuts during movement of the drive nut and/or drug delivery. In several embodiments, the protrusion may be located on the pump housing and the protrusion receptacle (e.g., groove, track, etc.) may be located on the drive nut. In some embodiments, the lack of rotation about the drive nut lowers rotational friction between the drive nut and the O-ring and/or the medicament cartridge plunger.

In some embodiments, as noted, the protrusion P1427a, P1427a of the first drive nut may be shaped differently from the protrusion P1427b, P1427b of the second medicament drive nut. In some variants the first and second grooves P1428a, 1428b, 21428a, 2428b (e.g., tracks) may be shaped differently from each other and may be configured to engage the first and second protrusions P1427a, P1427b, P2427a, P2427b of the first and second drive nuts respectively. In some embodiments, tracks may be provided on the drive nut and the tongue (e.g., protrusion) may be provided below the drive nut and on the housing in a position that engages the track of the drive nut.

In some embodiments, as shown in FIG. 2G, the first drive nut P1142 (e.g., elongated cylinder, piston shaft, etc.) may comprise an elongate head P1142a, with one or more barbs P1142b (e.g., 1, 2, 3, 4, or more). In the embodiment show in FIG. 2G, the second drive nut (e.g., elongated cylinder, piston shaft, etc.) has a flat head P1144a. In some embodiments, the plunger M1005 of the first cartridge M1001 (e.g., the insulin cartridge) may be threaded. In some embodiments, as the drive nut is urged forward, the elongate head P1142a slides within the plunger M1005 of the first cartridge and the barbs engage the distal threads within the plunger M1005, securing the plunger to the drive nut P1142. In some embodiments, these barbed features help prevent lift-off of the plunger from the drive nut. In some embodiments, the plunger M1105 may have sufficient friction within the second cartridge M1101 to avoid lift off. Thus, in some embodiments, the second drive nut lacks barbs and the second cartridge lacks a threaded plunger. In some embodiments, the second drive nut may or may not include an elongate head with one or more barbs. In some embodiments, the plunger of the second medicament cartridge (e.g., for glucagon) may or may not include threads.

In some embodiments, as shown in FIG. 2C, one of more of the cylinders P1142, P1144 comprise attachment features P1142c, P1144c (e.g., tracks, traction points, grips, etc.). In some embodiments, these attachment features provide a grip for one or more drive nut attachment tools. In some embodiments, the drive nut attachment tools are used to test the pull force (during retraction) or push force (during extension) of the drive nuts. In some embodiments, the attachment tool is used to pull the drive nut through the drive nut aperture P1100a, P1110a of the housing during assembly, allowing proper positioning of for example, the lead screws.

As shown in, for example, FIG. 2A, in some embodiments, the motors P1060 rotate and/or move a drive gear P1071 (e.g., a pinion gear) in a gear assembly. As shown in FIG. 2B, in some embodiments, each gear assembly P1070 (of which there are two pictured, a first and a second) comprises four gear components P1071, P1072, P1073, P1074 and facilitates turning of lead screws P1152, P1154 within the internal area of the pump. In some embodiments, the gear ratios of laterally adjacent and/or engaged gear wheels in the gear assembly may be equal to or at least about: 3:1, 4:1, 5:1, 8:1, or ratios spanning and/or including the aforementioned ratios. In some embodiments, as shown in FIG. 2B, the gear configuration in the assembly from the motor pinion to the drive pinion on the lead screw is 4:1, 5:1, 5:1 (e.g., for a total effective gear ratio of 100:1). In several embodiments, radially adjacent and/or stacked gear configurations give the infusion pump a compact design. In several embodiments, the total effective gear ratio of the gear assembly is equal to or at least about: 200:1, 100:1, 75:1, 50:1, or ratios spanning and/or including the aforementioned ratios.

In some variants, as shown, a gear assembly in the pump may comprise both small gear wheels P1071a, P1072a, P1073a and large gear wheels P1072b, P1073b, P1074b. In several embodiments, as shown in FIG. 2C, the gear assembly P1070 comprises one or more stepped gear components P1072, P1073. A stepped gear comprises a larger gear wheel P1072b, P1073b and a smaller gear wheel P1072a, P1073a on the same gear component. In some embodiments, the ratio of the diameter of the larger gear wheel and smaller gear wheel of a stepped gear may be equal to or at least about: 3:1, 4:1, 5:1, 8:1, or ratios spanning and/or including the aforementioned ratios. In some embodiments, as disclosed elsewhere herein, a laterally traversing gear assembly with multiple gear steps advantageously allows the height of the pump to be reduced. Additionally, the motors can be placed laterally adjacent to their drive nut, adding to the compactness of the design.

In some embodiments, the diameters of each of the large gear wheels are similar to one another. This feature advantageously allows the height of the pump to be reduced. For example, if an effective gear ratio of 100:1 is desired, a smaller diameter gear wheel can be achieved using three lateral steps (as in FIG. 2C), rather than a simple single step of 100:1. In some embodiments, the diameters of each of the large gear wheels are within about 20% of one another. In some embodiments, the diameters of the large gear wheels differ by equal to or less than 40%, 30%, 20%, 10%, 5%, 0%, or ranges spanning and/or including the aforementioned values. In some embodiments, the diameter of the largest gear wheel in the gear assembly and the diameter of the second largest gear wheel in the gear assembly differ by equal to or less than 40%, 30%, 20%, 10%, 5%, 0%, or ranges spanning and/or including the aforementioned values. In some embodiments, the diameter of the largest gear wheel in the gear assembly and the diameter of the third largest gear wheel in the gear assembly (e.g., where there are two gear wheels larger than it in the gear assembly) differ by equal to or less than 40%, 30%, 20%, 10%, 5%, 0%, or ranges spanning and/or including the aforementioned values.

In some embodiments, the size of the motor casing relative to the size of the larger gear wheels are within about 20% of one another. In some embodiments, the diameters of the large gear wheels and the diameter of the motor casing differs by equal to or less than 40%, 30%, 20%, 10%, 5%, 0%, or ranges spanning and/or including the aforementioned values. This also advantageously lowers the height of the pump.

In some embodiments, the small gear wheels have diameters that are no more than half that of the large gear wheels. For instance, the largest of the small gear wheels will have a diameter that is less than or equal to half the diameter of the smallest large wheel. In some embodiments, the diameters of each of the small gear wheels are similar to one another. In some embodiments, the diameters of each of the small gear wheels are within about 20% of one another. In some embodiments, the diameters of the small gear wheels differ by equal to or less than 40%, 30%, 20%, 10%, 5%, 0%, or ranges spanning and/or including the aforementioned values. In some embodiments, the diameter of the smallest gear wheel in the gear assembly and the diameter of the second smallest gear wheel in the gear assembly differ by equal to or less than 40%, 30%, 20%, 10%, 5%, 0%, or ranges spanning and/or including the aforementioned values. In some embodiments, the diameter of the smallest gear wheel in the gear assembly and the diameter of the third smallest gear wheel in the gear assembly (e.g., where there are two gear wheels smaller than it in the gear assembly) differ by equal to or less than 40%, 30%, 20%, 10%, 5%, 0%, or ranges spanning and/or including the aforementioned values.

In some embodiments, the number of gear components P1071, P1072, P1073, P1074 in the gear assembly P1070 is equal to or at least about: 2, 3, 4, 5, 6, or more. In some embodiments, as shown in FIG. 2B, the pump may comprise 4 gear components per gear assembly. In some embodiments, the number of gears (e.g., gear wheels) including the pinion and the driving gear attached to the lead screw is equal to or at least about: 2, 3, 4, 5, 6, or more. As shown in FIG. 2B, there may be 6 gear wheels in the gear assembly P1070. In some embodiments, the number of gear steps between the pinion and the driving gear attached to the lead screw is equal to or at least about: 2, 3, 4, 5 or more. As shown in FIG. 2B, there may be 3 gear steps in the gear assembly P1070. In some implementations, the stepped pinion gears in the gear assembly are stacked, as shown in FIG. 2C.

In some embodiments, a stacked configuration (e.g., a laterally stacked configuration) means that at least one line drawn laterally through a particular gear assembly can pass radially through each gear component in the stack (as shown by the line P1070' in FIG. 2C). In some embodiments, as shown in FIG. 2C, at least one line (shown as a dashed line) drawn laterally through a stacked gear assembly passes radially through at least four gear wheels in the assembly. In some embodiments, as shown in FIG. 2C, a different line (shown as a dotted line) drawn laterally through a stacked gear assembly may pass radially through at least two gear wheels in the assembly. In some embodiments, a line drawn laterally through a stacked gear assembly passes radially through 3, 4, 5, or more gear wheels in the assembly.

In some embodiments, the gears in a stacked configuration interact small gear to large gear in alternating fashion (as shown in FIG. 2C). In some embodiments, as shown in FIG. 2C, a large gear is laterally adjacent and/or radially adjacent to a small gear. In some embodiments, a small gear wheel of a stepped gear P1073 is laterally adjacent and/or radially adjacent to at least two large gear wheels of adjacent gears P1074, P1072. The drive axis of the motor and the lead screws are each configured to be parallel to each other and in the same axis as the reservoirs. In some embodiments, the motor axis and the lead screw axis are parallel and on the same side of the drive train. In some embodiments, the stacked configuration allows the gear to extend laterally past the motor of the pump. In some embodiments, as mentioned elsewhere herein, the stacked configuration allows for a compact height (e.g., to achieve the desired gear ratio, multiple gears do not necessitate any individual gear wheel to have a large and length of the pump.

In some embodiments, the stacked configuration of gears engages a lead screw, threaded inserts, and drive nuts to provide a along a telescoping arrangement of the drive nut and the lead screw. In some embodiments, this also contributes to the compact design of the pump system. In some embodiments, the length of the drive nut and the medicament chamber together (e.g., collectively shown as P(l–P/C) in FIG. 2I) make up a majority of (and/or substantially all of) the total length P(l) of the pump. In some embodiments, the ratio of P(l–P/C) to P(l) is equal to or at least about: 5:6, 6:7, 7:8, 9:10, or ratios spanning and or including the aforementioned ratios.

In some embodiments, as disclosed elsewhere herein, the pump housing P1001 houses one or more of a printed circuit board (PCB) P1080, one or more lead screws P1152, P1154, a gear assembly P1070 comprising one or more gears P1071, P1072, P1073, P1074 for the one or more lead screws P1152, P1154, one or more motors P1060, one or more medicament cartridge receptacles P1100, P1101, a power source P1050, and an antenna P1200. The pump housing P1001 can also house a memory, such as firmware, to store the various user settings, control schemes, and algorithms, as well certain instructions and/or settings related to various characteristics of the patient. For example, the memory can include instructions and/or settings regarding when and how much to dose to the patient, and otherwise. The pump P1000 can be configured such that a patient or doctor can modify (e.g., update, program, or otherwise) the memory, such as by connecting the pump to a computer (e.g., a smartphone, laptop, etc.) that is equipped with software or an "app" that is configured to enable the computer and/or pump to perform any of the functions, tasks, and/or steps described and/or illustrated herein.

As shown in FIGS. 3A and 3B, the display screen P1007 may have a length P(dl) and a width P(dw). In some embodiments, as shown in Figures P1(Q) and P1(R), the area A(d) of the display screen P1007 (as measured by multiplying the length P(dl) and the width P(dw)) makes up a majority of the area A(f) of the face of the pump P1002 (as measured by multiplying the length of the face P(fl) and the width of the face P(fl)) and/or substantially all of the face P1002 of the pump 1000. The area of the face A(f) is shown in FIG. 3B bounded by broken lines and the area of the display A(d) is shown bounded by a dotted line. In some embodiments, the ratio of the area of the display to the area of the face is equal to or at least about: 4:5, 17:20, 9:10, 19:20, or ratios spanning and/or including the aforementioned values. In some embodiments, the ratio of the length to the width of the display (e.g., the aspect ratio) is greater than or equal to about: 4:3, 25:16, 16:9, 21:9, or ratios spanning and/or including the aforementioned values. In some embodiments, the ratio of the length to the width of the pump (e.g., the aspect ratio) is equal to or about the same as the aspect ratio of the display. In some embodiments, the ratio of the length to the width of the pump (e.g., the aspect ratio) is greater than or equal to about: 4:3, 25:16, 16:9, 21:9, or ratios spanning and/or including the aforementioned values.

As shown in FIGS. 3C and 3D, the pump housing may have one or more rounded corners when viewed from the bottom P1001$b$ or from the front P1001$f$. In some embodiments these rounded corners provide a transition from the side surfaces of the pump to the lower side surface of the pump. It has also been noted that corners having particular radii of curvature impart additional strength to the pump housing. This feature is especially important where a pump has a large display as disclosed elsewhere herein (e.g., a display that makes up a substantial portion of the area of the face of a pump). In some embodiments, the pump housing has more than one radius of curvature (e.g., two or more) when viewed from different angles. For example, the pump housing may have a radius of curvature $P(r)^b$ as viewed from the bottom of the pump (shown in FIG. 3C, e.g., the radius of curvature of P1001$b$) and a radius of curvature $P(r)^f$ as viewed from the front of the pump (shown in FIG. 3D, e.g., the radius of curvature of P1001$f$). In some embodiments, $P(r)^b$ is less than $P(r)^f$. In some embodiments, the ratio of the radius of curvature $P(r)^b$ of a rounded corner viewed from the bottom and the width of the pump P(w) is equal to or at least about 1:9, 1:6, 1:4, or ranges including and/or spanning the aforementioned values. In some embodiments, the ratio of the radius of curvature of a rounded corner $P(r)^f$ viewed from the front and the height of the pump P(h) is equal to or at least about 1:2, 5:9, 2:3, or ranges including and/or spanning the aforementioned values.

Figure 5A:
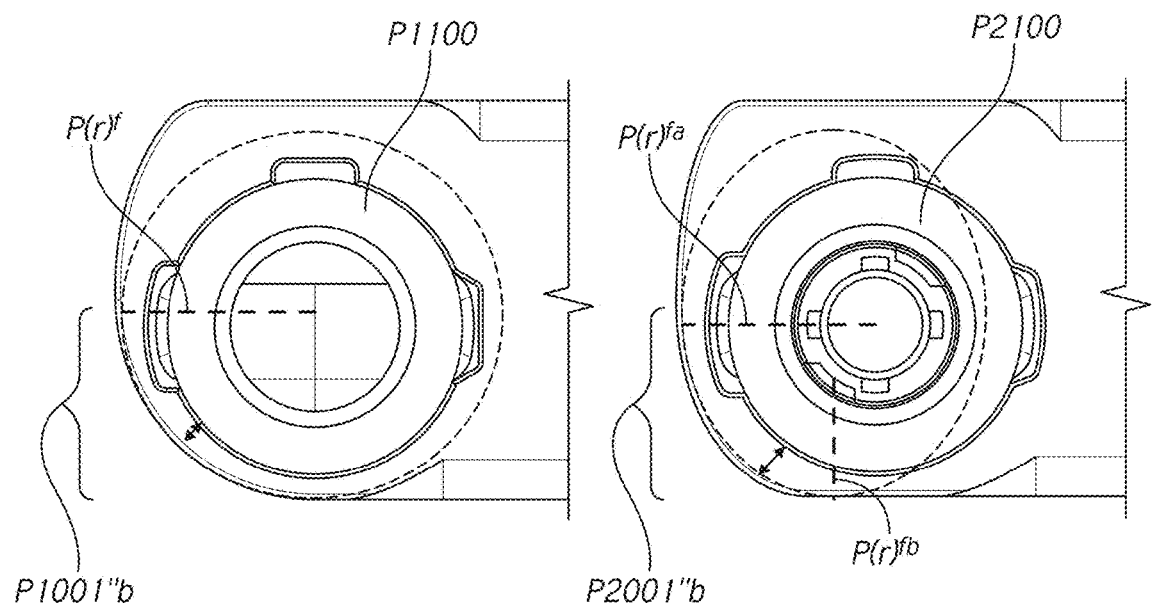
FIG. 5A shows a view of the upper side surface of the embodiment of FIG. 1A and FIG. 4A, respectively.

In some embodiments, as shown in FIG. 5A, the bottom section P1001"b of the lower portion P1001" of the pump housing P1001 of the embodiment of FIG. 1A has a radius of curvature $P(r)^f$ coinciding to a circle (shown with the dashed line). In some embodiments, the bottom section P1001"b is defined by the section of the pump that is the lower half of the height P(h) of the pump 1000. In some embodiments, as shown in FIG. 5A, the bottom section P2001"b of the lower portion P2001" of the pump housing P2001 of the embodiment of FIG. 4A has a multiple radii of curvature $P(r)^{fa}$, $P(r)^{fb}$ coinciding to an elliptical shape of the pump housing P2001, which is shown with the dashed line. It has been noted that, by including an elliptical shape (as with the embodiment of FIG. 4A) around the receptacle inlet port P2100', increased housing strength is achieved. In several embodiments, advantageously, this increased housing strength protects the pump and its components from breakage during an accidental drop (e.g., display shatter or cracking, etc.).

In some variants, the increased housing strength is realized using an elliptical shape characterized by a lower radius of curvature $P(r)^{fb}$ and an upper radius of curvature $P(r)^{fa}$. In some embodiments, increased housing strength is realized where the lower radius of curvature $P(r)^{fb}$ is smaller than the upper radius of curvature $P(r)^{fa}$. In some embodiments, the ratio of the lower radius of curvature $P(r)^{fb}$ to the upper radius of curvature $P(r)^{fa}$ is equal to or at least about: 1:2, 2:3, 4:5, 9:10, or ratios spanning and/or including the aforementioned values. In some embodiments, an elliptical configuration adds housing material between the receptacle inlet ports P2100' and a periphery of the pump P2001 (shown by the double headed arrows of FIG. 5A).

Capacitive Touch Sensor

As disclosed elsewhere herein, FIG. 1A depicts an embodiment of an ambulatory pump P1000. In some embodiments, the finger pad P1010 is a curved indentation and provides access to a capacitive sensor wake feature. In several embodiments, the wake feature is activated by touching a fingerprint recognizing pad, a haptic sensor, and/or by depressing a button provided by the curved indentation P1010. In several embodiments, the capacitive sensor of the finger pad P1010 may be located close to the curved indentation so that it may sense the change in capacitance that occurs when a finger is placed in the curved indentation P1010. In several implementations, the surface of the curved indentation P1010 is closer to the inner electronics of the ambulatory medical device than the surface (e.g., the lower side surface P1005) around the curved indentation. The capacitive sensor may be placed such that the capacitive sensor is only activated when the curved indentation P1010 is pressed or touched by a user. The curved indentation P1010 may be shaped, as shown in FIG. 1A, in a concave manner and/or to fit a finger (or shaped to fit different body parts, such as a thumb).

As shown, the curved indentation P1010 may be formed in the bezel P1001' of the pump P1000. One advantage of having the curved indentation P1010 shaped into the bezel P1001' is that the curved indentation P1010 for the wake button does not add water ingress points to the pump P1000. In some embodiments, as shown, the curved indentation P1010 is placed on the lower portion P1005 of the pump 1000, though it may be located on any other surface P1002, P1003, P1004, P1006', P1006" of the pump 1000.

In several implementations, as described else wherein herein, the pump may be made into various shapes. As shown in FIG. 1A, the pump may have a flat bricklike shape with six faces. When the curved indentation P1010 is placed on an end face P1004, P1005 or a side face P1006', P1006" of the pump 1000, the curved indentation P1010 does not take space up one of the larger faces P1002, P1003, leaving more space for the display screen and/or an inductive charging pad.

Figure 5B:
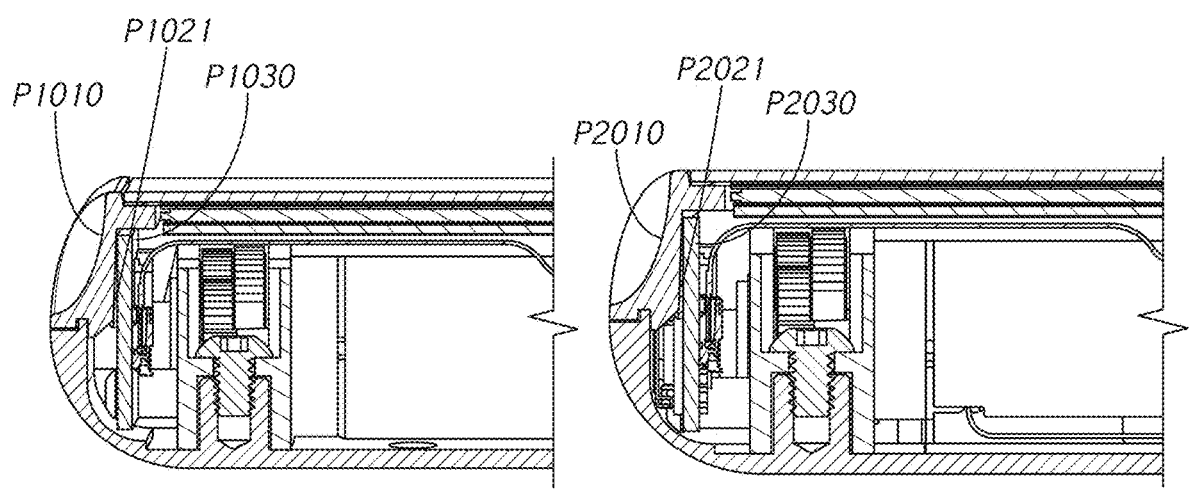
FIG. 5B is a bisected side view of a portion of the pump of FIGS. 1A and 4A.

FIG. 5B includes cross-sectional views of embodiments of pumps P1000, P2000 cut by a plane running the length and height of the pumps and passing through a width. As shown in FIG. 5B, the curved indentation P1010, P2010 is bisected and the electronics behind the curved indentation P1010, P2010 are visible. In several embodiments, as shown in FIGS. 5B-6B, the capacitive sensor pad 1020, 2020 contacts at least a part of the internal portion (e.g., internal to the pump housing and pump) of the finger pad P1010, P2010 through an intermediate material P1021. In several embodiments, a capacitance signal is received by the finger pad P1010, P2010 is transmitted to the capacitive sensor pad P1020, P2020 and on to a board P1030, P2030 that is in electronic communication with the PCB P1080, P2080.

In several embodiments, the capacitive sensor pad P1020, P2020 may be any conductive metal pad providing a conductive path from the finger pad P1010, P2010 to the board P1030, P2030. In some embodiments, the capacitive sensor pad P1020, P2020 is a copper pad. In several embodiments, the close proximity of the capacitive sensor pad P1020, P2020 to the curved indentation of the finger pad P1010, P2010 allows the capacitive sensor pad P1020, P2020 to detect the change in capacitance caused by a user placing a finger on the curved indentation P1010, P2010. In several embodiments, the logic level of the capacitance signal is reversible.

Figure 6A:
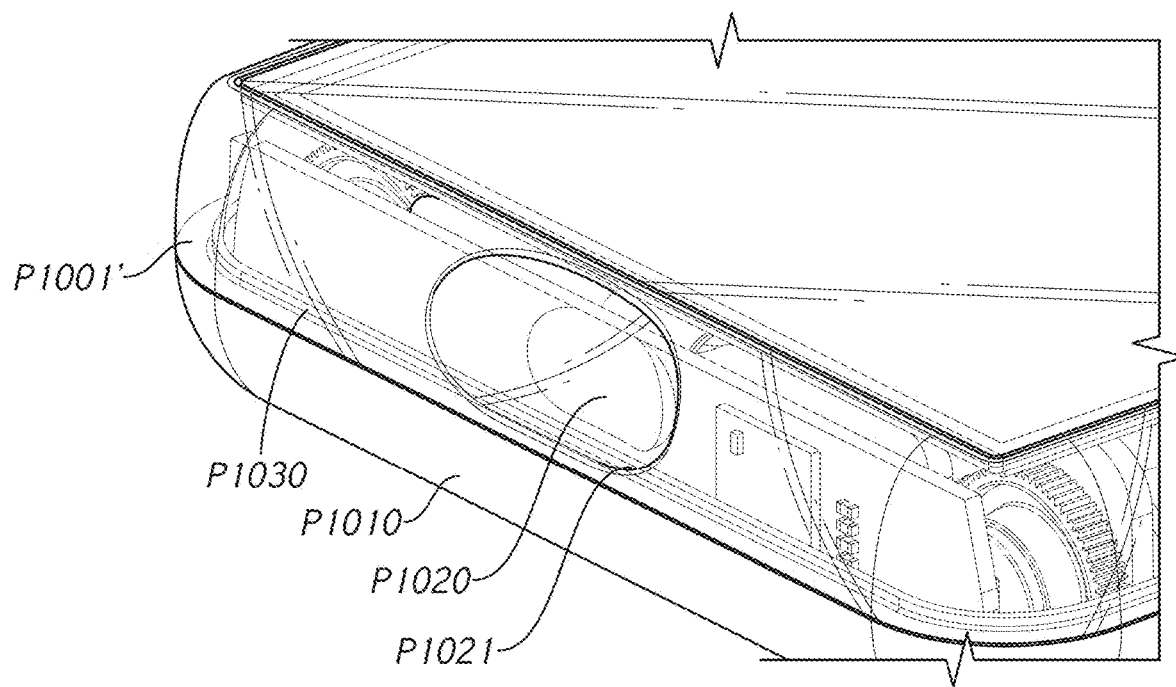
FIGS. 6A and 6B are illustrations of the pump of FIG. 1A with the bezel shown clear or with a cross-section taken along the width of the pump, respectively.
Figure 6B:
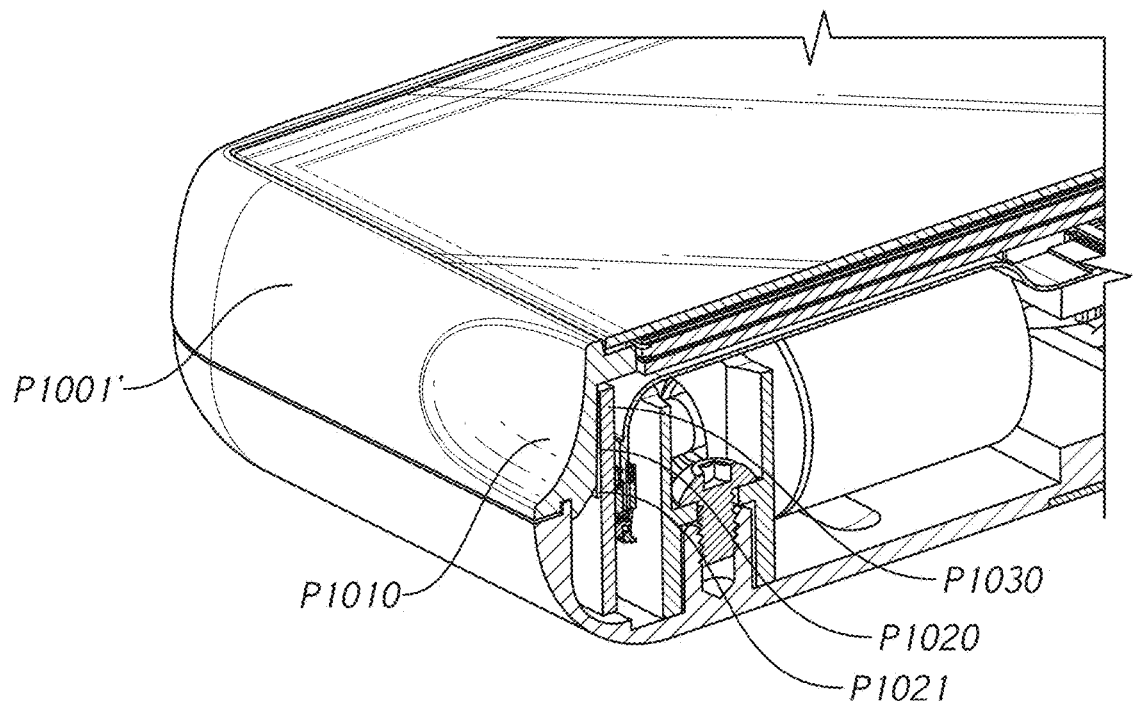

In some embodiments, a conductive foam (e.g., an intermediate material) is placed between the capacitive sensor pad P1020, P2020 and the curved indentation P1010, P2010. An embodiment of a conductive foam P1021 is foam is shown in FIG. 6A. As shown, the conductive foam P1021 is crushed and or deformed between the curved indentation P1010 and the capacitive touch pad P1020, thereby forming a large amount of contact between the curved indentation P1010 and the capacitive touch pad P1020. FIG. 6B shows another view of the conductive foam, which is sandwiched between the bezel and the board P1030. There are various conductive foam materials that may be placed between the capacitive sensor pad P1020, P2020 and the curved indentation P1010, P2010. In several embodiments, the conductive foam material is a polyurethane foam coated with nickel and copper. In several embodiments, the foam is a sponge-like material. In some embodiments, when installed, the foam becomes deformed and/or crushed to provide contact between the finger pad P1010, P2010 and the capacitive sensor pad P1020, P2020. The conductive foam may serve multiple purposes. In several embodiments, the conductive foam is configured to allow the capacitive sensor pad P1020, P2020 to be placed farther away from the curved indentation P1010, P2010. In several embodiments, this feature creates more space tolerance in the device. In some variants, the conductive foam is configured to decrease the sensitivity of the capacitive sensor pad P1010, P2010 and/or to tune the sensitivity of the capacitive sensor pad P1020, P2020.

In several variants, a capacitance signal is transmitted through the capacitive sensor pad P1020, P2020 to the board P1030, P2030. In several implementations, the board P1030, P2030 is configured to transmit the signal to an integrated circuit. In some embodiments, the integrated circuit has programmable thresholds that are configured to compare changes in capacitance. In some implementations, when a programmable threshold is met, the integrated circuit may transmit a signal corresponding to the programmable threshold that was met to a signal processing component of the pump 1000, 2000. In some implementations, the signal processing component may be configured to generate a wake signal when the signal processing component receives a signal from the integrated circuit. The signal processing component may be further configured to only generate a wake signal if specific programmable thresholds are met by the integrated circuit.

In certain variants, the curved indentation P1010, P2010, as disclosed elsewhere herein, is shaped to fit the finger of a user. The curved indentation P1010, P2010 may be shaped to various sizes to fit various sized fingers of different users. In some implementations, increased surface area of the curved indentation P1010, P2010 may fulfill the purpose of increasing the potential change in capacitance that is created by the finger of a user. Thus, in some embodiments, the indentation may be configured to interact generally with a finger the size of an adult or the finger the size of a child. In some implementations, the curved indentation is configured to recognize a fingerprint of a user. In certain implementations, fingerprint recognition serves as a safety feature and may ensure that only certain users are allowed to gain access to particular functions of the pump and/or to wake the system (e.g., in order to set specific pump and/or control parameters).

In some embodiments, as disclosed elsewhere herein, the curved indentation P1010, P2010 of the pump 1000, 2000 prevents inadvertent activation of the ambulatory medical device by only permitting shapes that match the curved indentation P1010, P2010 to press against the surface of the curved indentation. In some embodiments, because the curved indentation is relatively narrow, appendages of the user besides the fingers of the user, such as the arm or elbow of the user, are not likely to penetrate the curved indentation (e.g., accidental activation is prevented or minimized). In some embodiments, a concave shape of the curved indentation P1010, P2010 may provided with dimensions that prevent inadvertent touching against the surface of the curved indentation because objects larger than the curved indentation may not enter the curved indentation. In some embodiments, as noted above, the curved indentation P1010, P2010 may be configured to recognize particular users by virtue of fingerprints. In some embodiments, fingerprint recognition can also prevent a user from inadvertently activating the system.

FIG. 6A is an illustration of the pump 1000 with a capacitive sensor wake button shown with a transparent bezel. The bezel P1001' connects a display to the pump 1000. In some embodiments, where the bezel is nonmetallic, a change in capacitance may be measured when a finger is pressed against it. The transparent bezel in FIG. 6A provides a view of the components under the bezel. The curved indentation P1020, which is integrated into the bezel is also transparent in FIG. 6A. A user may press a finger into the curved indentation to generate a wake signal in the ambulatory medical device (e.g., or in the pump thereof). In some embodiments, the capacitance sensor pad P1020 may detect the change in capacitance that the finger of a user creates when the finger of the user is pressed into the curved indentation of the finger pad P1010. In some embodiments, the capacitance sensor pad P1020 is mounted on a board P1030. In some variants, signals that are generated at the capacitance sensor pad are transmitted to the board and then transmitted to an integrated circuit. Several variations of integrated circuits that are configured to detect a change in capacitance are publicly available for purchase. In some embodiments, the integrated circuit detects a change of capacitance of a signal that is transmitted to the integrated circuit, into the ambulatory medical device (e.g., pump). The integrated circuit may detect a change in capacitance by measuring a change in measured voltage on a circuit.

In various embodiments, the conductive foam P1021 may be positioned on the capacitance sensor pad P1020. As noted elsewhere herein, the conductive foam P1021 may effectively extend the range of the capacitance sensor pad P1020 by approximately the size of the conductive foam P1021. In some embodiments, the conductive foam P1021 may be used to lower the sensitivity of the capacitance sensor pad P1020 and/or the conductive foam P1021 may be used to fine tune the sensitivity of the capacitance sensor pad P1020.

Figure 6C:
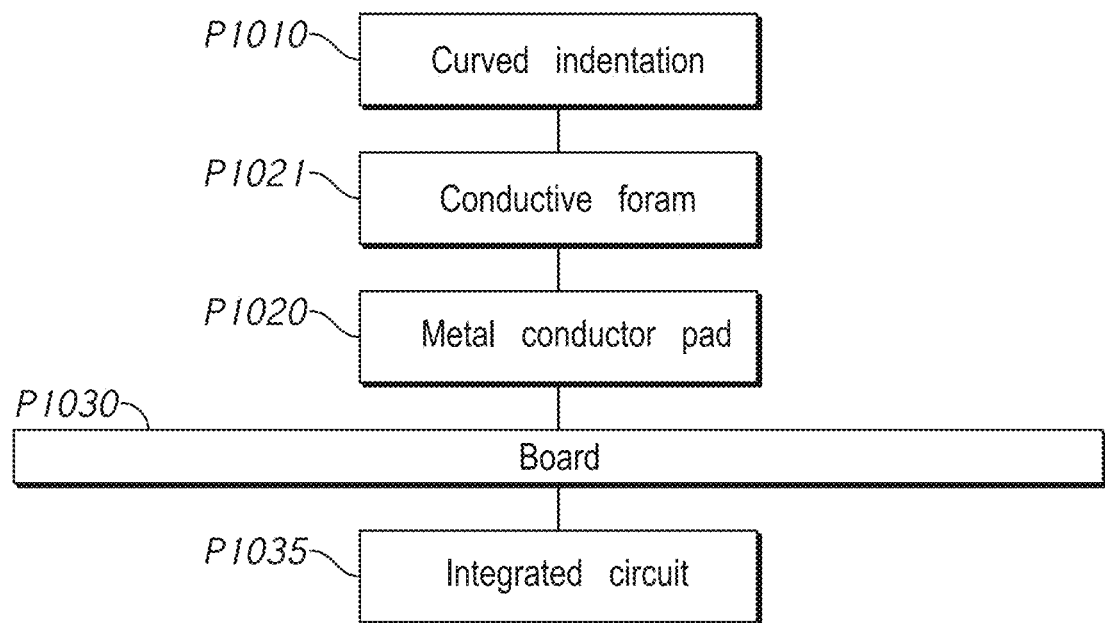
FIG. 6C is a schematic diagram illustrating the components of a capacitive sensor in the ambulatory medical device.

FIG. 6C is a schematic diagram illustrating the components of an embodiment of a capacitive sensor in the pump. The capacitive sensor may include one or more of a curved indentation P1010, a conductive foam P1021, a metal conductor pad P1020, a board P1030, and an integrated circuit board P1035. In some embodiments, as shown, the curved indentation P1010 may be a rounded depression in the surface of the bezel of a pump. In some embodiments, the curved indentation P1010 is incorporated into the bezel such that the curved indentation P1010 is seamless with no points of ingress for liquids. In some embodiments, the curved indentation P1010 may be shaped to fit the tip of the finger of a user as the finger of the user is pressed into the curved indentation.

In some embodiments, the conductive foam P1021 sits atop the metal conductor pad P1020. In some implementations, capacitance is measured at the metal conductor pad P1020. In several variants, the conductive foam P1021 sits atop the metal conductor pad P1020 and effectively extends the capacitance sensing range of the metal conductor pad P1020 to the length that the conductive foam P1021 that extends from the metal conductor pad P1020. In several variants, the conductive foam P1021 may be used to decrease the sensitivity of capacitance that is measured at the metal conductor pad P1020. In several embodiments, because the conductive foam P1021 may be used to decrease the sensitivity of capacitance measured at the metal conductor pad P1020, the sensitivity of capacitance may be tuned by adjusting the size of the conductive foam P1021. In several embodiments, the metal conductor pad P1020 may be made of and/or comprise a conductive metal such as copper. In several embodiments, the conductive foam P1021 may be made of a foam material that is conductive. In some embodiments, the conductive foam is a polyurethane material that is coated with copper and/or nickel. In various embodiments, the conductive foam P1021 is a polyurethane foam that is surrounded with a conductive fabric.

In several embodiments, as noted elsewhere herein, the signal generated at the metal conductor pad P1020 is transmitted to a board P1030. In some variants, the board P1030 may connect the metal conductor pad P1020 to an integrated circuit P1035. In some variations, the integrated circuit P1035 may be configured to determine that the signal generated by the metal conductor pad P1020 represents a change in capacitance. The integrated circuit P1035 may detect the change in capacitance by measuring the change in voltage in a circuit that connects the integrated circuit P1025 through the board P1030 to the metal conductor pad P1020 and the conductive foam P1021.

Figure 6D:
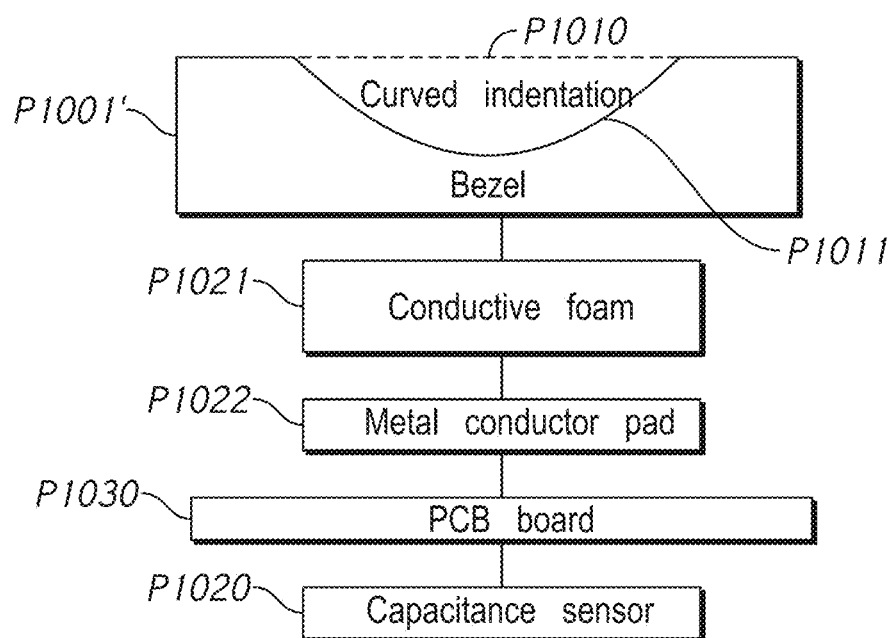
FIG. 6D is a schematic diagram illustrating the components of the ambulatory medical device with a capacitive sensor.

FIG. 6D is a schematic diagram illustrating the components of the pump 1000 with a capacitive sensor. The pump with a capacitive sensor includes a bezel P1001' with a curved indentation P1010, a conductive foam P1021, a metal conductor pad P1020, a secondary PCB board P1030, and a capacitance sensor P1020. In some embodiments, the bezel P1001' partially covers the outside of the pump 1000. In several embodiments, the curved indentation P1010 in the bezel P1001' is where the finger of the user may be pressed to generate a wake signal. As shown, in some embodiments, the conductive foam sits atop the metal conductor pad. In some embodiments, a change in capacitance may be detected at the metal conductor pad. In some embodiments, the conductive foam may extend the range that capacitance may be measured at the metal conductor pad P1022 by the size of the conductive foam P1021. In some embodiments, the metal conductor pad P1022 will detect a stronger change in capacitance by a finger pressing into the curved indentation P1010 if the conductive foam P1021 is moved closer to the curved indentation P1010 in proximity. Thus, in several embodiments, the distance from the bottom of the curved indentation P1011 is small to increase the detectable change in capacitance. In some embodiments, the capacitance signal detected by the metal conductor pad P1022 may be transmitted through PCB board to the capacitance sensor P1020 where the signal is converted into computer readable data. In some embodiments, the capacitance sensor P1021 may create a computer readable data for the capacitance measured at the metal conductor pad P1021 by measuring the change in the voltage on a circuit that goes through the metal conductor pad P1022. In some embodiments, the capacitance sensor P1020 may be programmed to send an activation signal at a variable level of capacitance.

Figure 6E:
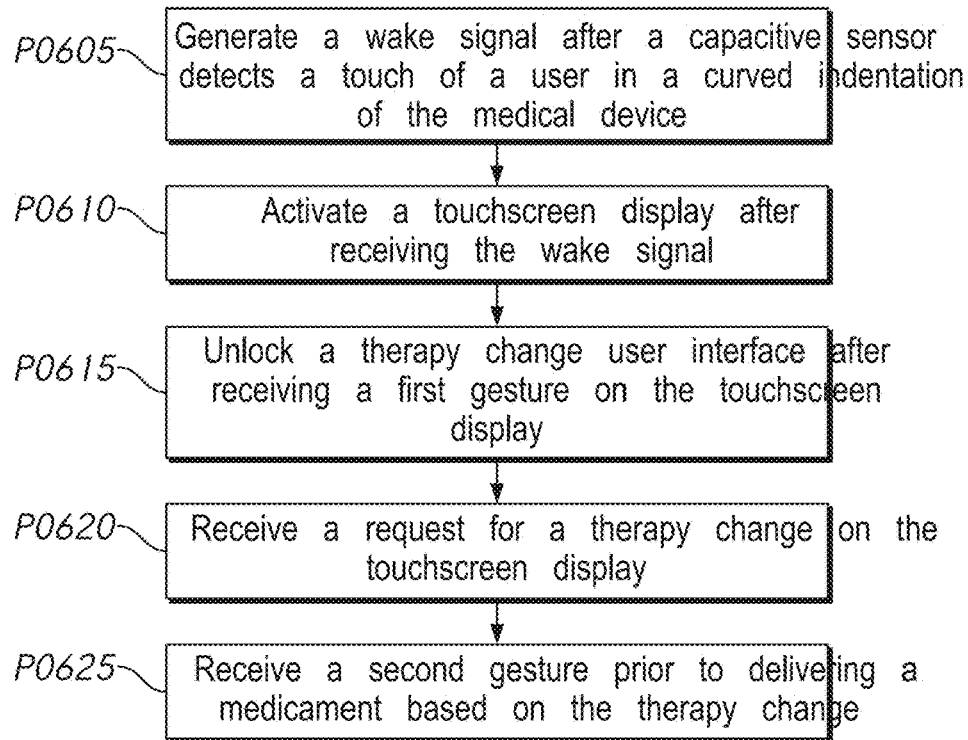
FIG. 6E is a flow diagram of a process for preventing inadvertent therapy on an ambulatory device.

FIG. 6E is a flow diagram of a process for preventing inadvertent therapy on an ambulatory infusion system (e.g., a system including an infusion pump as described elsewhere herein and/or the pump itself). The pump includes a curved indentation and a capacitive sensor. At step P0605 the pump may generate a wake signal after a capacitive sensor detects a touch of a user in the curved indentation of the medical device. The curved indentation is a concave indention in the bezel of the ambulatory system. The finger of the user may press into the curved indentation to create the wake signal. The capacitive sensor may detect the change in capacitance that is generated by the finger of the user. Once the capacitive sensor detects a change in capacitance, the ambulatory medical device may generate the wake signal. At step P0610, the pump may activate a touchscreen display after receiving the wake signal. In some embodiments, the touchscreen display may prompt the user to enter a first gesture after the pump generates a wake signal. The first gesture may be a series of inputs that the user may enter onto the touchscreen display of the pump. At step P0615 the pump (and/or the infusion system) may unlock a therapy change user interface after receiving a first gesture on the touchscreen display. In some embodiments, the first gesture is a series of inputs that are entered onto the touchscreen display. In various embodiments, the touchscreen display shows an alpha numeric pad where the user may type a pass key. At step P0620, the pump may receive a request for a therapy change on the touchscreen display. The request for the therapy change may be made by a user selecting the therapy change. The therapy change may be for various medicaments. In some embodiments, the therapy change is a hormone that the pump (and/or infusion system) may deliver into the user. At step P0625, the pump (and/or another component of the infusion system) may receive a second gesture prior to delivering a medicament based on the therapy change. The second gesture may be a series of inputs. In some embodiments, the second gesture includes the detection of a change in capacitance by the user pressing the curved indentation. Alternatively, in various embodiments, pressing the curved indentation after receiving a request for a therapy change, and before the second gesture is received, may cancel the therapy change and lock the ambulatory medical device.

Figure 6F:
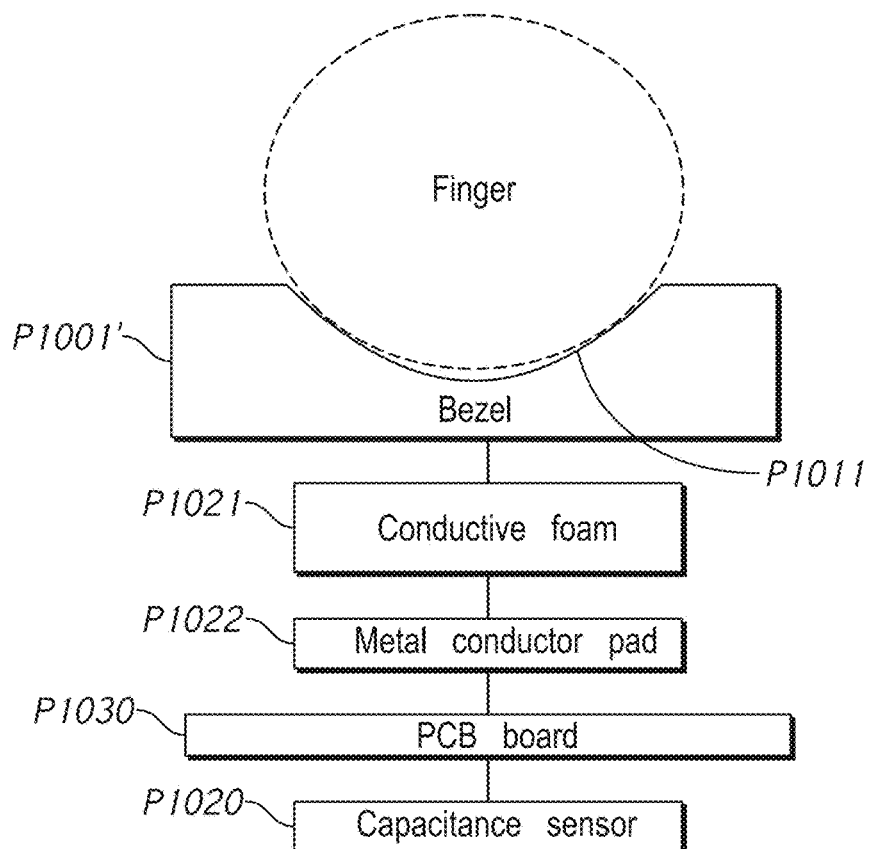
FIG. 6F is a schematic diagram illustrating the components of the ambulatory medical device with a capacitive sensor that is being activated by a user.

FIG. 6F is another a schematic diagram illustrating the components of the pump P1000 with a capacitive sensor that is being activated by a user. In some embodiments, the finger of the user may be pressed into the curved indentation P1010 to activate the ambulatory medical device (e.g., the pump of the infusion system and/or the infusion system). In some embodiments, the curved indentation P1010 portion of the bezel P1001' has a larger surface area than the portion of the bezel P1001' that is not curved. In some embodiments, the increased surface area of the curved indentation P1010 allows for a higher capacitance to be detected when the finger of the user is pressed into the curved indentation P1010. In some embodiments, the metal conductor pad P1022 may detect the capacitance of the finger when the user presses the curved indentation P1010. In some embodiments, space requirements in the ambulatory medical device may prohibit close placement of the metal conductor pad P1022 to the curved indentation P1010. In some embodiments, a conductive foam P1021 may be placed in between the curved indentation P1010 and the metal conductor pad P1022 to extend the capacitance measurement range of the metal conductor pad P1022. In some embodiments, the conductive foam P1021 may be a foam material that is conductive. In some embodiments, polyurethane foam that is coated with nickel and copper is used as the conductive foam P1021. In various embodiments, the conductive foam P1021 is a polyurethane foam that is covered in a conductive fabric. In some embodiments, the capacitance signal that is initialized by the user pressing a finger into the curved indentation P1010 is detected at the metal conductor pad P1022 and transmitted through PCB board P1030 to a capacitance sensor P1020. The capacitance sensor P1020 may be programmed to transmit an activation signal when it detects various capacitance measurements. In some embodiments, the capacitance sensor may be programmed to transmit an activation signal from a capacitance signal that is generated when the curved indentation P1010 is substantially covered by human skin.

Figure 6G:
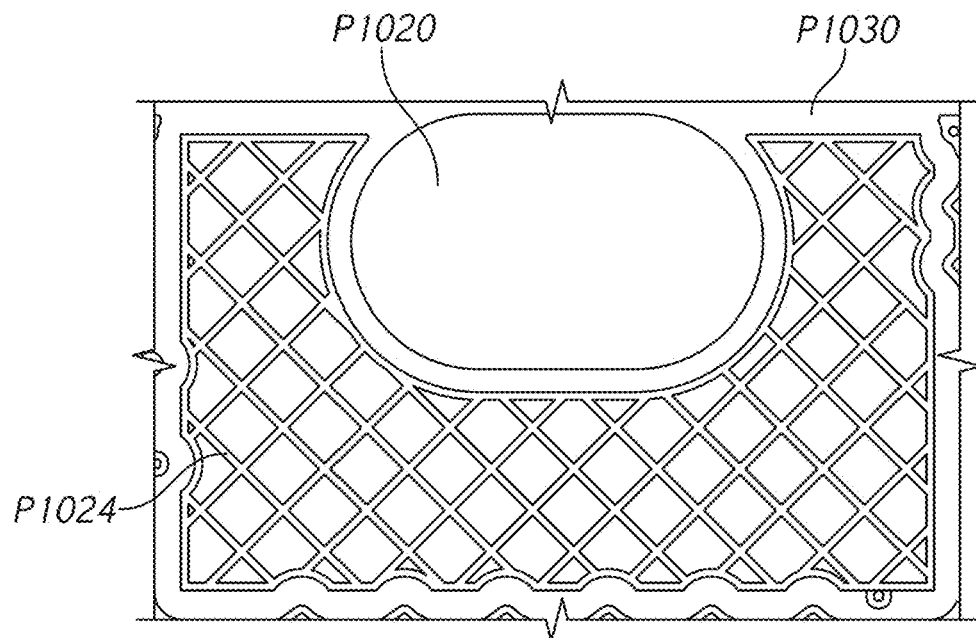
FIG. 6G is an illustration of a capacitance sensing pad on PCB board.

FIG. 6G is an illustration of a capacitance sensing pad P1020 on PCB board P1030. In some embodiments, the capacitance sensing pad P1020 may be made of various conducting metal or metal alloy materials. In some embodiments, the capacitance sensing pad P1020 is copper. In some embodiments, the capacitance sensing pad P1020 may be connected through the bottom of the PCB board P1030 to an integrated circuit that can convert a capacitance signal into machine readable data. In some embodiments, the capacitance sensing pad P1022 may detect a change in capacitance as the surface of a finger of a user is pressed close to the surface of the capacitance sensing pad. The PCB board P1030 may have a square GND hatch P1024 that surrounds the capacitance sensing pad P1020. In some embodiments, the GND hatch P1024 is a square pattern of copper on the PCB board P1030 that may act to isolate the capacitance sensing pad P1020 from other sensors and traces in the PCB board P1030.

In some embodiments, in order to prevent inadvertent activation of a therapy change (e.g., a medicament delivery schedule setting change, etc.) the pump, it is desired to strike a balance between ease of use and complexity to avoid inadvertent actions. In several embodiments, the described subject matter prevents inadvertent activations of therapy changes by requiring a series of activations. In several embodiments, the activations must be combined in a particular order to activate a therapy change. In several embodiments, the pump includes a wake button (e.g., the finger pad P1010) and a touchscreen display (e.g., the display screen P1007). In several embodiments, the wake button may be any type of button that registers a single input to generate a wake signal. An example of the wake button may be a capacitive button. Another example of the wake button is a mechanical button. In various embodiments, the wake signal is generated by a sensor. In some variants, the wake signal may be generated by a biometric sensor such as a fingerprint reader or a retinal scanner. The wake signal may also be generated by a proximity sensor. The wake signal may be generated by an accelerometer or a gyroscope or a combination accelerometer and gyroscope. The wake signal may also be generated by an optical sensor. In various embodiments, the wake signal is generated by entering a pass key into an alphanumeric pad. In various embodiments, the wake signal is generated by use of facial recognition. In various embodiments, the wake signal may be generated by a wireless signal such as RFID and Bluetooth.

In some variants, the touchscreen display may be any input surface that shows graphic images and text and registers the position of touches on the input surface. Graphic images and text may be shown by any display technology including, but not limited to OLED, LCD, or e-ink. Touches may be registered by any type of technology. An example of a touchscreen display that registers touches is a capacitive display screen. Another example of the touchscreen display that registers touches is a resistive display screen.

In some embodiments, the wake button is a capacitive touch sensor. The capacitive touch sensor is located within a curved indentation. In some embodiments, the curved indentation is a convex indentation that is unlikely to be accidentally pressed by brushing against the ambulatory medical device. The capacitive touch sensor may comprise a copper pad on a circuit board as close as possible to the surface that is touched by a finger. A capacitive sensing control integrated circuit measures the capacitance of the copper pad by applying a voltage to the circuit. In some embodiments, when a finger is present, the finger will add capacitance to the circuit and the capacitive sensing control integrated circuit will detect a change in voltage. The capacitive sensing control integrated circuit has programmable thresholds that are used to compare changes in capacitance and determine when a finger is present on the wake button. In some embodiments, the logic level of the capacitance signal is reversible and will return to a low capacitance measurement when the finger is removed from the wake button.

In some embodiments, to achieve high capacitance when a finger is placed on the capacitive touch sensor (maximum signal to noise), the design includes a scallop or curved indentation to shrink the gap between the touchable surface and the capacitive sensing surface. In some embodiments, the touchable surface is the outside wall of the device. In some variants, the outside wall of the device is in a plastic housing or bezel. In some embodiments, the capacitive sensing surface is the copper pad. In some embodiments, the curved indentation also provides a visual and tactile cue that guides the finger to the optimal position for adding capacitance to the sensor. Also, to increase maximum signal to noise, the surface area of the copper pad is maximized where it will be placed nearly parallel to the finger when the finger is pressed into the curved indentation. In some embodiments, to increase maximum signal to noise, the circuit board with the copper pad is shifted as close of possible to the curved indentation while maintaining the tolerances and mechanical requirements of the ambulatory medical device. In some embodiments, to increase signal to noise, a conductive foam is added to the copper pad (as disclosed elsewhere herein), which effectively raises the capacitive sensing surface of the copper pad closer to the curved indentation and the location of the finger.

In some embodiments, pressing the wake button is sufficient to engage the display screen to change device settings. In other embodiments, a series of activations is required. In some embodiments, the series of activations begins by pressing a wake button for a set amount of time to unlock a medical device. In various embodiments, the wake button must be pressed for at least 0.5 seconds and less than 1.5 seconds to unlock the device. In some embodiments, the device may provide a haptic feedback to indicate that the wake button was held for a required period of time.

In some embodiments, after pressing the wake button (and/or, as the case may be, if held for the correct period of time) the touchscreen display becomes activated. In various embodiments, touches on the touchscreen display are not registered until the wake button unlocks the touchscreen display. In some embodiments, the touchscreen display is still locked from accepting any user input until a gesture is performed on the display screen. In some embodiments, the gesture (e.g., a finger swipe, series of swipes, touching specific areas of the screen, etc.) unlocks the device settings.

In some embodiments, after the display is active, the next activation is a gesture (e.g., a complex gesture) to unlock a therapy change user interface. In some embodiments, the complex gesture may be any series of inputs on a touchscreen display. One example of the complex gesture is a swipe. Another example of a complex gesture is entering a predetermined sequence of touches (e.g., a combination of swipes, swiping to form a shape, pressing a code alphanumerically, etc.). Once the therapy change user interface is unlocked by the correct complex gesture, therapy change interactions may be initiated using the touchscreen display. In some embodiments, the therapy change interaction will allow a user to select a therapy change. In some embodiments, once the therapy change is selected, another final activation may be made to deliver the therapy change. In an exemplary embodiment, the final activation is a second complex gesture. The second complex gesture may be a swipe, a predetermined sequence of touches, or any other series of touches on the touchscreen display. In some embodiments, the therapy change will be effectuated once the second complex gesture is successfully completed.

In some embodiments, the initial or final activation is made by a sensor. In some embodiments, the initial or the final activation is made by a biometric sensor such as a fingerprint or retinal scanner. In another example, the initial or the final activation is made by a proximity sensor. In some embodiments, the initial or the final activation is made by an accelerometer, a gyroscope, or a combination of accelerometer and gyroscope. In some embodiments, the initial or the final activation is made by an optical sensor such as a visible light sensor or an IR sensor. Also, in an exemplary embodiment, the initial or the final activation is made by a positive facial recognition. Also, in an exemplary embodiment, the initial or the final activation may be made by entering a pass key on an alphanumeric keypad. Also, in an exemplary embodiment, the initial or the final activation may be made by a wireless signal such as RFID or Bluetooth.

In some embodiments, the pump and/or system may have a time-out such that if no interaction occurs for a set period of time, the screen will turn off and the therapy change request process must be reinitiated (e.g., to make a change). In some embodiments of the time-out, if no interaction occurs for more than 10 seconds, 15 seconds, 30 seconds or more after the wake button activation and before the second gesture, the touchscreen display deactivates. In some embodiments, the touchscreen display deactivates if no interaction occurs for more than 30 seconds after the wake button activation and before the first gesture. In some embodiments, the touchscreen display deactivates if no interaction occurs for more than 30 seconds after the first gesture and before the second gesture. Also, in some embodiments, a pressing of the wake button while the touchscreen display is activated will deactivate the touchscreen display.

Pump Housing Bezel and Antenna

As noted elsewhere herein, FIG. 1C provides a view of the pump that may be a part of an ambulatory infusion system. In some embodiments, a portion of the housing may be metal, molded plastic, or other suitable materials (e.g., the lower portion P1006', etc.). In some embodiments, a metal housing forms the exterior portion or at least a portion of the exterior portion (e.g., the lower portion P1001") of the pump P1000. In some embodiments, the metal housing is the lower portion P1001" of the pump and forms at least the bottom and the sides of the pump P1000. In some embodiments, the bezel is attached to the lower portion of the housing such that together they form a waterproof seal (as disclosed elsewhere herein). In some embodiments, the bezel P1001' is made of a plastic material or non-metallic material, though, in other embodiments, the bezel may be metal. In some embodiments, the bezel includes the curved indentation P1010 for activating a capacitive touch interface (as disclosed elsewhere herein). In some embodiments, the bezel holds the display P1007 (e.g., touchscreen display). In some embodiments, as disclosed elsewhere herein, the finger pad P1010 provides a depression (e.g., a concave portion, a curved indentation, etc.) to accommodate a finger of a user. In other embodiments, the finger pad is elevated, convex, and/or flush with the surrounding bezel (but called out with a traction pad, dimpling, an indentation running around the perimeter of the touch pad, etc.). In some embodiments, as disclosed elsewhere herein, the curved indentation P1010 may detect a finger touch by sensing the changes in capacitance using the capacitive sensor located on the circuit board under the bezel.

Figure 7A:
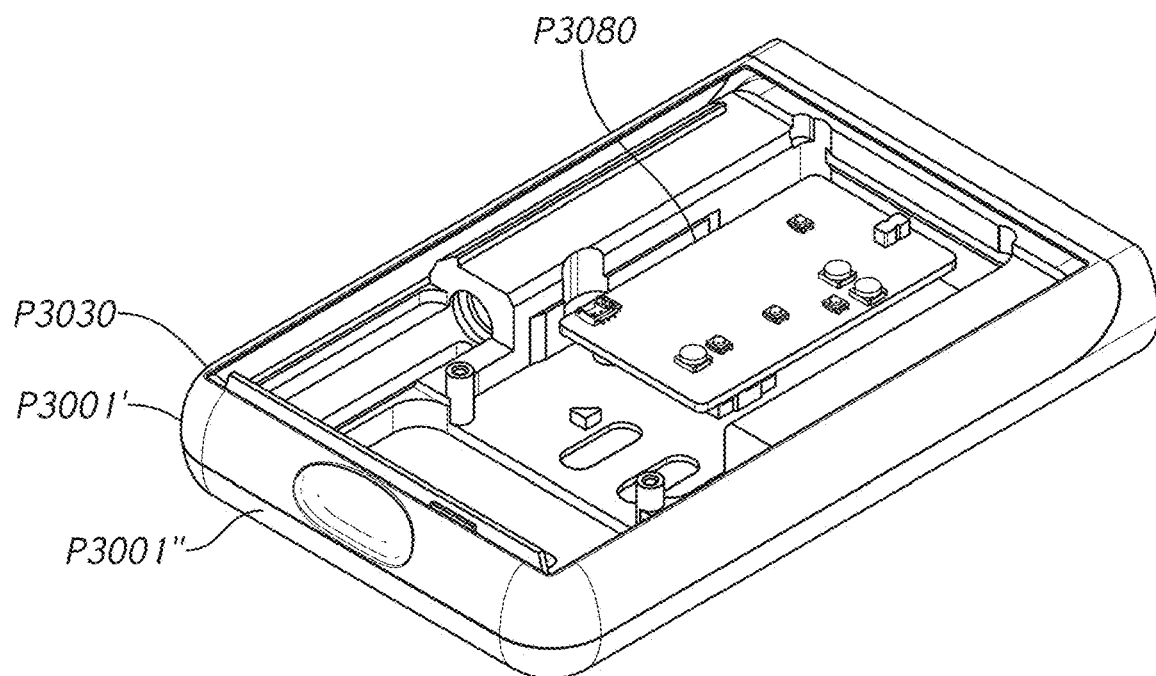
FIG. 7A is an illustration of another embodiment of a pump, shown without the display.

FIG. 7A is an illustration of another pump P3000 embodiment. As noted, for brevity not all of the features of each pump embodiment is mentioned, though any pump 1000, 2000, 3000 may have each feature described with respect another pump embodiment (except where a feature is explicitly distinguished). Additionally, as noted above, it should be recognized that, throughout this disclosure, similar and/or identical features for separate embodiments of a device or system component (e.g., pump, connectors, etc.), though not described for each different embodiment, are merely offset numerically by a factor of 1000 in the drawings (though they share hundreds, tens, and ones numerical values). For example, features of the receptacles P3100, P3110 of the pump P3000 of FIG. 7A may be common to those of the receptacle P1100, P1110 of the pump P1000 of FIG. 1A (or vice versa), though the features of the pump P3000 of FIG. 7A may not be detailed specifically where they are redundant. Likewise, features of the receptacles P3100, P3110 of the pump P3000 of FIG. 7A may be common to those of the receptacle P2100, P2110 of the pump P2000 of FIG. 4A (or vice versa), though the features of the pump P3000 of FIG. 7A may not be detailed specifically where they are redundant. Additionally, even where specific features are not highlighted with numerical called-outs in the figures, they may be present as will be apparent from the drawings themselves.

As shown, the pump P3000 is provided with the display removed. The lower portion P3001" of the housing P3001 forms the exterior portion of the ambulatory medical device. The bezel P3001' (which provides an upper portion of the housing) is attached on top of the lower portion P3001" of the housing. In several embodiments, a circuit board P1030 is attached to the inside of the bezel P3001'. In some embodiments, as disclosed elsewhere herein, the circuit board P3030 has a capacitive sensor that is in line with the curved indentation for the capacitive touch. In several variants, the circuit board P3030 is perpendicular to the metal housing the lower side surface of the housing and parallel to a portion of the bezel. The bezel may be made of a material that allows RF signals to pass through. The main board P3080 (e.g., primary PCB board P1080) controls any functions of the infusion system that are not controlled by the circuit board P1030.

Figure 7B:
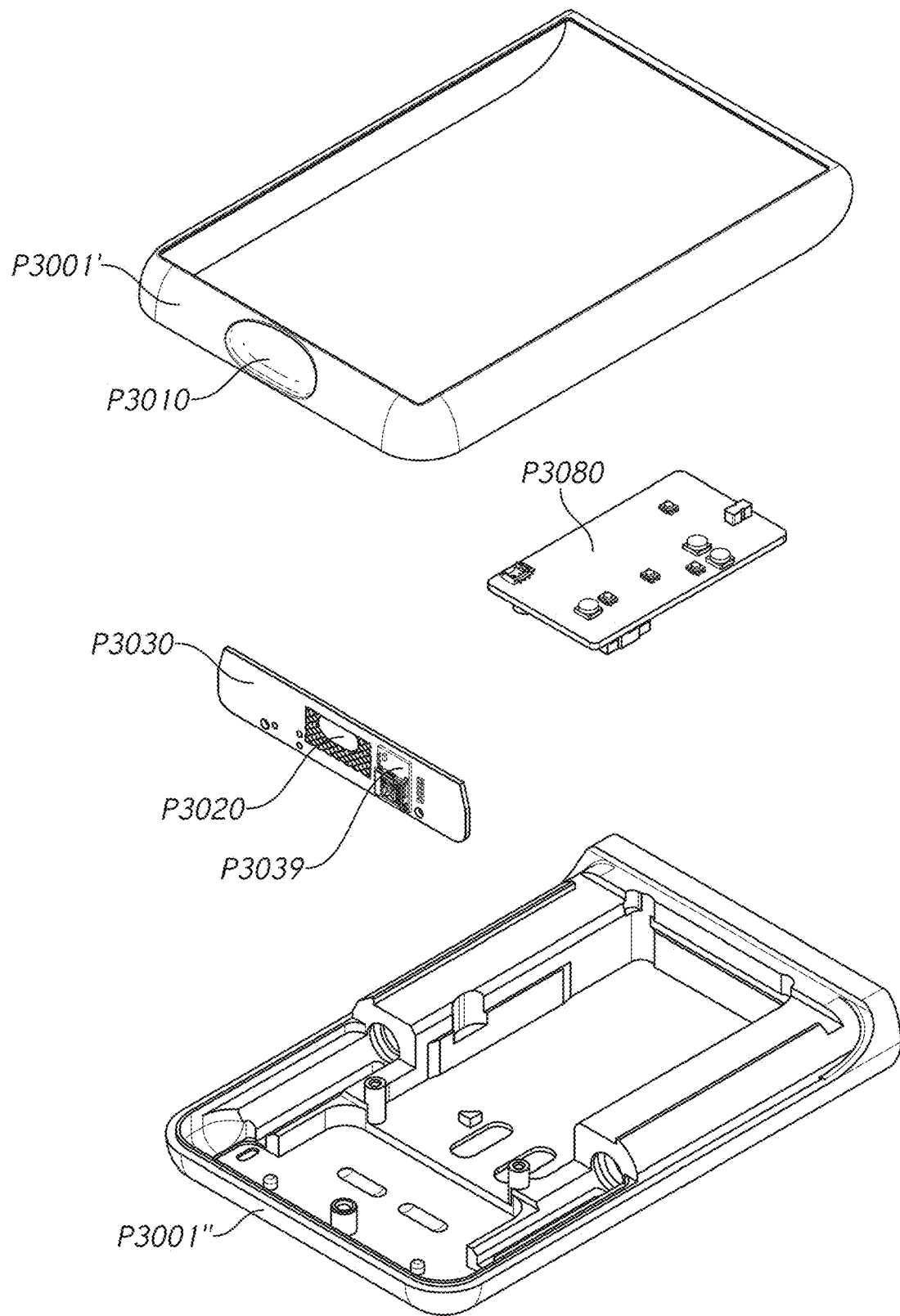
FIG. 7B is an illustration of an exploded view of the pump of FIG. 7A.

FIG. 7B is an illustration of an exploded view of portions of a pump. The lower portion of the housing P3001" (e.g., a metal portion of the housing) is separated from the bezel P3001' on top. As shown, in some embodiments, an antenna P3039 is provided. In several variants, the antenna P3039 is affixed to a secondary circuit board P3030, as shown. In several embodiments, the antenna P3039 sends and receives wireless signals (e.g., radio frequency, blue tooth, etc.). In several embodiments, the antenna P3029 is parallel to the bezel to receive wireless signals and/or runs along a length of a portion of the bezel. In some embodiments, the main board P3080 controls the pump features not controlled by the secondary circuit board P3030. In several embodiments, the secondary circuit board P3030 may have a capacitive touch pad P3020 and may sense changes in capacitance when a user places a finger into the curved indentation for capacitive touch P3010.

Figure 7C:
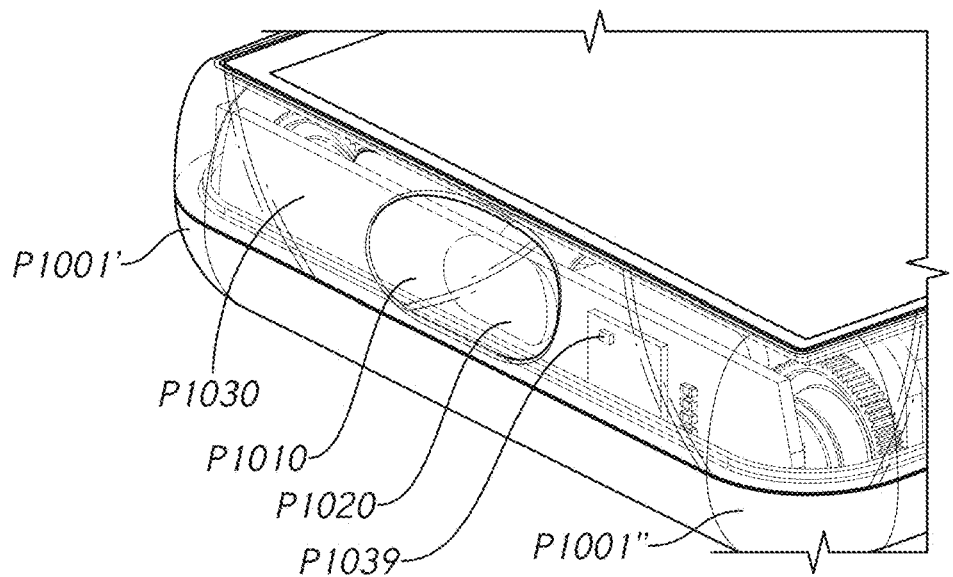
FIG. 7C is an illustration of the pump of FIG. 1A with a transparent bezel.

FIG. 7C is an additional illustration of the pump (of FIG. 1A) where the bezel has been made transparent. In some variants, the lower portion of the housing P1001" forms at least the bottom and sides of the pump. The clear bezel P1001' is attached on top of the lower portion of the housing P1001". In some embodiments, the circuit board P1030 is parallel to the clear bezel and the lower portion of the housing. In some embodiments, the antenna chip P1039 is attached to the circuit board P1030 that runs parallel to and in line with a capacitive sensor pad P1020 that is configured to receive input from the finger pad P1010. In several embodiments, the antenna chip P1039 is a protruding structure that is perpendicular to the bezel. In several embodiments, the antenna chip P1039 may receive and send wireless signals using Bluetooth, LTE, 3G, etc. In several embodiments, the signals produced by the pump are transmitted wirelessly to a user (e.g., a medical practitioner, parent of a child, the patient/wearer of the device, etc.) interface on a phone or computer, etc. In several embodiments, the lower portion of the housing is located below the antenna chip P1039 (e.g., the portion of the lower portion proximal and/or adjacent to the antenna chip terminates at a height that is lower than the height of the antenna chip). In some embodiments, the location of the antenna with respect to the housing P1001" substantially avoids, substantially prevents, and/or prevents interference with wireless signals. In some implementations, no metal portion of the housing intersects with a signal to the antenna. In some variants, the antenna chip P1039 is parallel to the curved indentation P1010. In several embodiments, the curved indentation P1010 is above (at a higher height than) the capacitive touch pad P1020.

Figure 7D:
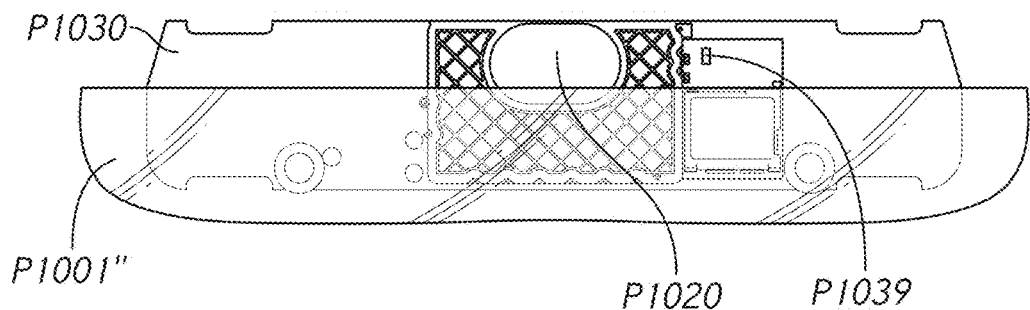
FIG. 7D is an illustration of the pump of FIG. 1A with a transparent metal housing and the bezel removed.

FIG. 7D is an illustration of the pump having the bezel removed and with the lower portion of the housing shown transparent. As noted elsewhere herein, in some embodiments, the lower portion of the housing P1001" is metal. In some variants, the metal housing P1001" forms at least the lower portion of the pump. The antenna P1039 is located above the metal housing and is attached to the circuit board P1030. The antenna P1039 is above the metal housing P1001" such that the antenna P1039 may receive and send wireless signals without interference. In some embodiments, the antenna P1039 may receive and send wireless signals using Bluetooth, LTE, or 3G. In some implementations, the capacitive touch pad P1020 is parallel to the antenna P1039.

In some embodiments, at least a portion of a sidewall of the pump is only covered by the bezel. In some embodiments, a circuit board is positioned adjacent to an inner surface of the bezel. In some embodiments, the wireless antenna is affixed to the circuit board such that the wireless antenna is positioned toward the portion of the sidewall of the ambulatory medical device that is only covered by the bezel. In some embodiments, a conducting layer of the circuit board is removed from a portion of the circuit board that is affixed to the wireless antenna. In some embodiments, a portion of the circuit board is positioned inside the portion of the sidewall of the ambulatory medical device that is only covered by the bezel. In some embodiments, the wireless antenna extends toward the portion of the side of the ambulatory medical device that is only covered by the bezel.

Error Detection System

Figure 7E:
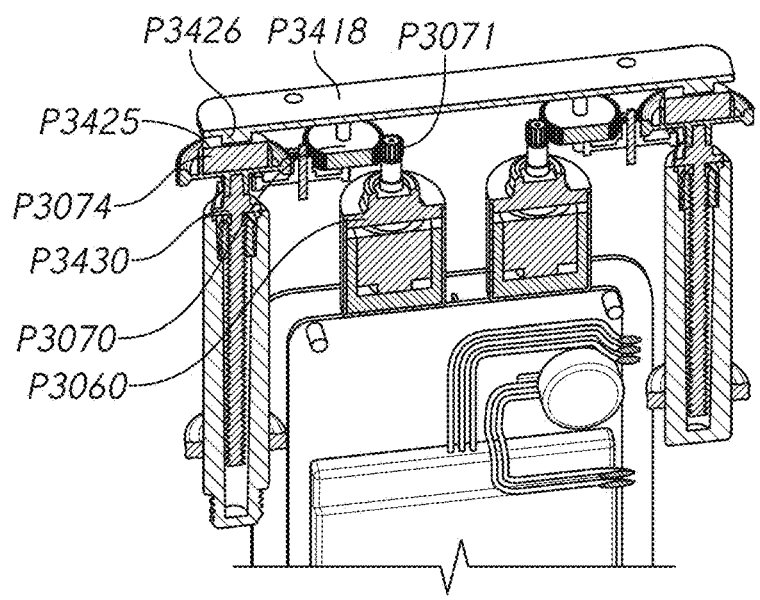
FIG. 7E is an illustration of the pump of FIG. 7A with an output shaft angular position error detection system.

FIG. 7E is an illustration of a portion of the pump P3000. In some embodiments, the pump P1000, P2000, P3000 as disclosed herein comprises an error detection system. In some embodiments, the error detection system is configured to determine when the calculated medicament distribution rate and/or amount (as indicated by, for example, the energy input to a motor) is different than the actual medicament distribution rate or amount (as calculated by revolutions of the lead screw). The view of 7E shows an embodiment of an output shaft angular position error detection system. In some implementations, the output shaft angular position error detection system determines that there is an error in the delivery of medicament from the pump. For example, in some embodiments, a sensor P3426 allows the pump to determine if the rotation of a lead screw P3430 is not in sync with the rotation of a motor P3060 (and/or is not calibrated correctly). In some embodiments, the pump comprises more than one sensor and/or the distribution of each medicament is monitored by a sensor. In some embodiments, for each motor, a sensor in the motor P3060 (e.g., a Hall sensor or mechanical sensor) records the number of rotations of the motor P3060. In some embodiments, the motor P3060 turns a gear P3071 that is a part of a gear assembly P3070. In some embodiments, part of the gear assembly P3070 is an output gear P3074. In some embodiments, the output gear P3074 has attached to it or on it a magnet P3425 that rotates on the coaxial axis of the output gear. In some embodiments a rotary position sensor P3426 detects the rotation of that magnet P3425 to determine the actual rotation of the lead screw P3430.

For example, the motor P3060 is controlled by Hall counts and monitors itself. However, the lead screw extension distributes the medicament. The rotary position sensor P3426 provides an independent precise understanding of the exact motion of the lead screw. In some embodiments, it is a redundant encoder that monitors the lead screw. This monitoring allows the user to diagnose any problems between the motors and the least screw (e.g., a broken gear, etc.). For example, if there was binding in the gear trains, disconnection, etc., without this sensor system, such an issue would not be registered. The encoder also provides real time monitoring of the movement of the lead screw. In some embodiments, any delays between communication to the motor from the display (or elsewhere) can be noted with the magnetic encoder.

In certain variants, the output gear P3074 turns an output shaft P3430 (e.g., lead screw), which operates to deliver a medicament to a user. In several embodiments, a magnet P3425 measures the angular position of the output gear P3074 by determining the angle of the magnet that is on the output gear P3074. In certain variants, the rotary position sensor P3426 is attached to a circuit board P3418. In some embodiments, data from the rotary position sensor P3426 and data from the sensor in the motor P3060 is transmitted to a computer in the pump (e.g., in a wired fashion or wirelessly using the antenna, etc.). In several embodiments, the computer may determine that the output shaft P3430 is not rotating in sync with the motor P3060 and generate an error based on the determination. In several embodiments, the computer may also determine the amount of medicament that the ambulatory medical device has infused into the user based on data from the rotary position sensor P3426 and the sensor in the motor P3060. The computer may determine the amount of medicament that has been infused into the user by multiplying the number of rotations of the motor P3060 by a predetermined volume of medicament per revolution of the motor P3060. The computer may also determine the amount of medicament that has been infused into the user by multiplying the number of rotations of the output shaft P3430 by a predetermined volume of medicament per rotation of the output shaft. The number of revolutions of the motor P3060 may be determined based on data from the sensor in the motor P3060. The number of rotations of the output shaft may be determined by data from the rotary position sensor P3426. In some embodiments, in response to an error determination, the computer may adjust the rotation of the motor pinion gear to provide a corrected dosing rate.

Figure 7F:
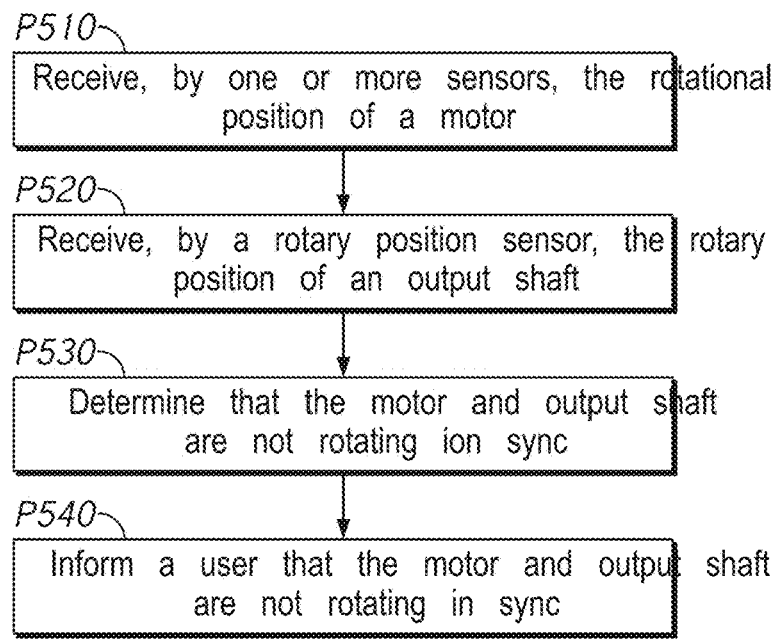
FIG. 7F is a flow diagram for a process of determining that there is an error in the delivery of medicament in the ambulatory medical device.

FIG. 7F provides a flow diagram for the process of determining that there is an error in the delivery of medicament in the pump. At step P510, the pump may receive, by one or more sensors, the rotational position of a motor in the ambulatory medical device. The motor operates to deliver medicament to the user. The sensor in the motor may be a Hall sensor that measures the number of rotations of the motor. At step P520, the ambulatory medical device may receive, by a rotary position sensor, the rotary position of an output shaft. In several embodiments, the output shaft is connected to the motor through a gear assembly. In some variants, the gear assembly may create a mechanical advantage that results in the output shaft rotating at a slower rate than the motor. At step P530, the ambulatory medical device may determine that the motor and output shaft are turning in sync based on the mechanical advantage created by the gear assembly. At step P540, the pump may inform a user that the motor and output shaft are not rotating in sync. In some embodiments, the pump may shut down the delivery of medicament to the user or may recalibrate to provide the correct distribution of medicament. Alternatively, the pump may display an error to the user while the system continues to deliver medicament to the user. In various embodiments, the pump may deactivate the motor that produced an error and activate a second motor in the ambulatory medical device. In some embodiments, where one type of medicament is being delivered using both medicament chambers, where an error is noted, the motor in the infusion line where the error occurred may deactivate in favor of the other motor (where an error did not occur).

Figure 7G:
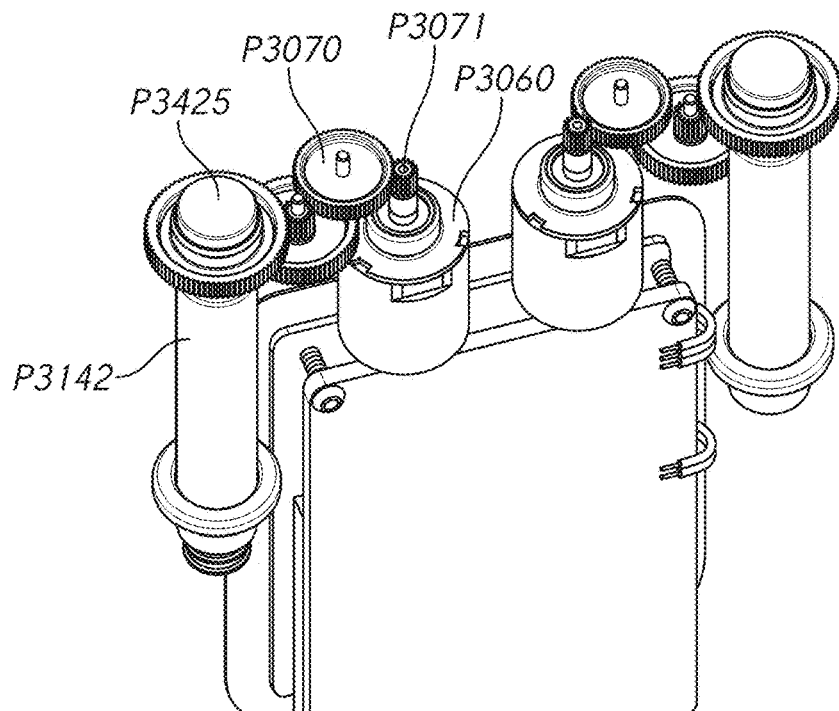
FIG. 7G is an illustration of the pump with an output shaft angular position error detection system.

FIG. 7G is an illustration of a portion of the pump showing the output shaft angular position error detection system. In several embodiments, as disclosed elsewhere herein, the pump may include a motor P3060, a gear P3071 attached to the motor, a gear assembly P3070, a magnet attached to an output shaft P3430 assembly with a piston P3142 (e.g., sheath, extendible shaft, etc.). In certain implementations, the motor P3060 has a sensor that determines the number of rotations of the motor P3060. In several embodiments, the sensor is a Hall sensor. In some embodiments, the motor turns a gear P3071 within the gear assembly P3070 and translating rotation to the fourth gear within the gear assembly P3074. In several embodiments, the gear assembly P3070 may create a mechanical advantage that operates to rotate the output shaft P3430 (e.g., lead screw) at a slower rate than the motor P3060. As the output shaft rotates, medicament is pushed out of a medicament cartridge and delivered into a user. In some embodiments, the magnet attached to the output shaft rotates P3430 with the output shaft. A rotary position sensor measures the angular position of the output shaft. Data from both the angular position of the output shaft and the number of rotations of the motor P3060 is compared by a computer in pump. The computer may generate an error if the computer determines that the output shaft P3430 and motor P3060 are not turning in sync. The computer may factor the mechanical advantage created by the gear assembly P3070 as the computer determines that the output shaft and motor P3060 are not turning in sync. Data from the angular position of the output shaft may also be used to determine volume of medicament that has been delivered to the user.

Figure 7H:
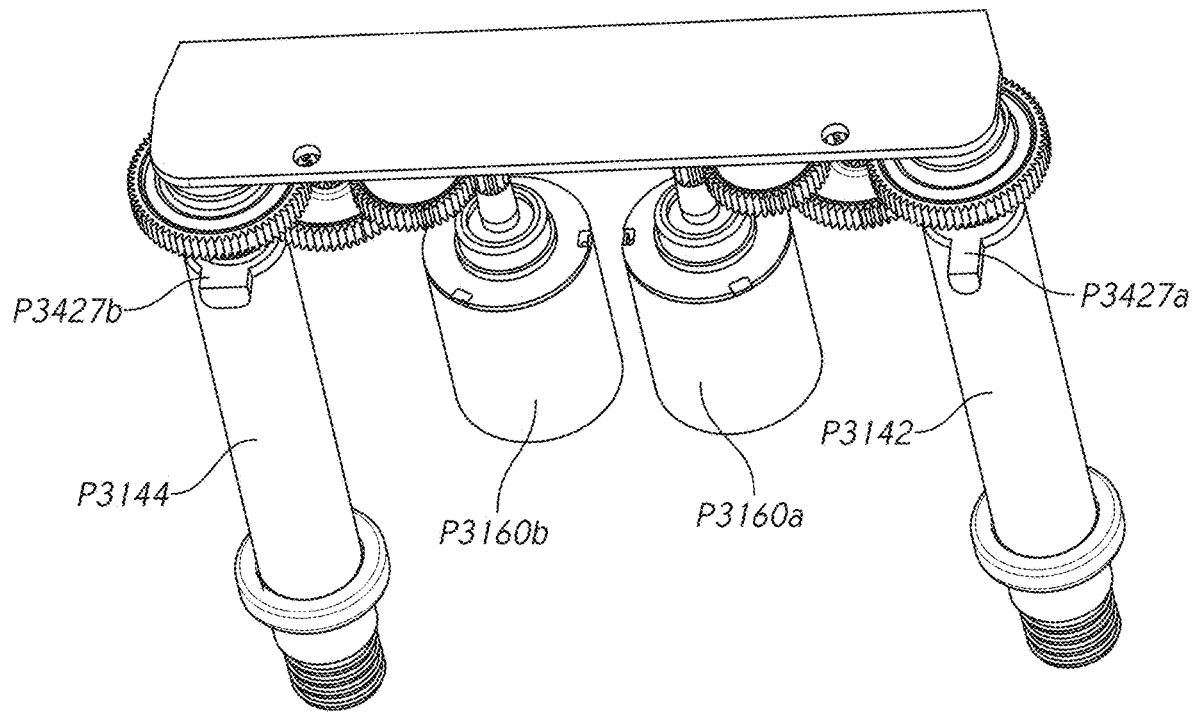
FIG. 7H is an illustration of a pump with two or more medicament cartridges.

FIG. 7H is an illustration of a portion of the pump showing two drive nuts configured to engage with two or more medicament cartridges. In some embodiment, the pump includes a first medicament piston P3142, a second piston P3144, a first motor P3060a, and a second motor P3060b. In some embodiments, a magnet used by a first rotary sensor for the first medicament chamber P3100 interacts with another magnet on a the drive nut. In some embodiments, the magnet for the second medicament chamber P3110 a interacts with a second rotating magnet. In some embodiments, first medicament cartridge may contain medicament that may be infused into the user. In some embodiments, the medicament in the first medicament cartridge is infused by the rotation of the first motor P3060a. Likewise, medicament may be contained in the second medicament cartridge. In some embodiments, medicament in the second medicament cartridge may be infused into the user by the rotation of the second motor P3060b.

In some embodiments, the cartridge slots of the housing of the ambulatory medical device may be shaped to exclude one or more medicament cartridges from being inserted into the cartridge slots. For example, a first cartridge slot (e.g., cartridge receptacle) in the housing of the pump may be shaped to exclude the second medicament cartridge from being inserted into the first cartridge slot. The first cartridge slot of the housing may be shaped to accept a shape of an alignment protrusion of the first medicament cartridge as the first medicament cartridge 2710 is inserted into the housing. Likewise, a second cartridge slot of the housing may be shaped to accept the shape of an alignment protrusion of the second medicament cartridge as the second medicament cartridge is inserted into the housing.

Figure 7I:
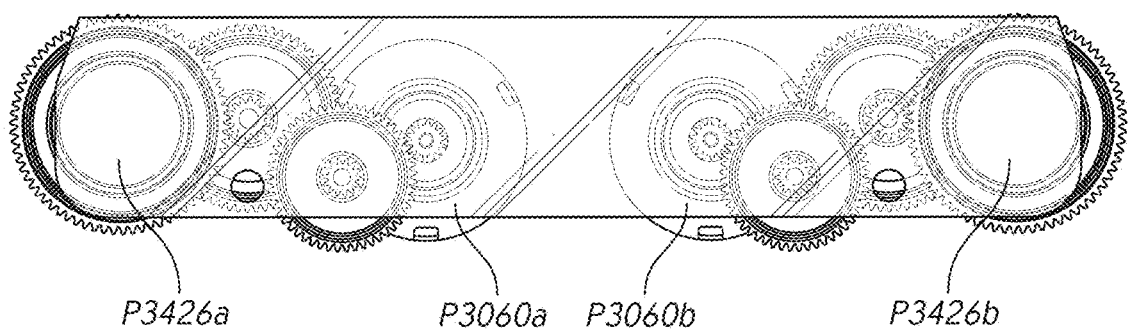
FIG. 7I is an illustration of an ambulatory medical device with an output shaft angular position error detection system.

FIG. 7I is an illustration of components of the pump with an output shaft angular position error detection system. In some embodiments, the pump includes a first motor P3060a, a second motor P3060b, a first rotary position sensor P3426a, and a second rotary position sensor P3426b. In several embodiments, a sensor in the first motor P3426a may determine the rate of rotation of the first motor P3060a. In several embodiments, the first rotary position sensor P3426a may determine the rate of rotation of a first output shaft. In several embodiments, a computer may determine that the first motor P3060a and first output shaft are not rotating in sync based on data from the sensor in the first motor P3060a and data from the first rotary position sensor P3426a. In several embodiments, the computer may switch the operating motor of the ambulatory medical device from the first motor P3060a to the second motor P3060b based on the determination. For example, the computer may deactivate the first motor P3060a and activate the second motor P3060b based on the determination that the first motor P3060a is not rotating in sync with the first output shaft. Likewise, the computer may determine that the second motor P3060b and second output shaft are not rotating in sync based on data from the sensor in the second motor P3060b and data from the second rotary position sensor P3426b. The computer may similarly deactivate the second motor P3060b and activate the first motor P3060a based on the determination that the second motor is not rotating in sync with the second output shaft.

O-Ring and Chambers

Various embodiments include one or more boundary sealing O-rings within the pump housing. In some embodiments, the placement of the O-ring seals the medicament chamber(s) from the internal portion of the pump. In several embodiments, however, the O-ring does not seal the cartridge receptacle(s) from the environment external to the pump. Thus, in several embodiments, an internal area of the cartridge receptacles is able to equalize with any atmospheric pressure outside and/or external to the pump. On the other hand, the area internal to the pump housing is sealed from the atmosphere (e.g., in an airtight and/or watertight manner) to prevent the ingress of harmful contaminants into the pump. Some embodiments have been designed in such a way to allow a drug cartridge to match the atmospheric pressure of the patient line and infusion site.

Differences in atmospheric pressures between the infusion site (e.g., an area external to the pump) and those felt at a drug cartridge sealed within an infusion pump can lead to under/over delivery of a medicament. For instance, in an embodiment where the pump cartridge chamber is sealed from the external atmosphere within the pump, the sealing of the cartridge chamber may occur at an atmospheric pressure eventually ends up being different than the atmosphere pressure of the external environment. If the patient seals the chamber at a high atmospheric pressure environment and moves to a lower pressure environment, a pressure differential may occur. In some embodiments, the pressure differential of high chamber pressure and low external pressure may force additional medicament to be distributed from the cartridge as the pressure within the pump attempts to equalize to the external pressure. To illustrate, if a patient loads a cartridge into an infusion pump at sea level (where atmospheric pressure is high) and then boards an airplane that proceeds to a cruising altitude, the pressure inside the cartridge chamber may be higher than the pressure outside pump at altitude (causing runaway and/or uncontrolled dosing of medicament). Alternatively, if the patient seals the cartridge chamber at a lower pressure atmosphere (e.g., at higher elevation, during low pressure weather events, in a plane, above sea level, at a mountain, etc.) and travels to a higher pressure atmosphere, (e.g., at or below sea level, during a high pressure weather event, etc.), a partial vacuum may be created within the cartridge receptacle (and pump) that impedes the movement of a plunger within the medicament cartridge, potentially leading to less medicament than is needed being delivered.

By providing a pump where the cartridge receptacle may equalize with the pressure external to the pump, these or other problems may be avoided. As noted elsewhere herein, some implementations provide an infusion pump (and/or infusion system) that is water-resistant or water-proof. Therefore, in several embodiments, where the cartridge chamber and the medicament cartridges themselves are not necessarily sealed from the environment (and/or are allowed to pressure equilibrate with the external environment) and because the cartridge chamber in the infusion pump may allow air and water to pass freely around the drug cartridges, the drug cartridge chamber and drug cartridge may be made airtight and/or watertight (or impervious or substantially impervious to the effects of the environment).

In some embodiments, the medicament cartridge chamber may be sealed substantially from the ingress of water (e.g., having a sealing mechanism that prevents water from infiltrating the cartridge area), but still, may allow air or gases to move through the seal to equalize the pressure differential between the infusion site and drug cartridge. In certain embodiments, the seal may be watertight but not airtight. In some embodiments, the seal provides an aperture between the cartridge connector that is sufficiently small so that the surface tension of water prevents its ingress, but does not prevent the ingress (or exiting) of air (or other gases).

In some embodiments, the quality of the seal between the medicament chamber and the internal area of the pump is characterized by an IP Code (or Ingress Protection Code, IEC standard 60529, sometimes interpreted as International Protection Code). An IP Code classifies and rates the degree of protection provided by mechanical casings against intrusion, dust, accidental contact, and water. The IP Codes provides two digits, one as a measure of solid particle barrier protection and the other as a measure of liquid barrier protection. The first digit following the "IP" in the IP code is indicative of the solid particle protection and the second is indicative of the liquid barrier protection. Thus, an IP code of IP 34 has a solid particle protection level of 3 and a liquid ingress protection of 4. For a solid particle, a level of 4 provides a seal against most wires, slender screws, large ants, etc. A level of 5 indicates that the ingress of dust is not entirely prevented, but it must not enter in sufficient quantity to interfere with the satisfactory operation of the equipment. A level of 6 indicates there is no ingress of dust; complete protection against contact (dust-tight). A vacuum must be applied. Test duration of up to 8 hours based on airflow. For liquid, a level of 1 indicates dripping water (vertically falling drops) shall have no harmful effect on the specimen when mounted in an upright position onto a turntable and rotated at 1 RPM. A level of 2 indicates vertically dripping water shall have no harmful effect when the enclosure is tilted at an angle of 15° from its normal position. A total of four positions are tested within two axes. A level of 3 indicates water falling as a spray at any angle up to 60° from the vertical shall have no harmful effect, utilizing either: a) an oscillating fixture, or b) a spray nozzle with a counterbalanced shield (test "a" is conducted for 5 minutes, then repeated with the specimen rotated horizontally by 90° for the second 5-minute test; test "b" is conducted (with shield in place) for 5 minutes minimum). A level of 4 indicates water splashing against the enclosure from any direction shall have no harmful effect, utilizing either: a) an oscillating fixture, or b) A spray nozzle with no shield. Test a) is conducted for 10 minutes. b) is conducted (without shield) for 5 minutes minimum. A level of 5 indicates water projected by a nozzle (6.3 mm (0.25 in)) against enclosure from any direction shall have no harmful effects. A level of 6 indicates water projected in powerful jets (12.5 mm (0.49 in)) against the enclosure from any direction shall have no harmful effects. A level of 7 indicates that the ingress of water in harmful quantity shall not be possible when the enclosure is immersed in water under defined conditions of pressure and time (up to 1 meter (3 ft 3 in) of submersion). A level of 8 indicates the equipment is suitable for continuous immersion in water under conditions (1 meter (3 ft 3 in) or more depth). A level of 9 indicates protection against powerful high-temperature water jets.

In some embodiments, the seal between the cartridge chamber and the internal area of the pump is characterized by a solid particle protection IP code number of greater than or at least: 4, 5, 6, or ranges spanning and/or including the aforementioned values. For example, the IP number for solid particle protection may range from 4 to 6. In some embodiments, the seal between the cartridge chamber and the internal area of the pump is characterized by a liquid ingress protection IP code number of greater than or at least: 2, 3, 4, 5, 6, 7, 8, 9, or ranges spanning and/or including the aforementioned values. For example, the IP number for liquid ingress protection may range from 2 to 6, from 4 to 8, from 3 to 9, etc. Additionally, the IP code may be IP42 to IP69, etc.

As disclosed elsewhere herein, some embodiments provide an infusion pump comprising an outer perimeter defined by the face P1002, backing P1003, lower side surface P1005, upper side surface P1004, first side surface P1006', and second side surface P1006" of the pump (as shown in FIGS. 1A-1D). In some embodiments, this outer perimeter provides the pump housing. In some embodiments, the pump comprises a bore, the bore having a first end and a second end and being configured to receive a first medicament cartridge. In some embodiments, the first end of the first bore defines an opening in the pump housing (e.g., a receptacle inlet port). In some embodiments, a side wall of the bore (e.g., a side wall of the cartridge chamber) extends longitudinally and internal into the housing to the second end of the bore. In some embodiments, the second end of the bore is located within the perimeter of the pump. In some embodiments, as disclosed elsewhere herein, a drive nut (e.g., an elongate shaft, a piston shaft, etc.) is disposed at least in part in the bore and is configured to engage and/or contact the first medicament cartridge when the first medicament cartridge is inserted into the first cartridge chamber. In some embodiments, the second end of the bore is an opening configured to accept an end of the drive nut. In some embodiments, in order to distribute a medicament from the pump, the drive nut extends into the bore via the second end of the bore and travels longitudinally toward the first end of the bore. In doing so, the piston urges a plunger of the first medicament cartridge forward, thereby distributing a medicament within the cartridge.

In certain implementations, as disclosed elsewhere herein, an O-ring is circumferentially disposed around the piston and provides a barrier and/or seal between the internal area of the pump and the external environment outside the pump. In some embodiments, a saddle for the O-ring abuts defines a bottom wall of the cartridge chamber at the second end of the bore. In some embodiments, the O-ring is positioned adjacent to the second end of the first bore, but outside the bore. In some embodiments, as disclosed elsewhere herein, the drive nut is configured to extend into the bore via rotation of a lead screw of the pump. In some embodiments, as the lead screw turns in one direction, the drive nut extends into the cartridge chamber along the bore. As the lead screw turns in the opposite direction, the drive nut retracts from the cartridge chamber along the bore. The O-ring may be fixed at a position adjacent to the second end of the bore and during movement of the drive nut.

In some embodiments, the pump also comprises a second bore with a first end and a second end. In some embodiments, the second bore shares one or more or all the features of the first bore but for the second bore being configured to distribute a medicament from a second cartridge. For example, the second bore may be configured to receive a second medicament cartridge. In some embodiments, the second bore is configured to receive a second drive nut. In some embodiments, the internal area of the pump is sealed from the external area of the pump by a second O-ring which forms a barrier to water and debris from entering the interior space of the pump. Where additional medicament chambers are provided, additional O-rings and drive nuts may be provided in similar fashion to those disclosed above.

In some embodiments, as disclosed herein, the O-ring may be configured to permit water or air movement around the medicament cartridge. In some embodiments, the O-ring is configured to permit pressure differential equalization between an infusion site and drug cartridge. In some embodiments, the O-ring exerts pressure on the elongated shaft when the O-ring is circumferentially disposed on the elongated shaft. In some embodiments, a lubricant to lubricate between the elongated shaft to reduce friction around between the O-ring and the elongated shaft is provided. In some embodiments, the O-ring is configured to maintain a pressure differential between ambient pressure and the interior space of the housing. In some embodiments, the O-ring is configured to maintain a pressure differential between the interior space of the housing and an interior of the bore. In some embodiments, the bore is configured to be exposed to an ambient pressure and equalize the ambient pressure. In some embodiments, the bore is configured to be exposed to an ambient pressure and equalize to the ambient pressure around the medicament cartridge. In some embodiments, the O-ring is compression fit over on the elongate shaft is configured to create a barrier to water and air ingress into the interior space of the housing.

Figure 7J:
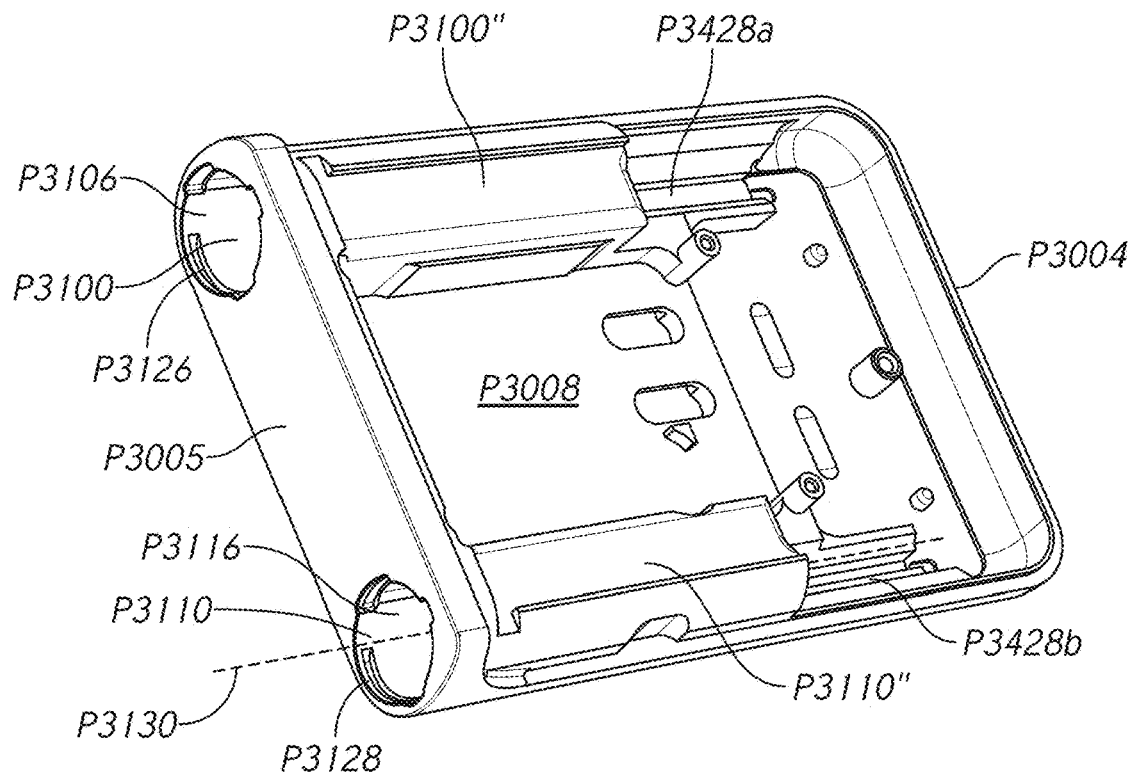
FIG. 7J is a perspective view of the interior space of an infusion pump housing, according to an exemplary embodiment.

As noted elsewhere herein, the infusion pump apparatus comprises a housing for various components. The housing can essentially take any shape suitable for receiving a medicament cartridge and incorporating components for dispensing the medicament from the cartridge. FIG. 7J shows the housing, with upper portion P3001' of the housing (e.g., the bezel and display P3007 removed. The interior of the pump P3008 may be designed to retain or receive certain components. In the example shown in FIG. 7J, the pump has an interior space P3008 as well as opposing top end making a part of the upper side surface P3004 and an opposing bottom end (e.g., the lower side surface P3005).

The infusion pump apparatuses of the exemplary embodiments may have one or more bores configured to receive a medicament cartridge. In general, the bores are cylindrical but may have any shape or modified features such as grooves or slots to receive features of a medicament cartridge as well as other components of the apparatus. FIG. 7J depicts an apparatus with a first and a second bore P3106 and P3116, respectively. Each bore has a first end (P3126, P3128) and a second end (not shown), where the first end defines an opening into the said housing and the second end is located in the interior space of the housing. The first openings are located at the first ends P3126 and P3128 of each bore P3122 and P3124, respectively. Each bore has a longitudinal axis P3130 along which other components translate (as further described below).

Figure 7K:
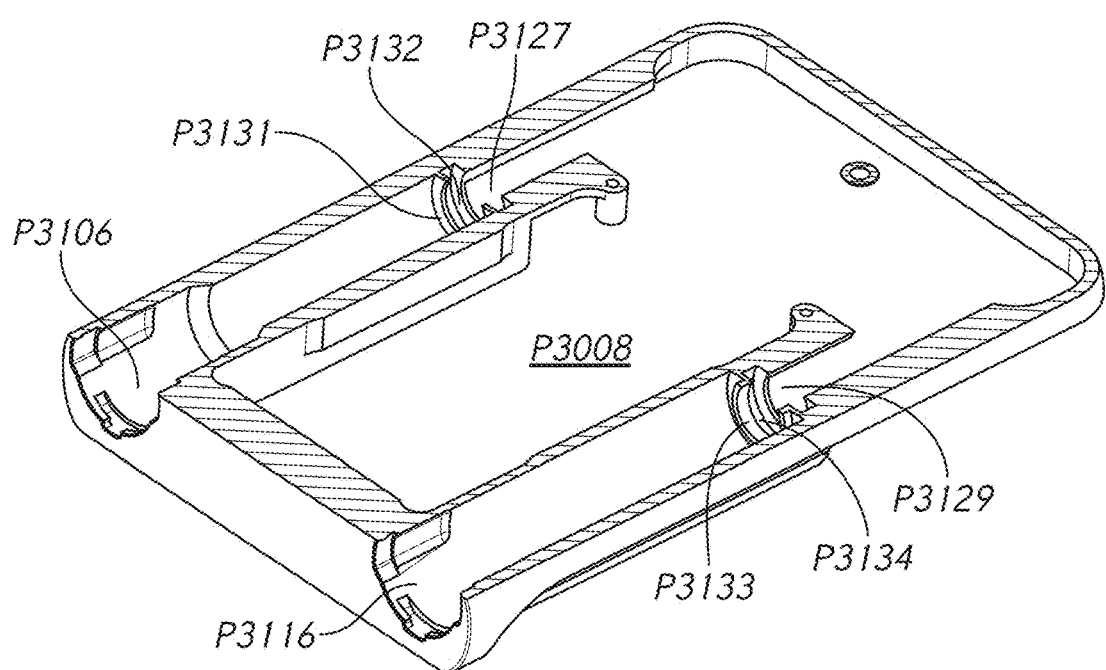
FIG. 7K is a cross-sectional view including the interior space of an infusion pump housing, according to an exemplary embodiment.
Figure 7L:
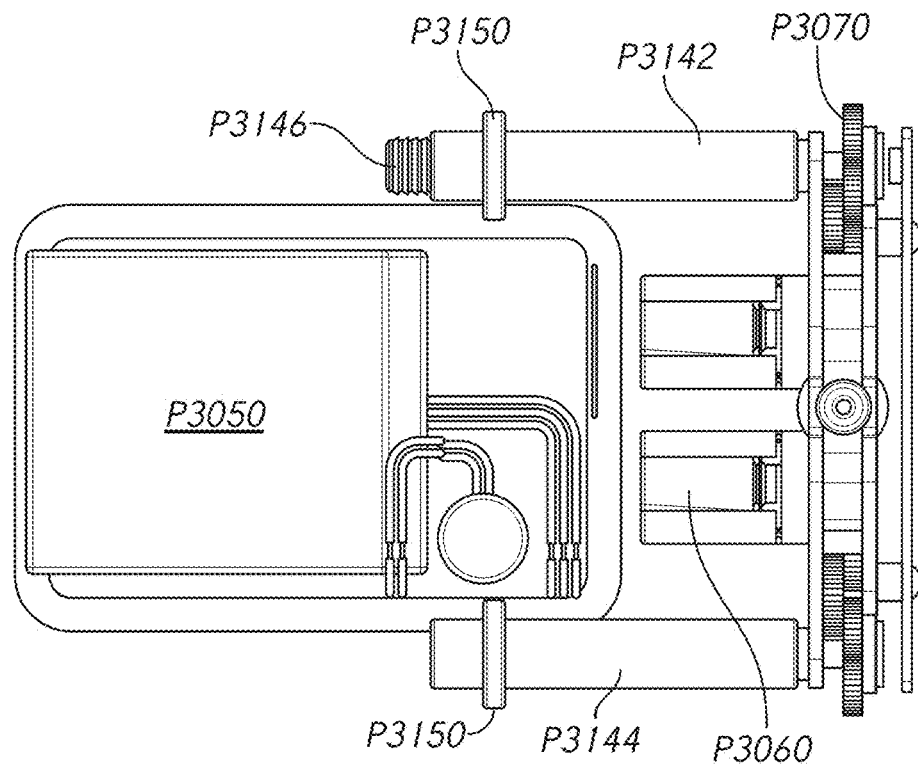
FIG. 7L is a top view of components in an infusion pump, according to an exemplary embodiment.

As shown in FIG. 7K, the O-rings (not shown) may be received by O-ring slots P3132 and P3134 (e.g., saddles, frames, etc.) that are located adjacent to the second ends P3127 and P3129 of the bores, respectively. Generally, the slots can take any shape that permits immobilizing the O-rings and forming a seal. For instance, the slots may be cylindrical and comprise a boundary which prevents the O-ring movement as the elongate shaft travels longitudinally in the bore. In some embodiments, the slots P3132 and P3134 may have a raised surface P3131, P3133 on both sides of the O-ring to immobilize the O-ring.

As shown in 7L, in some embodiments, the elongate shafts P3142 and P3144 which are disposed in the bores (not shown) may be driven by a motor P3060 and gears of a gear assembly P3070 to translate longitudinally within the bore. The motors may be powered by a battery P3050. In an exemplary embodiment, each elongate shaft comprises a lead screw that engages a drive nut (further described below) which engages a medicament cartridge (not shown). Moreover, as shown, one elongate shaft may further comprise a recognition portion P3146 (e.g., threads, nubs, openings, slots, etc.) or another end feature for identification of a coinciding medicament cartridge. This feature advantageously allows a user to determine which bore holds a particular medicament cartridge when different cartridges (e.g., glucagon and insulin) are disposed in the device concurrently. Also, shown are O-rings P3150 circumferentially disposed on each elongate shaft.

In several embodiments, the O-rings may be formed from any material suitable for achieving a seal and have different shape or thickness. In an exemplary embodiment, the O-ring for the elongate shaft comprises a polymeric material. In some embodiments, the O-ring is composed of a synthetic rubber, a thermoplastic, or combinations thereof. In some embodiments, the synthetic rubber comprises or consists of one or more of Butadiene rubber (BR), Butyl rubber (IIR), Chlorosulfonated polyethylene (CSM), Epichlorohydrin rubber (ECH, ECO), Ethylene propylene diene monomer (EPDM), Ethylene propylene rubber (EPR), Fluoroelastomer (FKM), Nitrile rubber, Perfluoroelastomer (FFKM), Polyacrylate rubber (ACM), Polychloroprene (neoprene) (CR), Polyisoprene (IR), Poly sulfide rubber (PSR), Polytetrafluoroethylene (PTFE), Sanifluor (FEPM), Silicone rubber, and/or Styrene-butadiene rubber. In some embodiments, the thermoplastic comprises or consists of one or more of Thermoplastic elastomer (TPE) styrenics, Thermoplastic polyolefin (TPO) LDPE, HDPE, LLDPE, ULDPE Thermoplastic polyurethane (TPU) polyether, polyester: Thermoplastic etheresterelastomers (TEEEs) copolyesters, Thermoplastic polyamide (PEBA) Polyamides, Melt Processible Rubber (MPR), and/or Thermoplastic Vulcanizate (TPV).

Moreover, the O-rings can be of different sizes as exemplified in 7N. In some embodiments, the differently sized O-rings engage differently sized drive nuts that are configured to engage differently sized medicament cartridges (e.g., cartridges with different circumferences). Further, the O-ring can be compression fit over the elongate shaft to create a barrier to water and air ingress into the interior space of the housing. For sealings, there are variations in cross-section design other than circular. In some embodiments, a cross section of the O-ring is X-shaped profile, square-shaped, or circular. In some embodiments, using the square (or quad shaped O-ring), when squeezed upon installation, they seal with multiple (1, 2, 3, or 4) contact surfaces (e.g., 2 small contact surfaces on the top and bottom, one on each side in the saddle).

Figure 7M:
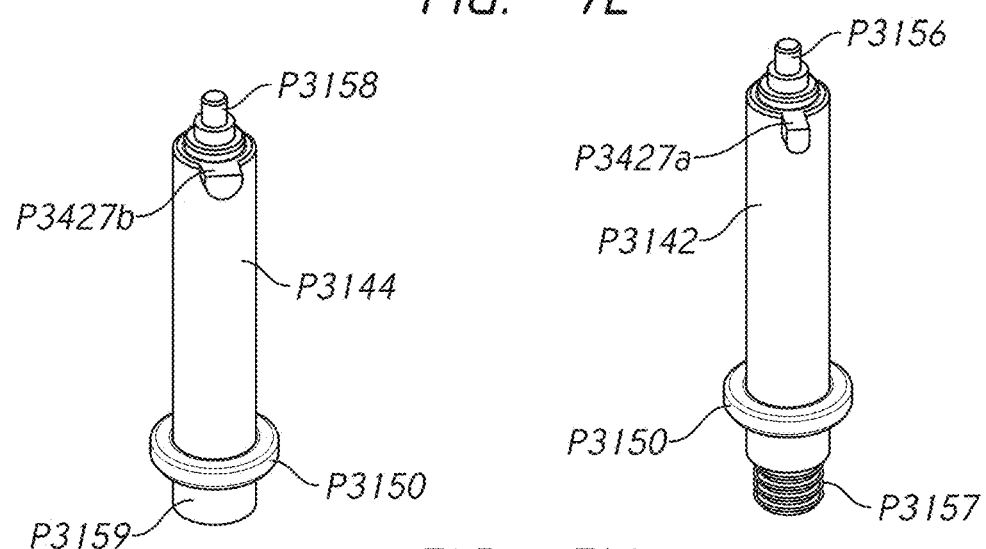
FIG. 7M is a perspective view of elongate shaft members of an infusion pump, according to an exemplary embodiment.
Figure 7N:
FIG. 7N is a perspective view of two O-rings of an infusion pump, according to an exemplary embodiment.
Figure 7O:
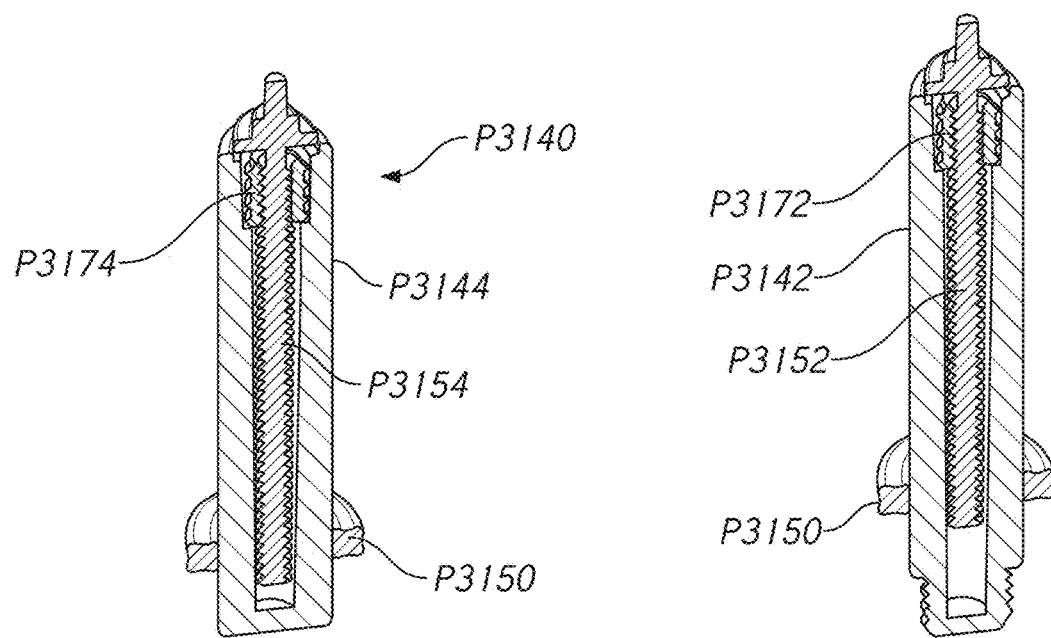
FIG. 7O is a cross-sectional view of elongate shaft members of an infusion pump, according to an exemplary embodiment.
Figure 7P:
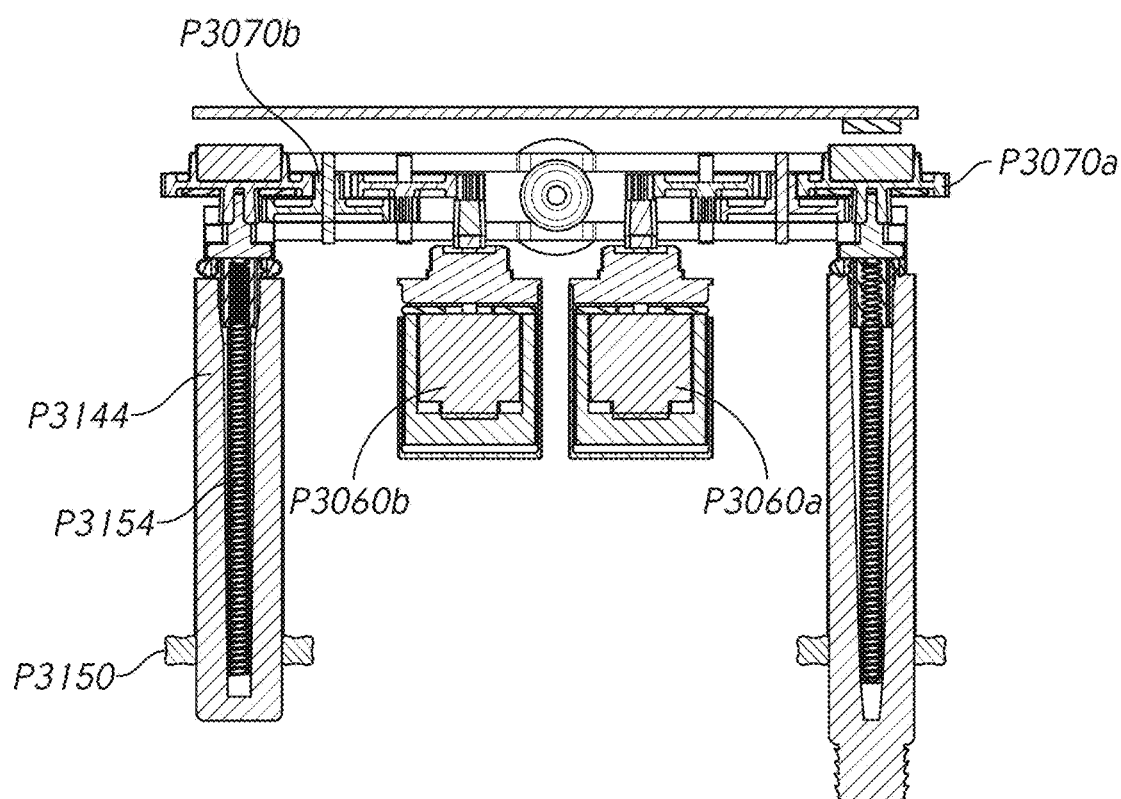
FIG. 7P is a top cross-sectional view of the components of an infusion pump, according to an exemplary embodiment.
Figure 7Q:
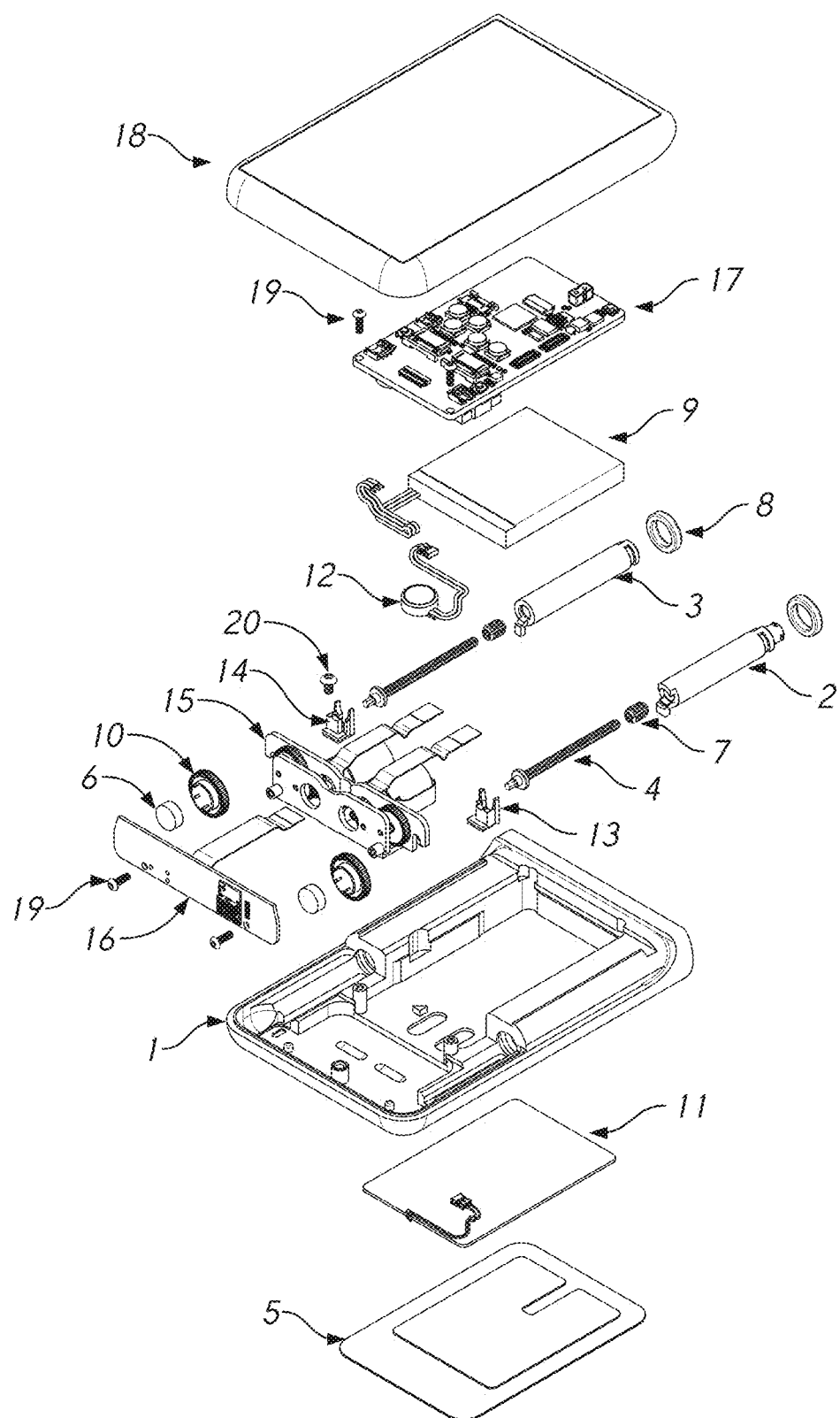
FIG. 7Q is an exploded view of the components of an infusion pump, according to an exemplary embodiment.

As shown in 7M, in some embodiments, the O-rings P3150 are near to the first ends P3157 and P3159 of two elongate shafts P3142 and P3144 when the shafts are fully retracted in the pump and opposite the seconds ends P3156 and P3158, respectively. In some embodiments, as shown in 7O, the elongate shafts P3142 and P3144 each comprise a lead screw P3152, P3154 threadedly engaged with the drive nut P3142, P3144 and/or with a treaded insert P3172, P3174. In some embodiments, the drive nut acts as a lead screw nut for the lead screw. In some embodiments, the lead screw P3152, P3154 engages the drive nut P3142, P3144 via the threaded insert P3172, P3174 shown in FIG. 7N. A piston assembly P3040 is shown for the second piston P3144. In some embodiments, as shown in 7M, 7N, and 7P, the motor P3160a, P3160b drives the gears P3070 engaging the lead screw P3154. In some embodiments, movement of the lead screw P3152, P3154 translates rotational energy to the threaded insert P3172, P3174. In some embodiments, the threaded insert P3172, P3174 is fixed within the drive nut P3142, P3144 and, as the lead screw P3152, P3154 rotates, the threaded insert P3172, P3174 creeps longitudinally along lead screw P3152, P154 causing the drive nut P3142, P3144 to extend within the medicament chamber longitudinally towards the first end of the bore (not shown). In some embodiments, as discussed elsewhere herein, the engagement between the drive nut and the threaded insert are fixed together (e.g., the threaded insert is sonically welded, glued, or otherwise fixed within the drive nut). In some embodiments, as the drive nut P3142, P3144 is urged forward or backward, the rotational motion of the lead screw P3152, P3154 against the threaded insert P3174 does not rotate the drive nut P3144. For instance, as shown in FIG. 7M, in several embodiments, the first and second drive nuts P3142, P3144 have first and second tongues P3427a, P3427b, respectively, that are seated within first and second grooves P3428a, 3428b (e.g., tracks) that prevent rotation of the drive nuts P3142, P3144. In some embodiments, the O-ring, which is immobilized in the bore, remains in place yet still circumferentially disposed on the lead screw nut P3172 portions of the elongate shaft during drug delivery. In some embodiments, the lack of rotation about the drive nut P3142, P3144 lowers rotational friction between the drive nut P3142, P3144 and the O-ring and/or the medicament cartridge plunger.

In some embodiments, protrusion P3427a of the first drive nut may be shaped differently from the protrusion P3427b of the second medicament drive nut. In some variants the first and second grooves P3428a, 3428b (e.g., tracks) may be shaped differently from each other and may be configured to engage the first and second protrusions P3427a, P3427b of the first and second drive nuts P3142, P3144, respectively. In some variants, the first and second grooves P3428a, 3428b (e.g., tracks) may be configured to not engage the second and first protrusions P3427a, P3427b, respectively.

In an exemplary embodiment, the O-ring seal exerts pressure on the elongated shaft when the O-ring is circumferentially disposed on the elongated shaft. A lubricant may be included to lubricate the elongated shaft to reduce the friction between the O-ring and the elongated shaft.

A non-limiting example of an embodiment is provided in 7Q. As shown, the housing portion bottom portion 1 engages the housing top portion 18, which comprises a display. The back cover 5 is included to fully encase the housing. A battery 9 powers the PCBA main board and vibrator 12. O-rings 8 are placed on the lead screw nuts 2 and 3. The lead screw nut 2 is attached via a threaded insert 7 to the lead screw 4. The piston 2 engages a glucagon cartridge while other piston 3 engages an insulin cartridge. The drive train assembly 15, and spur gear 10 act to mechanically actuate elongate shaft.

The features of the exemplary embodiments described in this disclosure provide various advantages. First, the O-ring seal around the elongate shaft forms a barrier to water and debris entering the interior space of the housing. This can prevent interference with the mechanical action of the pump and avoid potentially dispensing an incorrect amount of medicament.

Additionally, the position of the O-ring near the second end of the elongate shaft permits water or air movement around the cartridge whereby the pressure differential between the infusion site and the medicament cartridge is equalized.

Yet another advantage of the exemplary embodiments is that the infusion pump does not utilize an O-ring to seal the junction between the infusion set and the top of the medicament cartridge. In particular, the O-ring is not placed adjacent to the opening to the pump housing. This allows for a design which does not require a hydrophobic filter, as such filters become plugged, thereby affecting the pressure inside the pump housing. Moreover, a permanent installed hydrophobic filter would unlikely be able to last the full warranty period of the device, which forces the filter and complexity to be added to the disposable device which raises the costs and complexity on the disposable device.

The use of an O-ring as described can result in the pump apparatus being configured to maintain a pressure differential between the ambient pressure and the interior of the housing. Moreover, the pump apparatus can be configured to maintain a pressure differential between the interior of the housing and an interior of the bore. Yet another advantage is that the bore is configured to be exposed to the ambient pressure and equalize the ambient pressure around the medicament cartridge. Thus a seal at the bore first opening is not required. Additionally, the wiping action of the O-ring against the lead screw nut prevents water and dust ingress into the enclosure and provides a durable seal.

Other designs may include features that seal against the disposable cartridge or connector using O-rings to seal the pump surface to a flat surface on the disposable. One disadvantage of the previously mentioned design is that the sealing surface of the O-ring is exposed to the environment during set changes and can allow contamination to accumulate on the sealing surface of the O-ring causing the failure of the O-ring to provide adequate IPX sealing of the device. This can lead to seal failure and the ingress of water and fluids into the drug cartridge. The advantages of choosing the IPX seal boundary to not encompass allows the removal of the hydrophobic filter mechanism, as it is no longer needed. Water and air can freely move around the cartridge equalizing pressures. The O-ring seal thus provides the IPX seal to the device, preventing water and dirt from entering the electronic and motor/gear train enclosure. The O-ring application around the lead screw nut provides a smooth continuous surface for sealing and prevents exposure of the sealing surface to environmental contaminants. The wiping action of the O-ring against the lead screw nut prevents water and dust ingress into the enclosure and provides for a durable seal.

As disclosed elsewhere herein, in alternative embodiments, a seal (e.g., by an O-ring, polymeric sealing feature, etc.) is provided between a cartridge connector and the pump to seal the cartridge chamber from the external environment. In such an embodiment, pressure differentials may occur between the cartridge chamber and the external environment. In some embodiments, the seal between the cartridge chamber and the external atmosphere (outside the pump) is characterized by a solid particle protection IP code number of greater than or at least: 4, 5, 6, or ranges spanning and/or including the aforementioned values. For example, the IP number for solid particle protection may range from 4 to 6. In some embodiments, the seal between the cartridge chamber and the external atmosphere is characterized by a liquid ingress protection IP code number of greater than or at least: 2, 3, 4, 5, 6, 7, 8, 9, or ranges spanning and/or including the aforementioned values. For example, the IP number for liquid ingress protection may range from 2 to 7, from 5 to 8, from 4 to 9, etc.

Some embodiments pertain to a method comprising: implementing a seal between an interface of a medicament cartridge receiving chamber sand the medicament cartridge, the medicament cartridge receiving chamber being configured to mate with the medicament cartridge in an abutting relationship. In some embodiments, an O-ring is placed adjacent to a first end of an elongate shaft, opposite to a second end of the elongate shaft, engaging a lead screw of the elongate shaft, connected to a lead screw nut. In some embodiments, a gear engaging the lead screw is driven so as to translate the lead screw nut longitudinally towards the first end of the elongate shaft during medicament delivery. In some embodiments, the O-ring remains immobilized in a medicament cartridge receiving chamber and yet circumferentially disposed on the lead screw nut. In some embodiments, the O-ring exerts a pressure on the elongated shaft when the O-ring is circumferentially disposed on the elongated shaft. In some embodiments, a lubricant is used to lubricate the elongated shaft to reduce a friction between the O-ring and the elongated shaft. In some embodiments, the medicament cartridge is a glucagon cartridge. In some embodiments, the medicament cartridge is an insulin cartridge. In some embodiments, a drive train assembly and a spur gear act to mechanically actuate the elongate shaft. In some embodiments, the O-ring assists in maintaining a pressure differential between an ambient pressure and an interior of the medicament cartridge receiving chamber. In some embodiments, a position of the O-ring is configured to permit water or air movement around the medicament cartridge. In some embodiments, the O-ring comprises a polymeric material.

Vacuum to Avoid Lift-Off

Medicament vials having plungers are typically designed to have little or no resistance and/or friction between the plunger and the wall of the reservoir. Thus, the plunger can move and distribute medicament with very little force applied to the plunger (e.g., even by moving the cartridge, lifting the pump comprising the cartridge, etc.). This unwanted distribution is caused by the plunger lifting off the drive nut of a pump. In some embodiments, configurations described herein avoid issues with low friction plungers and/or lift-off. In some embodiments, to avoid lift-off, a vacuum is generated in the delivery chamber which is sufficient to restrain the plunger under conditions of free flow. In some embodiments, an air-tight seal between the lead screw nut and the housing is used. In some embodiments, an air-tight seal between the cartridge connector and the outside environment is used. In some embodiments, this makes a sealed chamber which contains the exposed portion of the lead screw, the cartridge, the plunger and the medicament. When the lead screw is advanced to dispense, some portion of the lead screw is exposed in the chamber, the plunger moved and medicament is moved out of the chamber. Since the lead screw is smaller than the plunger there is a net reduction in material volume in the sealed chamber resulting in a reduction in air pressure relative to the ambient air pressure. This results in a force being generated on the plunger that will resist the free flow condition.

In some embodiments, a certain amount of lead screw advancement is used to generate enough negative pressure to overcome the free flow, so the system can be designed to account for the total air volume in the chamber, the relative size of the lead screw and plunger and the volume of liquid evacuated during the prime to ensure that there is sufficient negative pressure after the prime. In some embodiments, the pressure will continue to decrease over the delivery resulting in increased force from the drive mechanism to overcome it. In some embodiments, the system is designed to ensure that the negative pressure generated is within the ability of the drive system to overcome. In an alternative embodiment, a check valve can be added to allow air to enter the chamber only if the pressure exceeds a negative limit.

Docking Station

Figure 8:
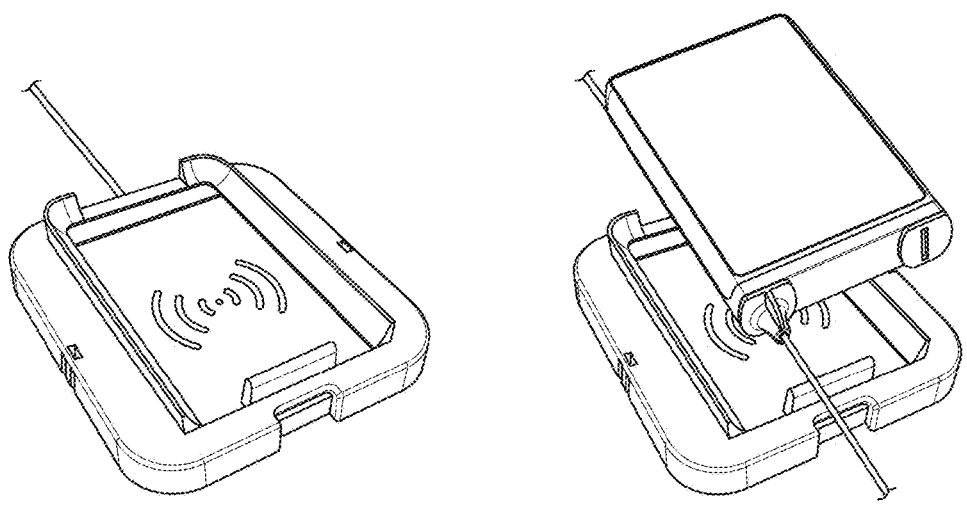
FIG. 8 is a perspective drawing of an embodiment of an inductive charger.

As noted elsewhere herein, in some embodiments an inductively chargeable battery is provided. In some embodiments, the pump 1000 comprises an inductive charging pad P1003' (shown in FIG. 1E) configured to allow charging of the inductively chargeable battery P1050. In some embodiments, the pump battery is not replaceable. In some embodiments, the pump is charged using an inductive charging pad/cradle and USB cable (as shown in FIG. 8). In some embodiments, the cradle is magnetized to hold the pump in place. In some embodiments, the cradle includes guide features, as shown, that aid in guiding the pump into place.

In some embodiments, to recharge a pump, one or more of the following steps can be performed: connect the wireless charging pad to the wall power outlet using the provided micro USB cable and plug, place the pump onto the supplied inductive charging pad, verify the touchscreen and the charging pad indicate that the pump is charging, and charge the pump with the supplied charging pad and cables.

In some embodiments, when placed on the charger, the touchscreen turns on and illuminates. In some embodiments, the touchscreen displays the state of charge and/or indicates that the pump is charging. In some embodiments, the light on the charging pad illuminates continuously while charging and blinks when it detects the presence of a pump but is not charging. In some embodiments, the pump indicates it is not charging and is not fully charged when the charging pad is blinking. In some embodiments, if the pump is not charging, the user can verify that the pump is properly aligned over the charging pad. In some embodiments, a depleted battery is configured to recharge in equal to or less than about 2 hours, 4 hours, or ranges including and/or spanning the aforementioned values.

In some embodiments, it may be beneficial to minimize the amount of time when the pump is without power. In some embodiments, when pump has no power, it will not be dosing insulin or providing the user with continuous glucose monitoring CGM values. In some embodiments, when the pump has run out of power, the Sleep/Wake button will not turn the screen on or off.

In some embodiments, for optimum battery life, it is recommended that the batter is recharged daily, regardless of what the battery level is reported as on the screen. In some embodiments, a fully charged battery can run several days for a typical user, but is dependent on amount of usage, especially of the backlight and volume of insulin delivered. In some embodiments, the user should monitor the battery charge level and alarms to determine what is typical battery life for the user. In some embodiments, the user should recharge the pump according to typical usage.

In some embodiments, the system includes a wireless charging interface that conforms to a Qi standard. In some embodiments, the wireless charging include Rezence (from the AirFuel Alliance) and Open Dots (from the Open Dots Alliance).

Certain embodiments may comprise the following specifications:

| Specification Name | Specification |
| --- | --- |
| USB Wall Charger, P/N | Q3002-US, UL Listing E141650 |
| Input | 100 to 240 Volts AC 50/60 Hz, 0.8 A Max |
| Output Voltage | 5 VDC/3.0 A, 9VDC/2.0 A, 12VDC/1.5 A |
| Output Connector | USB type A |

| Specification Name | Specification |
| --- | --- |
| Inductive Charging Pad w/USB Cable, P/N | TS511-S Choetech USB Cable USB A to USB Micro B, 1 meter |
| Input Volt/Current | 5 Volts/2 A, 9 V/1.8 A |
| Output Power | 10 W (Max) |
| Output Type | Qi Inductive Charger |
| Connector | USB Micro B |

Cartridge Connectors

As disclosed elsewhere herein, some embodiments, pertain to one or more cartridge connectors and/or a cartridge connector set (comprising cartridge connectors). In some implementations, the cartridge connector(s) (or cartridge connector set) is a part of lumen assembly (e.g., a multi-channel lumen assembly), as disclosed elsewhere herein. In some implementations, a cartridge connector (or a cartridge connector set) is a part of an ambulatory infusion system, as disclosed elsewhere herein. In some embodiments, an infusion system comprising the cartridge connector set is provided. In some embodiments, the connector set comprises a single cartridge connector. In some embodiments, the connector set comprises two, three, four, or more cartridge connectors that may be the same or different. In some embodiments, the cartridge connector set includes fluid conduits that are attached to the cartridge connectors. In some embodiments, the cartridge connector set further comprises infusion connectors that connect to an infusion set (which includes implements such as needles configured to infuse a subject with a medicament or medicaments).

FIG. 9A shows a cartridge connector set C1000 configured to engage the pump P1000 of FIG. 1A. In some embodiments, as shown in FIGS. 9A and 9B, the cartridge connectors C1001, C1101 comprise a body C1002, C1102. In some embodiments, the body C1002, C1102 comprises a piercing element C1003, C1103 (e.g., a needle). In some embodiments, the piercing element is configured to pierce the septum of a medicament cartridge and/or to receive a medicament from a medicament cartridge (e.g., when the cartridge is inserted into the connector). In some embodiments, the cartridge connectors C1001, C1101 comprise a lower surface portion C1004, C1104 extending circumferentially from the needle C1003, C1103 to a skirt C1005, C1105 (e.g., axially extending side wall, shroud, etc.) of the connector. In some embodiments, the shroud extends axially away from the lower surface portion. In some embodiments, the shroud is configured to receive and fit over a portion of a medicament cartridge.

Figure 10A:
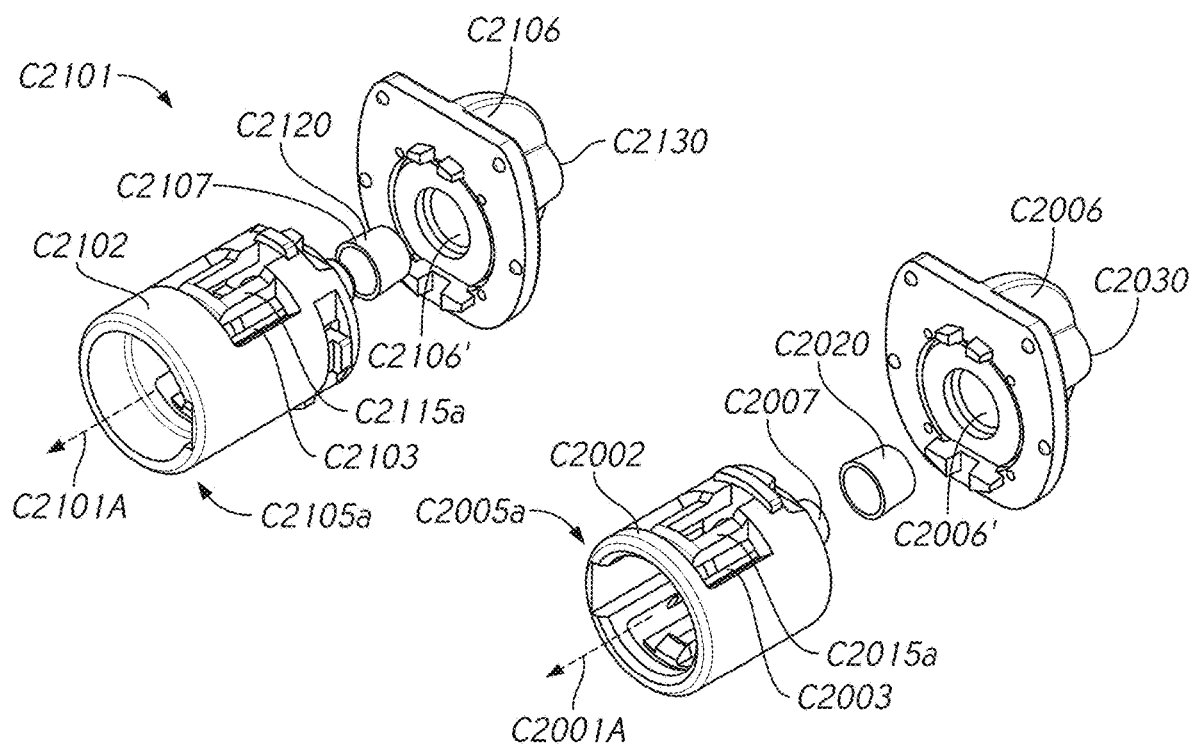
FIG. 10A is a view of another embodiment of a cartridge connector set comprising two cartridge connectors.

In several embodiments, the lower surface portion C1004, C1104 is located within the shroud C1005, C1105 and is configured to contact a cap of the medicament cartridge when the medicament cartridge is inserted into cartridge connector (e.g., within the shroud). In some embodiments, as shown, the needle C1003, C1103 extends axially from the lower surface portion C1004, C1104 within the shroud C1005, C1105. In some embodiments, the needle does not extend passed the shroud. FIGS. 9A and 10A provide views of a cartridge connector shroud and skirt ring at the bottom of the shroud (e.g., distal from the lower surface portion C1004, C1104 of the connector).

Figure 9C:
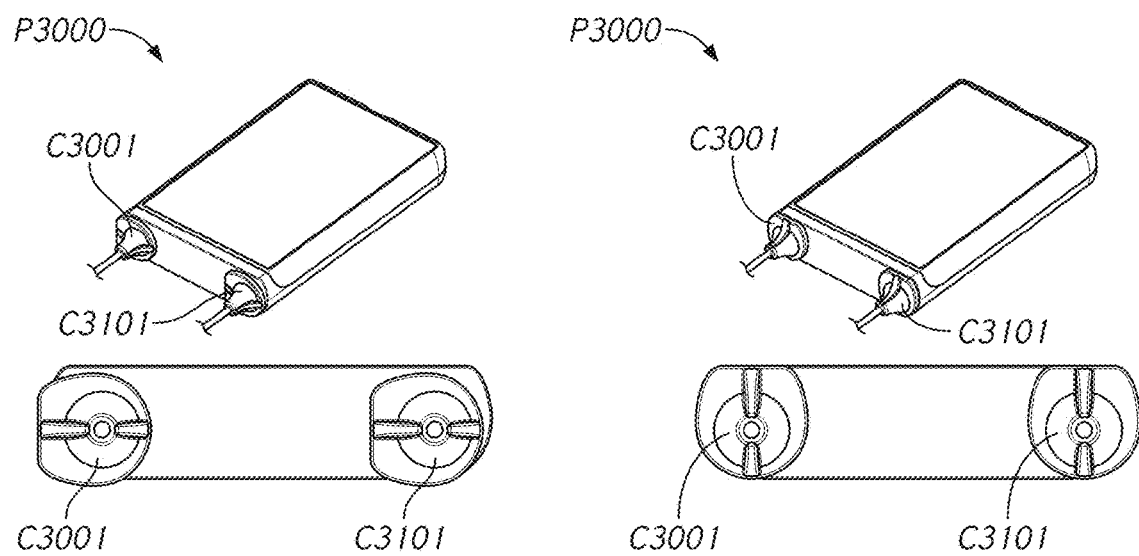
FIG. 9C illustrates an embodiment of the cartridge connector providing a visual indication of when the connectors from the connector set are unlocked or locked within the pump chamber, respectively.
Figure 9D:
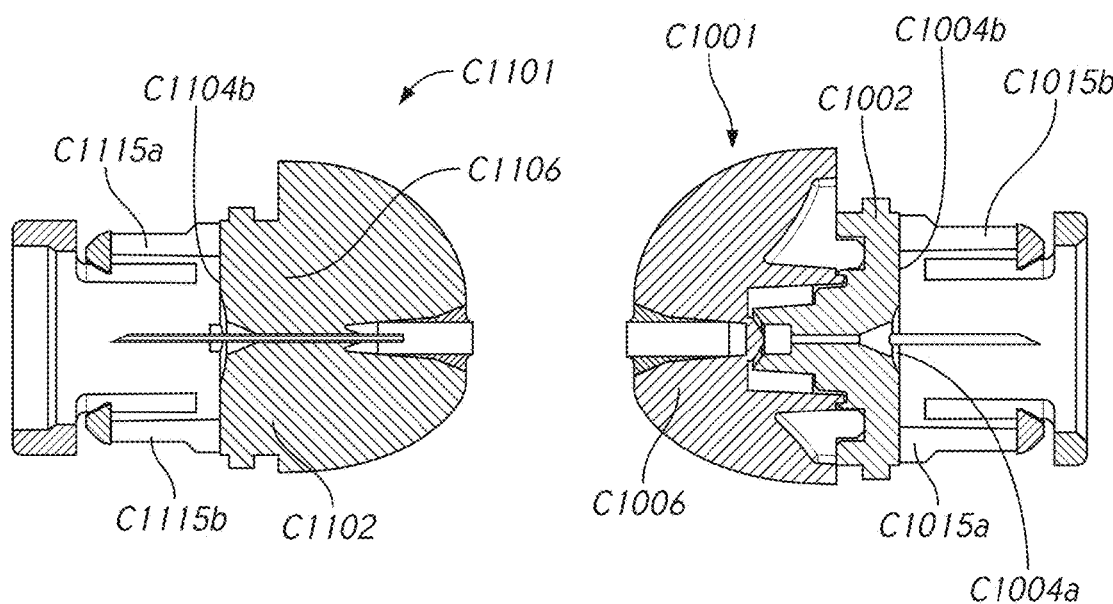
FIG. 9D illustrates a cross-sectional view of the connectors of FIG. 9A.

In some embodiments, the shroud C1005, C1105 comprises a distal end that is away from the lower surface portion C1004, C1104 of the connector C1001, C1101. In some embodiments, as shown, the distal end of the shroud C1005a, C1105a, shown with emphasis, is unbroken (e.g., lacks any spaces, gaps, is a ring) and extends circumferentially around an axis of the connector C1001A, C1101A (shown in FIG. 9A). In some variants, the shroud forms an uninterrupted ring around the bottom of the cartridge connector. In some embodiments, as shown, the needle is recessed within the connector above the shroud. In some embodiments, the unbroken end of the shroud aids in proper placement of a medicament cartridge into the connector C1001, C1101. For example, if the shroud was broken (not shown), a cartridge could be inserted into the connector at an angle more easily. If inserted at an angle and with the medicament cartridge not travelling along the axis of the cartridge connector, the piercing element of the cartridge could pierce the septum at a location that is off-center. Then, as the cartridge is inserted to a point where it abuts the lower surface C1004, C1104, the cap of the vial would become flush to the lower surface C1004, C1104, tearing and/or forming a gap at the septum where medicament could egress. In some embodiments, the skirt ring is unbroken and is configured to ensure that the cartridge connector shroud is perpendicular to the cartridge before the needle penetrates the cartridge seal. In some embodiments, non-perpendicular needle penetration has been shown to cause leakage at the seal. Additionally or alternatively, in some embodiments, a connector C1001, C1101 can comprise a bowl shape or a concavity C1004a, C1104a on or within the lower surface C1004, C1104. As shown in FIG. 9D, the concavity C1004a, C1104a may provide a portion of the lower surface C1004, C1104, and the remainder of the lower surface C1004, C1104 may include a lip C1004b, C1104b (e.g., configured to contact and/or abut the cap of an appropriate medicament cartridge). In some embodiments, unlike connectors lacking a bowl feature, this bowl feature puts distances the inflection point and/or the flex point of the needle from the septum. In some embodiments, this small distance from the septum allows the piercing element to flex in a manner that it can accept an incoming medicament vial without tearing or distorting the hole the needle makes in the septum.

In some embodiments, the connector C1001, C1101 comprises a knob C1006, C1106. In some embodiments, as shown in FIGS. 1A and 9A, the knob can be of irregular shape (e.g., partially oval with a flat portion, etc.) such that when inserted into the pump P1000, a portion of the knob hangs over the pump to provide a lip that gives tactile feedback that the knob is not correctly positioned and/or is not fully engaged. In some embodiments, as disclosed elsewhere herein, when twisted a quarter turn to engage the pump, the knob of the cartridge connector then aligns so that the lip is no longer present and the knob is in alignment with the pump (as shown in FIG. 1A). In some implementations, the knob C1006, C1106 is in the shape of a cam and having a flattened portion C1006', C1106'.

In some implementations, the knob C1006, C1106 comprises a rib portion C1006", C1106" (e.g., a ridge, a finger hold, wing, etc.). In some embodiments, the rib provides a handle making the cap more easily manipulated between the fingers. In some embodiments, the knob is a protrusion or ridge. In some embodiments, the knob allows a user to grip the cartridge connector easily between the finger in the thumb to facilitate placement in the pump chamber and to facilitate locking in the chamber. In some embodiments, as noted elsewhere herein, the cartridge is locked and/or secured in the pump chamber by providing a quarter turn twist to the knob. In some embodiments, the grip ribs help the user develop the torque needed to connect the cartridge connector to the pump. In some embodiments, the detents and/or lugs give tactile feedback when the connection is made. In some embodiments, a shallow cam within the pump chamber is provided for the detent as it rotates into the connected position keeps the connection forces low. In some embodiments, a steep cam for the detent is used to cause the disconnect forces to be higher that the connection forces. This is intended to minimize inadvertent disconnection.

As disclosed elsewhere herein, some embodiments provide for each of the cartridge connectors being shaped so as to provide a visual and/or tactile indication of when the cartridge connector is locked with the pump chamber. For example, in some embodiments, a knob or other physical structure on the cartridge may indicate the orientation of the cartridge and whether the cartridge is in a locked position once the cartridge is inserted into the pump chamber. FIG. 9C illustrates an example of the cartridge connector providing a visual indication of when the connector is locked to the pump chamber. The depiction on the left shows cartridges inserted in, but not locked to, the pump chamber. The depiction on the right shows cartridges aligned with pump chamber after quarter turn to indicate locked state. In some embodiments, as shown in FIG. 9C, the ridges may also provide visual feedback. In some embodiments, the ridges are perpendicular to the pump face when in the locked position. In this embodiment, unlike the embodiments shown in FIGS. 1B and 4A, both knobs of the connectors C3001, C3101 are rotated in a clockwise fashion to lock the connectors in the pump P3000. In other embodiments, the cartridge connectors and pump openings may be configured to require a clockwise turn to lock one cartridge connector (and cartridge) in place and counterclockwise turning to lock the other cartridge connector (and cartridge) in place. Thus, another indicator that allows a user to avoid mischanneling may be added.

Figure 9E:
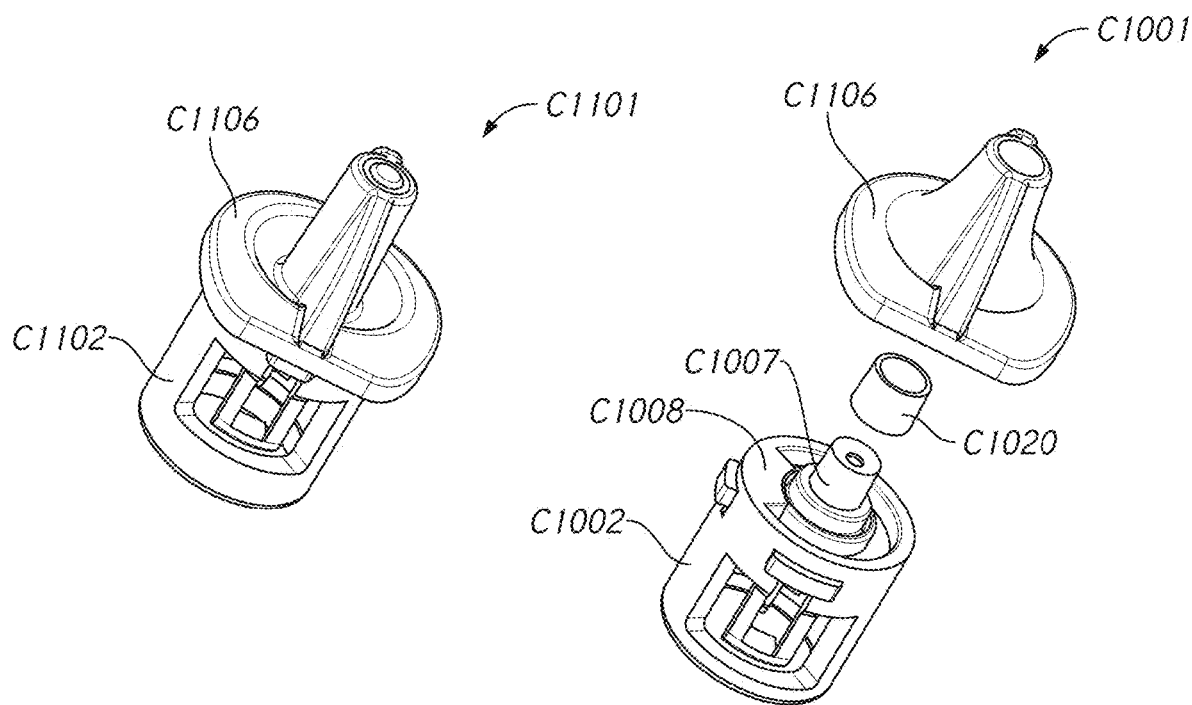
FIG. 9E illustrates a view of the connectors of FIG. 9A where the body of one connector has been separated from its knob.
Figure 9F:
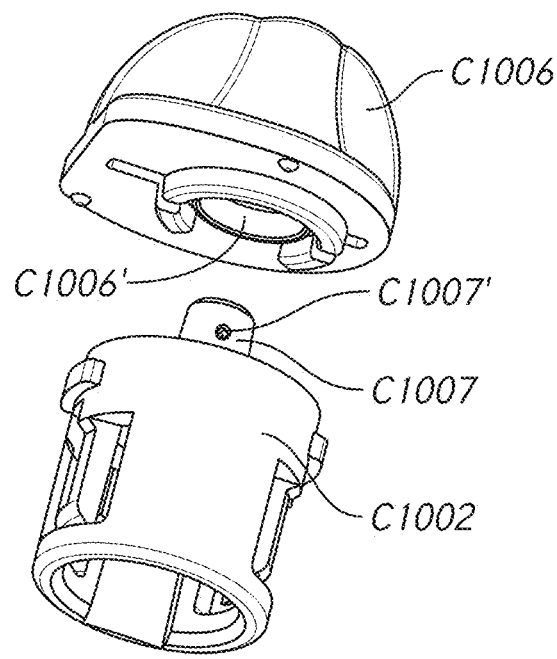
FIG. 9F-G illustrate views of one of the connectors of FIG. 9A where the body of the connector has been separated from its knob.
Figure 9G:
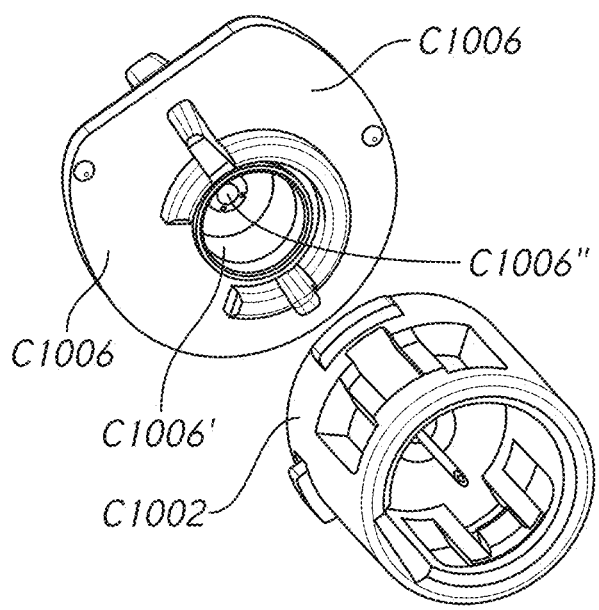

In some embodiments, as shown in FIGS. 9D and 9E, the knob C1106 and the body C1102 of one connector C1101 may be one piece (e.g., a molded, unitary piece). Alternatively, in some embodiments, as apparent in FIGS. 9D-10A, the knob C1006, C2006, C2106 and the body C1002, C2002, C2102 of a connector C1001, C2001, C2101 may be separately molded pieces fixed together (e.g., using an adhesive, sonic welding, etc.). As shown in FIG. 9E, the connector set can comprise either or both types of connectors (unitary or fixed together).

In some embodiments, as shown in FIGS. 9E-10A a connector C1001, C2001, C2101 may comprise a projection C1007, C2007, C2107 extending axially upwardly from an upper surface of the body C1008, C2008, C2108. In some embodiments, the projection C1007, C2007, C2107 comprises a fluid outlet C1007', C2007' C2107' (e.g., connected to a through-hole or passage extending radially outward from, for example, a central fluid conduit in the projection). In some embodiments, the knob C1006, C2006, C2106 comprises a receptacle section C1006', C2006', C2106'. In some embodiments, the receptacle section C1006', C2006', C2106' is configured to extend over and receive at least a portion of the projection of the body C1007, C2007, C2107. In some embodiments, the receptacle section C1006', C2006', C2106' comprises a knob inlet C1006", C2006", C2106" configured to receive the medicament a medicament that passes through the fluid outlet C1007', C2007', C2107' of the connector body C1002, C2002, C2102. In some embodiments, an interstitial space C1009, C2009, C2109 is located between the projection of the body C1007, C2007, C2107 and the receptacle section C1006', C2006', C2106' of the knob C1006, C2006, C2106. In some embodiments, a flexible membrane C1020, C2020, C2120 is located within the interstitial space C1009, C2009, C2109 and extending over at least a portion of the projection of the body C1007, C2007, C2107. In some embodiments, as disclosed elsewhere herein, the flexible membrane C1020, C2020, C2120 is configured to allow fluid to pass from the body outlet C1007' and into the knob inlet C1006" only after a threshold fluid pressure of the medicament is reached.

As noted elsewhere herein, medicament vials having plungers are typically designed to have little or no resistance and/or friction between the plunger and the wall of the reservoir. Thus, the plunger can move and distribute medicament with very little force applied to the plunger (e.g., even by moving the cartridge, lifting the pump comprising the cartridge, etc.). This unwanted distribution is caused by the plunger lifting off the drive nut of a pump. In some embodiments, configurations described herein avoid issues with low friction plungers and/or lift-off. In some embodiments, the membrane C1020, C2020, C2120 acts as a one-way valve and/or prevents lift-off. In some embodiments, the one-way valve (e.g., check valve) allows fluid to pass only after reaching a threshold pressure (e.g., a crack pressure) at the membrane. In some embodiments, the threshold pressure needed to allow fluid flow passed the check valve is greater than any gravitationally induced hydrostatic pressure differential that might develop between the patient and the infusion system. For instance, hydrostatic pressure can develop when the infusion system is connected to a patient via the infusion base and the patient (or user) lifts the loaded pump (containing one or more medicament vial(s)) to an elevation over the infusion base. By force of gravity, the elevation of the vial pushes fluid from the vial through the conduit and into the patient via the infusion base set. The amount of hydrostatic force applied is determined by the elevation of the medicament vial over the infusion set. The amount of hydrostatic force, therefore, is usually limited by the length of the fluid conduit (which ultimately connects the medicament vial to the infusion set). In some embodiments, a standard length of the fluid conduit is about 110 cm or about 60 cm. In some embodiments, the check valve is sufficiently resilient to remain closed when a vial of medicament in the infusion system is elevated over the infusion set by a distance of at least: about 220 cm, about 110 cm, about 60 cm, values between the aforementioned values, or ranges spanning those values. In some embodiments, the check valve is designed such that the threshold pressure gradient needed to allow fluid flow passed the check valve is greater than any hydrostatic pressure differential that might arise due to any other changes in the hydrostatic pressure between the patient and the infusion system (e.g., force caused by an airplane changing elevation, a carnival ride, bungee jumping, physical activity, etc.).

Figure 9H:
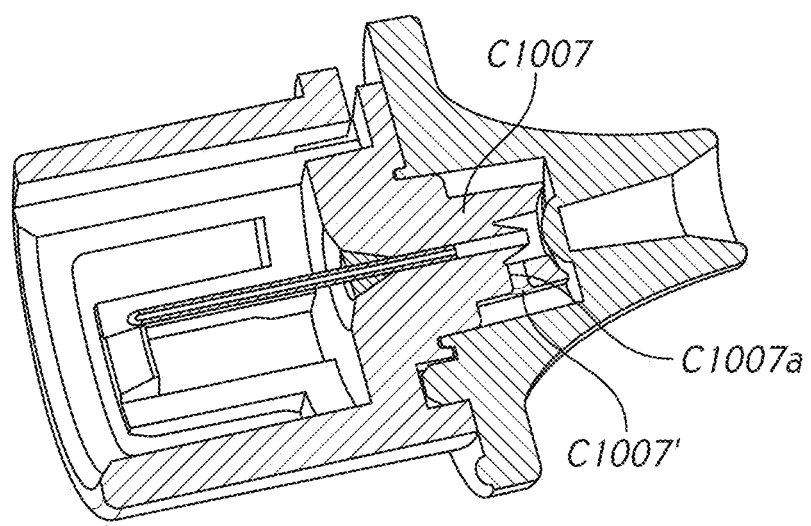
FIG. 9H illustrates a cross-sectional view of one of the connectors of FIG. 9A.
Figure 10B:
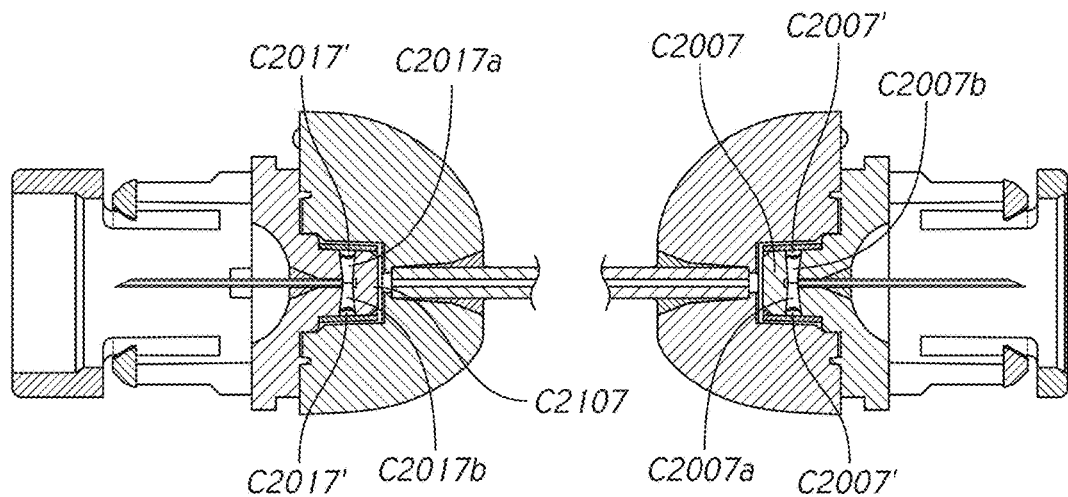
FIG. 10B illustrates cross-sectional views of the connectors of FIG. 10A.

In some embodiments, as shown in FIGS. 9H and 10B, one or more radially extending passages C1007a, C2007a, C2007b, C2107a, C2107b (e.g., tunnels, fluid conduits, etc.) pass through the projection C1007 terminating at a fluid outlet C1007'. In some embodiments, tunnel(s) provides a fluid path through the projection C1007, C2007, C2107 of the cartridge connector body C1002, C2002, C2102 ending at a side hole C1007' or a plurality of side holes C2007', C2107'. In some embodiments, the side hole abuts the membrane C1020, C2020, C2120.

Figure 10C:
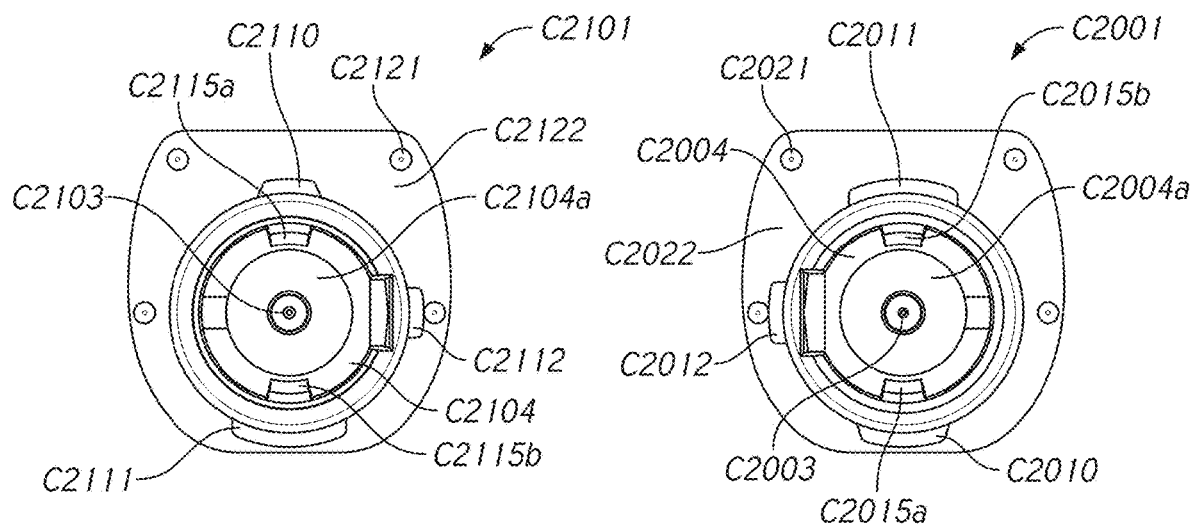
FIG. 10C illustrate a bottom view of the connectors of FIG. 10A.
Figure 10D:
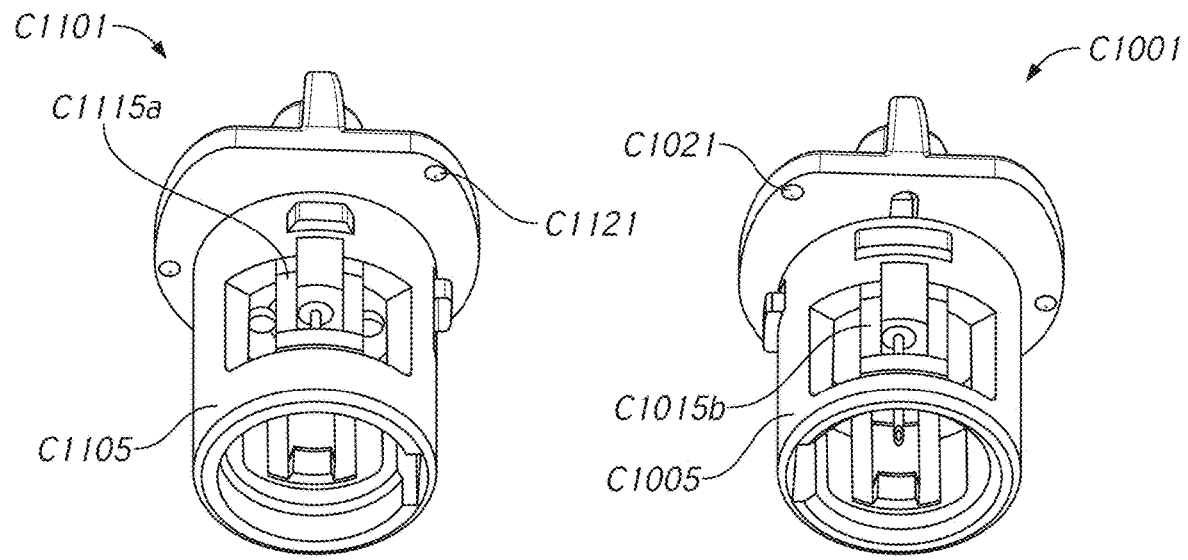
FIGS. 10D-E illustrate views of the connectors of FIGS. 9A and 10A.
Figure 10E:
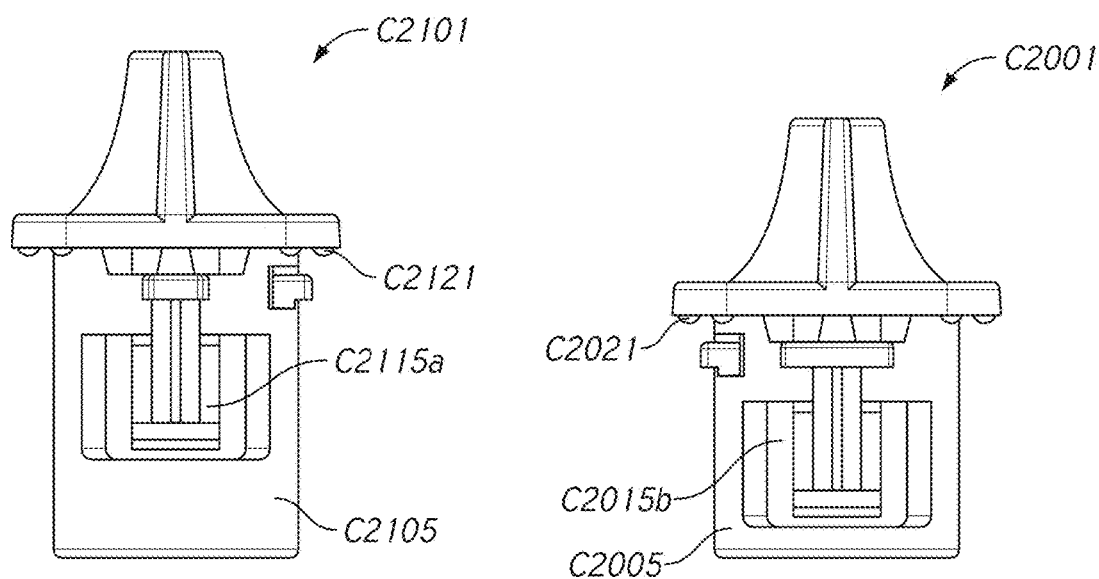
Figure 10F:
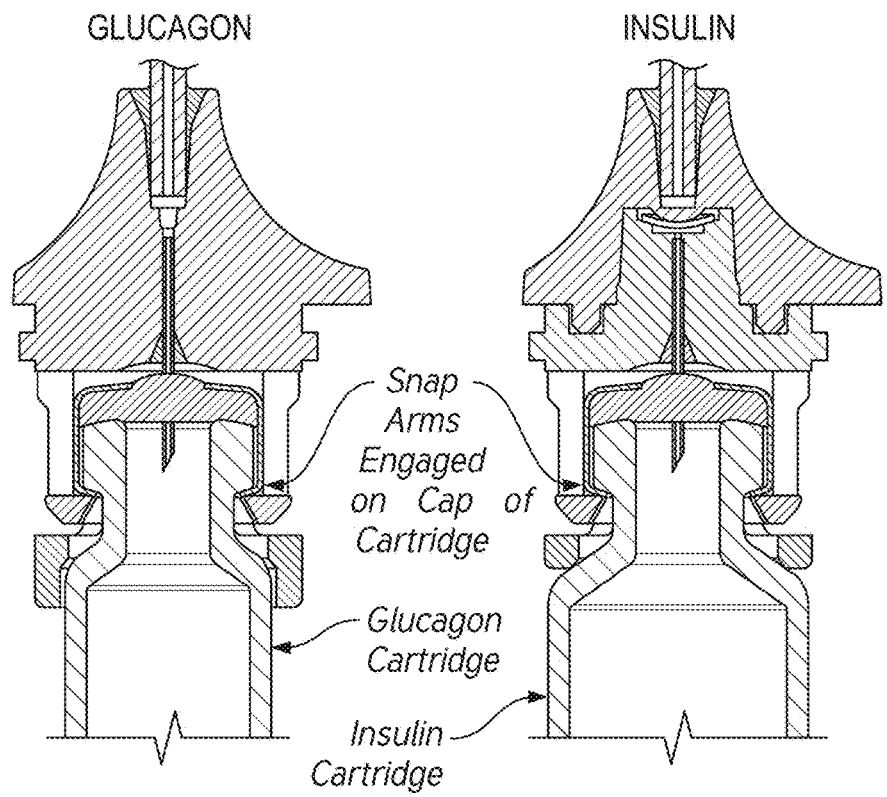
FIG. 10F illustrates a cross-sectional view of an embodiment of a connector set engaged to medicament cartridges.
Figures 10G, 10H:
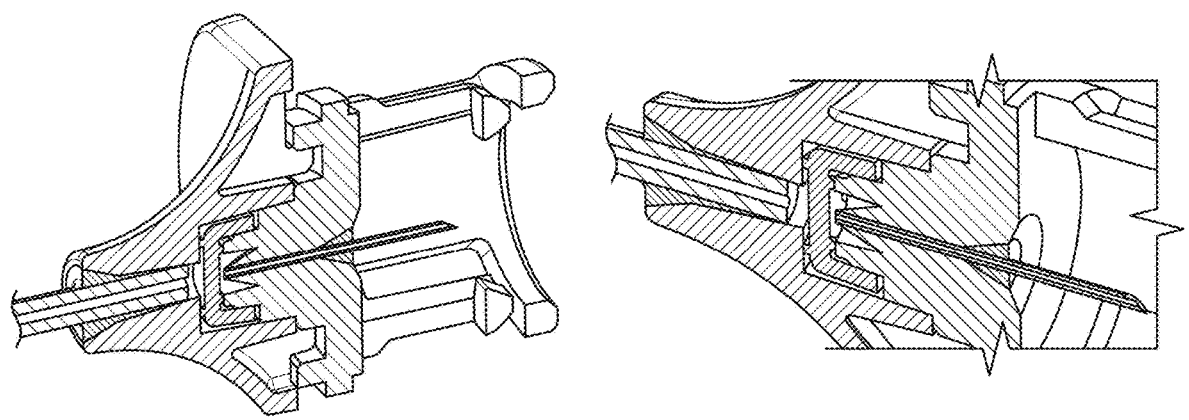
FIGS. 10G-10H show views of a connector having a check-valve.

FIGS. 10G and 10H show views of another example of a cartridge connector including a check valve including standoff bumps and a fluid path flowing from the concave side of a check valve, around a proximal end of the check valve, and towards a convex side of the check valve. In some embodiments, as shown, a modified sheath (e.g., cap feature) is provided over an entry port into the cartridge connector and under the knob. Fluid moves under the sheath via spaces made between the pictured standoff bumps (which are distributed around the sheath) the provide a path to the end of the cap feature. In some embodiments, fluid flows up the needle (from the drug cartridge). In some embodiments, the fluid abuts the sheath. In some embodiments, when sufficient fluid pressure is generated by the plunger of the cartridge pushing out the fluid, then the perimeter of the sheath opens to relieve the pressure. In some embodiments, the fluid then flows up the tube on its way to the patient. In some embodiments, the valve provides checked flow, where in the event that the fluid attempts to flow the other direction (i.e. from the tube back into the drug cartridge), the valve will remain closed stopping this flow. The check valve can be made of silicone or another material.

In some embodiments, where the knob and body are unitary, the connector C1101 is configured to receive the medicament through the needle C1103 and to deliver the medicament out of the knob C1106 from the fluid outlet C1130. In some embodiments, in a connector C1001, C2001, C2101 comprising a flexible membrane C1020, C2020, C2120 the connector C1001, C2001, C2101 is configured to receive the medicament through the needle C1003, C2003, C2103 and to deliver the medicament out of the connector through a fluid outlet of the connector C1030, C2030, C2130. In some embodiments, the needle C1003, C1103, C2003, C2103 and the fluid outlet of the connector C1030, C1130, C2030, C2130 are in fluidic communication and provide a fluid path through the connector C1001, C1101, C2001, C2101.

Figure 9I:
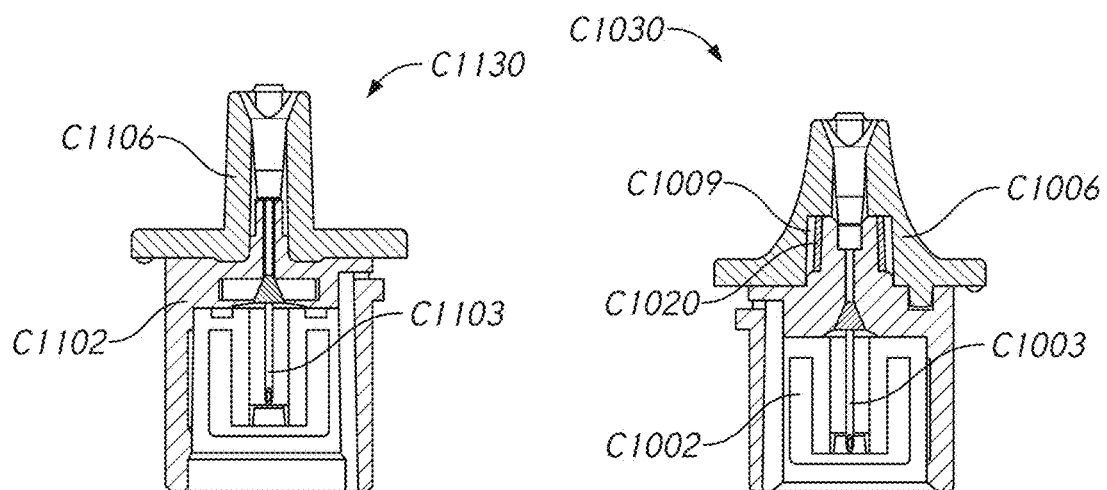
FIG. 9I illustrates an additional cross-sectional view of the connectors of FIG. 9A.

In some embodiments, as shown in FIG. 10A, where more than one connector C2001, C2101 is provided, each connector may comprise a projection C2007, C2107 extending axially upwardly from an upper surface of the body C2008, C2108, a receptacle section C2006', C2106', a knob inlet C2006", C2106", an interstitial space C2009, C2109 located between the projection of the body and the receptacle section of the knob C2006, C2106 and a flexible membrane C2020, C2120. In some embodiments, each connector and or a plurality of connectors in a connector set may comprise a one-way valve. As shown in FIG. 9I, where more than one connector C1001, C1101 is provided, a single connector may comprise a one-way valve (and not both and/or and not more than one).

In some embodiments, as shown in FIGS. 9B and 10C, an underside of the knob C1022, C1122, C2022, C2122 may comprise one or more nubs C1021, C1121, C2021, C2121 (e.g., crushable protrusions, small lumps, protuberances, etc.). In some embodiments, these nubs are crushable and/or malleable. In certain embodiments, these nubs ensure a tight (e.g., snug, flush, space-free vibration-free, and/or rattle-free) engagement of a connector to the pump. For example, in some embodiments, as the connector is turned into place within a connector receptacle and as the lugs of the connector pass along the feature tracks P1101', P1103', P1111', P1113', the longitudinally extending threads (e.g., traveling distally down the bore) cinch the connectors closer and closer to the pump until the connectors substantially abut the upper side surface P1004 of the pump. In some embodiments, the nubs ensure that at least a portion of the connectors contact the upper side surface of the pump to hold the connectors tightly in place against the upper side surface. It has been noted that, in the absence of nubs and where space exists between the cartridge connector and the pump housing, the cartridge connector can inadvertently be pushed flush against the pump housing (e.g., at the upper side surface) which, in turn, pushes the cartridge within the pump against the drive nut, delivering a small bolus. In some embodiments, the nubs allow the connectors to mold to the upper side surface of the pump (so that each attachment and reattachment of a connector provides a flush connection without space between the pump and the cartridge connector).

In some embodiments, the nubs, in combination with the detent cams (or lug cams) provide added stability to the system. Additionally, manufacturing tolerances for the cartridge connectors (which may be disposable) is increased through use of the nubs. For example, the cartridge connectors need not be manufactured to exactly conform to a particular upper surface of a pump as the nubs aid in forming a snug/tight fit between the upper surface of the pump and the cartridge connector.

As shown in FIGS. 1D-1I, 4A, 9A-9B and 10A, recognition features P1101, P1102, P1103, P1111, P1112, P1113, C1010, C1011, C1110, C1111, C1012, C1112 may be provided and can be configured to prevent or inhibit mischannelling. As shown in FIGS. 9A-9B, cartridge connectors C1001, C1101 corresponding to the pump receptacles P1100, P1110, respectively, comprise coinciding protrusions C1010, C1011, C1110, C1111, C1012, C1112 (e.g., tabs, lugs, detents) to the openings of the pump chambers P1101, P1102, P1103, P1111, P1112, P1113. In some embodiments, these protrusions include lugs C1010, C1011, C1110, C1111 and/or detents C1012, C1112. Likewise, as shown for the pump 2000 of FIG. 4A and in FIGS. 10A and 10C, cartridge connectors C2001, C2101 corresponding to the pump receptacles P2100, P2110, respectively, comprise coinciding protrusions (e.g., tabs, lugs, detents). In some embodiments, these protrusions include lugs C2010, C2011, C2110, C2111 and/or detents C2012, C2112. In some embodiments, as disclosed elsewhere herein, the protrusions (e.g., projections) are configured to mate with (e.g., slide into) coinciding openings configured to receive such projections. As shown, the features may be protruding features (e.g., protrusions, tabs, lugs, detents) configured to engage corresponding divots (e.g., apertures, pass-through spaces, detent slots, lug slots, radial notches, carve-outs, etc.) of a receptacle. These mating features facilitate attachment of and/or to prevent connection of in appropriate components.

As illustrated in FIG. 9B, each cartridge connector may have a plurality of recognition features. In the illustrated embodiment, each connector C1001, C1101 comprises three radially extending protrusions (lugs and detents) configured to engage coincidingly shaped carve-outs of corresponding cartridge receptacles. These recognition features may be configured to engage an appropriate receptacle, to prevent or inhibit engagement of an improper cartridge connector (e.g., that is not corresponding and that lacks one or more coinciding protrusions), or both. While in the embodiment shown in FIG. 9B each connector has three radially extending protrusions as recognition features, in some embodiments, each connector can independently have one, two, three, four five, or more recognition features (e.g., divots and/or protrusions) configured to engage and/or receive coinciding recognitions features (e.g., protrusions and/or divots) from corresponding pump chambers. Additionally, while the cartridge connectors have been described as comprising circumferentially distributed protrusions and the pump chambers as comprising circumferentially distributed divots, the opposite configuration is also possible (where protrusions are on the cartridge connectors and divots on the receptacles). Likewise, in some embodiments, types of recognition features could be mixed and matched on a particular cartridge connector (so the connector comprises both protrusions and divots and the corresponding receptacle has coinciding divots and protrusions). In yet another variation, a cartridge connector can comprise only divots and a different cartridge connector in the same connector set can comprise only protrusions. In such an embodiment, the corresponding cartridge receptacle can comprise coinciding protrusions and a cartridge receptacle can comprise coinciding divots, respectively.

In some embodiments, as shown in FIGS. 9B and 10C, the lugs and detents may be various different sizes (e.g., circumferential lengths, radial heights, etc.). For example, as shown in FIG. 9B, a lug of one cartridge connector may be of one length lug(cl'), a second may be of a second length lug(cl"), these lengths may be different from each other and/or from the lug lengths of a second cartridge connector lug(cl'"), lug(cl""). As shown, a detent of one cartridge connector may be of one length det(cl') that is different from a detent length det(cl") of the other cartridge connector. In some embodiments, these lugs and detents are configured to insert into correspondingly sized (e.g., of coinciding lengths) openings located on corresponding cartridge receptacles.

As shown in FIGS. 9B and 10C, detents and lugs of two different connectors may have corresponding positions (e.g., when the middle feature is rotated to 12 o'clock, a first lug is at 9 o'clock, a detent is at 12 o'clock, and a second lug is at 3 o'clock, etc.). In some variants, the lugs and detents are not in corresponding positions or only a portion of the lugs and detents are in corresponding positions. In some embodiments, even where lugs and detents are in corresponding positions on separate connectors, the attachment of an incorrect cartridge connector can be prevented and/or substantially hindered by providing different sizes of those equivalently positioned features. It has been found that that by providing a feature on a first connector (e.g., a lug opening, a detent opening, a lug, a detent, etc.) that is has a size difference of at least 15% (e.g., is 15% longer or shorter) than an equivalent feature on a second connector (e.g., a feature that is in the same relative position), mischanneling can be prevented and/or substantially inhibited. In certain implementations, the ratio of the length of a feature of one connector as compared to the length of an equivalent feature on a different connector is equal to or at least about: 3:1, 5:2, 2:1, 5:3, 4:3, 20:17, or ranges spanning and/or including the aforementioned ratios.

In certain embodiments, as shown in FIG. 9B, a plurality of recognition features (e.g., lugs, detents, openings configured to receive lugs or detents, etc.) may be distributed around the periphery of cartridge connectors C1001, C1101 (e.g., circumferentially). For example, as shown in FIG. 9B, the mid-point of one recognition feature C1012 may be positioned at the 9 o'clock position and an adjacent recognition feature may have a midpoint at 12 o'clock C1011, thereby being separated by 90°. In some embodiments, adjacent recognition features of the connectors C1001, C1101 may be separated by values independently selected from equal to or less than about: 180°, 160°, 140°, 120°, 100°, 90°, 80°, 70°, 60°, 50°, 40°, 30°, 20°, 10°, values between the aforementioned values or otherwise. As shown in FIG. 9B, in some embodiments, non-adjacent recognition features of the connectors C1001, C1101 may be separated by values independently selected from equal to or less than about: 180°, 160°, 140°, 120°, 100°, 90°, 80°, 70°, 60°, 50°, 40°, 30°, 20°, 10°, values between the aforementioned values or otherwise.

As disclosed elsewhere herein, as noted elsewhere herein, the cartridge connectors may include, instead of and/or in additional to protrusions, divots (not shown). In some embodiments, the divots may open to tracks (e.g., slots, paths, etc.). In some embodiments, as shown for the receptacle inlets elsewhere herein, these paths may travel and/or are positioned circumferentially around the connectors. In certain variants, once a cartridge connector is inserted into the pump chamber opening, the connector is rotated to lock the cartridge connector into the receptacle (as disclosed elsewhere herein).

Figure 11A:
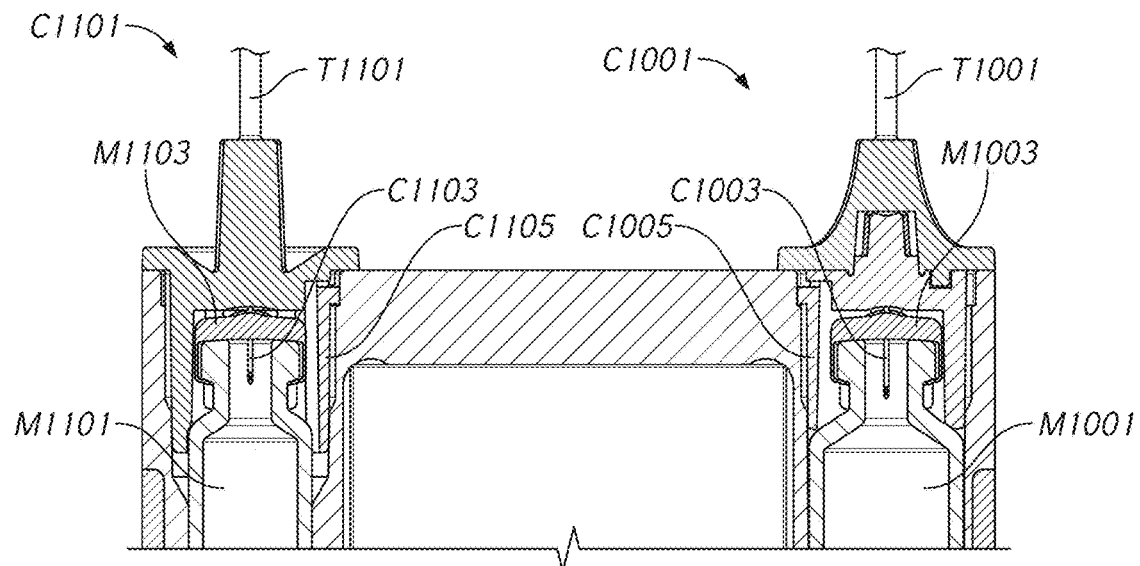
FIGS. 11A-11B illustrate cross-sectional views of embodiments of connector sets engaged to medicament cartridges within a pump.
Figure 11B:
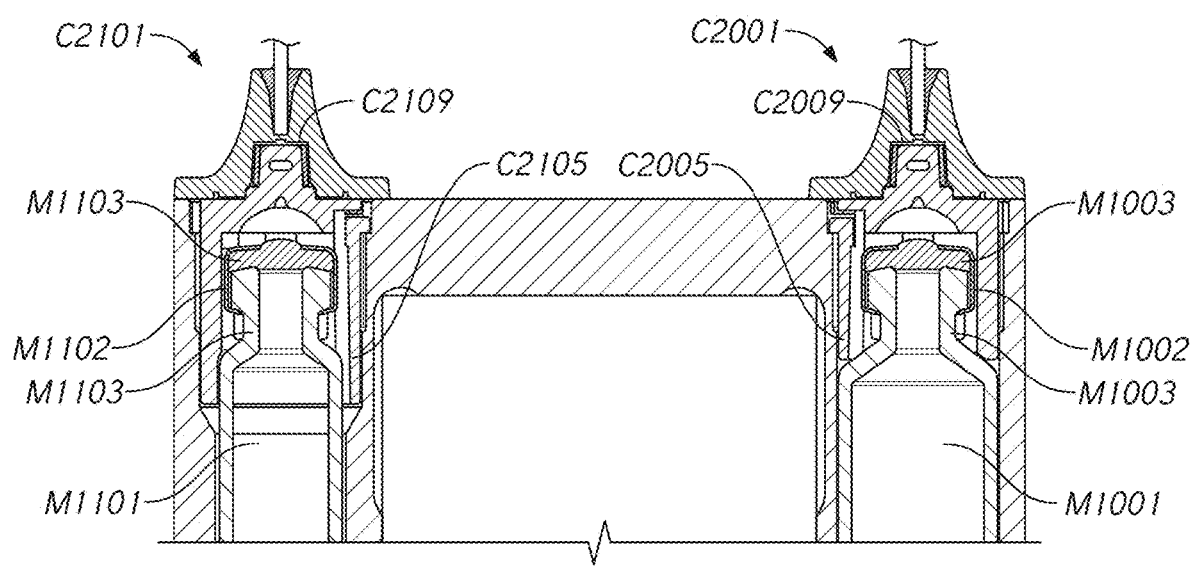
Figure 11C:
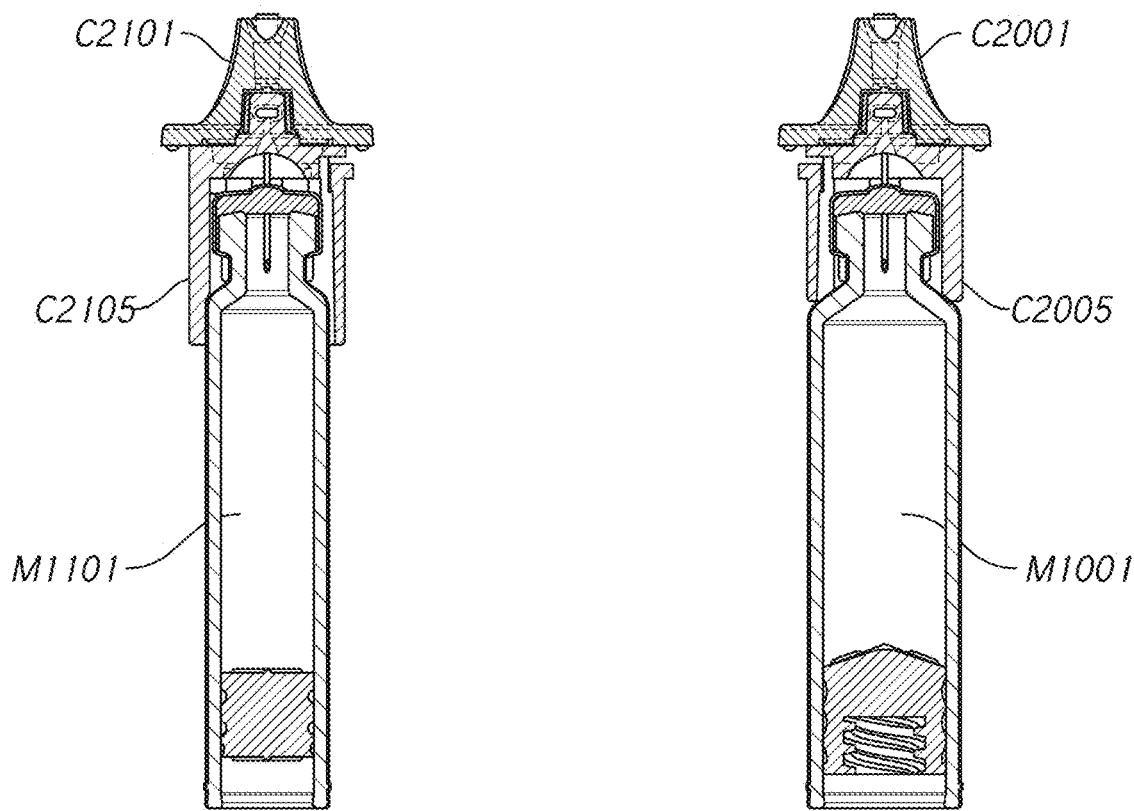
FIGS. 11C-11D illustrate cross-sectional views of embodiments of connector sets engaged to medicament cartridges.
Figure 11D:
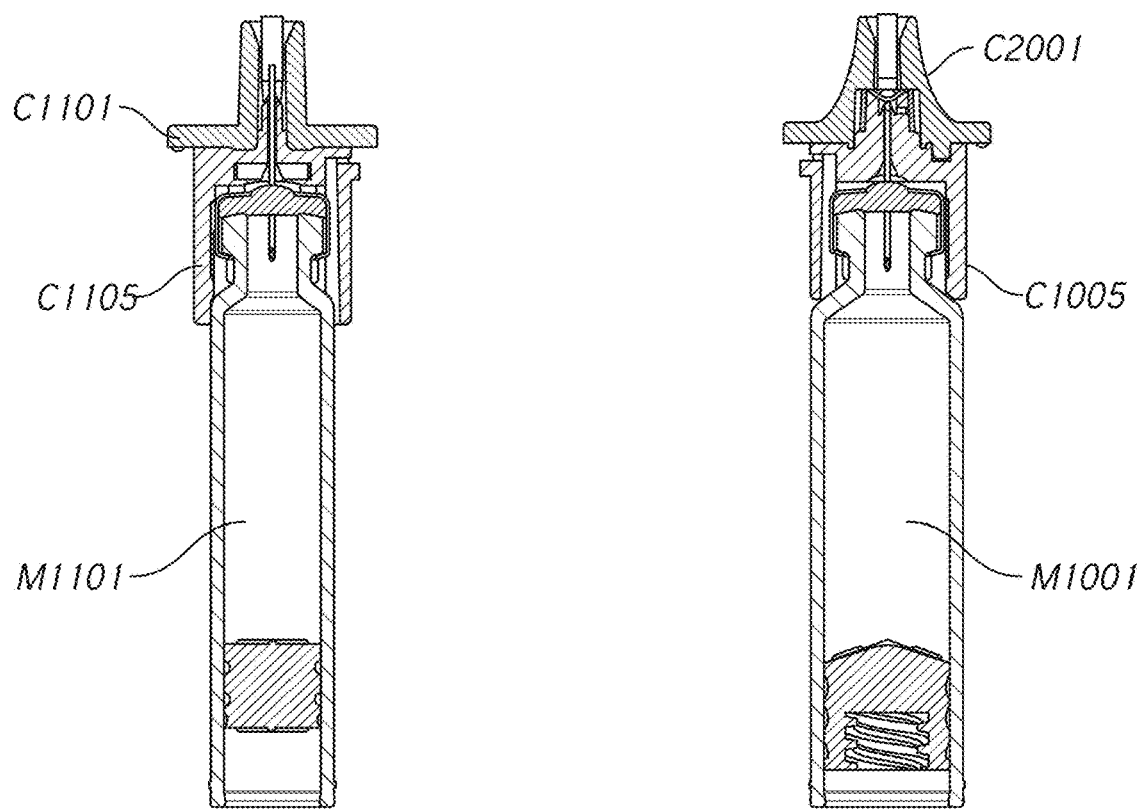
Figure 11E:
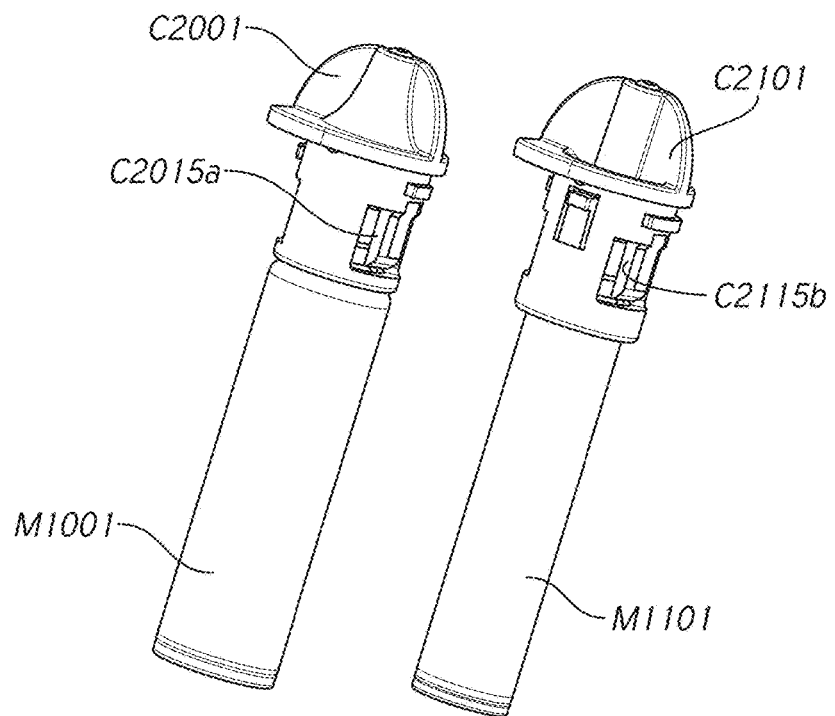
FIG. 11E illustrates a view of an embodiment of a connector set engaged to medicament cartridges.

In some embodiments, as shown in FIGS. 10D, 10E, and 11D, the individual cartridge connector shrouds (and/or the individual medicament cartridges) may be formed to prevent attachment of the incorrect cartridge connector with the incorrect medicament cartridge. For example, as illustrated in FIGS. 10D, 10E, and 11D, a first cartridge connector may have a shorter skirt. In some embodiments, a second cartridge connector C1101, C2101 (e.g., a glucagon cartridge) may be formed to have a longer shroud (e.g., skirt) than the first cartridge connector C1001, C2001 (e.g., an insulin cartridge connector). In some embodiments, not shown, one connector can have a wider diameter the other a smaller diameter. In some embodiments, alternatively, a first cartridge M1001 (e.g., the insulin cartridge) may be formed to have a wider diameter than a second cartridge M1101 (e.g., the glucagon cartridge). As such, the longer shroud C2105 of the cartridge connector C2101 would abut against a larger diameter vial of the first medicament cartridge M1001; thus, preventing the snap arms and needle cannula of the glucagon cartridge connector from engaging and connecting to the insulin cartridge (see FIG. 10F). In other embodiments (not shown), the shroud of the insulin cartridge is longer to avoid engaging a glucagon cartridge that may be wider than the insulin cartridge.

In some embodiments, as shown in FIGS. 9A, 9D, and 10A, additional features of the connectors may include one or more of a needle that is recessed within the connector above the shroud. In some embodiments, this feature, and others, prevent the vial from being pressed into the connector and/or may prevent improper puncture of the vial septum. In some embodiments, the needle recessed within the shroud makes the needle touchproof, avoiding pricks of the finger or other parts of the user's body.

In some embodiments, as disclosed elsewhere herein, the connector set comprises one or more cartridge connectors that couple the fluid conduits (shown in FIGS. 11A and 11B) to the medicament reservoirs. In some variants of the system, as disclosed elsewhere herein, the reservoirs (or reservoir) are located in (and/or can be placed in) a pumping device configured to distribute the medicament from the reservoirs (or reservoir) to the conduit, thereby supplying the system with medicaments. In some embodiments, the fluid conduits provide separate pathways that terminate at designated delivery members (e.g., needles, cannulas, etc.) within the base, thereby enabling independent delivery (e.g., subcutaneous or otherwise) of medicaments separately.

As shown in FIGS. 9A-10F, in some embodiments, there are one or more snap arms C1015a, C1015b, C2015a, C2015b, C1115a, C1115b, C2115a, C2115b, (e.g., 1, 2, 3, 4, or more) molded into the body of the cartridge connector. In some embodiments, these arms snap onto the cap M1002, M1102 (e.g., around the cap) or into the neck area M1003, M1103 of a drug cartridge when the cartridge connector is attached. In some embodiments, the snap-arm comprises a lip (e.g., a tooth, ridge, etc.) configured to engage the cap and/or neck of a cartridge. In some embodiments, these snap arms are in a position that ensures the cartridge is extracted from the pump when the cartridge connector is disconnected. In some embodiments, without this connection, the cartridge could be stuck in the pump by the forces on the Plunger/Pump connection. As shown, the longer skirt of a cartridge connector (e.g., glucagon) will hit a larger diameter cartridge (e.g., insulin) preventing the snap connection of the snap arms. In some embodiments, the first medicament cartridge is configured to receive insulin. In some embodiments, the second medicament cartridge is configured to receive glucagon. In some embodiments, the cartridge connector cannot rotate into the locked position within a pump if the cartridge snaps are not closed. In some embodiments, as shown, there are one or more snap arms (1, 2, 3, 4, or more) molded into the body section. In some embodiments, these arms snap onto the cap of the drug cartridge when the cartridge connector is attached. In some embodiments, a recognition feature of the second cartridge connector (e.g., the skirt ring, snap arms, etc.) is configured to block attachment of the second cartridge connector within the first pump receptacle. In some embodiments, a recognition feature of the first cartridge connector is configured to block attachment of the first cartridge connector within the second pump receptacle.

In some embodiments, as shown in FIGS. 10F, 11A 11B, and 11D-11E, features of a cartridge (e.g., its diameter, neck position, etc.) and/or of a connector are configured to block engagement of an improper cartridge with an improper connector. In some embodiments, features of a second cartridge M1101 (e.g., its diameter, neck position, etc.) are configured to block engagement of the second cartridge M1101 with a first connector C1001, C2001. In some embodiments, the first cartridge M1001 is configured to interact with the first cartridge connector C1001, C2001 and/or not the second cartridge connector C1101, C2101. In some embodiments, the second cartridge M1101 is configured to interact with the second cartridge connector C1101, C2101 and/or not the first cartridge connector C1001, C2001. In some embodiments, features of the cartridges (e.g., diameter, neck position, cap width and length, etc.) are configured to block engagement of a non-corresponding cartridge with the incorrect cartridge connector. FIGS. 10F, 11A 11B, and 11D-11E show exemplary features. As shown in FIG. 11A, when properly seated in the connector, the needle C1003, C1103 of the connector C1001, C1101 pierces the septum M1004, M1104 substantially perpendicularly.

Some embodiments pertain to methods of making a cartridge connector. In some embodiments, the cartridge connector is made by employing one or more of the following steps: a needle is bonded to the body; a tube is bonded to the knob; a check valve (e.g., a flapper valve) is set onto the "Valve Seat" of the body and/or a membrane is stretched over the connector projection; the knob and body are fixed together (e.g., sonically welded together, etc.). In some embodiments, the tube mounting hole in the knob may be tapered so that the tube will contact the wall around the perimeter before bottoming out in the hole. This creates a seal to prevent adhesive from running down into the check valve area when gluing the tube into the knob. In some embodiments, the cartridge connector can be made by employing one or more of the following steps: the Needle is bonded to the Body; the Tube is bonded to the Knob.

Multi-Channel Lumen Assembly

As disclosed elsewhere herein, some embodiments, pertain to a lumen assembly. In some embodiments, the lumen assembly comprises one or more lumens (or tubes). In some embodiments, the lumen assembly is a multi-lumen assembly comprising a plurality of tubes (e.g., 1, 2, 3, or more). In some implementations, the lumen assembly comprises a cartridge connector (or a cartridge connector set). In some implementations, the lumen assembly comprises an infusion site connector (or an infusion set). In some implementations, the lumen assembly is a part of an ambulatory infusion system, as disclosed elsewhere herein. In some embodiments, an infusion system comprising the lumen assembly set is provided.

Figure 12A:
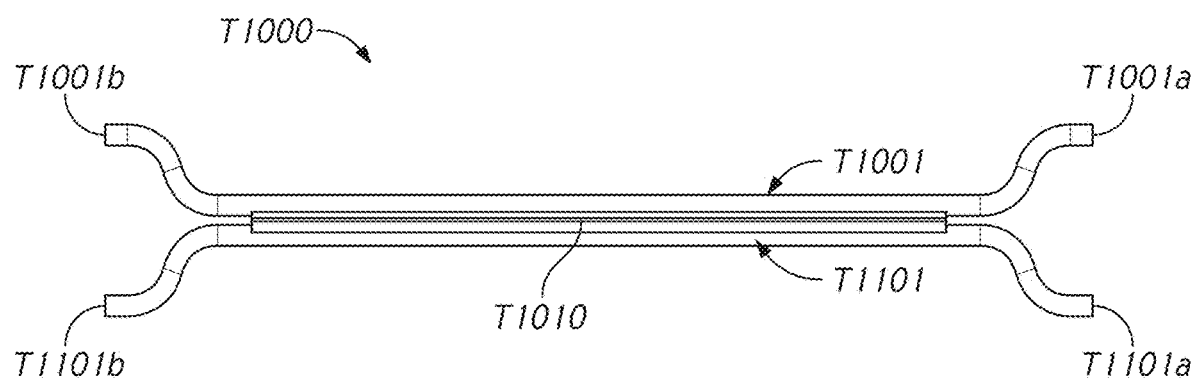
FIG. 12A illustrates an embodiment of a dual lumen portion of a multi-channel lumen assembly.

A lumen assembly T1000 of a multi-lumen assembly is shown in FIG. 12A with the cartridge connectors and/or infusion site connectors removed. The illustrated multi-channel lumen assembly includes a first tube T1001 and a second tube T1101, respectively, forming medicament passages or channels. For example, in several embodiments, the first tube T1001 forms a first medicament channel and the second tube T1101 forms a second medicament channel. In several embodiments, of the multi-channel lumen assembly, the first and second tubes comprise the first and second cartridge connectors C1001, C1101, respectively. For example, the first end portion T1001a may be configured to engage or may be fused with the first connector C1001. In several embodiments, the first end portion T1101a of the second tube T1101 may be configured to engage or may be fused with the second connector C1101. As disclosed elsewhere herein, in several embodiments, the second end portion T1001b of the first tube T1001 may be configured to engage or may be fused with a first infusion connector 2533. In several embodiments, the second end portion T1101b of the second tube T1101 may be configured to engage or may be fused with a second infusion connector 2432.

In several embodiments, the first ends of the first and second tubes, respectively, form the infusion pump side of the multi-channel lumen assembly. The second ends of the first and second tubes, respectively, may form the infusion set side of the multi-channel lumen assembly. The tubes of the multi-channel lumen assembly can be configured so as to be able to be coupled together and then, if desired, be detached or decoupled from each other. This can preferably be done repeatedly. As shown in FIG. 12A, the tubes can have formed thereon mating connecting features T1010 that allow the tubes to be coupled together over at least a portion of the length of the tubes. For example, the first tube can employ a surface feature, such as a tongue-like rail portion, that is formed on and extends outwardly from the main body of the tube. The ability to repeatedly couple and decouple the tubes of the multi-channel lumen assembly allows the patient significant flexibility in using the infusion system, and especially the multi-channel lumen assembly. In several embodiments, the patient can replace one or both of the tubes as needed rather than dispose of both tubes at the same time as is required in systems where the tubes are permanently connected. In other embodiments, the tubes of the multi-channel lumen assembly may be fused and/or permanently affixed to one another.

In some implementations, the lumen assembly comprises a cartridge connector (or a cartridge set) but not an infusion site connector. In some implementations, the lumen assembly comprises an infusion site connector (or an infusion set), but not a cartridge connector.

Point of Care Filling

Figure 13A:
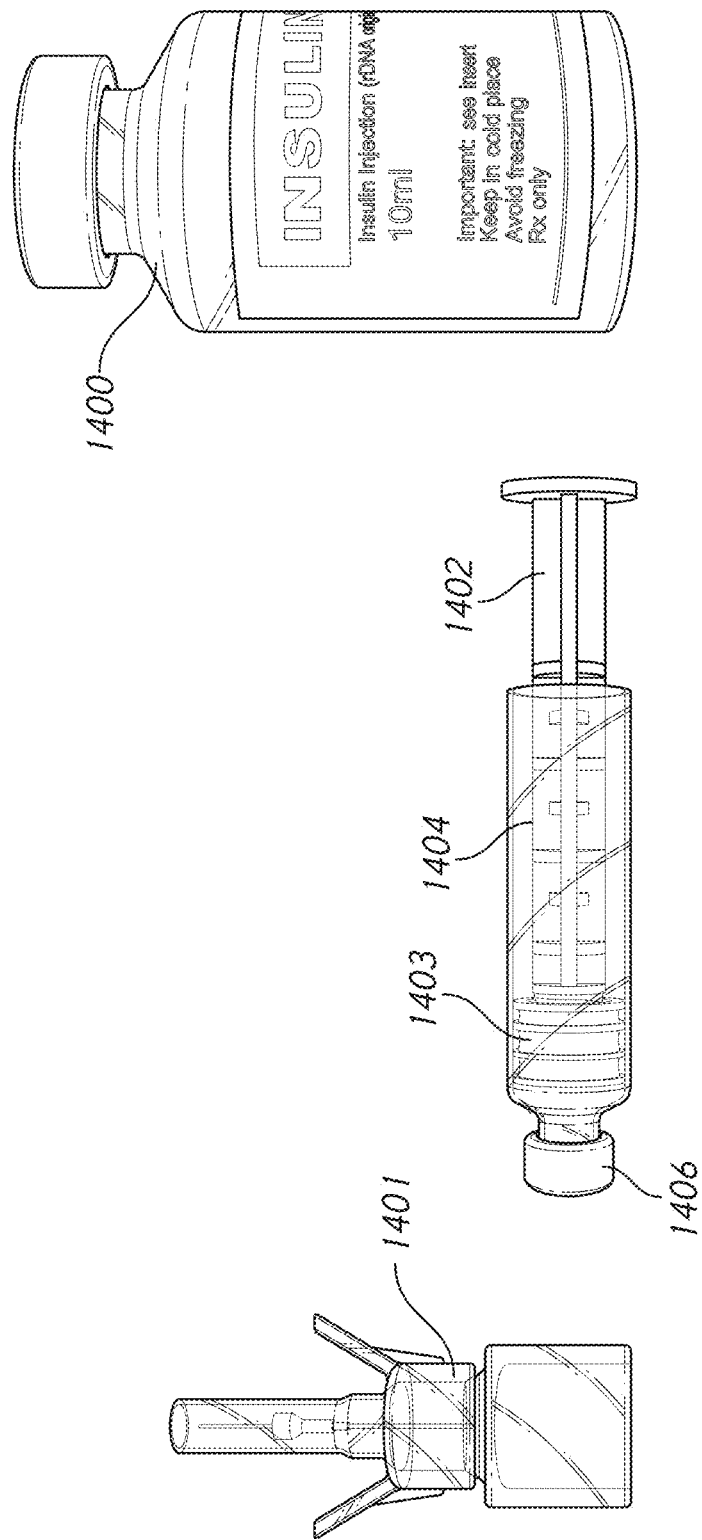
FIG. 13A illustrates components and steps for filling or refilling a medicament cartridge.

In some embodiments, the cartridges can be filled at the point of care with different medicaments (or may be pre-filled with different medicaments, for example, at a pharmaceutical company). Some embodiments, pertain to a method and components used to fill a vial at a point of care (e.g., by a doctor, nurse, or patient). In some embodiments, as shown in FIG. 13A, one or more of an empty medicament cartridge 1404 (or substantially empty from prior use), a medicament vial 1400, and a transfer hub are collected. In some embodiments, a pushrod 1402 is provided with the cartridge 1404 (when the cartridge is being filled a first time without prior use) and in other embodiments, the pushrod 1402 is engaged to the elastomeric plunger 1403 by a user before use. In some embodiments, the pushrod 1402 is engaged by threading it into a cavity of the plunger using threads on the pushrod.

Figure 13B:
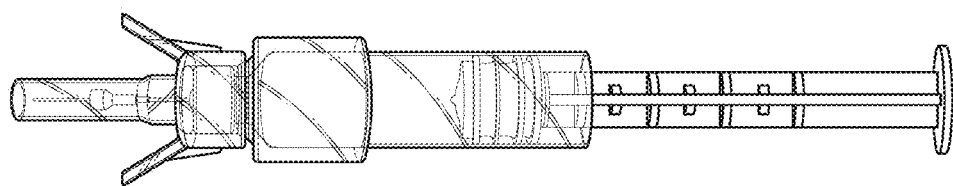
FIG. 13B illustrates additional components and steps for filling or refilling a medicament cartridge.
Figure 13B:
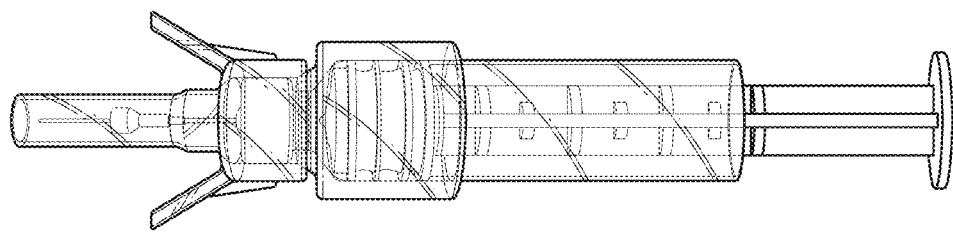
Figure 13B:
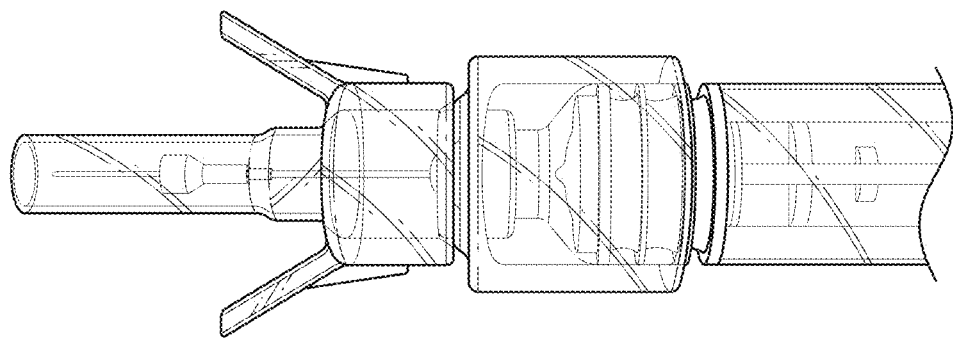
Figure 13C:
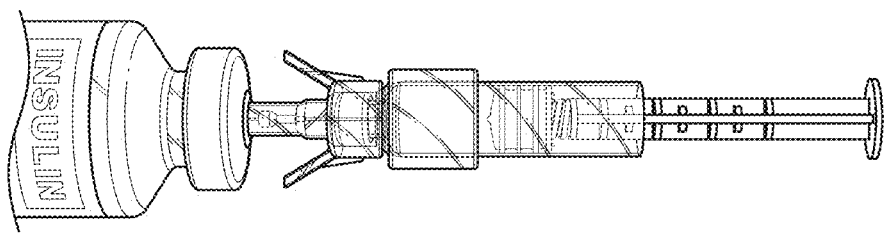
FIG. 13C illustrates additional components and steps for filling or refilling a medicament cartridge.
Figure 13C:
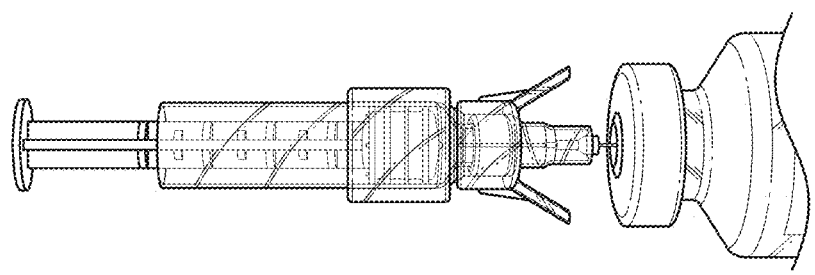
Figure 13C:
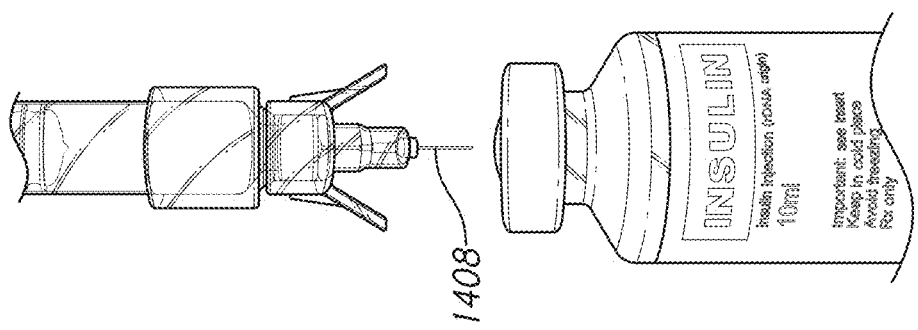
Figure 13C:
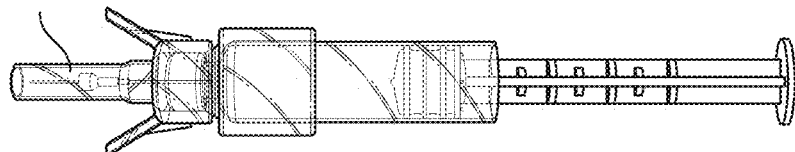
Figure 13D:
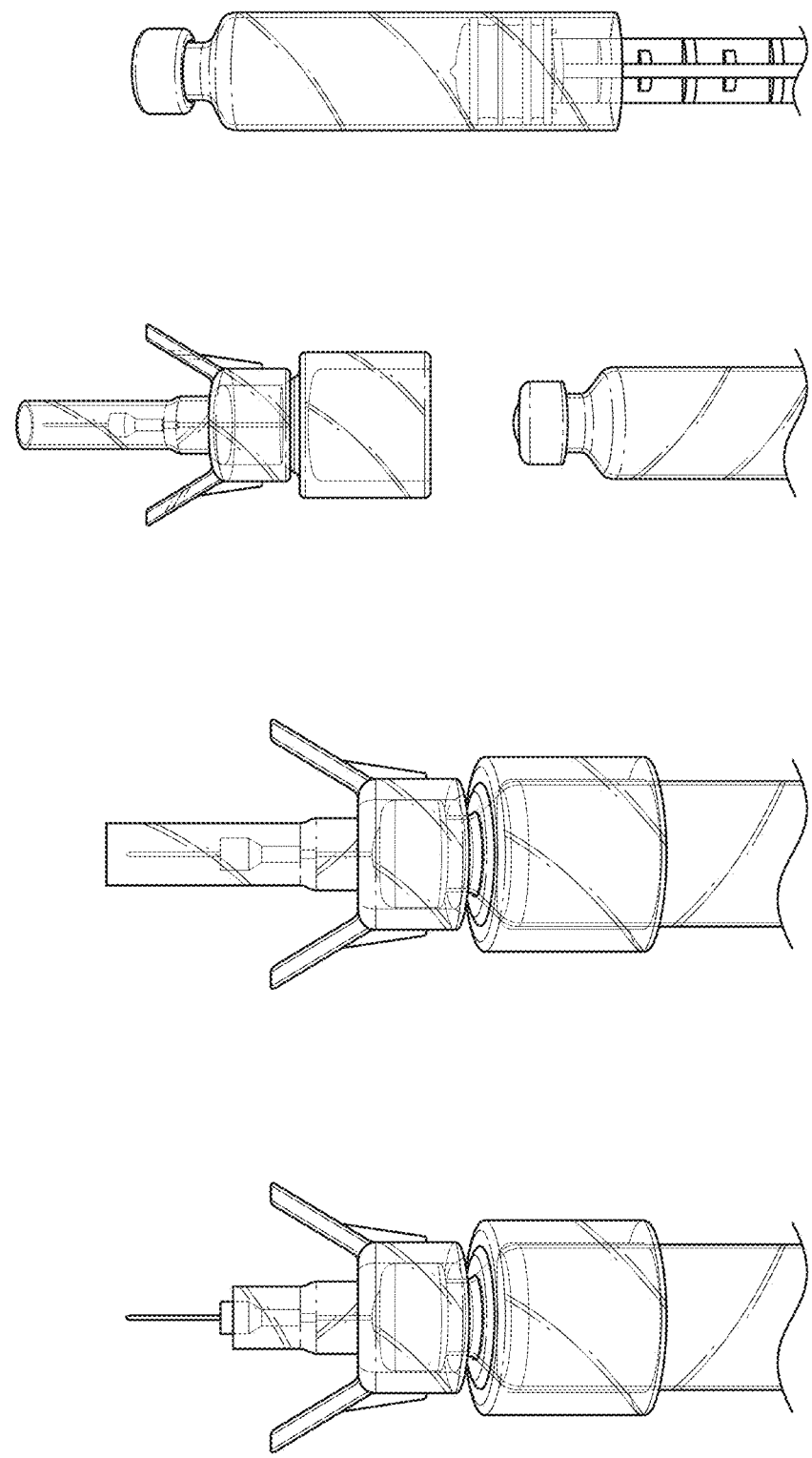
FIG. 13D illustrates additional components and steps for filling or refilling a medicament cartridge.
Figure 13E:
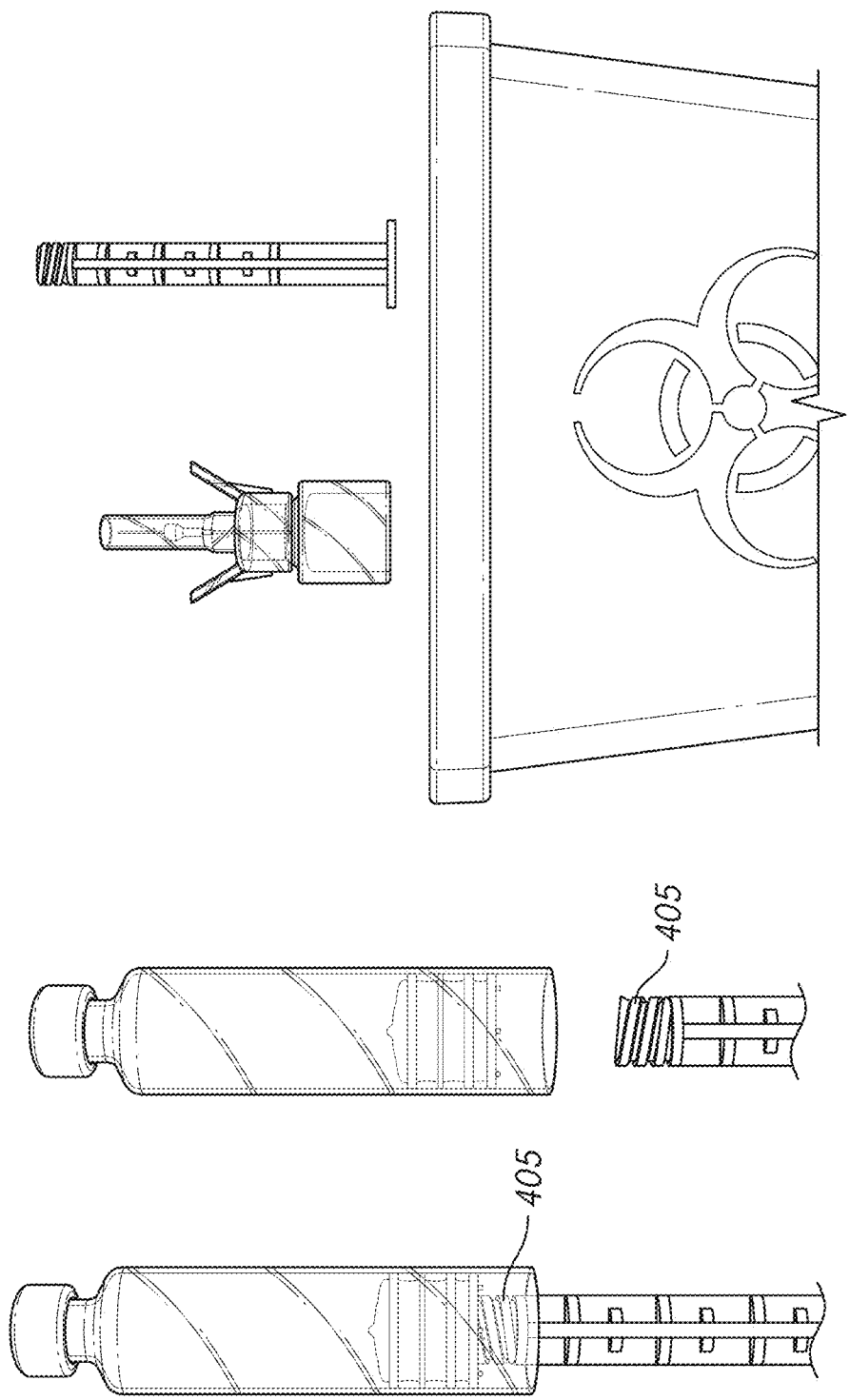
FIG. 13E illustrates additional components and steps for filling or refilling a medicament cartridge.

In some embodiments, as shown in FIGS. 13B-13C, the transfer hub 1401 is connected to a cap 1406 of the cartridge 1404. In some embodiments, once engaged to the plunger, the pushrod is withdrawn to pull air into the cartridge 1404. In some embodiments, as shown, the needle protector 1407 is removed from the needle 408, to expose the needle 1408. In some embodiments, the needle is used to then puncture a septum (or cap) of the vial 1400 and the air in the cartridge 1404 is pushed into the vial 400 to produce a positive pressure in the vial 1400. The medicament vial 1400 is then turned at an angle (e.g., upside down) to submerge the needle. The medicament is then withdrawn, as shown, into the cartridge 1404. The needle is then withdrawn and resheathed as shown in FIGS. 13D-13E. The pushrod is then removed, as shown, to provide the filled medicament cartridge. The cartridge can be engaged to a cartridge connector and inserted into a pump.

In some embodiments, as disclosed herein, the pushrod can be connected directly to the plunger by means of a threads and, upon completion of the filling procedure, the pushrod can be disconnected and discarded (or reused), leaving the elastomeric plunger. In some embodiments, the threads could have a uni-directional burred surface (not shown) that would allow it to easily thread into the elastomeric plunger, but would resist being threaded out of the elastomeric plunger. In some embodiments, the pushrod has a thread-locking barb (not shown). In some embodiments, the pushrod and transfer hub are disposed of in a biohazard container.

Infusion Set

As disclosed elsewhere herein, some embodiments, pertain to one or more infusion connectors, an infusion connector set, and/or an infusion base or bases. In some implementations, an infusion connector (or an infusion connector set) is a part of an ambulatory infusion system, as disclosed elsewhere herein. In some embodiments, the infusion system comprises an infusion set and/or infusions bases and one or more of a cartridge connector set, medicament cartridges, and an infusion pump.

Figure 14A:
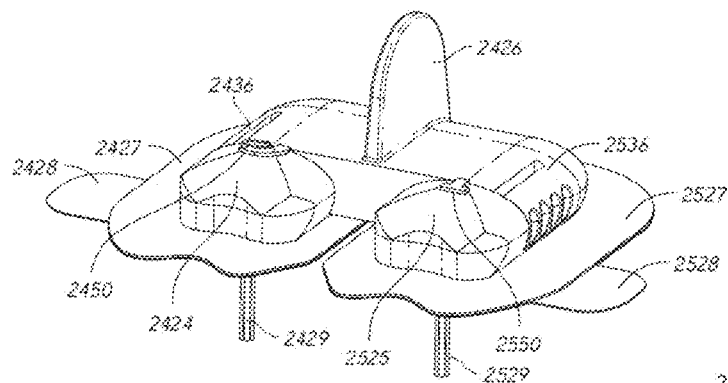
FIGS. 14A-B illustrate perspective views of a dual infusion set base where 14A also illustrates an insertion implement.
Figure 14B:
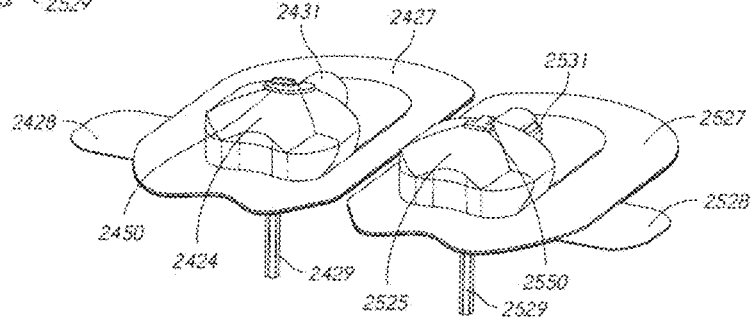

FIGS. 14A-B are isometric views showing a portion of a dual-medicament infusion set. FIG. 14A shows an embodiment of a dual-medicament site base inserter 2426 attached. In FIG. 14B the dual-medicament site base inserter 2426 has been removed. In some embodiments involving two medicaments, the dual-medicament site base inserter 2426 couples two disjoint halves: the right site base 2424 (e.g., the second base, the glucagon base, etc.), and the left site base 2525 (e.g., the first base, the insulin base, etc.). In some embodiments, the inserter 2426 provides a handle for the application of the dual-medicament infusion site base 2401. In some embodiments, the base 2401 includes one or more needle guards 2429, 2529. In some embodiments, the infusion set base 2401 comprises one or more release liners 2428, 2528. In some embodiments, the infusion set base 2401 comprises an adhesive 2427, 2527 (e.g., a tape, gel, rubber adhesive, etc.). In some embodiments, once the two needle guards 2429, 2529 and the two release liners 2428, 2528 have been removed and discarded, the dual-medicament site base inserter 2426, can be used to apply the dual-medicament infusion set base 2401. In some embodiments, the adhesive tape 2427, 2527 can be used to adhere the dual-medicament infusion set 2401 to the surface of the skin. In some embodiments, after insertion, the dual-medicament site base inserter 2426 is disposable and is removed by activating the two living hinges 2436, 2536 and sliding the dual-medicament site base inserter 2426 out of the retention slots 2430, 2530 (shown in FIG. 16B) to reveal the two posts 2431, 2531 that are now ready to accept site connectors (see FIGS. 15A-B). In some embodiments, as shown in FIG. 14B, the posts 2431, 2531 are asymmetric. In some embodiments, the infusion set inserter 2426 is reusable and can be reattached to the site bases 2424, 2525.

Figure 15A:
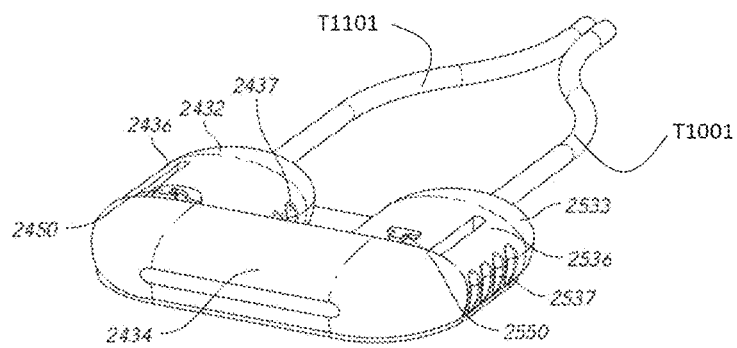
FIGS. 15A-B illustrate perspective views of dual medicament distribution connectors where 15A also illustrates a cover for the distribution connectors.

In some embodiments, the infusion set includes a connector cover 2434. FIG. 15A is an isometric view showing the dual-medicament infusion site connectors 2432, 2533 with a dual-medicament site connector cover 2434 attached. In some embodiments, as shown, fluid conduits from the cartridge connectors may be attached to the infusion site connectors.

Figure 15B:
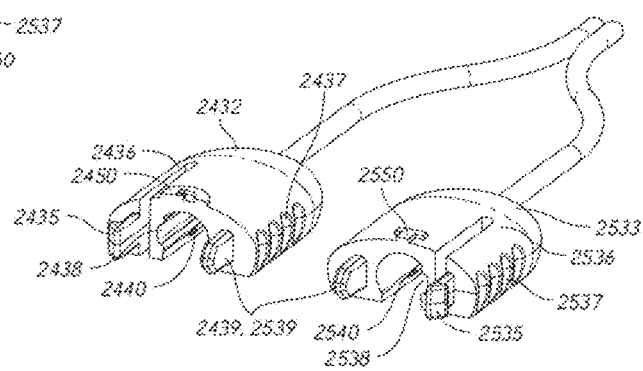

FIG. 15B shows the dual-medicament infusion site connectors after the dual-medicament site connector cover 2434 has been removed. In some embodiments, the dual-medicament site connector cover 2434 couples the two disjoint halves: the second site connector 2432, and the first site connector 2533. In some embodiments, the site connector cover 2434 protects the site connectors 2432, 2533 from exposure (e.g., to dust, dirt, abrasion, physical damage, etc.) when they are not connected to the dual-medicament infusion site base 2401 (shown in FIG. 14A). In some embodiments, the first site connector 2533 can be disconnected from the dual-medicament site connector cover 2434 by activating the living hinge 2536 to release the retention clip 2535 and then sliding the first site connector 2533 out of the retention slot 2530 (shown in FIG. 16B). Disconnection of the first site connector 2533 from the dual-medicament site connector cover 2434 reveals the alignment posts 2539 and the asymmetric post receptacle 2538 which mate with corresponding features on the left site base 2525 (shown in FIG. 14B). The same procedure can be used to disconnect the second site connector 2432 from the dual-medicament site connector cover 2434, using corresponding features and similarly tens-place enumerated features (e.g., 2436 corresponds to 2536). The order of disconnection from the dual-medicament site connector cover 2434 and reconnection to the dual-medicament infusion site set base 2401 is arbitrary.

Figure 21A:
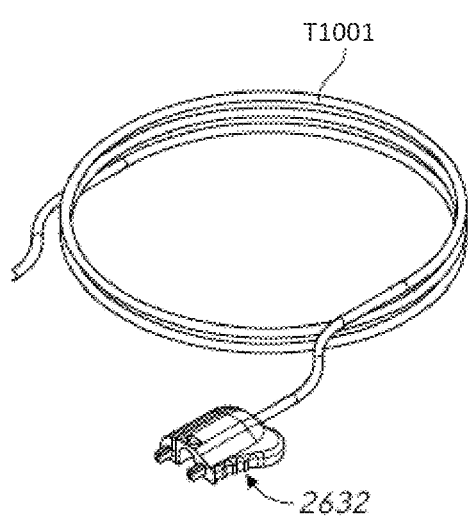
FIG. 21A illustrates a perspective view of a medicament distribution connector.

In some embodiments (as shown in FIG. 21), the infusion site connector 2632 (e.g., the first infusion site connector, as shown, or the second infusion site connector) comprises an ergonomic feature (e.g., a flared-out edge, a finger hold, a bulbous end, etc.). In some embodiments, the ergonomic feature allows the infusion site connector to be easily grasped and pulled from the infusion base. In some embodiments, as shown in FIG. 21, the infusion site connector 2632 can have a thin section and a thick section, with the thick section being located proximal (towards) the tubing, and the thin section being proximal to base connection point. In some embodiments, this design feature, similar to the ergonomic feature, allows the infusion site connector to be easily grasped by the finger tips and slid away from the infusion base.

Figure 16A:
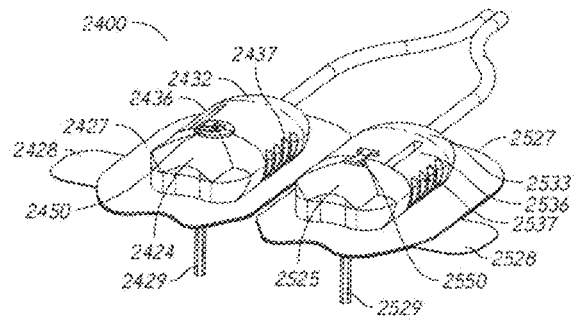
FIGS. 16A-B illustrate views of a dual medicament infusion set where 16B is a cross-sectional view from the top.
Figure 16B:
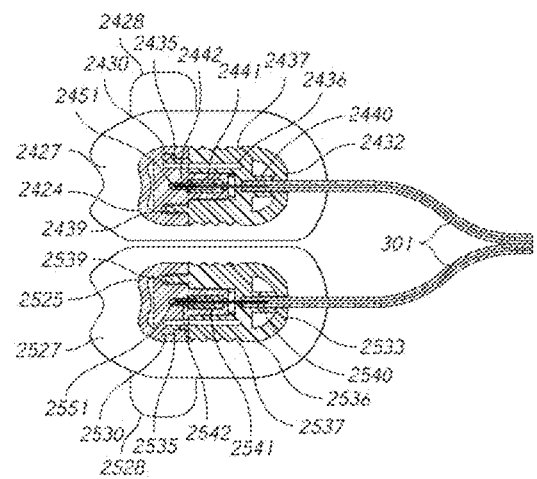

FIG. 16A shows an isometric view of the complete dual-medicament infusion set 2400 including the dual-medicament infusion site base 2401 assembled with the dual-medicament infusion site connectors. In some embodiments, as shown, the infusion set comprises a second infusion assembly comprising a second base and a second connector and a first infusion assembly comprising a first base and a first connector. In some embodiments, having the bases separate prevents needle pull in a system where both needles are fixed to a single base. In some embodiments, this feature increases comfort when the infusion set is placed on an area where movement, pulling, and discomfort can occur. FIG. 16B shows a cross-sectional view revealing the internal components of the dual-medicament infusion set 2400. In some embodiments, after connection of the second site connector 2432 and the first site connector 2533, to the second site base 2424 and the left site base 2525, respectively, two closed, independent, patent, and continuous fluid paths are created. In some embodiments, the fluid paths terminate at 90 degree, beveled, hollow, piercing members 2442, 2542 (stainless steel needles). In some embodiments, each fluid path can begin in many types of connections to a fluid reservoir such as luer locks or custom cartridge connectors that eventually communicate with the lumen of the tubing 301 which is bonded together with a straight, beveled, hollow, stainless steel needle 2440, 2540 and an infusion site connector 2432, 2533, respectively. In some embodiments, upon connecting an infusion site connector(s) to an infusion site base(s), the straight, beveled, hollow, stainless steel needle 2440, 2540 pierces a site base septum 2441, 2541 respectively, allowing fluid to be pushed through the 90 degree, beveled, hollow, stainless steel needle 2442, 2542 for delivery to the patient. In some embodiments, lettering (or other visual indicators) 2450, 2550 are present on the infusion set 2400. In some embodiments, for example as shown in FIG. 16A, the indicators 2442, 2542 provide convenience to a user, though, in some embodiments, misconnection of components is still mechanically prevented. In some embodiments, the 90 degree, beveled, hollow, stainless steel needle 2442, 2542 is placed using a sub-assembly consisting of itself, a soft durometer tube 2451, 2551 and the site base septum 2441, 2541 which is then secured with a plug (not shown).

Figure 17A:
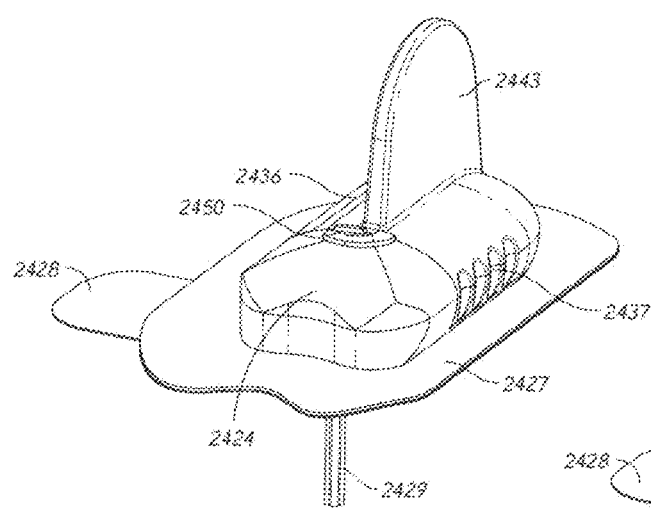
FIGS. 17A-B illustrate a single medicament infusion housing set base where an insertion implement is attached (17A) or detached (17B).
Figure 17B:
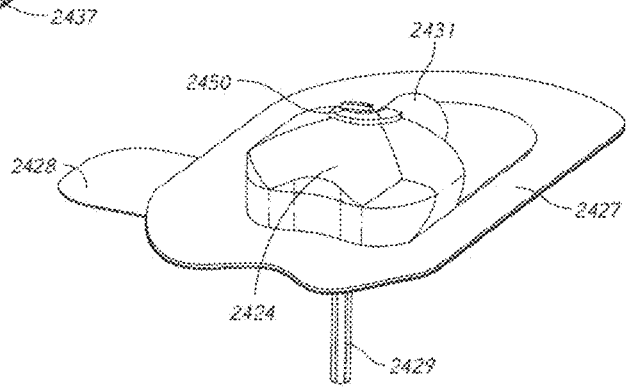

FIG. 17A is an isometric view showing the second site base 2424 (shown in FIG. 15B), as it would be used in the single-medicament configuration. In some embodiments, a second site base inserter 2443 can be attached as shown. FIG. 16B shows the second base 2424 after the second site base inserter 2443 has been removed. In some embodiments, the second site base inserter 2443 provides a handle for the application of the single-medicament infusion site base 2424. In some embodiments, after insertion, the second site base inserter 2443 is removed by activating the living hinge 2436 and sliding the right site base inserter 2443 out of the retention slot, 2430, to reveal the asymmetric post, 2431 that is now ready to accept a site connector 2432. Although only the half of the dual-medicament infusion site base 2401 (shown in FIG. 17B) is shown, the other half 2433 could also be used in a single-medicament configuration. In some embodiments, the other half 2433 could be attached using the same strategy, but with components having uniquely pairing features, hinges, etc.

FIG. 18A shows an isometric view of the second site connector 2432 (shown in FIG. 15), as it would be used in the single-medicament configuration, with the second site connector cover 2446. FIG. 18B shows the second site connector 2432 after the second site connector cover 2446 has been removed. In some embodiments, the second site connector cover 2446 protects the second site connector 2432 from exposure (e.g., to dirt, grime, debris, physical damage from bumps, etc.) and can be removed by activating the living hinge 2436, to release the retention clip 2435 and then sliding the second site connector 2432 out of the retention slot 2430 (shown in FIG. 19B). In some embodiments, disconnection of the second site connector 2432 from the second site connector cover 2446 reveals the alignment post 2439 and the asymmetric post receptacle 2438, which mate with corresponding features on the second site base 2424 (shown in FIG. 17). Although this depiction describes only the second half of the dual-medicament infusion site connectors (shown in FIG. 15), the first half could also be used in a single-medicament configuration with similarly numbered features.

FIG. 19A shows an isometric view of the complete single-medicament infusion set 2400' including the single-medicament infusion site base 2424 assembled with the single-medicament infusion site connector 2432. FIG. 19B shows a cross-sectional view revealing the internal components of the single-medicament infusion set 2400'. In some embodiments, after connection of the second site connector 2432 to the second site base 2424, a closed, independent, patent, and continuous fluid path is created. In some embodiments, the closed fluid path terminates in a 90 degree piercing member, 2442 (e.g., a beveled, hollow, stainless steel needle). In some embodiments, the fluid path can begin in many types of connections to a fluid reservoir such as luer locks or custom cartridge connectors that eventually communicate with the lumen of the tubing 301. In some embodiments, the tubing 301 is bonded together with a straight piercing element 2440 (e.g., a beveled, hollow, stainless steel needle) and, in this depiction, the second site connector 2432. In some embodiments, upon connecting the second site connector 2432 to the right site base 2424, the straight, beveled, hollow, stainless steel needle 2440 pierces the site base septum 2441, allowing fluid to be pushed through the 90 degree, beveled, hollow, stainless steel needle 2442, for delivery to the patient. In some embodiments, although this depiction is analogous only to the second half of the dual-medicament infusion set (shown in FIGS. 16A-B), the first half of the infusion set (e.g., the left half) could also be used in a single-medicament configuration. In some embodiments, lettering or other visual indicators 2450, 2550 are present and provide convenience to a user. In some embodiments, beside the visual indicators, mis-connection of components is still mechanically prevented. In some embodiments, the 90 degree, beveled, hollow, stainless steel needle 2442 is placed using a sub-assembly consisting of itself, a soft durometer tube 2451 and the site base septum 2441 which is then secured with a plug (not shown).

Figure 20A:
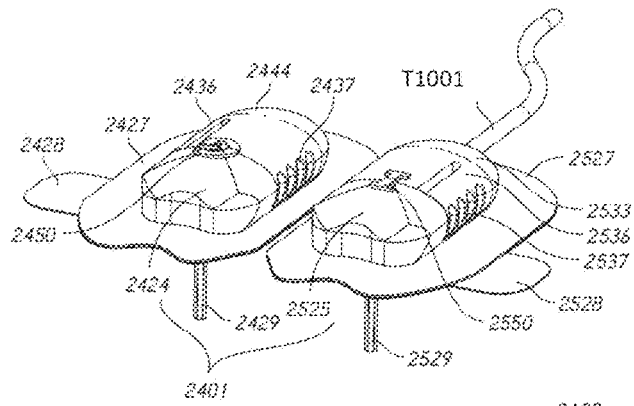
FIGS. 20A-E illustrate various configurations of dual medicament infusion set bases, connectors, and covers.
Figure 20B:
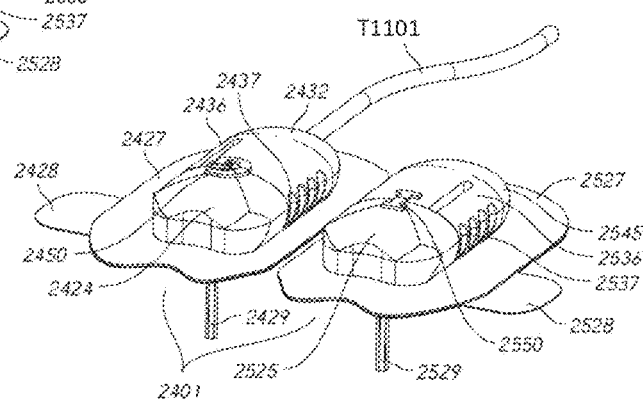
Figure 20C:
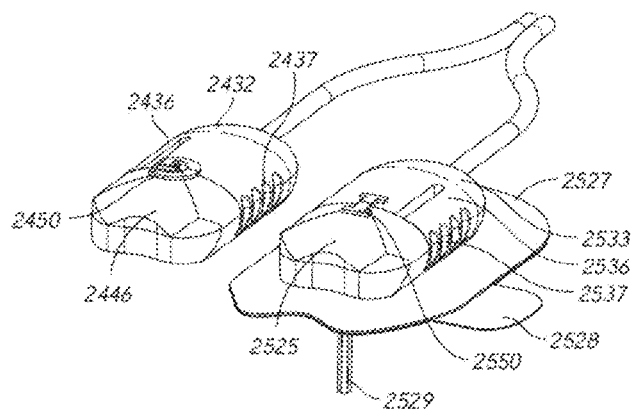
Figure 20D:
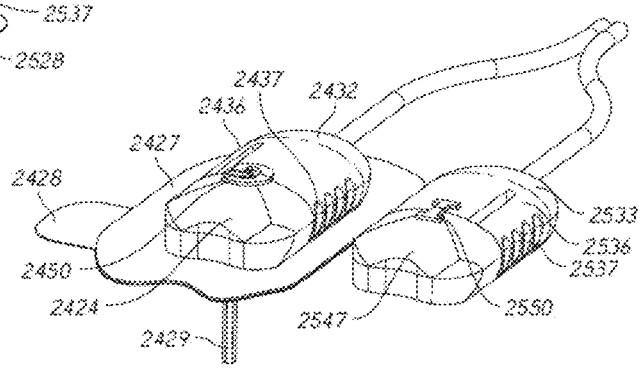
Figure 20E:
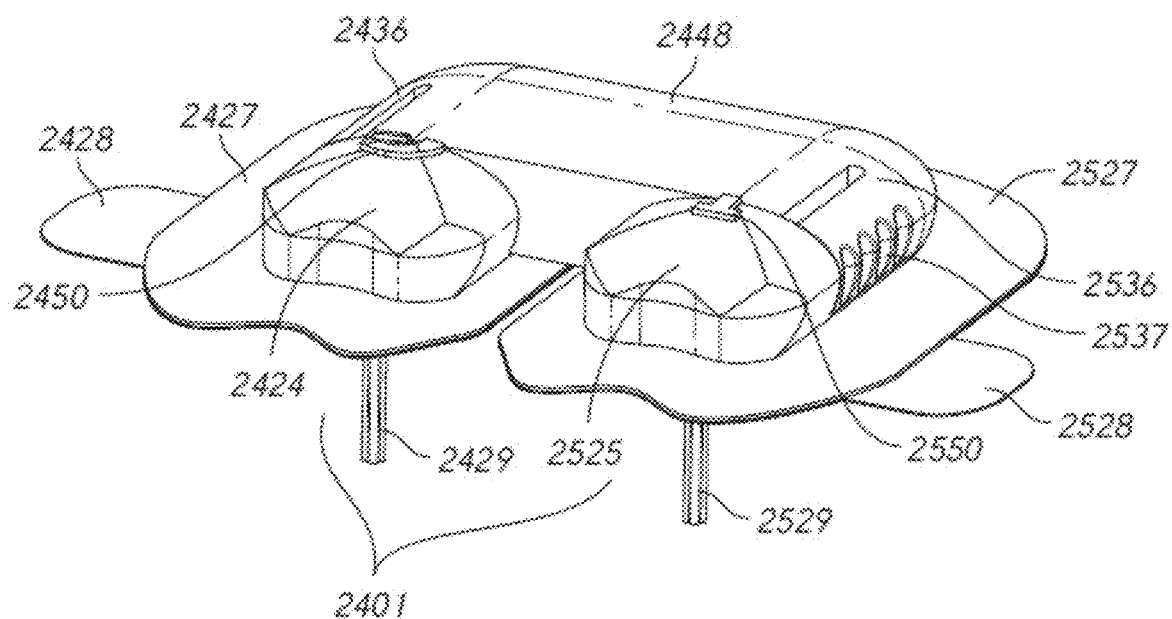

FIGS. 20A-E show isometric views of embodiments of a dual-medicament infusion set. FIG. 20A with the right site base 2424, connected to a right site base cover 2444. FIG. 20B shows the first site base 2525 connected to a first site base cover 2545. FIG. 20C shows the second site connector 2432 connected to a second site connector cover 2446. FIG. 20D shows the first (left) site connector 2533 connected to a first (left) site connector cover 2547. FIG. 20E shows the dual-medicament infusion site base 2401 connected to a dual-medicament site base cover 2448. In some embodiments, when an individual site connector must be replaced, it can be disconnected from its site base and a site base cover can be temporarily connected to the site base thereby protecting it from exposure (as in A and B) until the site connector can be replaced. In some embodiments, if both site connectors are removed together, a dual-medicament site base cover 2448 can be connected temporarily to both site bases to protect them from exposure until the site connectors can be replaced (as in E). In some embodiments, when any individual site base must be replaced, it can be disconnected from its site connector and a site connector cover is temporarily connected to the site connector thereby protecting it from exposure (as in C and D) until the site base can be replaced. In some embodiments, if both site bases are removed together, a dual-medicament site connector cover can be connected temporarily to both site connectors to protect them from exposure until the site bases can be replaced (as in FIG. 15A). A single-medicament embodiment could operate in the same manner as the right site half of A and C or the left site half of B and D.

In some embodiments, a single-medicament implementation of the infusion system that infuses only medicament A can use one of the two single-medicament infusion site connectors of the dual-medicament infusion site connectors. Similarly, the other single-medicament infusion site connector, which is distinct from the single-medicament infusion site connector for medicament A, can be used for a single-medicament implementation of the infusion system that infuses only medicament B. In some embodiments, asymmetric features in the dual-medicament infusion site connectors, such as any combination of asymmetric posts, asymmetric post receptacles, retention clips, alignment posts, and/or keys and keyways can be used to differentiate the single-medicament infusion site connector for medicament A from medicament B. In some embodiments, such features can also be used to ensure that a single-medicament implementation of the infusion system that infuses only medicament A uses only the medicament A chamber in the pump housing, and a single-medicament implementation of the infusion system that infuses only medicament B uses only the medicament B chamber in the pump housing. In some embodiments, in this way, the same molds used to manufacture the dual-medicament infusion site connectors will serve for the single-medicament infusion site connectors for a single-medicament implementation of the infusion system that infuses only medicament A or only medicament B. Thus, the constituent components of the dual-medicament infusion site base, dual-medicament infusion site connectors, tubing, and needle connectors, which serve a dual-medicament implementation of the infusion system, can be used to serve one of two distinct single-medicament implementations of the infusion system, one for medicament A and one for medicament B.

In some embodiments, software (either integrated into the infusion system or run on an auxiliary device such as a smart-phone or tablet) can be used to configure (automatically and/or manually) the infusion system to be configured either as a dual-medicament infusion system, as a single-medicament infusion system that uses only the medicament A chamber in the pump housing, or a single-medicament infusion system that uses only the medicament B chamber in the pump housing. In some embodiments, once any of these three configurations is implemented, the dual-medicament infusion site connectors or appropriate single-medicament infusion site connectors (either pertaining to medicament A or medicament B) can be chosen to match the particular configuration.

In some embodiments involving a site connector or site connectors, each site connector can be designed to connect to a site base by the action of at least one retention clip. Connection of a site connector to a site base allows a straight, beveled, hollow, stainless steel needle to pierce a septum in the site base (as in FIGS. 16 and 19). In some embodiments, once the straight, beveled, hollow, stainless steel needle in a site connector pierces the site base septum in a site base, it is brought into fluid continuity with a 90 degree, beveled, hollow, stainless steel needle, which can deliver the medicament to the delivery space. In some embodiments, this arrangement creates, for each medicament, a closed, independent, patent, and continuous fluid path from the medicament reservoir to the patient (e.g., for delivery transdermally, intradermally, subcutaneously, intramuscularly, intravenously, etc.). In some embodiments, each site base can be physically independent and can connect to or disconnect from a site connector repeatedly.

In some embodiments involving the use of a site base, the 90 degree, beveled, hollow, stainless steel needle can be overmolded, bonded, press-fitted, glued, solvent bonded, insert molded, or otherwise attached to the site base. In some embodiments, as an example other than insert molding, such a 90-degree, beveled, hollow, stainless steel needle may be sheathed with a soft durometer tube, which is in turn press-fit into the site base septum to create a sub-assembly outside the site base. In some embodiments, this sub-assembly can then be placed into a cavity in the site base (as shown in FIGS. 16 and 19) and a plug (not shown) can be used to hold the sub-assembly firmly in place while simultaneously ensuring a fluid seal.

In some embodiments involving the use of a site base, the 90 degree, beveled, hollow, stainless steel needle, the needle may be designed to protrude from the center or near the center of the site base. In some embodiments, this arrangement increases the likelihood that the site base will remain adhered to the surface of the skin for the entirety of its intended use.

In some embodiments involving multiple medicaments where a site connector can be connected to or disconnected from a site base, the site connectors and site bases can contain features such as lettering or other visual indicators to help prevent mis-connection of a site base or a site connector to incorrect site connectors or site bases. In some embodiments, such lettering or other visual indicators (colors, etc.) can be used in addition to physical features that mechanically prevent mis-connection. In some embodiments, the lettering or other visual indicators can be raised and colored differently from the base material to enhance visibility.

In some embodiments involving multiple medicaments where a site connector can be connected to or disconnected from a site base, the site connectors and the site bases can contain features such as asymmetric post receptacles, retention clips, alignment posts, and/or keys and keyways that prevent mis-connection of a site base or a site connector to incorrect site connectors or site bases.

In some embodiments involving a site connector or site connectors, each site connector can be designed to connect to a site base by the action of at least one retention clip that fits into at least one retention slot. In some embodiments involving two medicaments where only one retention clip and retention slot pair is used on each site connector and site base pair, the retention clips and retention slots may be present on the medial or lateral (as in FIGS. 14-17) sides of the site connectors and site bases. If the retention clips and retention slots are present on the lateral side of one site connector and site base pair, and on the medial side of the other site connector and site base pair, convenience is afforded to the user by allowing for the same finger to activate the living hinges. In this case, mis-connection of the site connectors to incorrect site bases is still prevented by the presence of the asymmetric posts and asymmetric post receptacles.

In some embodiments involving two medicaments, a right site connector and a left site connector (as in FIGS. 15, 16, and 20) comprise the dual-medicament infusion site connectors, can be physically independent, and can contain features such as asymmetric post receptacles, retention clips, alignment posts, and/or keys and keyways that prevent mis-connection of the dual-medicament infusion site connectors to a dual-medicament infusion site base.

In some embodiments involving two medicaments, a right (second) site base and a left (first) site base (as in FIGS. 15, 16, and 20) comprise the dual-medicament infusion site base, can be physically independent, and can contain features such as retention slots (shown in FIG. 19), asymmetric posts, and alignment post receptacles that prevent mis-connection of the dual-medicament infusion site connectors to the dual-medicament infusion site base.

In some embodiments the site connectors and site bases are designed such that any site connector and site base pair from a multiple medicament configuration can be used individually in a single medicament configuration (as in FIGS. 17-19) such that the single medicament site connectors and site bases can be manufactured from the same tools as the multiple medicament site connectors and site bases.

In some embodiments involving multiple medicaments, the site connectors can be supplied with one or more site connector covers that may couple all of the site connectors, certain groups of the site connectors, or none of the site connectors such that each site connector can be supplied with its own site connector cover. The site connector cover can be connected to and disconnected from the site connectors repeatedly and protects them from exposure (as in FIG. 15A). Likewise, the site bases can be supplied with one or more site base covers that may couple all of the site bases, certain groups of the site bases, or none of the site bases such that each site base can be supplied with its own site base cover. The site base cover can be connected to and disconnected from the site bases repeatedly and protects them from exposure (as in FIG. 20).

In some embodiments involving a single medicament or multiple medicaments wherein each site base is supplied with its own site base cover and each site connector is supplied with its own site connector cover, the site base covers and the site connector covers could be manufactured from the same tools as the site bases and the site connectors respectively. In some embodiments, each site base cover may not contain the straight, beveled, hollow, stainless steel needle and the tubing and each site connector cover may not contain the 90 degree, beveled, hollow, stainless steel needle and the site base septum.

In some embodiments involving a single medicament or multiple medicaments, the site base or site bases can be supplied with a site base inserter that connects to the site base or site bases in the same manner as the site connectors and provides a handle for the application of site base or site bases (as in FIGS. 14 and 18). In some embodiments, the handle provided by the site base inserter may be used to apply the site base manually or to load the site base(s) into an automated insertion device, such as a spring loaded inserter. In some embodiments, in the case of multiple site bases, one or more site base inserters may couple all of the site bases, certain groups of the site bases, or none of the site bases such that each site base can be supplied with its own site base inserter. In some embodiments, removal of a site base inserter would decouple any coupled site bases.

In some embodiments, the infusion pump may be equipped with a cartridge detection hardware-software system that would detect, separately, whenever each cartridge is fully loaded and secured in its corresponding pump chamber. In some embodiments, since the design described herein can ensure that only the correct medicament cartridge can be fully loaded and secured in its corresponding pump chamber, the cartridge detection system can, when functioning in conjunction with the design described herein, effectively and conclusively inform the infusion pump system of which specific medicaments are available for potential infusion. In some embodiments, the availability status of each medicament for potential infusion at any point in time would also allow the infusion pump system to set its mode of operation accordingly. In some embodiments, for example, in the case of a dual-chamber pump, the detection of both cartridges being in place would allow the infusion pump system to operate in dual-infusion mode, whereas the detection of one cartridge being in place but not the other would lead the infusion pump system to operate in a single-infusion mode that is specific to the medicament that corresponds to the cartridge that is detected to be in place. In some embodiments, this detection capability would be determined autonomously in real time, including when a cartridge is in place or out of place transiently or temporarily.

In some embodiments, the infusion pump may also be equipped with a delivery occlusion hardware-software detection system that would detect, separately, whenever the fluid-delivery path associated with each cartridge is impeded or obstructed anywhere from the cartridge, all the way through the corresponding tubing, and out to the distal end of the corresponding site base. In some embodiments, since the design described herein can ensure that only the correct tubing assembly and site base can be connected to their corresponding cartridge, the occlusion detection system would, when functioning in conjunction with the design described herein, effectively and conclusively inform the infusion pump system of which specific medicaments have a patent fluid-delivery path.

In some embodiments, with both cartridge and occlusion detection systems simultaneously present, the infusion pump may at any point in time conclusively determines which medicament is possible to deliver to the user. In some embodiments, the infusion pump could then autonomously set its mode of operation, as per the detection of which of the cartridges are in place along with the patency of their corresponding fluid-delivery paths. In some embodiments, in a specialized example of a dual-chamber pump that autonomously controls blood glucose levels by delivering insulin or an insulin analog, as well as a counter-regulatory agent (e.g. glucagon, a glucagon analog, or dextrose), such cartridge and occlusion detection systems, when functioning in conjunction with the design described here, would practically allow the infusion pump system to be prescribed in a particular configuration to deliver only insulin, or only the counter-regulatory agent, or both. Moreover, in some embodiments, such an implementation would also allow the dual-chamber infusion pump system to autonomously switch its mode of operation in real time whenever either delivery channel becomes unavailable for delivery (whether informed by cartridge detection, occlusion detection, or both), including in cases where channel availability may alternate in real time. In some embodiments, the cartridge and occlusion detection methods could be realized through a variety of hardware and software implementations, including, but not limited to, techniques that rely on magnetic field or electrical signal feedback in the case of cartridge detection, or techniques that rely on back pressure detection or flow sensor technology in the case of occlusion detection, to mention but a few.

In some embodiments, the features described in the context of one base, connector, housing, inlet connector, inlet connector cover, collar, medicament reservoir, or pump assembly can be mixed and matched and used in different combinations on other bases, connectors, housings, inlet connectors, inlet connector covers, collars, medicament reservoirs, or pump assemblies. For instance, any feature described above to prevent mischanneling can be deleted from or added to other embodiments. Redundant features can be added or deleted from the components of the medicament delivery systems.

The examples shown here are meant to be representative of a general approach to the design of an infusion system for multiple medicaments and various connectors, tubes, and cartridges to ensure proper channeling of each medicament to the patient. The geometric shapes, sizes, orientations, locations, and number of tabs, protrusions, and features, as well as the corresponding cavities, grooves, keyways, or slots are merely meant to be examples of a much greater abundance of variations on the particular examples shown here.

For instance, as described elsewhere herein, the degrees of separation between the tabs, protrusions, and features on the cap connectors and on the corresponding cavities, grooves, keyways, or slots in the pump housing, or the degrees of separation between the tabs, protrusions, and features on the pre-fitted collar assembly and the corresponding cavities, grooves, keyways, or slots on the cap connector shown here can be generalized to be placed closer together or farther apart than in the examples shown here. Additionally, the number of tabs, protrusions, and features on the cap connectors and on the corresponding cavities, grooves, keyways, or slots in the pump housing, or the number of tabs, protrusions, and features on the pre-fitted collar assembly and the corresponding cavities, grooves, keyways, or slots on the cap connector designs shown here can be generalized to one, two, three or more such features, which might have different sizes, shapes, orientations, and locations from the examples shown here. Moreover, as discussed above, the locations of the tabs, protrusions, and features on the pre-fitted collar assembly and the corresponding cavities, grooves, keyways, or slots on the cap connector designs shown here need not be limited to the neck or head (or crown) regions of the cartridge. For instance, the point of engagement between the pre-fitted collar assembly and the cap connector could alternatively occur elsewhere on the body of the cartridge, or extend over the entire length of the cartridge. In some embodiments, the tabs, protrusions, and features on the pre-fitted collar assemblies described here could instead appear directly on the surface of the cartridge (such as in the case of an injection molded cartridge), which is either pre-filled with medicament or not pre-filled with medicament.

In some embodiments, the cartridges described here can either be pre-filled with medicament or not pre-filled with medicament before or after the pre-fitted collar assemblies described here are installed onto the cartridge. In the case of the latter, such cartridges can be filled with medicament sometime after the manufacturing process, including at the point of care.

In some embodiments, for example in the case of a cartridge that is filled with medicament at the point of care, the cap connector might not contain a recessed needle, but rather might couple with said cartridge using a standard luer lock or other mechanism, in which the medicament flows directly from the cartridge into the tubing without first passing through a needle. In this case, the tabs, protrusions, and features on the pre-fitted collar assemblies described here would still appear on the surface of the cap connector.

In some embodiments, mischanneling of medicaments can still be avoided if one cartridge is prefilled with one medicament and a second cartridge is filled at the point of care with a different medicament. So long as only one cartridge needs to be filled with medicament at the point of care, and all other cartridges are pre-filled with medicaments, the designs described here can prevent medicament mischanneling.

In some embodiments, the features and components described above are applicable to reusable injection pens (e.g., insulin pens, etc.). In some embodiments, each collar, cap, input connector, etc. could be applied to prevent incorrect dosing of drugs delivered by injection pens. For example, one unique cartridge, having a first set of unique features as described above could be used to deliver long-acting insulin to a patient via a mated injection pen. Another unique cartridge, with a second set of unique features as described above could be used to deliver fast-acting or ultra-rapid insulin analogs to a patient via a different mated injection pen. As a further example, these features can be used to differentiate between more and less concentrated insulin analogs (e.g. U100, U200, or U500 insulin analogs).

The medicament described above for any embodiment can include any suitable compound or drug for treating, regulating, controlling or addressing one or more conditions of the patient. While diabetes mellitus is a target, other conditions can be addressed as well (e.g., pancreatic misfunction). The medicament can include for example a regulating agent, such as insulin, for regulating the blood glucose levels in the patient and/or a counter-regulatory agent, such as glucose or glucagon, for more effective blood glucose regulation in certain circumstances. Other type of agents can be used as well.

In some embodiments, an infusion system for multiple medicaments involving various needle sites, connectors, tubes, and cartridges that ensure proper channeling of each medicament to the patient is provided. In some embodiments, the infusion system comprises an infusion pump. In some embodiments, the infusion system comprises an infusion pump with two or more pump chambers. In some embodiments, the infusion system comprises cartridges that can be filled at the point of care with different medicaments (or may be pre-filled with different medicaments). In some embodiments, the infusion system comprises connectors and tubing that connect the cartridges to the infusion pump in such a way as to prevent mischanneling or cross-channeling of medicaments. In some embodiments, each type of cartridge for each type of medicament has unique differentiating sizes, shapes, and/or geometrical features (either as an integral part of the cartridge or as a component attached or affixed to the cartridge) that allow for unique coupling with a type of connector that itself has unique differentiating features that engage corresponding features in the pump housing and only allow for insertion of the proper cartridge into the proper pump chamber within the infusion pump.

In some embodiments, the systems described above can be used for the delivery of single medicaments, or combinations of medicaments. For instance, in some embodiments, the infusion set can be used to deliver agent A (e.g., insulin), while the features of that infusion set would be incompatible with the medicament reservoir for agent B (e.g., glucagon). Alternatively, in some embodiments, the infusion set can be used to deliver agent B, while the features of that infusion set would be incompatible with the medicament reservoir for agent A. Additionally, in some embodiments, as described above, dual medicaments can be delivered without mischanneling (e.g., bi-hormonal delivery, dual drug delivery, etc.). As is apparent from the disclosure above, configurations for the delivery of a plurality of medicaments (e.g., two, three, four, or more) without mischanneling can be provided.

In some embodiments, methods of making the infusion systems disclosed herein are provided. In some embodiments, various needle sites, connectors, tubes, and cartridges that ensure proper channeling of each medicament to the patient are assembled. In some embodiments, the method comprises assembling an infusion system with an infusion pump. In some embodiments, the method comprises assembling an infusion system with a pump having two or more pump chambers. In some embodiments, the method comprises assembling an infusion system with connectors and tubing that connect the cartridges to the infusion pump in such a way as to prevent mischanneling or cross-channeling of medicaments. In some embodiments, each type of cartridge for each type of medicament is assembled to have unique differentiating sizes, shapes, and/or geometrical features (either as an integral part of the cartridge or as a component attached or affixed to the cartridge) that allow for unique coupling with a type of connector that itself has unique differentiating features that engage corresponding features in the pump housing and only allow for insertion of the proper cartridge into the proper pump chamber within the infusion pump. In some embodiments, a pump housing is prepared by connecting a bezel to a lower portion of the pump. In several embodiments, a display screen is connected to the bezel. In several embodiments, one or more of the o-rings, lead screws, drive nuts, motors, power sources, and gear assemblies are added to the pump housing. In some embodiments, the body of a connector is affixed to a knob. In several embodiments, a membrane is placed between the knob and the body. In some embodiments, a needle is affixed to the body. In several embodiments, a fluid conduit is affixed to the connector. In several embodiments, a fluid conduit is affixed to an infusion site connector.

It should be appreciated that any of the features of the cartridge connectors, pumps, and/or cartridges disclosed herein (e.g., retention lugs (shape, size, and position), detents (shape, size, and position), skirts (length and diameter), threading (e.g., different directional, such as clockwise counter clockwise), cartridge connectors (shape, size, and position), coinciding receiving portions on the pump receptacles, etc.) may be used in combination to provide multiple cartridge connectors and pumps that avoid mischanneling. Likewise, one or more of features disclosed herein for the cartridge connectors (e.g., retention lugs and detents) could instead be provided on the pump receptacle and the coinciding pump features described above (lug and detent tracks) could instead be provided on the cartridge connectors. Moreover, as disclosed elsewhere herein, the cartridge connectors, pumps, and/or cartridges disclosed herein could lack one or more features disclosed herein.

Any terms generally associated with circles, such as "radius" or "radial" or "diameter" or "circumference" or "circumferential" or any derivatives or similar types of terms are intended to be used to designate any corresponding structure in any type of geometry, not just circular structures. For example, "radial" as applied to another geometric structure should be understood to refer to a direction or distance between a location corresponding to a general geometric center of such structure to a perimeter of such structure; "diameter" as applied to another geometric structure should be understood to refer to a cross sectional width of such structure; and "circumference" as applied to another geometric structure should be understood to refer to a perimeter region. Nothing in this specification or drawings should be interpreted to limit these terms to only circles or circular structures.

What is claimed is:
1. A cartridge connector comprising:
a body comprising:
  a needle;
  a lower surface portion extending circumferentially outwardly from the needle, the lower surface comprising a bowl-shaped concavity and a surrounding lip, wherein the needle protrudes out of and extends away from the bowl-shaped concavity;
  a shroud extending axially away from a circumference of the lower surface portion and configured to receive and fit over a portion of a first medicament cartridge that is configured to hold a first medicament;
  wherein the lower surface portion is located within the shroud;
  wherein the needle extends axially from the lower surface portion and within the shroud;
  wherein the body comprises a projection extending axially upwardly from an upper surface of the body, the projection comprising a fluid outlet; and
  wherein the body is configured to receive the first medicament through the needle and to deliver the first medicament out of the body from the fluid outlet of the projection, the needle and the fluid outlet of the projection being in fluidic communication and providing a fluid path through the body;
a knob portion comprising:
  a receptacle section, the receptacle section of the knob portion configured to extend over and receive at least a portion of the projection of the body;

a fluid inlet located within the receptacle section, the fluid inlet of the knob portion being configured to receive the first medicament; and a fluid outlet, the fluid outlet of the knob portion being configured to deliver the first medicament to a position outside the cartridge connector;

wherein the cartridge connector comprises an interstitial space located between the projection of the body and the receptacle section of the knob portion and a flexible membrane located within the interstitial space, the flexible membrane extending over at least a portion of the projection of the body and being configured to allow fluid to pass from the fluid outlet of the projection and into the fluid inlet of the knob portion only after a threshold fluid pressure of the first medicament is reached; and wherein the cartridge connector is configured to engage a first pump receptacle of an infusion pump.

2. The cartridge connector of claim 1, wherein the lower surface portion of the body is configured to contact a cap of the first medicament cartridge when the first medicament cartridge is inserted into the cartridge connector within the shroud.

3. The cartridge connector of claim 1, wherein the knob portion comprises a perimeter having a flattened portion and wherein, once inserted into the first pump receptacle, the cartridge connector is configured to be positioned within the first pump receptacle using a quarter turn that aligns the flattened portion of the perimeter of the knob portion with a coinciding flat surface of the infusion pump to indicate to a user that the cartridge connector is correctly positioned in the infusion pump.

4. The cartridge connector of claim 1, wherein the knob portion comprises a lower side extending circumferentially outwardly from the shroud of the body and wherein the lower side of the knob portion comprises one or more protrusions configured to contact an upper side surface of the infusion pump.

5. The cartridge connector of claim 1, wherein the shroud comprises one or more of a snap arm configured to engage a cap of the first medicament cartridge, a detent configured to engage a corresponding detent track in the first receptacle of the infusion pump, and a lug configured to engage a corresponding lug track in the first receptacle of the infusion pump.

6. The cartridge connector of claim 1, wherein the cartridge connector is configured to not engage a second medicament cartridge.

7. The cartridge connector of claim 1, wherein the cartridge connector is configured to not engage a second pump receptacle of the infusion pump.

8. The cartridge connector of claim 1, wherein the shroud comprises a snap arm configured to engage a cap of the first medicament cartridge, a detent configured to engage a corresponding detent track in the first receptacle of the infusion pump, and a lug configured to engage a corresponding lug track in the first receptacle of the infusion pump.

9. The cartridge connector of claim 1, wherein the shroud comprises a snap arm configured to engage a cap of the first medicament cartridge.

10. The cartridge connector of claim 1, wherein the shroud comprises a detent configured to engage a corresponding detent track in the first receptacle of the infusion pump.

11. The cartridge connector of claim 1, wherein the shroud comprises a lug configured to engage a corresponding lug track in the first receptacle of the infusion pump.

12. The cartridge connector of claim 1, wherein the first medicament cartridge is an insulin cartridge.

13. The cartridge connector of claim 1, wherein the first medicament cartridge is a glucagon cartridge.

14. The cartridge connector of claim 1, wherein the fluid outlet of the projection comprises a passage extending radially outward from a central fluid conduit of the projection of the body, the passage terminating at an aperture that provides the fluid outlet of the projection.

15. The cartridge connector of claim 1, wherein the bowl-shaped concavity of the lower surface portion of the body is configured to allow the needle to flex in a manner that allows the cartridge connector to accept the first medicament cartridge without tearing a septum within a cap of the first medicament cartridge.

16. An infusion system comprising a first cartridge connector and a second cartridge connector;

wherein the first cartridge connector is the cartridge connector of claim 1; and wherein the second cartridge connector comprises:

a second cartridge connector needle;

a lower surface portion extending circumferentially outwardly from the needle;

a shroud extending axially away from a circumference of the lower surface portion of the second cartridge connector and configured to receive and fit over a portion of a second medicament cartridge that is configured to hold a second medicament, the second medicament cartridge being of a different shape than the first medicament cartridge; and a knob portion comprising a fluid outlet, the fluid outlet of the knob portion of the second cartridge connector being configured to deliver the second medicament to a position outside the second cartridge connector.

17. The infusion system of claim 16, wherein the first cartridge connector comprises a first recognition feature, wherein the first recognition feature of the first cartridge connector is configured to engage the first medicament cartridge and to block attachment of the second medicament cartridge to the first cartridge connector.

18. The infusion system of claim 17, wherein the second cartridge connector comprises a first recognition feature, wherein the first recognition feature of the second cartridge connector is configured to engage the second medicament cartridge and to block attachment of the first medicament cartridge to the second cartridge connector.

19. The infusion system of claim 18, wherein the first cartridge connector comprises a second recognition feature, wherein the second recognition feature of the first cartridge connector is configured to engage a corresponding recognition feature of the first pump receptacle of the infusion pump.

20. The infusion system of claim 19, wherein the second recognition feature of the first cartridge connector is configured to block attachment of the first cartridge connector to a second pump receptacle of the infusion pump.

21. The infusion system of claim 20, wherein the second cartridge connector comprises a second recognition feature, wherein the second recognition feature of the second cartridge connector is configured to engage a corresponding recognition feature of the second pump receptacle of the infusion pump.

22. The infusion system of claim 21, wherein the second recognition feature of the second cartridge connector is configured to block attachment of the second cartridge connector to the first pump receptacle of the infusion pump.

23. The infusion system of claim 22, wherein the second recognition feature of the first cartridge connector is a protrusion or a protrusion shaped-opening.

24. The infusion system of claim 23, wherein the second recognition feature of the second cartridge connector is a protrusion or a protrusion shaped-opening.

25. The infusion system of claim 18, wherein the system comprises the first medicament cartridge and the second medicament cartridge.

26. The infusion system of claim 18, wherein the first recognition feature of the first cartridge connector is a snap-arm or a skirt ring.

27. The infusion system of claim 26, wherein the first recognition feature of the second cartridge connector is a snap-arm, a skirt ring, or the shroud of the second cartridge connector.

28. The infusion system of claim 16, further comprising a multi-channel lumen assembly comprising:

a first tube comprising an inlet port and an outlet port, the inlet port of the first tube being in fluidic communication with the fluid outlet of the knob portion of the first cartridge connector and providing a first fluid path from the first cartridge connector; and a second tube comprising an inlet port and an outlet port, the inlet port of the second tube being in fluidic communication with the fluid outlet of the knob portion of the second cartridge connector and providing a second fluid path from the second cartridge connector.

29. The infusion system of claim 28, further comprising an infusion set configured to deliver the first and second medicaments to a patient, the infusion set being in fluidic communication with the multi-channel lumen assembly via the outlet port of the first tube and the outlet port of the second tube.

* * * * *